US012600775B2

(12) United States Patent
Bot et al.

(10) Patent No.: US 12,600,775 B2
(45) Date of Patent: Apr. 14, 2026

(54) CHIMERIC ANTIGEN RECEPTOR T CELL THERAPY

(71) Applicant: KITE PHARMA, INC., Santa Monica, CA (US)

(72) Inventors: Adrian Bot, Beverly Hills, CA (US); John Rossi, Newbury Park, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 389 days.

(21) Appl. No.: 17/091,039

(22) Filed: Nov. 6, 2020

(65) Prior Publication Data

US 2021/0161959 A1 Jun. 3, 2021

Related U.S. Application Data

(60) Provisional application No. 63/089,930, filed on Oct. 9, 2020, provisional application No. 63/063,692, filed on Aug. 10, 2020, provisional application No. 63/056,369, filed on Jul. 24, 2020, provisional application No. 63/031,217, filed on May 28, 2020, provisional application No. 62/944,937, filed on Dec. 6, 2019, provisional application No. 62/931,636, filed on Nov. 6, 2019.

(51) Int. Cl.

| | |
|---|---|
| ***C07K 16/28*** | (2006.01) |
| ***A61K 9/00*** | (2006.01) |
| ***A61K 31/675*** | (2006.01) |
| ***A61K 31/7076*** | (2006.01) |
| ***A61K 38/17*** | (2006.01) |
| ***A61K 39/00*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***A61P 35/02*** | (2006.01) |
| ***C07K 14/705*** | (2006.01) |
| ***C07K 14/725*** | (2006.01) |
| ***C12N 5/0783*** | (2010.01) |
| ***G01N 33/50*** | (2006.01) |
| ***G01N 33/574*** | (2006.01) |

(52) U.S. Cl.

CPC ........ *C07K 16/2803* (2013.01); *A61K 9/0019* (2013.01); *A61K 31/675* (2013.01); *A61K 31/7076* (2013.01); *A61K 38/1774* (2013.01); *A61K 39/3955* (2013.01); *A61K 40/11* (2025.01); *A61K 40/31* (2025.01); *A61K 40/4211* (2025.01); *A61P 35/00* (2018.01); *A61P 35/02* (2018.01); *C07K 14/7051* (2013.01); *C07K 14/70521* (2013.01); *C12N 5/0636* (2013.01); *G01N 33/505* (2013.01); *G01N 33/57426* (2013.01); *A61K 2039/545* (2013.01); *A61K 2239/38* (2023.05); *A61K 2239/48* (2023.05); *C07K 2317/622* (2013.01); *C07K 2317/76* (2013.01); *C07K 2319/30* (2013.01); *C07K 2319/33* (2013.01); *C12N 2501/505* (2013.01); *C12N 2506/11* (2013.01)

(58) Field of Classification Search

CPC .... A61K 35/17; A61K 9/0019; A61K 31/675; A61K 31/7076; A61K 38/1774; A61K 39/3955; A61K 2039/545; A61P 35/00; C07K 14/7051; C07K 14/70521; C07K 16/2803; C12N 5/0636; G01N 33/505

See application file for complete search history.

(56) References Cited

U.S. PATENT DOCUMENTS

| | | | | |
|---|---|---|---|---|
| 5,591,827 | A | 1/1997 | Brakenhoff et al. | |
| 5,728,388 | A | 3/1998 | Terman | |
| 5,827,642 | A | 10/1998 | Riddell et al. | |
| 6,040,177 | A | 3/2000 | Riddell et al. | |
| 6,319,494 | B1 | 11/2001 | Capon et al. | |
| 6,797,514 | B2 | 9/2004 | Berenson et al. | |
| 6,867,041 | B2 | 3/2005 | Berenson et al. | |
| 6,905,874 | B2 | 6/2005 | Berenson et al. | |
| 7,741,465 | B1 | 6/2010 | Eshhar et al. | |
| 8,562,991 | B2 | 10/2013 | Igawa et al. | |
| 9,855,298 | B2 | 1/2018 | Bot et al. | |
| 2002/0006409 | A1 | 1/2002 | Wood | |
| 2004/0126363 | A1 | 7/2004 | Jensen et al. | |
| 2013/0287748 | A1 | 10/2013 | June et al. | |
| 2014/0050708 | A1 | 2/2014 | Powell et al. | |
| 2014/0099309 | A1 | 4/2014 | Powell, Jr. et al. | |
| 2014/0154228 | A1 | 6/2014 | Volk et al. | |
| 2014/0227237 | A1 | 8/2014 | June et al. | |
| 2015/0283178 | A1* | 10/2015 | June ..................... | A61K 31/436 424/85.2 |
| 2018/0371093 | A1 | 12/2018 | Bilic et al. | |
| 2022/0387492 | A1 | 12/2022 | Bot et al. | |

FOREIGN PATENT DOCUMENTS

| | | | | |
|---|---|---|---|---|
| WO | 2008/081035 A1 | 7/2008 | | |
| WO | 2012/079000 A1 | 6/2012 | | |
| WO | 2012/129514 A1 | 9/2012 | | |
| WO | 2015/120096 A2 | 8/2015 | | |
| WO | WO-2015157252 | 10/2015 | | |
| WO | WO-2016191755 | 12/2016 | | |
| WO | WO-2016191756 | 12/2016 | | |
| WO | 2017/070395 A1 | 4/2017 | | |
| WO | WO-2018102786 | 6/2018 | | |
| WO | WO-2018183927 A1 * | 10/2018 | ........... | A61K 31/436 |
| WO | WO-2019058348 A1 * | 3/2019 | ........... | A61K 31/352 |

OTHER PUBLICATIONS

Liu et al. Current approaches and advance in mantle cell lymphoma treatment. Stem Cell Investigation 2015;2:18 (Year: 2015).*

(Continued)

*Primary Examiner* — Janet L Andres
*Assistant Examiner* — Brian Hartnett
(74) *Attorney, Agent, or Firm* — Sheppard Mullin Richter & Hampton LLP

(57) ABSTRACT

Provided herein are methods for preparing, producing, processing, culturing, isolating, or making cells suitable for immune or cell therapy, and for their use in cell therapy.

9 Claims, 44 Drawing Sheets

(56) References Cited

OTHER PUBLICATIONS

Figure 1A:
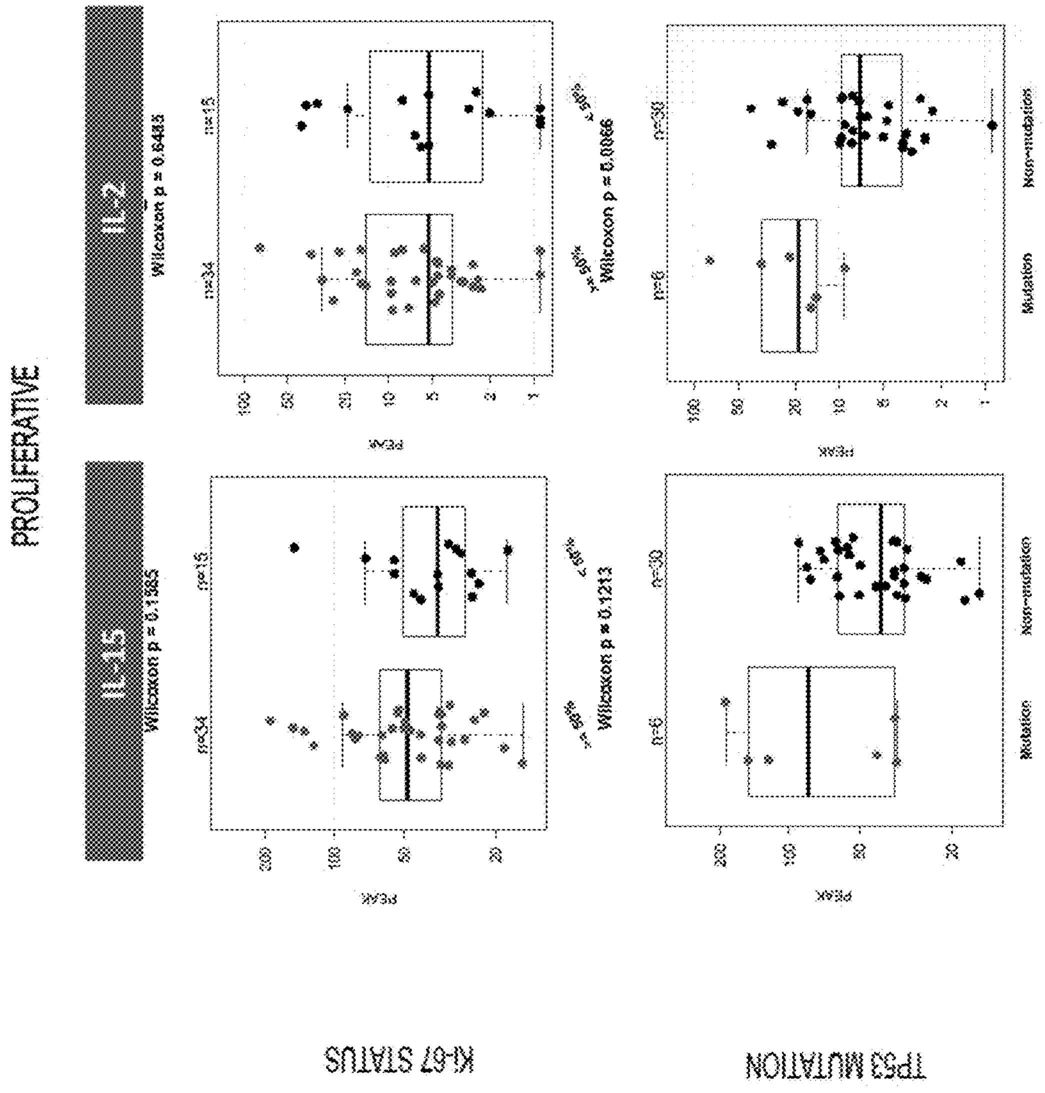
Figure 1B:
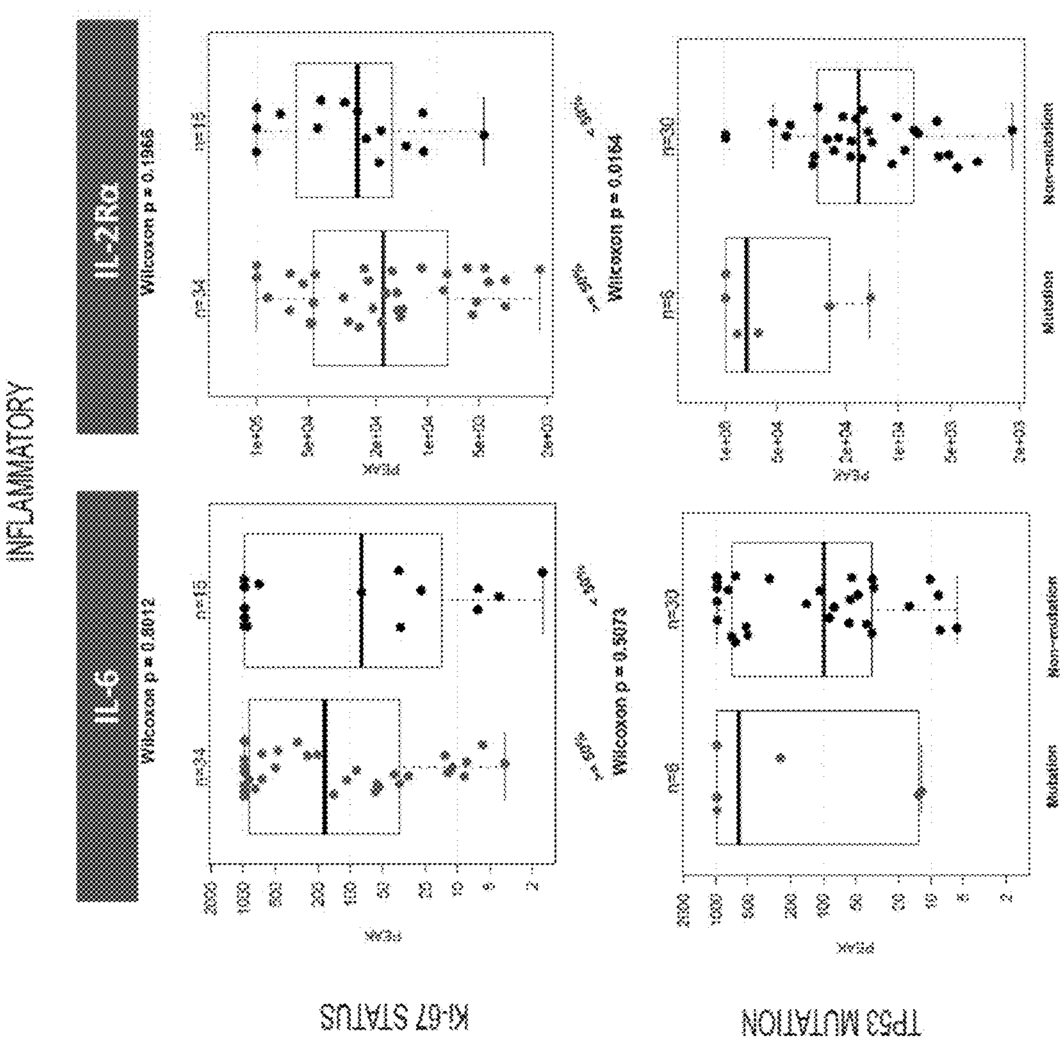
Figure 1C:
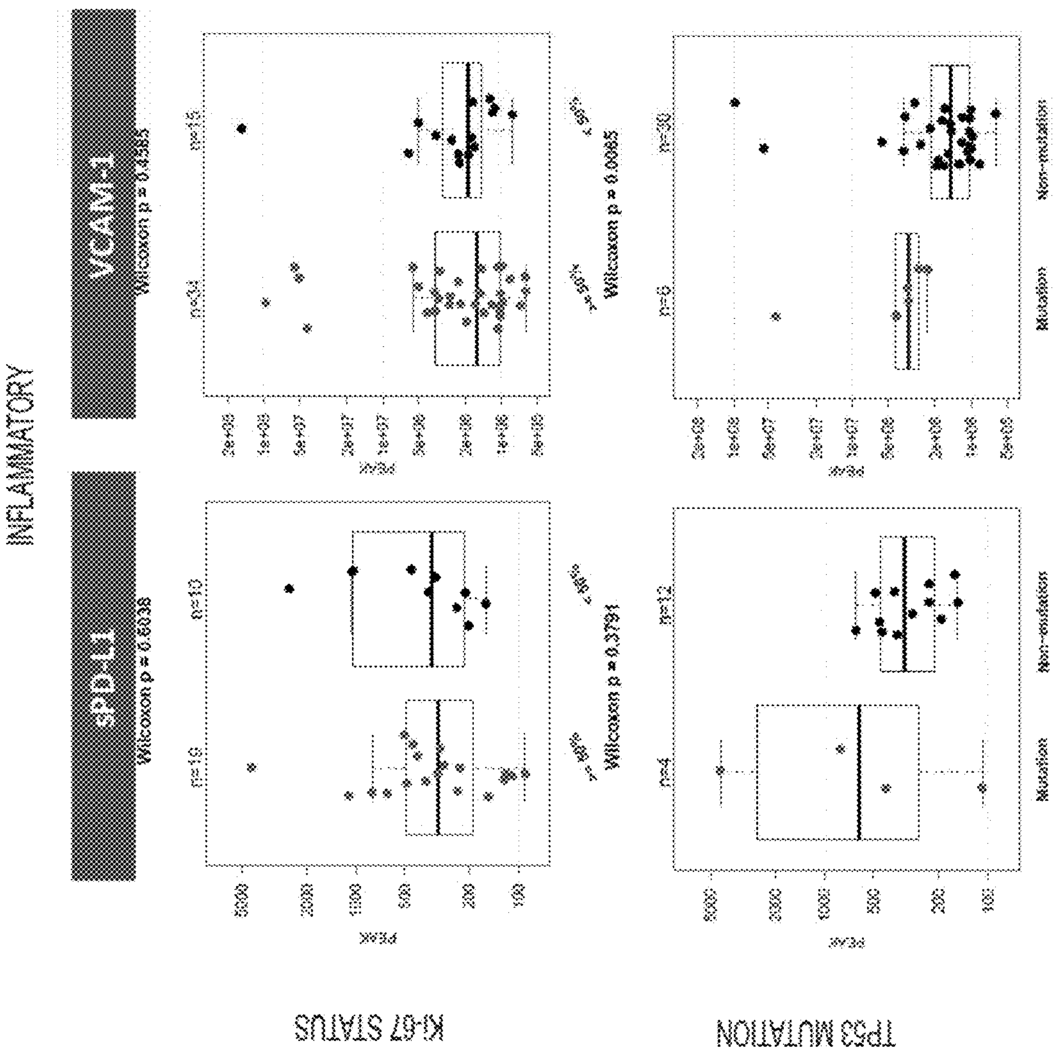
Figure 1D:
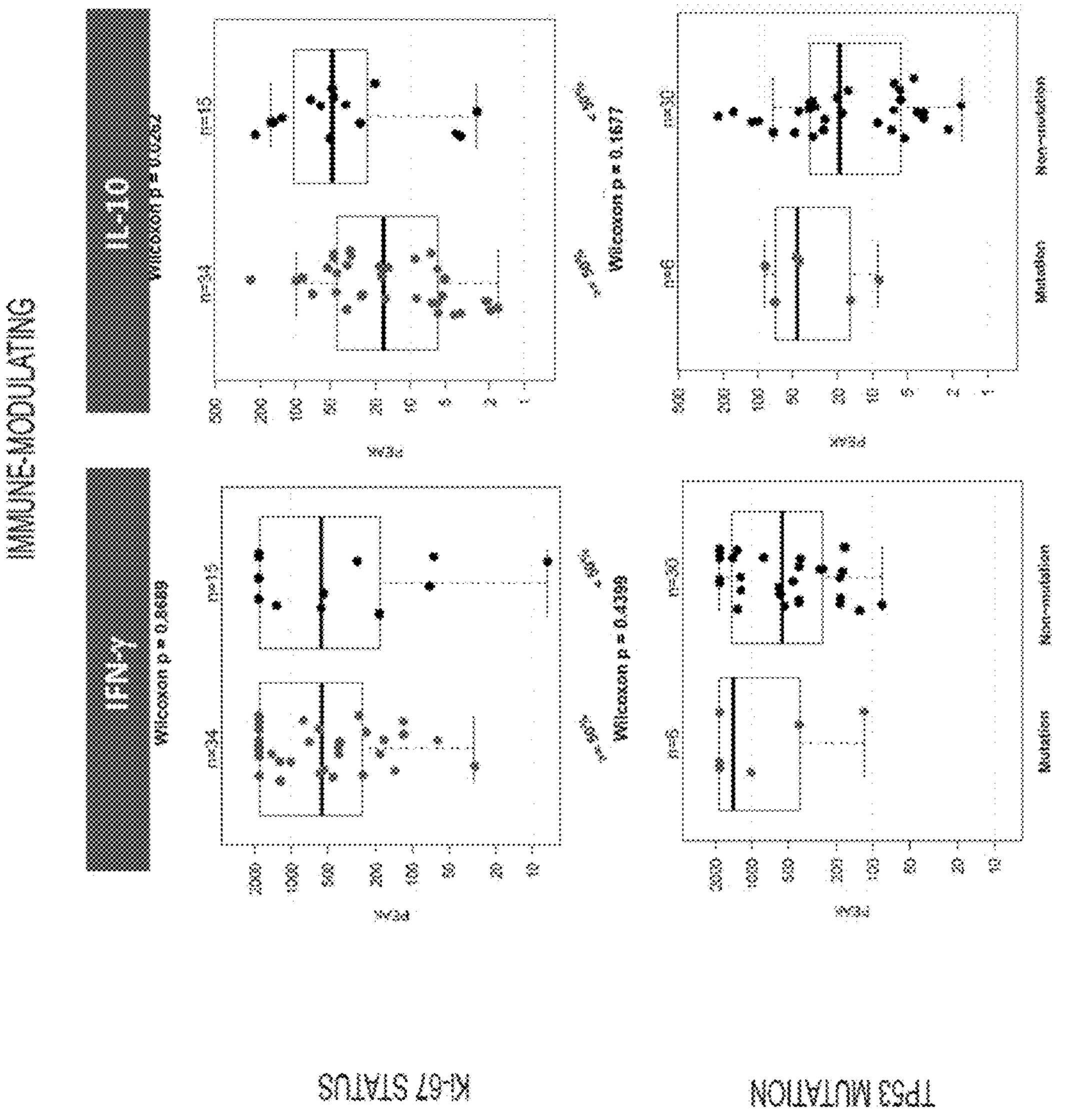
Figure 1E:
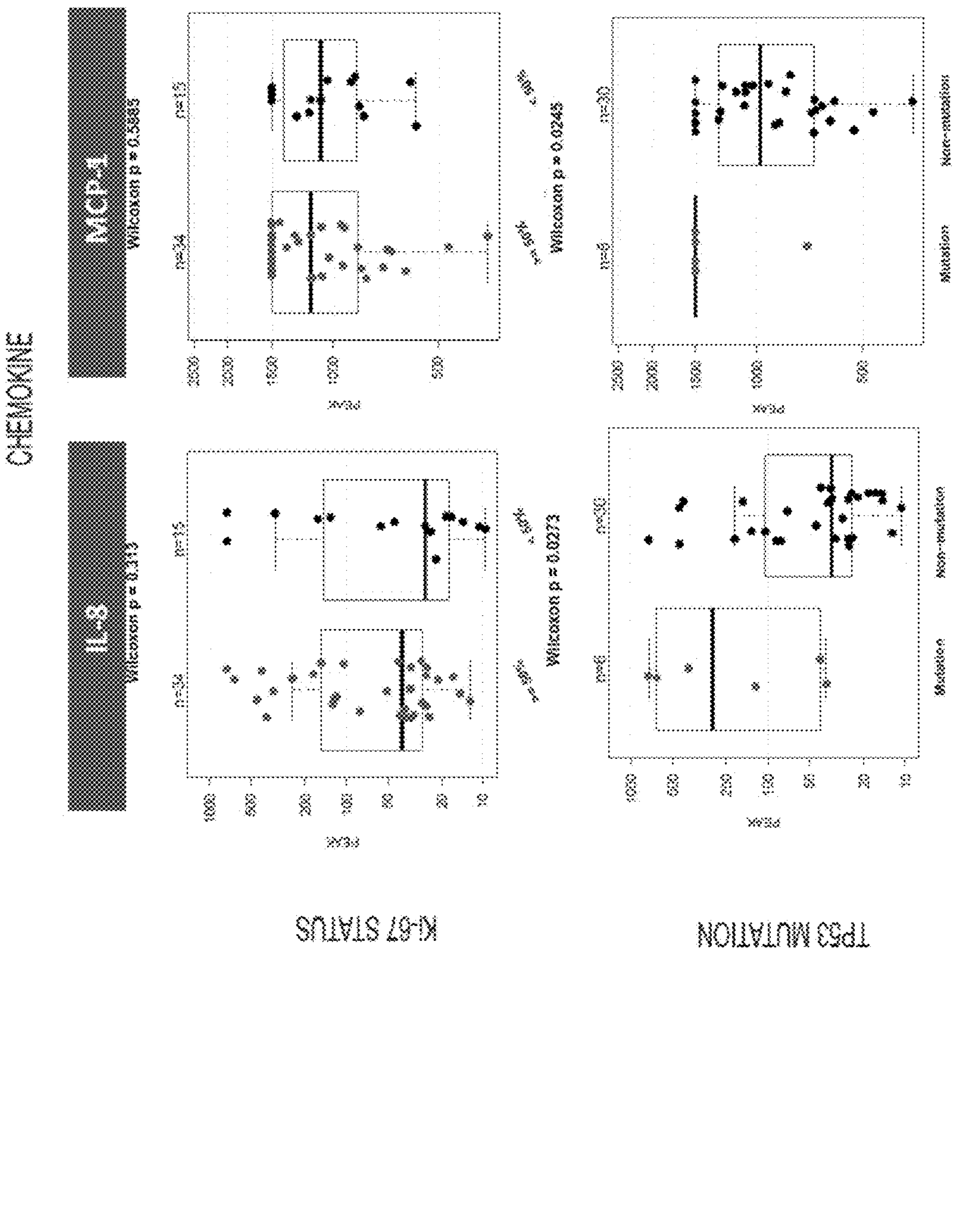
Figure 1F:
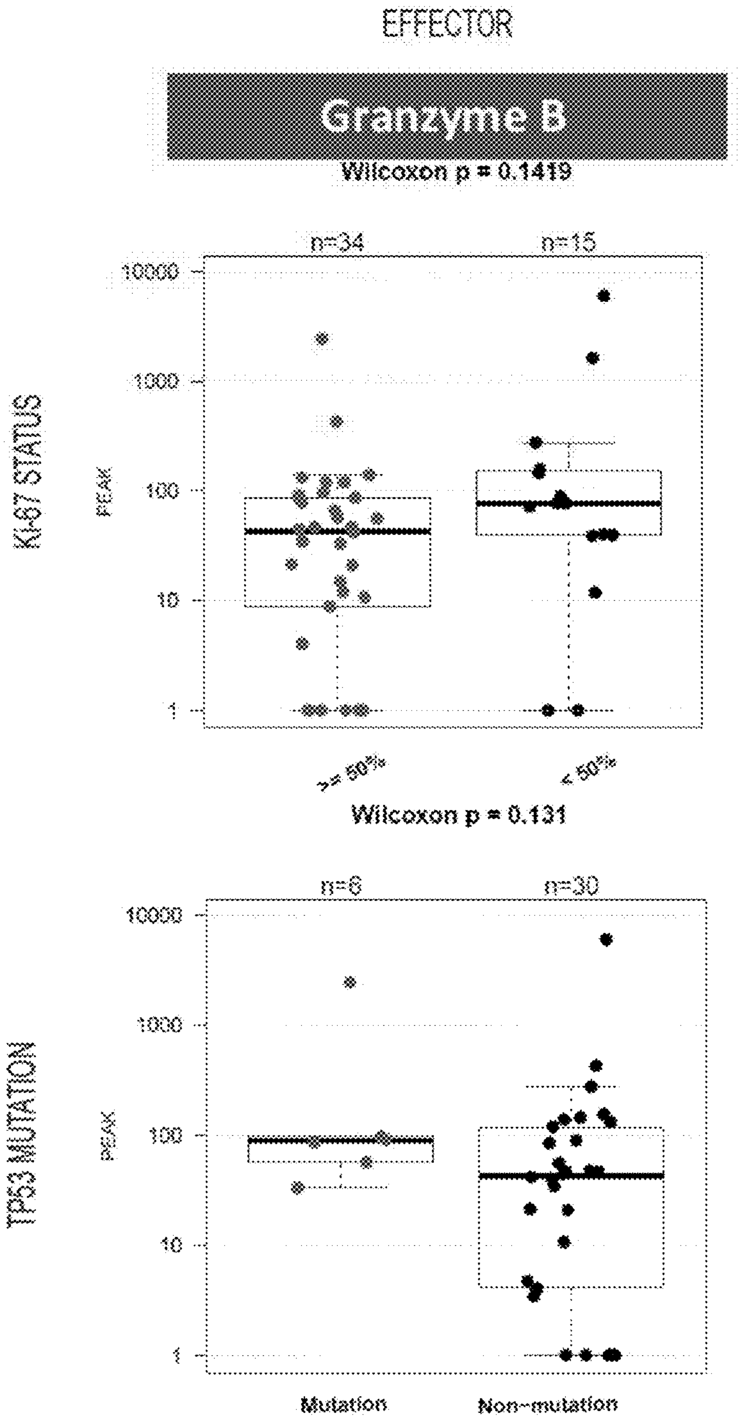
Figure 2A:
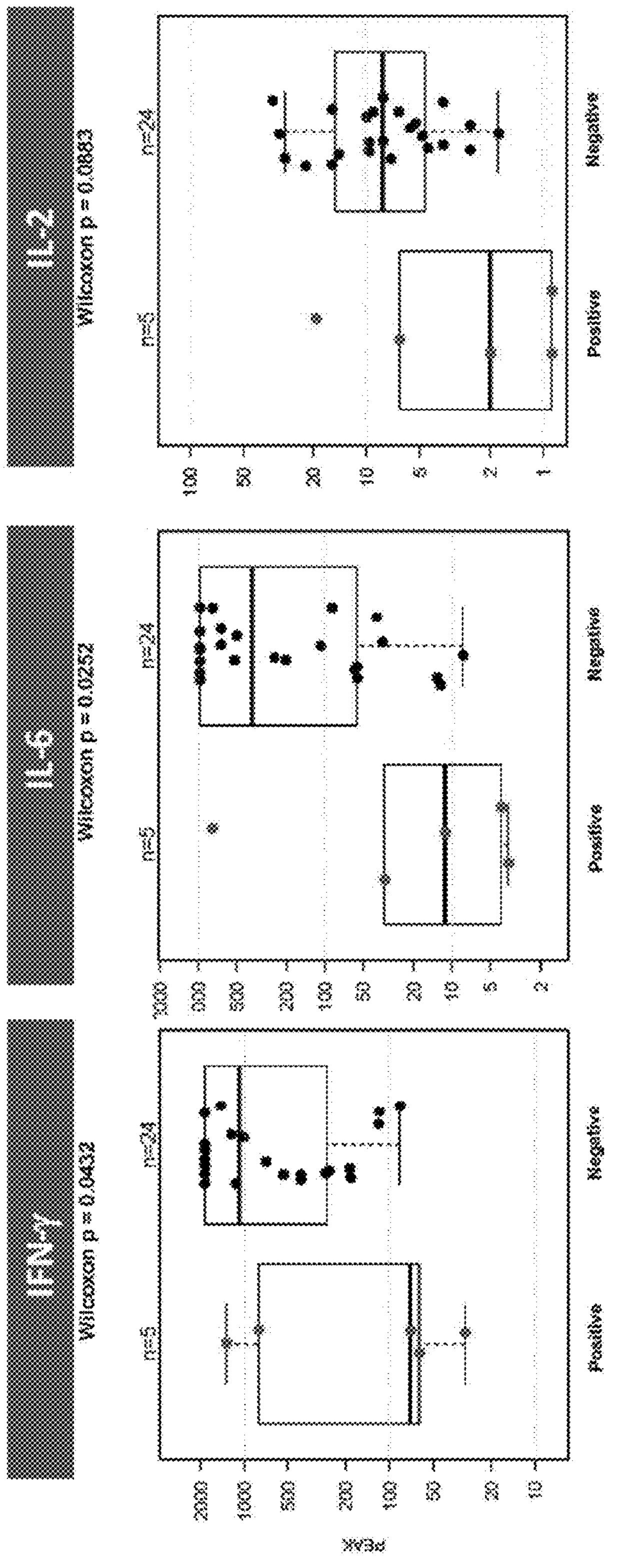
Figure 2B:
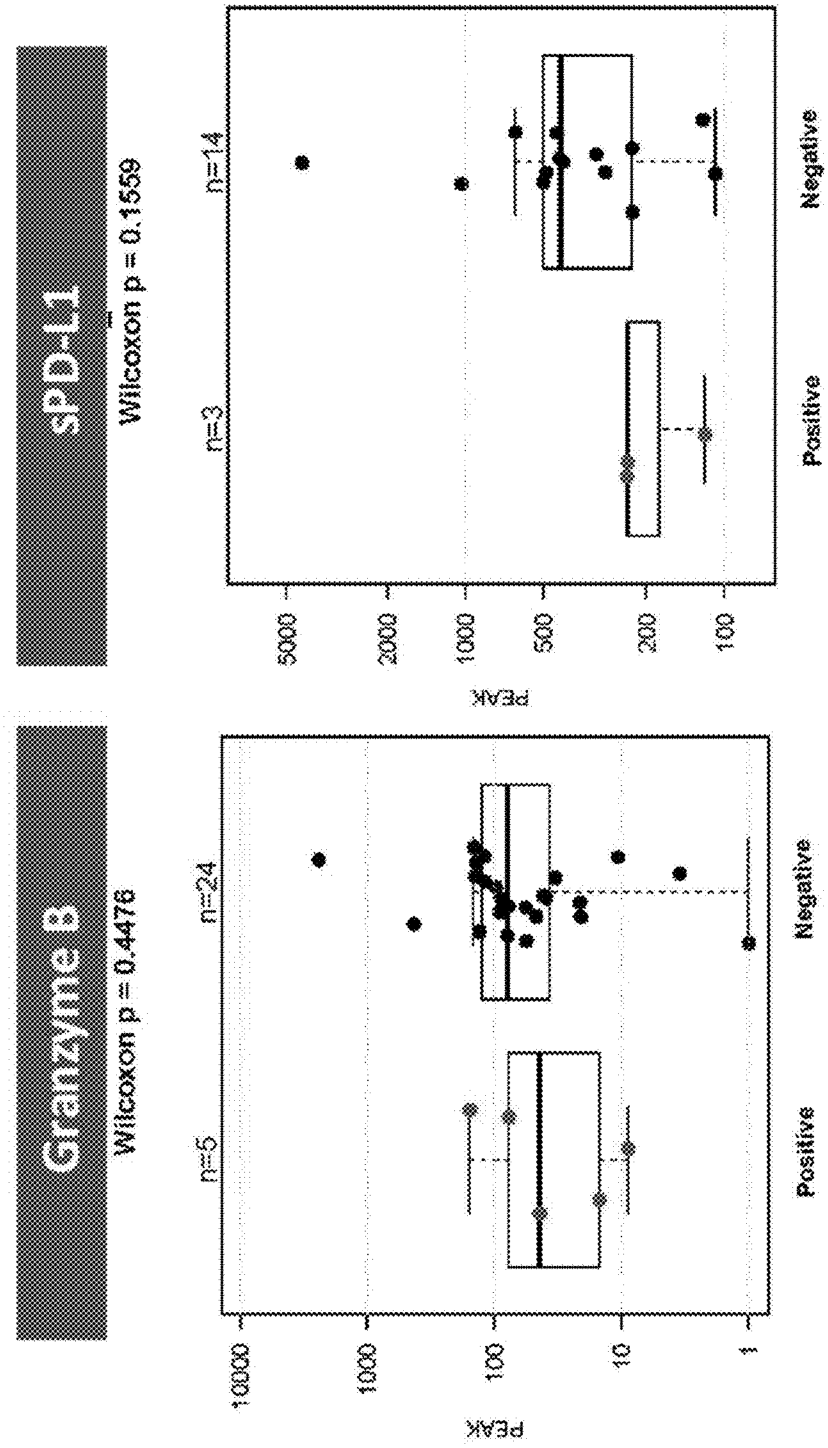
Figure 2C:
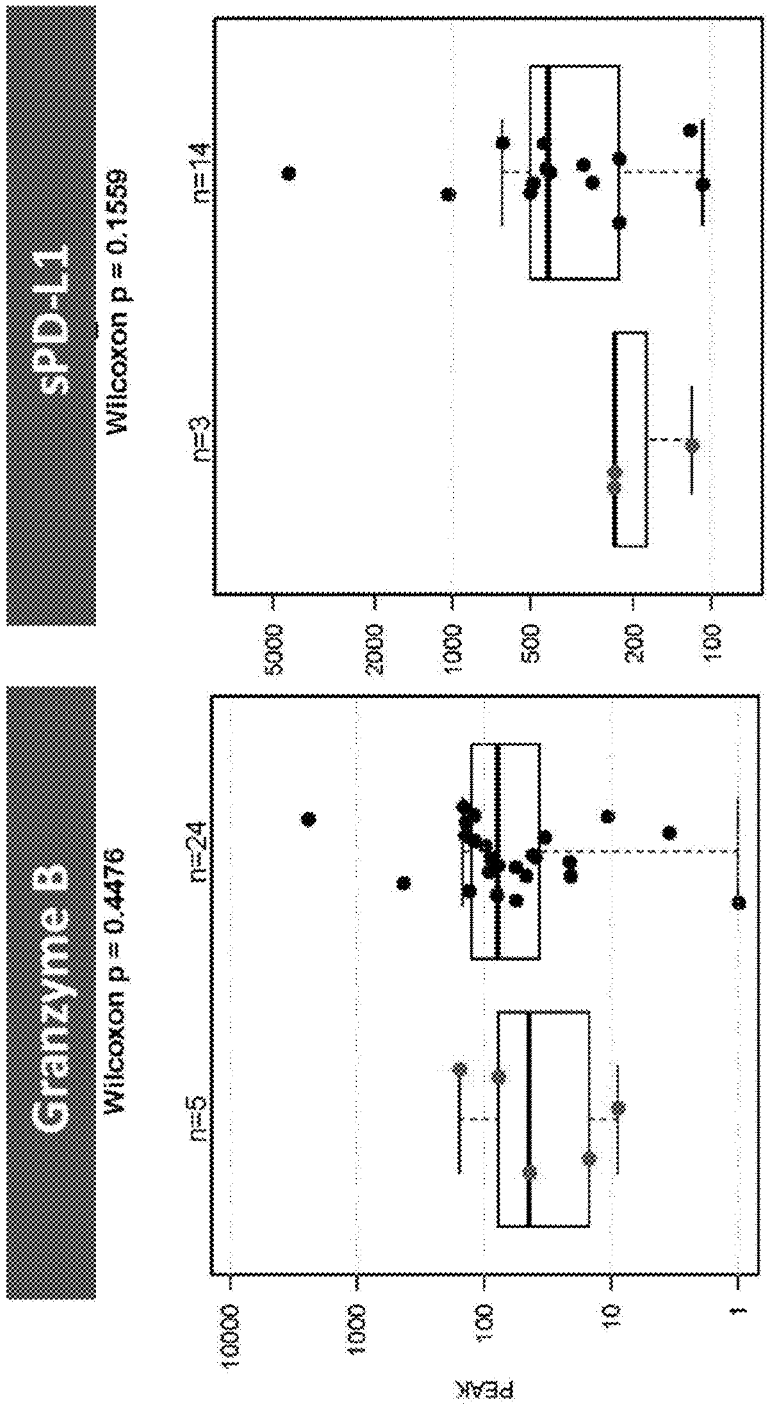
Figure 2D:
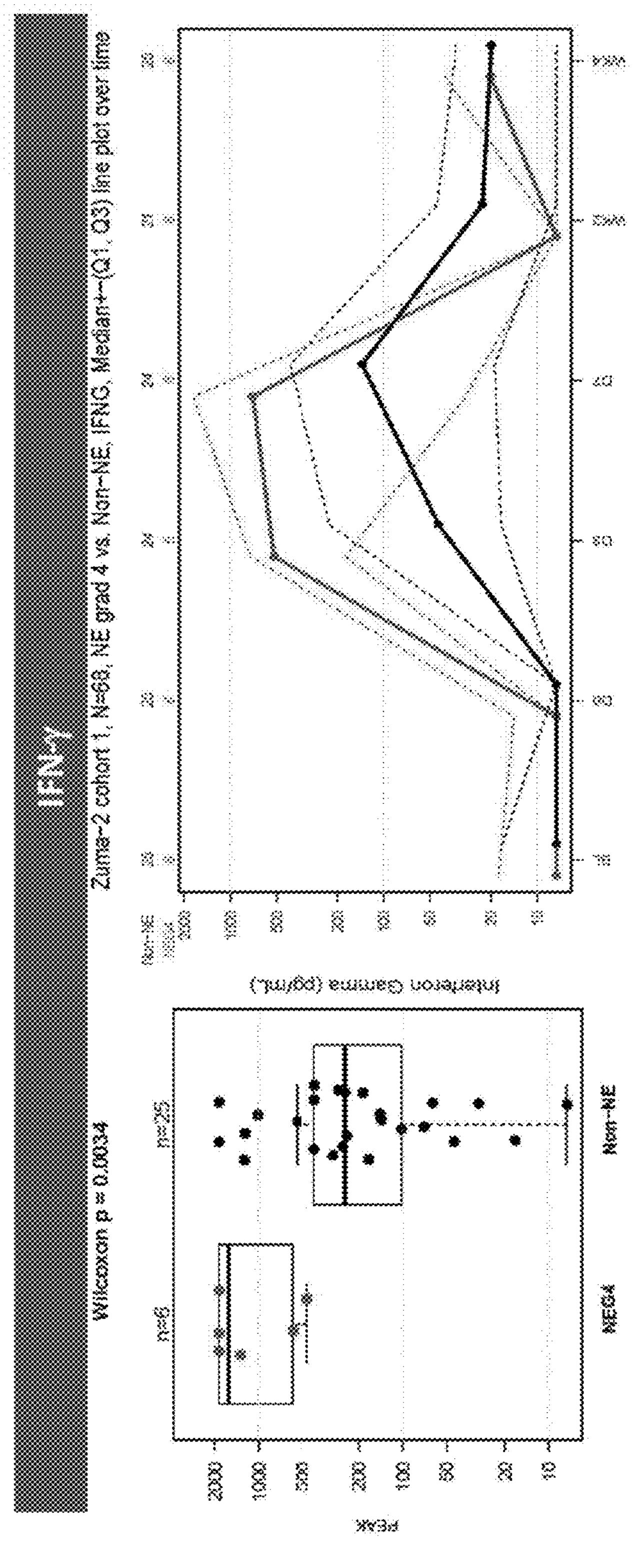
Figure 2E:
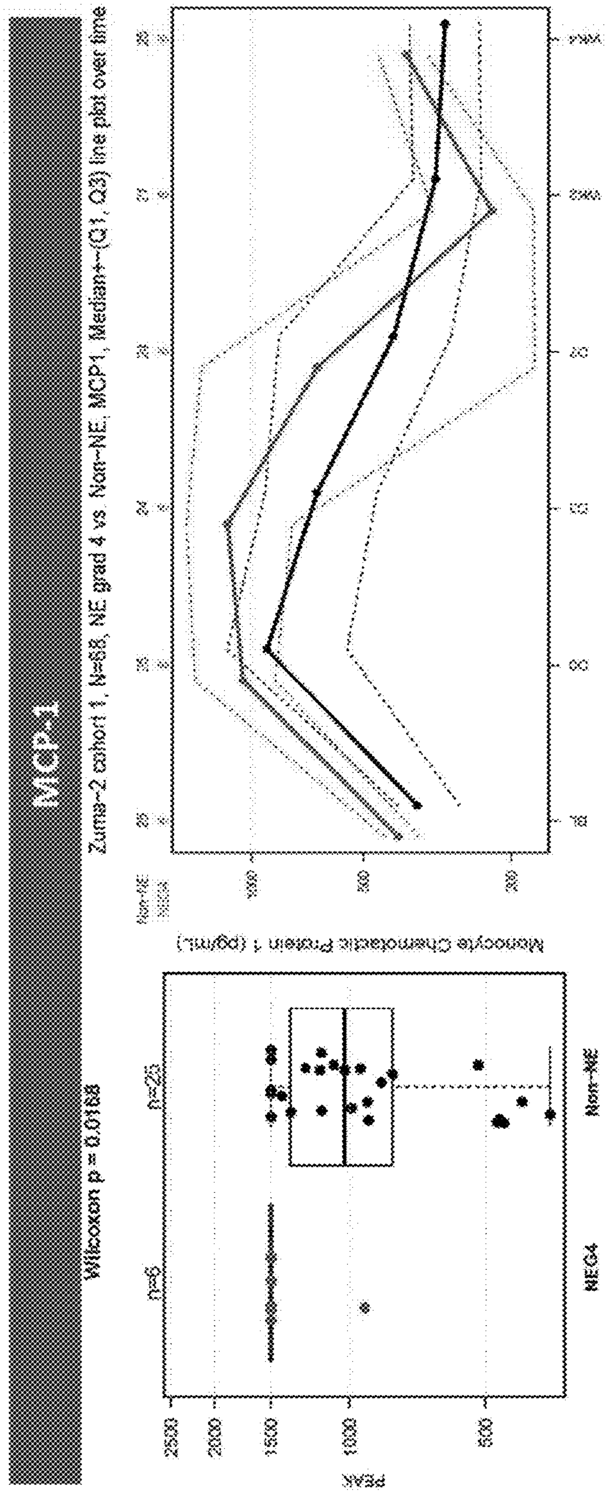
Figure 2F:
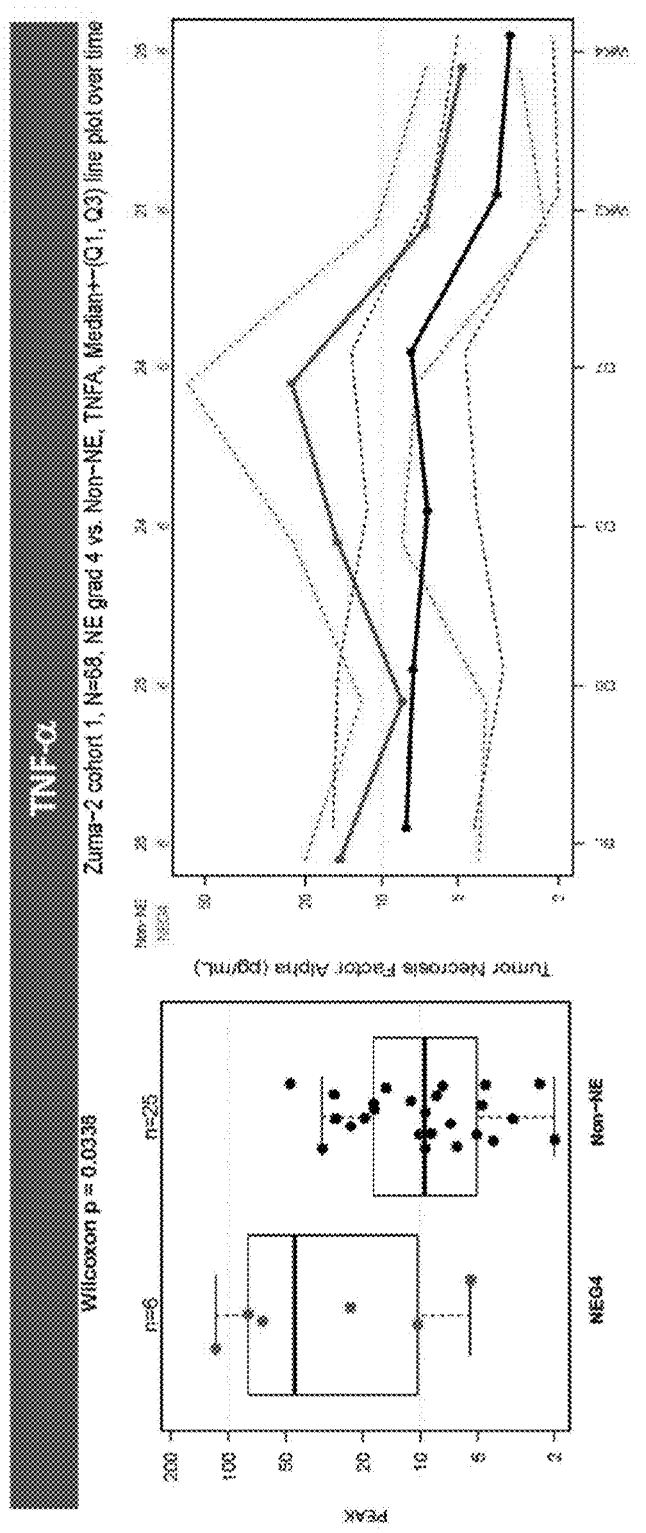
Figure 2G:
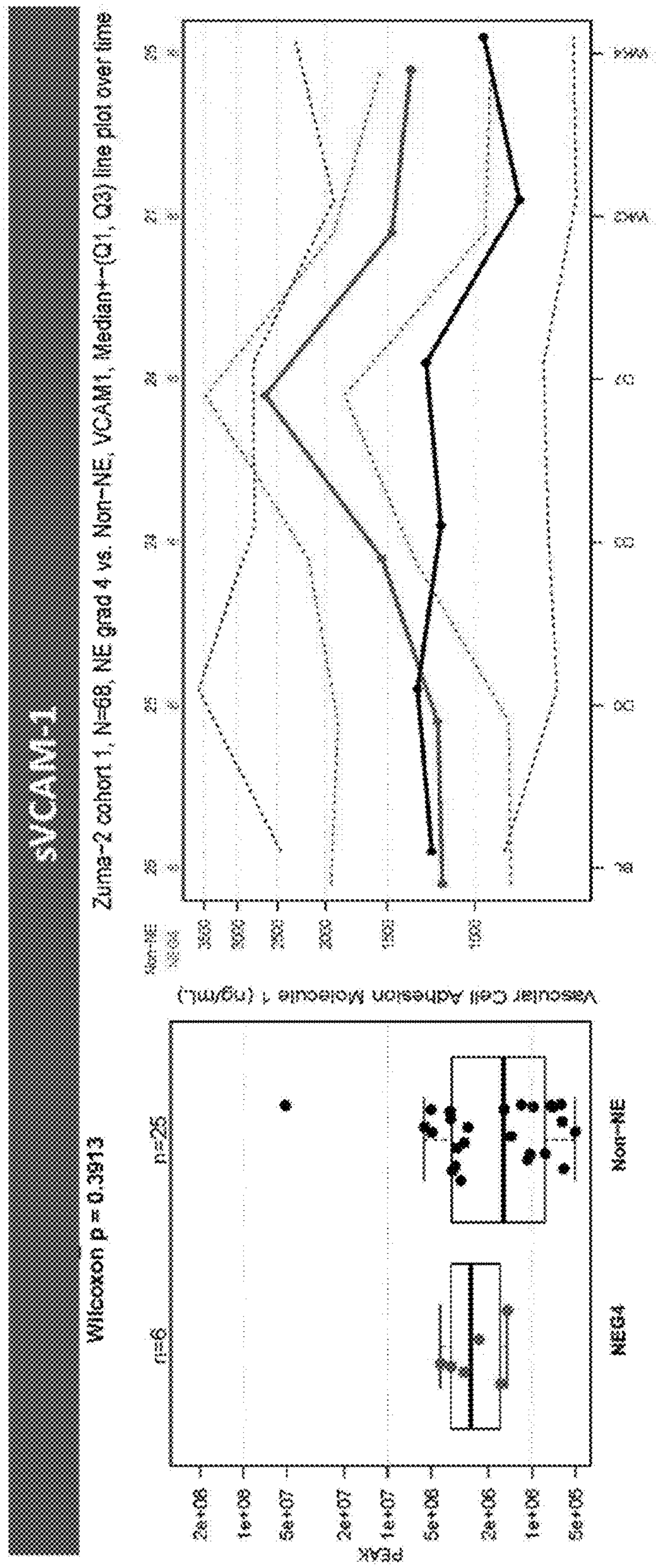
Figure 2H:
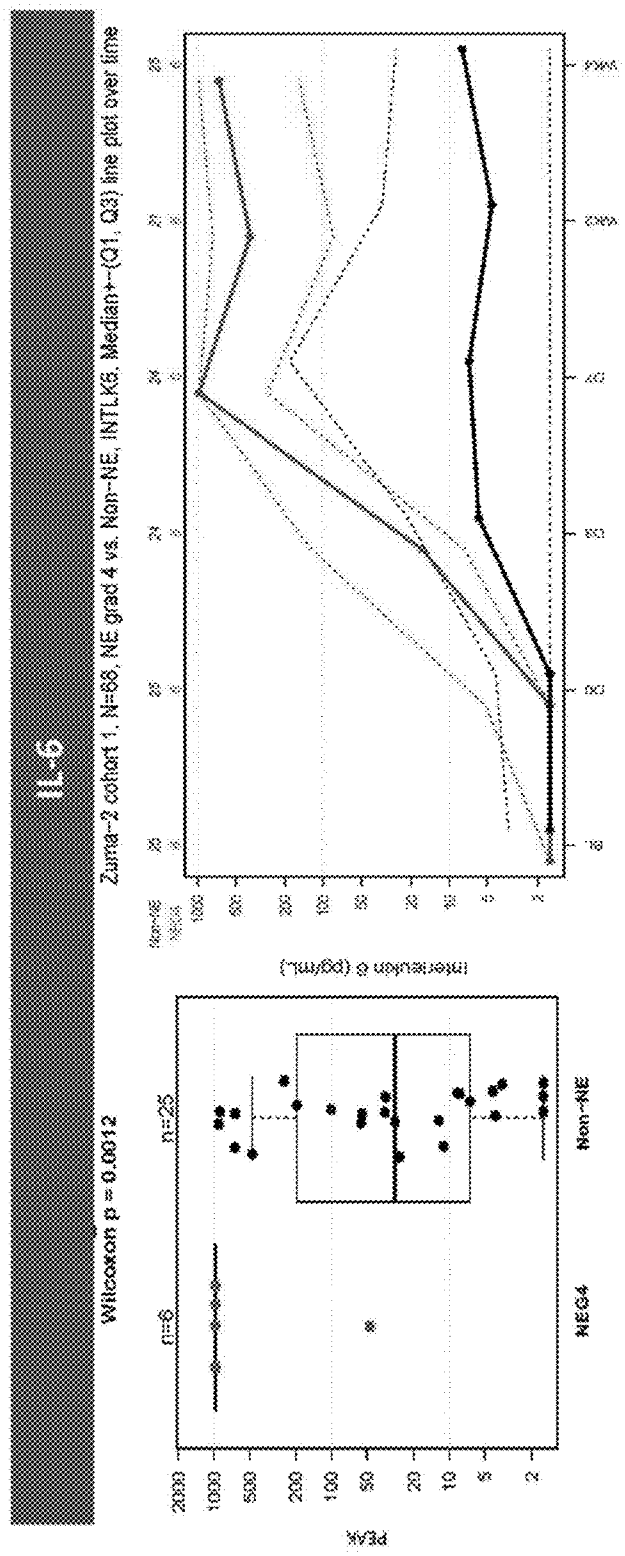
Figure 2I:
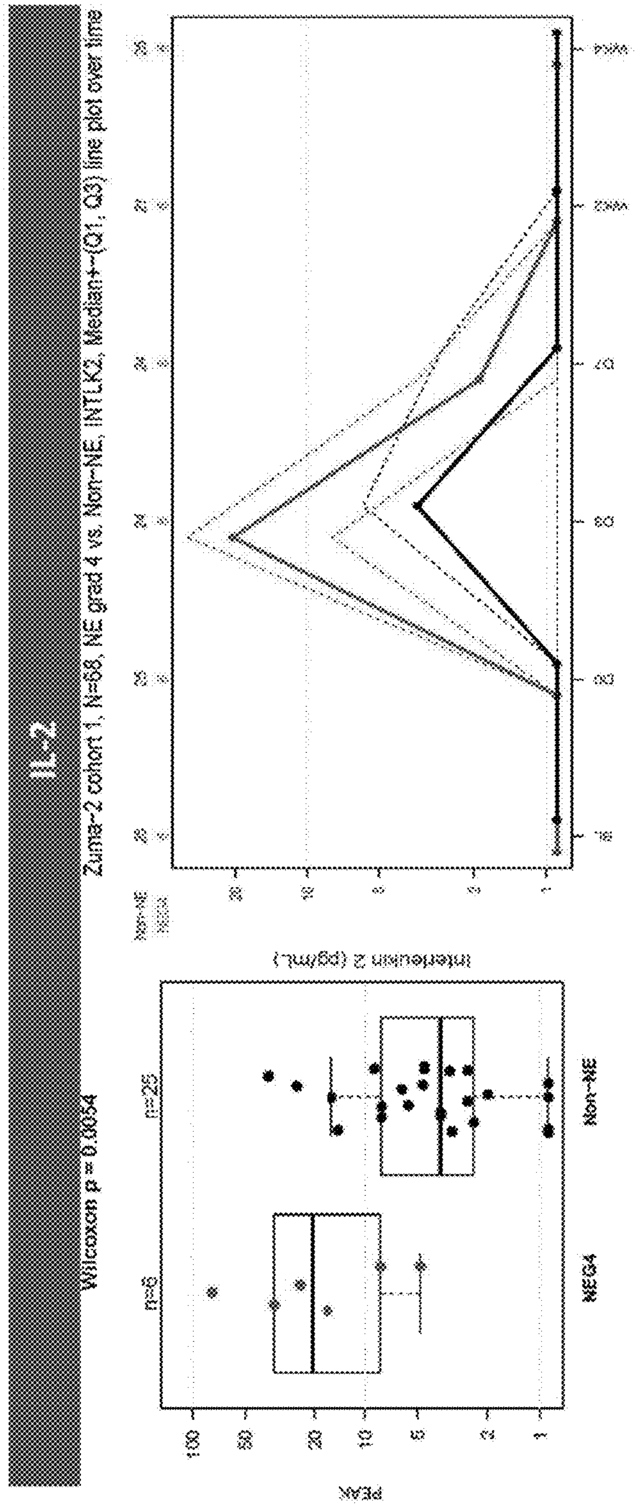

Jain et al. Mantle cell lymphoma: 2019 update on the diagnosis, pathogenesis, prognostication, and management. Am J Hematology. 2019;94:710-725. (Year: 2019).*
Neelapu et al. Axicabtagene Ciloleucel CAR T-Cell Therapy in Refractory Large B-Cell Lymphoma. n engl j med 377;26,Dec. 28, 2017 (Year: 2017).*
Schuster et al. Chimeric Antigen Receptor T Cells in Refractory B-Cell Lymphomas. n engl j med 377;26,Dec. 28, 2017. (Year : 2017).*
Locke et al. Phase 1 Results of ZUMA-1: A Multicenter Study of KTE-C19 Anti-CD19 CAR T Cell Therapy in Refractory Aggressive Lymphoma. Molecular Therapy vol. 25 No. Jan. 1, 2017. (Year: 2017).*
Wang et al. KTE-X19 CAR T-Cell Therapy in Relapsed or Refractory Mantle-Cell Lymphoma.n engl j med 382;14 nejm.org Apr. 2, 2020 (Year: 2020).*
Hay et al., Chimeric Antigen Receptor (CAR) T Cells: Lessons Learned from Targeting of CD19 in B-Cell Malignancies. Drugs 2017, doi 10.1007/s40265-017-0690-8. 9 pages.
International Search Report and Written Opinion for International Application No. PCT/US2020/059285 dated Apr. 12, 2021. 9 pages.
Lee et al. (2014), "Current concepts in the diagnosis and management of cytokine release syndrome", How I Treat Cytokine Release Syndrome, Blood, 124 (2) 188-195.
Juo, Pei-Show (2002) "Concise dictionary of biomedicine and molecular biology." second edition, Library of Congress Cataloging-in-Publication Data, CRC Press, 1163.
Topp et al. (2014), "Safety and activity of blinatumomab for adult patients with relapsed or refractory B-precursor acute lymphoblastic leukaemia: a multicentre, single-arm, phase 2 study", The Lancet, 16, 57-66.
Deangelo et al. (2017), "32nd Annual Meeting and Pre-Conference Programs of the Society for Immunotherapy of Cancer (SITC 2017): Part One," Journal for Immuno Therapy of Cancer, 5 (Suppl 2)(86), p. 217.
Lackie et al. (2013)The Dictionary of Cell and Molecular Biology, 5th edition, Academic Press, 748 pages.
Frey et al. (2019), "Optimizing Chimeric Antigen Receptor T-Cell Therapy for Adults With Acute Lymphoblastic Leukemia", Journal of Clinical Oncology, 1-10.
Maude et al. (2018), "Tisagenlecleucel in Children and Young Adults with B-Cell Lymphoblastic Leukemia", The New England Journal of Medicine, 378(5), 439-448.
Sabatino et al., "Production of Anti-CD19 CAR T Cells for ZUMA-3 and -4: Phase 1/2 Multicenter Studies Evaluating KTE-C19 in Patients With Relapsed/Refractory B-Precursor Acute Lymphoblastic Leukemia (R/R ALL)", Blood, 128 (2), 1-6.
Wang et al. (2020), "KTE-X19 CAR T-Cell Therapy in Relapsed or Refractory Mantle-Cell Lymphoma", The New England Journal of Medicine, 382(14), 1331-1342.
Kochenderfer et al. (2009), "Construction and Pre-clinical Evaluation of an Anti-CD19 Chimeric Antigen Receptor", NIH Public Access Author Manuscript, 32(7), 1-26.
Kochenderfer et al. (2010), "Eradication of B-lineage cells and regression of lymphoma in a patient treated with autologous T cells genetically engineered to recognize CD19", Blood, 116(20), 4099-4102.
Dolmans et al. (2003), "Photodynamic therapy for cancer", Nature Reviews, Cancer, 3, 380-397.
Ruella et al. (2016), "Chimeric Antigen Receptor T cells for B Cell Neoplasms: Choose the Right CAR for You", Curr Hematol Malig Rep, Spriger, 1-17.
Sadelain et al. (2013), "The Basic Principles of Chimeric Antigen Receptor Design", Review, Cancer Discovery, 388-398.
Locke et al. (2017), "Phase 1 Results of ZUMA-1: A Multicenter Study of KTE-C19 Anti-CD19 CAR T Cell Therapy in Refractory Aggressive Lymphoma", Molecular Therapy, 25(1), 285-295.
Kochenderfer et al. (2010), "Adoptive transfer of syngeneic T cells transduced with a chimeric antigen receptor that recognizes murine CD19 can eradicate lymphoma and normal B cells", Blood, 116(19), 3875-3886.
Lee et al. (2015), "T cells expressing CD19 chimeric antigen receptors for acute lymphoblastic leukaemia in children and young adults: a phase 1 dose-escalation trial", The Lancet, 385, 517-528.
Park et al. (2018), "Long-Term Follow-up of CD19 CAR Therapy in Acute Lymphoblastic Leukemia", The New England Journal of Medicine, 449-459.
Hunger et al. (2015), "Acute Lymphoblastic Leukemia in Children", The new england journal of medicine, 373(16), 1541-1552.
Sun et al. (2018), "Outcome of children with multiply relapsed B-cell acute lymphoblastic leukemia: a therapeutic advances in childhood leukemia & lymphoma study", Acute lymphoblastic leukemia, Springer Nature, 32, 2316-2325.
Rheingold et al. (2019), "Prognostic factors for survival after relapsed acute lymphoblastic leukemia (ALL): A Children's Oncology Group (COG) study", Journal of Clinical Oncology, List of Issues, 37(15), 1-5.
Oskarsson et al. (2016), "Relapsed childhood acute lymphoblastic leukemia in the Nordic countries: prognostic factors, treatment and outcome", Acute Lymphoblastic Leukemia, Haematologica, 101(1), 68-76.
Nguyen et al. (2008), "Factors influencing survival after relapse from acute lymphoblastic leukemia: a Children's Oncology Group study", Leukemia, 22, 2142-2150.
Crotta et al. (2018), "Survival after stem-cell transplant in pediatric and young-adult patients with relapsed and refractory B-cell acute lymphoblastic leukemia", Curr Med Resin, Opin., 34, 1-18.
Schrappe et al. (2012), "Outcomes after Induction Failure in Childhood Acute Lymphoblastic Leukemia", The New England Journal of Medicine, 366(15), 1371-1381.
Stackelberg et al. (2016), "Phase I/Phase II Study of Blinatumomab in Pediatric Patients With Relapsed/Refractory Acute Lymphoblastic Leukemia", Journal of Clinical Oncology, 34(36), 4381-4389.
Bhojwani et al. (2018), "Inotuzumab ozogamicin in pediatric patients with relapsed/refractory acute lymphoblastic leukemia", Leukemia, Acute lymphoblastic leukemia, accessed at https://doi.org/10.1038/s41375-018-0265-z, 1-9.
Borowitz et al. (2015), "Prognostic significance of minimal residual disease in high risk B-ALL: a report from Children's Oncology Group study AALL0232", Blood, 126(8), 964-971.
Brüggemann et al. (2017), "Minimal residual disease in adult ALL: technical aspects and implications for correct clinical interpretation", Blood Advances, 1(25), 2456-2466.
Gupta et al. (2018), "Flow-cytometric vs. -morphologic assessment of remission in childhood acute lymphoblastic leukemia: a report from the Children's Oncology Group (COG)", Leukemia, Springer Nature, accessed at https://doi.org/10.1038/s41375-018-0039-7, 1-10.
Cannarile et al. (2017), "Colony-stimulating factor 1 receptor (CSF1R) inhibitors in cancer therapy", Journal for Immuno Therapy of Cancer, 5(53), 1-13.
Hamilton, John A (2015), "GM-CSF as a target in inflammatory/autoimmune disease: current evidence and future therapeutic potential", Expert Reviews, Clin. Immunol., Early online, accessed at 10.1586/1744666X.2015.1024110, 1-9.
Wicks et al. (2015), "Targeting GM-CSF in inflammatory diseases", Nature Reviews, Rheumatology, 1-12.
Neelapu et al. (2018), "Chimeric antigen receptor T-cell therapy—assessment and management of toxicities", Nature Reviews, Clinical Oncology, 15, 47-62.
Kochenderfer et al. (2014), "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor", Journal Of Clinical Oncology, 1-11.
Neelapu et al. (2017), "Axicabtagene Ciloleucel CAR T-Cell Therapy in Refractory Large B-Cell Lymphoma", The New England Journal of Medicine, 2531-2544.
Schuster et al. (2019), "Tisagenlecleucel in Adult Relapsed or Refractory Diffuse Large B-Cell Lymphoma", The New England Journal of Medicine, 380(1), 45-56.

(56) References Cited

OTHER PUBLICATIONS

Cheson et al. (2014), "Recommendations for Initial Evaluation, Staging, and Response Assessment of Hodgkin and Non-Hodgkin Lymphoma: The Lugano Classification", Journal of Clinical Oncology, 1-10.

Cheson et al. (2007), "Revised Response Criteria for Malignant Lymphoma", Journal of Clinical Oncology, 25(5), 579-586.

Jain et al. (2019), "Mantle cell lymphoma: 2019 update on the diagnosis, pathogenesis, prognostication, and management", Annual Clinical Updates in Hematological Malignancies, 94, 710-725.

Kochenderrfer et al. (2017), "Lymphoma Remissions Caused by Anti-CD19 Chimeric Antigen Receptor T Cells Are Associated With High Serum Interleukin-15 Levels", Journal of Clinical Oncology, 35(16), 1803-1813.

Wang et al. (2017), "Acalabrutinib in relapsed or refractory mantle cell lymphoma (ACE-LY-004): a single-arm, multicentre, phase 2 trial", The Lancet, 1-9.

Martin et al., "Postibrutinib outcomes in patients with mantle cell lymphoma", Clinical Trials and Observations, Blood, vol. 127, No. 12, Mar. 24, 2016, pp. 1559-1563.

Kantarjian et al. (2017), "Blinatumomab versus Chemotherapy for Advanced Acute Lymphoblastic Leukemia", The New England Journal of Medicine, 376(9), 836-847.

Sotillo et al. (2015), "Convergence of Acquired Mutations and Alternative Splicing of CD19 Enables Resistance to CART-19 Immunotherapy", Cancer Discovery, OF1-OF14.

Chen et al., Anti-CD19 Chimeric Antigen Receptor T Cells Improve Responses to Chemotherapy- Refractory Mantle Cell Lymphoma: A Case Report, Blood 2016, vol. 128, No. 22: 5393, DOI: 10.1182/blood.V128.22.5393.5393. 2 pages.

Enblad et al., A Phase I/IIa Trial Using CD19-Targeted Third-Generation CAR T Cells for Lymphoma and Leukemia, Clinical Cancer Research 2018, vol. 24, No. 24, pp. 6185-6194, DOI: 10.1158/1078-0432.CCR-18-0426.

Shah et al., A Phase 1 Study with Point-of-Care Manufacturing of Dual Targeted, Tandem Anti-CD19, Anti-CD20 Chimeric Antigen Receptor Modified T (CAR-T) Cells for Relapsed, Refractory, Non-Hodgkin Lymphoma, Blood 2018, vol. 132, (Supplement 1): 4193, DOI: 10.1182/blood-2018-99-110194. 4 pages.

Turtle et al., Immunotherapy of non-Hodgkin lymphoma with a defined ratio of CD8+ and CD4+ CD19-specific chimeric antigen receptor-modified T cells, Science Translational Medicine 2016, vol. 8, No. 355, doi:10.1126/scitranslmed.aaf8621. 24 pages.

Wang et al., ZUMA-2: A phase 2 multi-center study evaluating the efficacy of KTE-C19 (Anti-CD19 CAR T cells) in patients with relapsed/refractory mantle cell lymphoma (R/R MCL), Annals of Oncology, 2016, vol. 27(Supplement 6): vi326, doi:10.1093/annonc/mdw375.40. 2 pages.

Abramson et al., High Durable CR Rates in Relapsed/Refractory (R/R) Aggressive B-NHL Treated with the CD19-Directed CAR T Cell Product JCAR017 (Transcend NHL 001): Defined Composition Allows for Dose-Finding and Definition of Pivotal Cohort, Blood 2017, vol. 130, Supplement 1, p. 581.

Brudno et al., Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease, Journal of Clinical Oncology 2016, vol. 34, No. 10, pp. 1112-1121.

Brudno et al., Chimeric antigen receptor T-cell therapies for lymphoma, Nature Reviews Clinical Oncology 2018, vol. 15, pp. 31-46.

Cao et al., Anti-CD19 Chimeric Antigen Receptor T Cells in Combination With Nivolumab Are Safe and Effective Against Relapsed/Refractory B-Cell Non-hodgkin Lymphoma, Frontiers in Oncology 2019, vol. 9, article 767.

Fraietta et al., Determinants of response and resistance to CD19 chimeric antigen receptor (CAR) T cell therapy of chronic lymphocytic leukemia, Nature Medicine 2018, vol. 24, pp. 563-571.

Gilead Sciences Announces Fourth Quarter and Full Year 2018 Financial Results?Gilead?Feb. 4, 2019?https://s24.q4cdn.com/804398512/files/doc_news/archive/829f46cd-0ddb-43d5-bedb-3771670d8102.pdf.

Hirayama et al., The response to lymphodepletion impacts PFS in patients with aggressive non-Hodgkin lymphoma treated with CD19 CAR T cells, Blood 2019, vol. 133, No. 17, pp. 1876-1887.

Jain et al., Axicabtagene ciloleucel (KTE-C19), an anti-CD19 CAR T therapy for the treatment of relapsed/refractory aggressive B-cell non-Hodgkin's lymphoma, Therapeutics and Clinical Risk Management 2018, vol. 14, pp. 1007-1017.

Larson et al., Pre-clinical development of gene modification of haematopoietic stem cells with chimeric antigen receptors for cancer immunotherapy, Human Vaccines & Immunotherapeutics 2017, vol. 13, No. 5, 1094-1104.

Li et al., A good response of refractory mantel cell lymphoma to haploidentical CAR T cell therapy after failure of autologous CAR T cell therapy, Journal for ImmunoTherapy of Cancer 2019, vol. 7, No. 51. 7 pages.

Partial Supplementary European Search Report for European Application No. 20886085.8 dated Apr. 5, 2024. 23 pages.

Ruella et al., The Addition of the BTK Inhibitor Ibrutinib to Anti-CD19 Chimeric Antigen Receptor T Cells (CART19) Improves Responses against Mantle Cell Lymphoma, Clinical Cancer Research, 2016, 22(11):2684-2696.

Sadelain et al., CD19 CAR Therapy for Acute Lymphoblastic Leukemia, American Society of Clinical Oncology Educational Book 2015, e360-e363.

Wang et al., 247 Safety and Preliminary Efficacy in Patients With Relapsed/Refractory Mantle Cell Lymphoma Receiving Lisocabtagene Maraleucel in Transcend NHL 001, Hematological Oncology, Wiley, 2019.

Wang et al., Safety and preliminary efficacy in patients (pts) with relapsed/refractory (R/R) mantle cell lymphoma (MCL) receiving lisocabtagene maraleucel (Liso-cel) in Transcend NHL 001, Journal of Clinical Oncology, vol. 37, No. 15_suppl, May 26, 2019.

Guedan et al., "Engineering and Design of Chimeric Antigen Receptors," Molecular Therapy: Methods & Clinical Development, 2019, vol. 12, pp. 145-156.

Shah et al., "End of phase I results of ZUMA-3, a phase 1/2 study of KTE-X19, anti-CD19 chimeric antigen receptor (CAR) T cell therapy, in adult patients (pts) with relapsed/refractory (R/R) acute lymphoblastic leukemia (ALL)," 2019, Meeting Abstract: 2019 ASCO Annual Meeting I, Journal of Clinical Oncology, vol. 37, No. 15 Supp., 3 pages.

* cited by examiner

| | 2 × $10^6$ cells/kg (n = 6) | | 1 × $10^6$ cells/kg Original AE Management (n = 14) | | 1 × $10^6$ cells/kg Revised AE Management (n = 9) | | 0.5 × $10^6$ cells/kg (n = 16) | |
|---|---|---|---|---|---|---|---|---|
| | | | | | | | | |
| CCL17 (TARC), pg/mL | | | | | | | | |
| Median | 881.2 | 786.2 | 241.6 | 389.5 | 76.0 | 114.1 | 215.2 | 864.9 |
| Range | 93.3 – 4480.0† | 220.1 – 1902.5 | 55.4 – 4480.0† | 40.2 – 4480.0† | 3.3* – 4480.0† | 45.8 – 4480.0† | 3.3* – 4480.0† | 3.3* – 4480.0† |
| **CRP, mg/L** | | | | | | | | |
| Median | 79.1 | 193.0 | 17.1 | 93.0 | 10.0 | 94.8 | 59.5 | 138.4 |
| Range | 2.7 – 496.0† | 7.3 – 272.1 | 0.5 – 183.5 | 3.5 – 496.0† | 0.8 – 101.6 | 10.5 – 216.5 | 1.3 – 270.6 | 4.0 – 496.0† |
| **CXCL10, pg/mL** | | | | | | | | |
| Median | 230.8 | 2000.0† | 289.1 | 2000.0† | 298.9 | 1635.3 | 377.9 | 2000.0† |
| Range | 113.3 – 515.5 | 663.3 – 2000.0† | 88.6 – 2000.0† | 525.3 – 2000.0† | 134.6 – 1569.1 | 276.8 – 2000.0† | 30.8 – 1682.4 | 309.5 – 2000.0† |
| **Eotaxin-1, pg/mL** | | | | | | | | |
| Median | 96.2 | 100.6 | 135.0 | 183.1 | 143.2 | 185.1 | 121.1 | 265.5 |
| Range | 12.3* – 480.9 | 12.3* – 222.3 | 12.3* – 277.6 | 59.9 – 346.2 | 74.6 – 342.0 | 69.0 – 636.2 | 59.4 – 401.8 | 77.0 – 594.7 |
| **Eotaxin-3, pg/mL** | | | | | | | | |
| Median | 10.2* | 10.2* | 10.2* | 10.2* | 10.2* | 10.2* | 10.2* | 10.2* |
| Range | 10.2* – 10.2* | 10.2* – 10.2* | 10.2* – 10.2* | 10.2* – 10.2* | 10.2* – 96.3 | 10.2* – 307.4 | 10.2* – 10.2* | 10.2* – 326.3 |
| **Ferritin, ng/mL** | | | | | | | | |
| Median | 6963.1 | 20611.3 | 3126.7 | 14271.5 | 2769.1 | 7545.3 | 3816.9 | 9706.2 |
| Range | 2487.5 – 25000.0 | 9565.8 – 25000.0 | 0.8 – 17725.5 | 2758.8 – 25000.0 | 625.3 – 5299.5 | 1516.7 – 31620.0† | 747.3 – 14020.1 | 875.2 – 31620.0† |
| **GM-CSF, pg/mL** | | | | | | | | |
| Median | **1.9*** | **11.9** | **1.9*** | **3.5** | **1.9*** | **1.9*** | **1.9*** | **5.7** |

FIG. 10A

| | | | | | | | | |
|---|---|---|---|---|---|---|---|---|
| Range | 1.9* – 1.9* | 1.9* – 78.9 | 1.9* – 1.9* | 1.9* – 239.7 | 1.9* – 1.9* | 1.9* – 64.6 | 1.9* – 5.9 | 1.9* – 189.1 |
| **Granzyme A, pg/mL** | | | | | | | | |
| Median | 1194.1 | 685.9 | 20.0* | 20.0* | 20.0* | 20.0* | 20.0* | 20.0* |
| Range | 20.0* – 4634.0 | 20.0* – 5018.1 | 20.0* – 5804.6 | 20.0* – 3925.8 | 20.0* – 1818.5 | 20.0* – 2019.0 | 20.0* – 8664.7 | 20.0* – 14,625.9 |
| **Granzyme B, pg/mL** | | | | | | | | |
| Median | 1.0* | 43.4 | 1.0* | 51.5 | 1.0* | 29.6 | 1.0* | 16.1 |
| Range | 1.0* – 117.5 | 1.0* – 473.8 | 1.0* – 394.3 | 1.0* – 2988.6 | 1.0* – 23.9 | 1.0* – 2499.7 | 1.0* – 14.4 | 1.0* – 10,000.0† |
| **ICAM-1, ng/mL** | | | | | | | | |
| Median | 691.0 | 1296.5 | 584.9 | 1236.0 | 572.6 | 882.7 | 711.4 | 1098.8 |
| Range | 395.1 – 1366.7 | 781.6 – 1777.4 | 313.5 – 1359.9 | 605.1 – 2332.3 | 137.1 – 857.4 | 270.7 – 3879.5 | 141.0 – 1538.5 | 543.5 – 4926.0 |
| **IFNγ, pg/mL** | | | | | | | | |
| Median | 7.5* | 703.6 | 7.5* | 1415.3 | 7.5* | 286.9 | 21.2 | 493.9 |
| Range | 7.5* – 7.5* | 99.1 – 1876.0† | 7.5* – 910.5 | 19.8 – 1876.0† | 7.5* – 31.2 | 39.3 – 1876.0† | 7.5* – 496.9 | 21.0 – 1876.0† |
| **IL-1RA, pg/mL** | | | | | | | | |
| Median | 357.6 | 1904.8 | 439.6 | 3360.9 | 308.3 | 1052.6 | 361.6 | 1154.6 |
| Range | 31.2 – 861.1 | 1034.7 – 4000.0 | 31.2 – 1672.7 | 431.2 – 4000.0 | 107.8 – 387.9 | 329.3 – 4224.3 | 31.2 – 975.7 | 371.3 – 4000.0 |
| **IL-1α, pg/mL** | | | | | | | | |
| Median | 2.9* | 2.9* | 2.9* | 2.9* | 2.9* | 2.9* | 2.9* | 2.9* |
| Range | 2.9* – 2.9* | 2.9* – 2.9* | 2.9* – 2.9* | 2.9* – 2.9* | 2.9* – 2.9* | 2.9* – 2.9* | 2.9* – 2.9* | 2.9* – 2.9* |
| **IL-1β, pg/mL** | | | | | | | | |
| Median | 2.1* | 2.1* | 2.1* | 2.1* | 2.1* | 2.1* | 2.1* | 2.1* |
| Range | 2.1* – 2.1* | 2.1* – 2.1* | 2.1* – 2.1* | 2.1* – 2.1* | 2.1* – 2.1* | 2.1* – 2.1* | 2.1* – 2.1* | 2.1* – 2.1* |
| **IL-10, pg/mL** | | | | | | | | |
| Median | **1.8** | **57.3** | **0.7*** | **47.0** | **0.7*** | **15.9** | **0.7*** | **27.2** |

FIG. 10B

| | | | | | | | | |
|---|---|---|---|---|---|---|---|---|
| Range | 0.7* – 7.7 | 0.7* – 113.8 | 0.7* – 85.2 | 3.0 – 466.0† | 0.7* – 6.2 | 5.6 – 466.0† | 0.7* – 16.8 | 0.7* – 466.0† |
| **IL-12 P40, pg/mL** | | | | | | | | |
| Median | 18.0 | 112.1 | 49.5 | 57.3 | 36.7 | 41.5 | 44.6 | 150.1 |
| Range | 5.7* – 83.7 | 16.6 – 177.1 | 14.2 – 466.3 | 5.7* – 418.4 | 5.7* – 372.8 | 5.7* – 283.5 | 5.7* – 674.6 | 5.7* – 4500.0† |
| **IL-12 P70, pg/mL** | | | | | | | | |
| Median | 1.2* | 1.2* | 1.2* | 1.2* | 1.2* | 1.2* | 1.2* | 1.2* |
| Range | 1.2* – 1.2* | 1.2* – 1.2* | 1.2* – 1.2* | 1.2* – 16.7 | 1.2* – 5.2 | 1.2* – 4.7 | 1.2* – 1.2* | 1.2* – 12.7 |
| **IL-13, pg/mL** | | | | | | | | |
| Median | 4.2* | 4.2* | 4.2* | 4.2* | 4.2* | 4.2* | 4.2* | 4.2* |
| Range | 4.2* – 4.2* | 4.2* – 4.2* | 4.2* – 4.2* | 4.2* – 13.1 | 4.2* – 4.2* | 4.2* – 4.2* | 4.2* – 4.2* | 4.2* – 20.0 |
| **IL-15, pg/mL** | | | | | | | | |
| Median | 8.3 | 66.3 | 7.3 | 39.6 | 4.5 | 39.6 | 6.8 | 52.8 |
| Range | 3.9 – 20.6 | 10.7 – 143.6 | 4.1 – 15.6 | 11.6 – 74.5 | 1.4* – 23.1 | 9.1 – 78.9 | 3.8 – 28.0 | 16.5 – 103.5 |
| **IL-16, pg/mL** | | | | | | | | |
| Median | 103.1 | 173.9 | 255.8 | 462.8 | 122.6 | 248.7 | 272.7 | 650.5 |
| Range | 68.5 – 362.6 | 58.4 – 842.5 | 73.6 – 2216.9 | 85.4 – 3740.0† | 71.2 – 935.7 | 92.5 – 803.7 | 88.3 – 3740.0† | 132.4 – 3215.8 |
| **IL-17, pg/mL** | | | | | | | | |
| Median | 9.3* | 9.3* | 9.3* | 9.3* | 9.3* | 9.3* | 9.3* | 9.3* |
| Range | 9.3* – 39.5 | 9.3* – 156.5 | 9.3* – 9.3* | 9.3* – 35.7 | 9.3* – 9.3* | 9.3* – 35.3 | 9.3* – 9.3* | 9.3* – 41.6 |
| **IL-2, pg/mL** | | | | | | | | |
| Median | 0.9* | 18.8 | 0.9* | 10.3 | 0.9* | 4.2 | 0.9* | 4.3 |
| Range | 0.9* – 0.9* | 0.9* – 110.6 | 0.9* – 3.0 | 0.9* – 159.1 | 0.9* – 0.9* | 0.9* – 49.5 | 0.9* – 3.8 | 0.9* – 359.1 |
| **IL-2Rα, pg/mL** | | | | | | | | |
| Median | 5795.9 | 14016.8 | 4973.6 | 12766.2 | 4468.3 | 17904.8 | 4495.2 | 15104.8 |
| Range | 1210.9 – 35644.4 | 8277.2 – 22719.1 | 78.0 – 36533.8 | 3759.5 – 48150.8 | 1420.9 – 10663.5 | 8502.9 – 71270.8 | 78.0 – 92941.7 | 4893.7 – 100000.0† |
| IL-4, pg/mL | | | | | | | | |

FIG. 10C

| | | | | | | | | |
|---|---|---|---|---|---|---|---|---|
| Median | 0.5* | 0.5* | 0.5* | 0.5* | 0.5* | 0.5* | 0.5* | 0.5* |
| Range | 0.5* – 0.5* | 0.5* – 0.5* | 0.5* – 0.5* | 0.5* – 4.0 | 0.5* – 0.5* | 0.5* – 5.6 | 0.5* – 0.5* | 0.5* – 5.6 |
| **IL-5, pg/mL** | | | | | | | | |
| Median | 6.3* | 6.3* | 6.3* | 23.5 | 6.3* | 6.3* | 6.3* | 24.1 |
| Range | 6.3* – 6.3* | 6.3* – 32.7 | 6.3* – 14.2 | 6.3* – 111.8 | 6.3* – 6.3* | 6.3* – 124.6 | 6.3* – 60.9 | 6.3* – 182.2 |
| **IL-6, pg/mL** | | | | | | | | |
| Median | 7.1 | 91.9 | 1.6* | 629.5 | 1.6* | 60.0 | 5.5 | 213.9 |
| Range | 1.6* – 297.4 | 7.4 – 210.1 | 1.6* – 45.6 | 8.6 – 976.0† | 1.6* – 19.8 | 16.8 – 976.0† | 1.6* – 74.0 | 1.6* – 976.0† |
| **IL-7, pg/mL** | | | | | | | | |
| Median | 5.3 | 21.3 | 5.3 | 28.7 | 6.9 | 18.4 | 5.2 | 25.6 |
| Range | 2.9 – 14.7 | 15.1 – 58.1 | 1.4* – 36.6 | 10.9 – 46.9 | 1.4* – 15.5 | 9.0 – 38.6 | 1.4* – 25.1 | 1.4* – 47.6 |
| **IL-8, pg/mL** | | | | | | | | |
| Median | 44.0 | 153.0 | 33.4 | 272.9 | 16.3 | 75.2 | 48.7 | 245.1 |
| Range | 6.5 – 130.5 | 29.0 – 750.0† | 7.0 – 657.3 | 58.5 – 750.0† | 13.3 – 258.0 | 37.1 – 750.0† | 3.9 – 418.4 | 25.2 – 750.0† |
| **MCP-1, pg/mL** | | | | | | | | |
| Median | 878.5 | 1500.0† | 872.2 | 1500.0† | 777.1 | 1281.9 | 809.1 | 1500.0† |
| Range | 786.5 – 1401.4 | 495.8 – 1500.0† | 242.5 – 1500.0† | 1090.8 – 1500.0† | 405.4 – 1500.0† | 495.8 – 1500.0† | 191.4 – 1500.0† | 627.4 – 1500.0† |
| **MCP-4, pg/mL** | | | | | | | | |
| Median | 77.3 | 189.0 | 83.5 | 245.8 | 70.1 | 112.3 | 102.0 | 214.4 |
| Range | 35.3 – 111.1 | 97.1 – 248.0 | 46.4 – 146.8 | 54.8 – 840.4 | 35.7 – 246.7 | 44.6 – 263.3 | 5.1* – 258.1 | 55.9 – 396.8 |
| **MDC, pg/mL** | | | | | | | | |
| Median | 88.3* | 600.8 | 395.0 | 396.1 | 392.8 | 407.2 | 238.1 | 445.7 |
| Range | 88.3* – 88.3* | 88.3* – 1928.8 | 88.3* – 2285.8 | 88.3* – 1337.5 | 88.3* – 1256.1 | 88.3* – 927.6 | 88.3* – 740.5 | 88.3* – 1163.4 |
| **MIP-1α, pg/mL** | | | | | | | | |
| Median | 13.8* | 47.5 | 13.8* | 75.0 | 13.8* | 13.8* | 13.8* | 58.8 |
| Range | 13.8* – 13.8* | 13.8* – 109.7 | 13.8* – 68.0 | 13.8* – 412.9 | 13.8* – 58.6 | 13.8* – 143.8 | 13.8* – 13.8* | 13.8* – 182.6 |

FIG. 10D

| | | | | | | | | |
|---|---|---|---|---|---|---|---|---|
| **MIP-1β, pg/mL** | | | | | | | | |
| Median | 102.3 | 228.0 | 103.0 | 462.9 | 102.2 | 241.6 | 98.4 | 246.3 |
| Range | 56.1 – 132.7 | 163.6 – 891.4 | 32.4 – 346.8 | 58.2 – 2877.6 | 54.7 – 189.3 | 56.7 – 1644.5 | 34.8 – 240.7 | 122.2 – 992.7 |
| **PDL1, pg/mL** | | | | | | | | |
| Median | N/A | N/A | N/A | N/A | 107.4 | 236.6 | 86.9 | 153.8 |
| Range | | | | | 69.7 – 196.0 | 120.5 – 1137.0 | 86.9 – 86.9 | 153.8 – 153.8 |
| **Perforin, pg/mL** | | | | | | | | |
| Median | 6263.5 | 7530.6 | 7811.5 | 22320.9 | 10674.7 | 20264.2 | 8418.8 | 16414.4 |
| Range | 2628.9 – 10482.2 | 3789.3 – 16842.9 | 2661.1 – 50032.0 | 6281.1 – 38643.4 | 7568.1 – 13712.9 | 5587.2 – 44195.4 | 2597.9 – 45816.7 | 5316.7 – 100000.0† |
| **SAA, ng/mL** | | | | | | | | |
| Median | 133028.2 | 359364.6 | 12121.4 | 116259.9 | 5984.5 | 176974.2 | 34725.5 | 250054.7 |
| Range | 44406.8 – 1380000.0† | 20584.4 – 762894.4 | 2286.7 – 458693.3 | 13770.4 – 1380000.0† | 2690.7 – 643970.0 | 15196.8 – 519874.5 | 2196.1 – 522644.6 | 12226.0 – 696334.1 |
| **SFASL, pg/mL** | | | | | | | | |
| Median | 10.0* | 10.0* | 10.0* | 10.0* | 10.0* | 10.0* | 10.0* | 10.0* |
| Range | 10.0* – 1687.2 | 10.0* – 1978.1 | 10.0* – 178.9 | 10.0* – 164.1 | 10.0* – 936.1 | 10.0* – 554.5 | 10.0* – 859.8 | 10.0* – 856.6 |
| **TNF-α, pg/mL** | | | | | | | | |
| Median | 3.6 | 8.0 | 4.8 | 12.6 | 3.0 | 5.6 | 4.1 | 8.3 |
| Range | 0.7* – 9.3 | 2.8 – 16.2 | 1.5 – 18.2 | 2.5 – 29.7 | 2.2 – 8.8 | 3.5 – 33.4 | 0.7* – 18.1 | 3.4 – 34.4 |
| **TNF-β, pg/mL** | | | | | | | | |
| Median | 1.2* | 1.2* | 1.2* | 1.2* | 1.2* | 1.2* | 1.2* | 1.2* |
| Range | 1.2* – 1.2* | 1.2* – 1.2* | 1.2* – 1.2* | 1.2* – 8.6 | 1.2* – 1.2* | 1.2* – 1.2* | 1.2* – 5.6 | 1.2* – 13.0 |
| **VCAM-1, ng/mL** | | | | | | | | |
| Median | 1116.4 | 1186.6 | 1445.2 | 1782.7 | 599.4 | 1189.0 | 1277.4 | 2206.1 |
| Range | 744.5 – 7813.7 | 956.2 – 4743.1 | 543.4 – 3528.0 | 1089.5 – 2433.7 | 0.04* – 1808.7 | 627.2 – 3994.6 | 496.6 – 4447.2 | 817.1 – 8469.2 |

*FIG. 10E*

| | | Cytokine Release Syndrome | | | Neurologic Events | | |
|---|---|---|---|---|---|---|---|
| Function | Peak Value - Median (range) | **Grade ≥3** | Grade 0 – 2 | *P* Value | **Grade ≥3** | Grade 0 – 2 | *P* Value |
| **Homeostatic/ proliferative** | IL-15, pg/mL | 31.9 (10.7 – 143.6) | 55.1 (9.1 – 103.5) | 0.0372 | 40.0 (21.2 – 84.0) | 49.5 (9.1 – 143.6) | 0.79 |
| | IL-2, pg/mL | 9.7 (0.9* – 110.6) | 6.6 (0.9* – 359.1) | 0.6846 | 10.9 (0.9* – 359.1) | 5.3 (0.9* – 110.6) | 0.1126 |
| Pro-inflammatory | IL-6, pg/mL | 213.9 (7.4 – 976.0†) | 210.1 (1.6* – 976.0†) | 0.7388 | 284.4 (7.4 – 976.0†) | 188.5 (1.6* – 976.0†) | 0.8596 |
| | CRP, mg/L | 96.0 (3.99 – 459.6) | 133.7 (3.5 – 496.0†) | 0.2646 | 145.7 (3.5 – 496.0†) | 109.1 (7.3 – 496.0†) | 0.708 |
| | SAA, mg/L | 173329.1 (14860.1 – 636991.2) | 176974.2 (12226.0 – 1380000.0†) | 0.3622 | 165464.6 (12226.0 – 1380000.0†) | 211371.4 (13770.4 – 696334.1) | 0.8621 |
| | IL-5, pg/mL | 6.3* (6.3* – 182.2) | 23.2 (6.3* – 124.6) | 0.6764 | 6.3* (6.3* – 86.5) | 19.7 (6.3* – 182.2) | 0.5092 |
| | Ferritin, ng/mL | 19490.9 (2758.8 – 29866.3) | 10014.5 (875.2 – 31620.0†) | 0.1643 | 9565.8 (2758.8 – 29866.3) | 11486.6 (875.2 – 31620.0†) | 0.8233 |

*FIG. 11A*

| | | | | | | | |
|---|---|---|---|---|---|---|---|
| | IL-1RA, pg/mL | 2227.8 (587.6 – 4224.3) | 1313.9 (329.3 – 4000.0) | 0.0925 | 2054.5 (431.2 – 4000.0) | 1235.3 (329.3 – 4224.3) | 0.2653 |
| | IL-2Rα, pg/mL | 17214.7 (5098.2 – 87978.1) | 13246.7 (3759.5 – 100000.0†) | 0.339 | 12776.3 (3759.5 – 87978.1) | 17268.4 (4893.7 – 100000.0†) | 0.1745 |
| **Immune-modulating** | GM-CSF, pg/mL | 7.3 (1.9* – 112.5) | 1.9* (1.9* – 239.7) | 0.6038 | 5.7 (1.9* – 239.7) | 1.9* (1.9* – 197.8) | 0.5088 |
| | IFNγ, pg/mL | 1365.8 (39.3 – 1876.0†) | 551.6 (19.8 – 1876.0†) | 0.3636 | 726 (19.8 – 1876.0†) | 511.2 (21.0 – 1876.0†) | 0.601 |
| **Chemokines** | IL-8, pg/mL | 277.9 (29.0 – 750.0†) | 199.0 (25.2 – 750.0†) | 0.4985 | 265.2 (52.6 – 750.0†) | 212.4 (25.2 – 750.0†) | 0.3532 |
| | CXCL10, pg/mL | 2000.0† (663.3 – 2000.0†) | 2000.0† (276.8 – 2000.0†) | 0.2668 | 2000.0† (525.3 – 2000.0†) | 2000.0† (276.8 – 2000.0†) | 0.3151 |
| | MCP-1, pg/mL | 1500.0† (452.8 – 1500.0†) | 1500.0† (495.8 – 1500.0†) | 0.3134 | 1500.0† (627.4 – 1500.0†) | 1500.0† (452.8 – 1500.0†) | 0.5301 |
| **Effector** | Granzyme B, pg/mL | 74.3 (1.0* – 10000.0) | 22.1 (1.0* – 2499.7) | 0.1124 | 57.5 (1.0* – 10000.0) | 24.6 (1.0* – 2988.6) | 0.4174 |

FIG. 11B

CHIMERIC ANTIGEN RECEPTOR T CELL THERAPY

CROSS-REFERENCE TO RELATED APPLICATIONS

This application claims the benefit of priority of U.S. Provisional Application No. 63/089,930 filed Oct. 9, 2020, U.S. Provisional Application No. 63/063,692 filed Aug. 10, 2020, U.S. Provisional Application No. 63/056,369 filed Jul. 24, 2020, U.S. Provisional Application No. 63/031,217 filed May 28, 2020, U.S. Provisional Application No. 62/944,937 filed Dec. 6, 2019, and U.S. Provisional Application No. 62/931,636 filed Nov. 6, 2019, the contents of all of which are hereby incorporated by reference in their entireties.

FIELD

The present application relates to CAR-T cells, methods of making them, and methods of using them to treat cancer.

BACKGROUND

Human cancers are by their nature comprised of normal cells that have undergone a genetic or epigenetic conversion to become abnormal cancer cells. Cancer cells express proteins and other antigens that are distinct from those expressed by normal cells. These aberrant tumor antigens may be used by the body's innate immune system to specifically target and kill cancer cells. However, cancer cells employ various mechanisms to prevent immune cells, such as T and B lymphocytes, from successfully targeting cancer cells. Human T cell therapies rely on ex-vivo-enriched or modified human T cells to target and kill cancer cells in a subject, e.g., a patient. Various technologies have been developed to prepare T cell populations with enriched concentrations of naturally occurring T cells capable of targeting a tumor antigen, remove circulating tumor cells, and/or genetically modifying T cells to specifically target a known cancer antigen, thus producing populations of chimeric antigen receptor (CAR)-T cells for cancer therapy. Some of these therapies have shown promising effects on tumor size and patient survival.

SUMMARY

Any aspect or embodiment described herein may be combined with any other aspect or embodiment as disclosed herein. While the present invention has been described in conjunction with the detailed description thereof, the description is intended to illustrate and not limit the scope of the present invention, which is partially defined by the scope of the appended claims. Other aspects, advantages, and modifications are within the scope of the following embodiments/claims.

Embodiment 1. A method for treating mantle cell lymphoma (MCL) or B cell ALL in a subject in need thereof comprising administering to the subject a therapeutically effective amount of a T cell product comprising autologous T cells expressing an anti-CD19 chimeric antigen receptor (CAR).

Embodiment 2. The method of embodiment 1, wherein the MCL and B cell ALL are relapsed or refractory MCL and B cell ALL, optionally wherein the MCL is classical, blastoid, and pleomorphic MCL.

Embodiment 3. The method of any one of embodiments 1 and 2, wherein the MCL and B cell ALL is refractory to, or has relapsed following, one or more of chemotherapy, radiotherapy, immunotherapy (including a T cell therapy and/or treatment with an antibody or antibody-drug conjugate), an autologous stem cell transplant, or any combination thereof.

Embodiment 4. The method of any one of embodiments 1 through 3, wherein the subject has received 1-5 prior treatments, optionally wherein at least one of the prior treatments is selected from autologous SCT, anti-CD20 antibody, anthracycline- or bendamustine-containing chemotherapy, and/or a Bruton Tyrosine Kinase inhibitor (BTKi).

Embodiment 5. The method of embodiment 4, wherein the BTKi is ibrutinib or acalabrutinib.

Embodiment 6. The method of any one of embodiments 1 through 5, wherein R/R B cell ALL is defined as refractory to first-line therapy (i.e., primary refractory), relapsed ≤12 months after first remission, relapsed or refractory after ≥2 prior lines of systemic therapy, or relapsed after allogeneic stem cell transplant (SCT), optionally, wherein the subject is required to have ≥5% bone marrow blasts, an Eastern Cooperative Oncology Group performance status of 0 or 1, and/or adequate renal, hepatic, and cardiac function.

Embodiment 7. The method of any one of embodiments 1 through 6, wherein if the B cell ALL subject has received prior blinatumomab, the subject is required to have leukemic blasts with CD19 expression ≥90%.

Embodiment 8. The method of any one of embodiments 1 through 7, wherein the subject receives bridging therapy after leukapheresis and before conditioning/lymphodepleting chemotherapy.

Embodiment 9. The method of any one of embodiments 1 through 8, wherein the MCL subject receives a lymphodepleting chemotherapy regimen of cyclophosphamide 500 mg/m2 intravenously and fludarabine 30 mg/m2 intravenously, both given on each of the fifth, fourth, and third days before T cell infusion.

Embodiment 10. The method of any one of embodiments 1 through 9, wherein the B cell ALL subject receives a lymphodepleting regimen of fludarabine intravenous (IV) 25 mg/m2/day on each of the fourth, third, second days before T cell infusion, and cyclophosphamide IV 900 mg/m2/day on the second day before infusion.

Embodiment 11. The method of any one of embodiments 8 through 10, wherein the MCL bridging therapy is selected from dexamethasone (e.g., 20-40 mg or equivalent PO or IV daily for 1-4 days); methylprednisolone, ibrutinib (e.g., 560 mg PO daily), and/or acalabrutinib (e.g, 100 mg PO twice daily); an immunomodulator; R-CHOP, bendamustine; alkylating agents; and/or platinum-based agents, wherein the bridging therapy is administered after leukapheresis and completed in, for example, 5 days or less before conditioning chemotherapy.

Embodiment 12. The method of any one of embodiments 8 through 10, wherein the B cell ALL subject may receive any one or more of the following bridging chemotherapy regimens:

| Predefined Bridging Chemotherapy Regimens | |
|---|---|
| Attenuated VAD | Vincristine non-liposomal (1-2 mg IV weekly) or liposomal (2.25 mg/$m^2$ IV weekly), and dexamethasone 20-40 mg IV or PO daily × 3-4 days per week. Optional doxorubicin 50 mg/$m^2$ IV × 1 (first week only) |
| Mercaptopurine (6-MP) | 50-75 mg/$m^2$/day by mouth (administer at bedtime on an empty stomach to improve absorption) |
| Hydroxyurea | Doses titrated between 15-50 mg/kg/day (rounded to the nearest 500 mg capsule and given as a single daily oral dose on a continuous basis) |
| DOMP | Dexamethasone 6 mg/$m^2$/day PO (or IV) divided BID days 1-5, vincristine 1.5 mg/$m^2$ (maximum dose 2 mg) IV on day 1, methotrexate 20 mg/$m^2$ PO weekly, 6-MP 50-75 mg/$m^2$/day PO daily |
| Attenuated FLAG/FLAG-IDA | Fludarabine 30 mg/$m^2$ IV days 1-2, cytarabine 2 g/$m^2$ IV days 1-2, G-CSF 5 μg/kg SC or IV starts on day 3 and can continue until day before the start of conditioning chemotherapy. With or without idarubicin 6 mg/$m^2$ IV days 1-2 |
| Mini-hyper CVAD (courses A and/or B) | Course A: Cyclophosphamide 150 mg/$m^2$ every 12 h × 3 days, dexamethasone 20 mg/d IV or PO daily days 1-4 and 11-14, vincristine 2 mg IV × 1<br>Course B: methotrexate 250 mg/$m^2$ IV over 24 hours on day 1, cytarabine 0.5 g/$m^2$ IV every 12 hours × 4 doses on days 2 and 3 |

Embodiment 13. The method of any one of embodiments 1 through 12, wherein the T cell product comprises CD4+ and CD8+ CAR T cells that are prepared from peripheral blood mononuclear cells (PBMCs) by positive enrichment and consequent partial or complete depletion of circulating cancer cells.

Embodiment 14. The method of embodiment 13, wherein the PBMC are enriched for T cells by positive selection for CD4+ and CD8+ cells, activated with anti-CD3 and anti-CD28 antibodies in the presence of IL-2, and then transduced with a replication-incompetent viral vector containing FMC63-28Z CAR, a chimeric antigen receptor (CAR) comprising an anti-CD19 single-chain variable fragment (scFv), CD28 and CD3-zeta domains.

Embodiment 15. The method of any one of embodiments 13 and 14, wherein the T cell product comprises fewer cancer cells than a T cell product comprising T cells from a leukapheresis product that have not been positively selected for CD4+ and CD8+ T cells.

Embodiment 16. The method of any one of embodiments 13 through 15, wherein the T cell product has other superior product attributes relative to a T cell product comprising T cells from a leukapheresis product that have not been positively selected/enriched for CD4+ and CD8+ T cells.

Embodiment 17. The method of embodiment 16, wherein the superior product attributes are selected from increased percentage of CDRA45+ CCR7+ (naïve-like) T cells, decreased percentage of differentiated T cells, increased percentage of CD3+ cells, decreased IFN-gamma production, decreased percentage of CD3− cells.

Embodiment 18. The method of any one of embodiments 1 through 17, wherein the MCL subject is administered one or more doses of 1.8×106, 1.9×106, or 2×106 CAR positive viable T cells per kg body weight, with a maximum of 2×108 CAR positive viable T cells (for patients 100 kg and above) and the B cell ALL subject is administered 0.5×106, 1×106, or 2×106 CAR positive viable T cells per kg body weight, with a maximum of 2×108 CAR positive viable T cells (for patients 100 kg and above).

Embodiment 19. The method of any one of embodiments 1 through 17, wherein if the subject has achieved complete response to the first infusion, the subject may receive a second infusion of anti-CD19 CAR T cells, if progressing following >3 months of remission, provided CD19 expression has been retained and neutralizing antibodies against the CAR are not suspected, wherein response is assessed using the Lugano classification.

Embodiment 20. The method of any one of embodiments 1 through 19, wherein the subject is monitored for signs and symptoms of cytokine release syndrome (CRS) and neurologic toxicity after T cell administration.

Embodiment 21. The method of embodiment 20, wherein the subject is monitored daily for at least seven days, preferably for four weeks, following infusion for signs and symptoms of CRS and neurologic toxicity.

Embodiment 22. The method of any one of embodiments 20 and 21, wherein the signs or symptoms associated with CRS include fever, chills, fatigue, tachycardia, nausea, hypoxia, and hypotension and the signs or symptoms associated with neurologic events include encephalopathy, seizures, changes in level of consciousness, speech disorders, tremors, and confusion.

Embodiment 23. The method of any one of embodiments 20 through 22, wherein cytokine release syndrome in MCL subjects is managed in accordance with the following protocol:

| CRS Grade | Tocilizumab | Corticosteroids |
|---|---|---|
| Grade 1<br>Symptoms require symptomatic treatment only (e.g., fever, nausea, fatigue, headache, myalgia, malaise). | If not improving after 24 hours, administer tocilizumab 8 mg/kg intravenously over 1 hour (not to exceed 800 mg). | Not applicable. |

-continued

| CRS Grade | Tocilizumab | Corticosteroids |
| --- | --- | --- |
| Grade 2<br>Symptoms require and respond to moderate intervention.<br>Oxygen requirement less than 40% FiO2 or hypotension responsive to fluids or low dose of one vasopressor or Grade 2 organ toxicity. | Administer tocilizumab 8 mg/kg intravenously over 1 hour (not to exceed 800 mg).<br>Repeat tocilizumab every 8 hours as needed if not responsive to intravenous fluids or increasing supplemental oxygen. Limit to a maximum of 3 doses in a 24-hour period; maximum total of 4 doses if no clinical improvement in the signs and symptoms of CRS.<br>If improving, discontinue tocilizumab. | Manage per Grade 3 if no improvement within 24 hours after starting tocilizumab.<br>If improving, taper corticosteroids. |
| Grade 3<br>Symptoms require and respond to aggressive intervention.<br>Oxygen requirement greater than or equal to 40% FiO2 or hypotension requiring high-dose or multiple vasopressors or Grade 3 organ toxicity or Grade 4 transaminitis. | Per Grade 2 | Administer methylprednisolone 1 mg/kg intravenously twice daily or equivalent dexamethasone (e.g., 10 mg intravenously every 6 hours) until Grade 1, then taper corticosteroids.<br>If improving, manage as Grade 2.<br>If not improving, manage as Grade 4. |
| Grade 4<br>Life-threatening symptoms.<br>Requirements for ventilator support or continuous veno-venous hemodialysis (CVVHD), or Grade 4 organ toxicity (excluding transaminitis). | Per Grade 2 | Administer methylprednisolone 1000 mg intravenously per day for 3 days.<br>If improving, taper corticosteroids, and manage as Grade 3.<br>If not improving, consider alternate immunosuppressants. |

Embodiment 24. The method of any one of embodiments 20 through 23, wherein neurologictoxicityinMCLsubjectsismanagedinaccordancewiththefollowingprotocol:

| Grading Assessment | Concurrent CRS | No Concurrent CRS |
| --- | --- | --- |
| Grade 2 | Administer tocilizumab per embodiment 15 for management of Grade 2 CRS.<br>If not improving within 24 hours after starting tocilizumab, administer dexamethasone 10 mg intravenously every 6 hours until the event is Grade 1 or less, then taper corticosteroids.<br>If still not improving, manage as Grade 3. | Administer dexamethasone 10 mg intravenously every 6 hours until the event is Grade 1 or less, then taper corticosteroids. |
| | Consider non-sedating anti-seizure medicines (e.g., levetiracetam) for seizure prophylaxis. | |
| Grade 3 | Administer tocilizumab per embod iment 15 for management of Grade 2 CRS.<br>In addition, administer dexamethasone 10 mg intravenously with the first dose of tocilizumab and repeat dexamethasone dose every 6 hours. Continue dexamethasone use until the event is Grade 1 or less, then taper corticosteroids.<br>If improving, discontinue tocilizumab and manage as Grade 2.<br>If still not improving, manage as Grade 4 (below). | Administer dexamethasone 10 mg intravenously every 6 hours.<br>Continue dexamethasone use until the event is Grade 1 or less, then taper corticosteroids.<br>If not improving, manage as Grade 4. |
| | Consider non-sedating anti-seizure medicines (e.g., levetiracetam) for seizure prophylaxis. | |

-continued

| Grading Assessment | Concurrent CRS | No Concurrent CRS |
|---|---|---|
| Grade 4 | Administer tocilizumab per embodiment 15 for management of Grade 2 CRS.<br>Administer methylprednisolone 1000 mg intravenously per day with first dose of tocilizumab and continue methylprednisolone 1000 mg intravenously per day for 2 more days.<br>If improving, then manage as Grade 3.<br>If not improving, consider alternate immunosuppressants. | Administer methylprednisolone 1000 mg intravenously per day for 3 days.<br>If improving, then manage as Grade 3.<br>If not improving, consider alternate immunosuppressants. |
| | Consider non-sedating anti-seizure medicines (e.g., levetiracetam) for seizure prophylaxis. | |

Embodiment 25. The method of any one of embodiments 1 through 24, wherein the MCL subject is a high-risk patient as determined by a Ki-67 tumor proliferation index ≥50% and/or presence of a TP53 mutation.

Embodiment 26. The method of any one of embodiments 20 through 22, wherein CRS in a B cell ALL subject is managed according to the following protocol:

| CRS Grade | Tocilizumab | Corticosteroids |
|---|---|---|
| Grade 1<br>Symptoms require symptomatic treatment only (e.g., fever, nausea, fatigue, headache, myalgia, malaise). | If not improving after 24 hours, administer tocilizumab 8 mg/kg intravenously over 1 hour (not to exceed 800 mg). | Not applicable. |
| Grade 2<br>Symptoms require and respond to moderate intervention.<br>Oxygen requirement less than 40% FiO2 or hypotension responsive to fluids or low dose of one vasopressor or Grade 2 organ toxicity. | Administer tocilizumab 8 mg/kg intravenously over 1 hour (not to exceed 800 mg).<br>Repeat tocilizumab every 8 hours as needed if not responsive to intravenous fluids or increasing supplemental oxygen. Limit to a maximum of 3 doses in a 24-hour period; maximum total of 4 doses if no clinical improvement in the signs and symptoms of CRS.<br>If improving, discontinue tocilizumab. | Manage per Grade 3 if no improvement within 24 hours after starting tocilizumab.<br>If improving, taper corticosteroids. |
| Grade 3<br>Symptoms require and respond to aggressive intervention.<br>Oxygen requirement greater than or equal to 40% FiO2 or hypotension requiring high-dose or multiple vasopressors or Grade 3 organ toxicity or Grade 4 transaminitis. | Per Grade 2 | Administer methylprednisolone 1 mg/kg intravenously twice daily or equivalent dexamethasone (e.g., 10 mg intravenously every 6 hours) until Grade 1, then taper corticosteroids.<br>If improving, manage as Grade 2.<br>If not improving, manage as Grade 4. |
| Grade 4<br>Life-threatening symptoms.<br>Requirements for ventilator support or continuous veno-venous hemodialysis (CVVHD), or Grade 4 organ toxicity (excluding transaminitis). | Per Grade 2 | Administer methylprednisolone 1000 mg intravenously per day for 3 days.<br>If improving, taper corticosteroids, and manage as Grade 3.<br>If not improving, consider alternate immunosuppressants. |

Embodiment 27. The method of any one of embodiments 20 through 22 and 26, wherein neurologic toxicity in a B cell ALL subject is managed in accordance with one of the following two protocols:

| NE Grade | Original Management Guidelines | Revised Management Guidelines |
|---|---|---|
| Grade 1 | Supportive care<br>Neurological examination and additional work-up as clinically indicated | Supportive care<br>Closely monitor neurologic status<br>Consider prophylactic antiepileptic |
| Grade 2 | Supportive Care and Evaluation<br>Neurological examination, brain MRI, and evaluation of CSF; consider EEG as clinically indicated<br>Consider prophylactic antiepileptic | Supportive Care and Evaluation<br>Continuous cardiac telemetry and pulse oximetry as indicated<br>Serial neurological examinations to include fundoscopy and Glasgow Coma Score, brain MRI, evaluation of CSF, EEG; consider neurology consult<br>Administer antiepileptics for patients with seizures |
| | Tocilizumab<br>Consider tocilizumab 8 mg/kg IV over 1 hour (not to exceed 800 mg) for patients with comorbid conditions (eg, grade ≥2 CRS) | Tocilizumab<br>For patients with concurrent CRS, administer tocilizumab 8 mg/kg IV over 1 hour (not to exceed 800 mg); repeat every 4-6 hours as needed if not responsive to IV fluids or increasing supplemental oxygen, for a maximum of 3 doses in 24 hours<br>Discontinue tocilizumab if patient improves |
| | Corticosteroids<br>N/A | Corticosteroids<br>For patients without concurrent CRS, administer dexamethasone 10 mg IV every 6 hours<br>For patients with concurrent CRS, if no improvement within 24 hours after starting tocilizumab, administer dexamethasone 10 mg IV every 6 hours<br>Taper corticosteroids if patient improves |
| Grade 3 | Supportive Care and Evaluation<br>Per grade 2<br>Monitor with continuous cardiac telemetry and pulse oximetry | Supportive Care and Evaluation<br>Manage in monitored care or ICU |
| | Tocilizumab<br>Consider tocilizumab 8 mg/kg IV over 1 hour (not to exceed 800 mg); repeat every 4-6 hours if symptoms have not stabilized or improved | Tocilizumab<br>Per grade 2<br>Discontinue tocilizumab if patient improves |
| | Corticosteroids<br>Consider corticosteroids (eg, dexamethasone 10 mg IV every 6 hours or methylprednisolone 1 mg/kg BID) for worsening symptoms despite tocilizumab | Corticosteroids<br>Administer dexamethasone 10 mg IV every 6 hours<br>Taper corticosteroids if patient improves |
| Grade 4 | Supportive Care and Evaluation<br>Per grade 2<br>Monitor with continuous cardiac telemetry and pulse oximetry | Supportive Care and Evaluation<br>Per grade 3<br>Mechanical ventilation may be required<br>Administer immunosuppresants if patient does not improve |
| | Tocilizumab<br>Administer tocilizumab per grade 3 if not previously administered | Tocilizumab<br>Per grade 2 |
| | Corticosteroids<br>Administer corticosteroids (eg, | Corticosteroids<br>Administer high-dose |

-continued

| NE Grade | Original Management Guidelines | Revised Management Guidelines |
|---|---|---|
| | methylprednisolone 1 g/d × 3 days, followed by 250 mg BID × 2 days, then 125 mg BID × 2 days, then 60 mg BID × 2 days) | corticosteroids (eg, methylprednisone 1 g/d × 3 days)<br>Taper corticosteroids if patient improves |

Embodiment 28. The method of any one of embodiments 1 through 27, wherein the B cell ALL subject may receive any one or more of the following bridging chemotherapy regimens:

| | Predefined Bridging Chemotherapy Regimens |
|---|---|
| Attenuated VAD | Vincristine non-liposomal (1-2 mg IV weekly) or liposomal (2.25 $mg/m^2$ IV weekly), and dexamethasone 20-40 mg IV or PO daily × 3-4 days per week. Optional doxorubicin 50 $mg/m^2$ IV × 1 (first week only) |
| Mercaptopurine (6-MP) | 50-75 $mg/m^2$/day by mouth (administer at bedtime on an empty stomach to improve absorption) |
| Hydroxyurea | Doses titrated between 15-50 mg/kg/day (rounded to the nearest 500 mg capsule and given as a single daily oral dose on a continuous basis) |
| DOMP | Dexamethasone 6 $mg/m^2$/day PO (or IV) divided BID days 1-5, vincristine 1.5 $mg/m^2$ (maximum dose 2 mg) IV on day 1, methotrexate 20 $mg/m^2$ PO weekly, 6-MP 50-75 $mg/m^2$/day PO daily |
| Attenuated FLAG/FLAG-IDA | Fludarabine 30 $mg/m^2$ IV days 1-2, cytarabine 2 $g/m^2$ IV days 1-2, G-CSF 5 μg/kg SC or IV starts on day 3 and can continue until day before the start of conditioning chemotherapy. With or without idarubicin 6 $mg/m^2$ IV days 1-2 |
| Mini-hyper CVAD (courses A and/or B) | Course A: Cyclophosphamide 150 $mg/m^2$ every 12 h × 3 days, dexamethasone 20 mg/d IV or PO daily days 1-4 and 11-14, vincristine 2 mg IV × 1<br>Course B: methotrexate 250 $mg/m^2$ IV over 24 hours on day 1, cytarabine 0.5 $g/m^2$ IV every 12 hours × 4 doses on days 2 and 3 |

Embodiment 29. Autologous T cells expressing an anti-CD19 CAR for use in a method for treating mantle cell lymphoma (MCL) or B cell ALL according to any one of embodiments 1 through 28.

Embodiment 30. Use of autologous T cells expressing an anti-CD19 CAR in the manufacturing of a medicament for treating mantle cell lymphoma (MCL) or B cell ALL according to any one of embodiments 1 through 28.

Embodiment 31. A method of predicting:

(i) objective response of a subject to a CAR T cell treatment (optionally, according to the method of any one of embodiments 1 through 28) comprising measuring peak CAR T cell levels and comparing them to a reference standard, wherein objective response is positively associated with peak CAR T cell levels, wherein objective response includes both complete response and partial response, and wherein all responses are assessed using the Lugano classification.

(ii) minimal residual disease (e.g., at week 4) in response to a CAR T cell treatment (optionally, according to the method of any one of embodiments 1 through 28) comprising measuring peak CAR T cell levels and comparing them to a reference standard, wherein negative minimal residual disease is associated with higher peak CAR T cell levels.

(iii) grade ≥3 CRS and/or grade ≥3 neurologic events (NE) in a subject receiving CAR T cell treatment (optionally, according to a method of any one of embodiments 1 through 28) comprising measuring peak CAR T cell expansion after treatment and comparing the levels to a reference value, wherein the higher the CAR T cell expansion, the higher the chance for grade ≥3 CRS and/or grade ≥3 NE events.

(iv) grade ≥3 CRS and/or grade ≥3 NE comprising measuring the peak levels of GM-CSF and IL-6 post-CAR T cell treatment (optionally, according to the method of any one of embodiments 1 through 28) and comparing them to a reference level, wherein the higher the peak level of these cytokines, the higher the chance for grade ≥3 CRS and/or grade ≥3 NE.

(v) grade ≥3 CRS in a subject receiving CAR T cell treatment (optionally, according to a method of any one of embodiments 1 through 28) comprising measuring the peak level of serum ferritin post-CAR T cell treatment and comparing it to a reference level, wherein the higher the peak level of ferritin, the higher the chance for grade ≥3 CRS.

(vi) grade ≥3 CRS comprising measuring the peak levels of serum IL-2 and IFN-gamma post-CAR T cell treatment (optionally, of any one of embodiments 1 through 28) and comparing them to a reference level, wherein the higher the peak level of IL-2 and IFN-gamma, the higher the chance for grade ≥3 NE.

(vii) grade ≥3 CRS comprising measuring the cerebrospinal fluid levels of C-reactive protein, ferritin, IL-6, IL-8, and/or vascular cell adhesion molecule (VCAM) post-CAR T cell treatment (optionally, of any one of embodiments 1 through 28) and comparing them to a reference level, wherein the higher the cerebrospinal fluid levels of C-reactive protein, ferritin, IL-6, IL-8, and/or vascular cell adhesion molecule (VCAM), the higher the chance for grade ≥3 NE (viii) grade ≥3 CRS post-CAR T cell treatment (optionally, according to a method of any one of embodiments 1 through 28) comprising measuring peak serum levels of IL-15, IL-2 Rα, IL-6, TNFα, GM-CSF, ferritin, IL-10, IL-8, MIP-1a, MIP-1b, granzyme A, granzyme B, and/or perforin after anti-CD19 CAR T treatment and comparing the levels to reference levels, wherein the peak serum levels of IL-15, IL-2 Rα, IL-6, TNFα, GM-CSF, ferritin, IL-10, IL-8, MIP-1a, MIP-1b, granzyme A, granzyme B, and/or perforin associate positively with grade ≥3 CRS.

(ix) grade ≥3 CRS post-CAR T cell treatment of B cell ALL (optionally, according to a method of any one of embodiments 1 through 28) comprising measuring peak serum level of IL-15 after anti-CD19 CAR T treatment and comparing the levels to reference levels, wherein the peak serum level of IL-15 associates negatively with grade ≥3 CRS.

(x) grade ≥3 CRS and/or grade ≥3 NE post-CAR T cell treatment (optionally, according to a method of any one of embodiments 1 through 28) comprising measuring peak serum levels of IL-6, TNFα, GM-CSF, IL-10, MIP-1b, and granzyme B after anti-CD19 CAR T treatment and comparing the levels to reference levels, wherein peak serum levels of IL-6, TNFα, GM-CSF, IL-10, MIP-1b, and granzyme B associate positively with grade ≥3 CRS and grade ≥3 NE.

(xi) whether a patient is going to be MRD ($10^{-5}$ sensitivity) negative at 4 weeks/one month post-CAR T cell treatment (optionally, of any one of embodiments 1 through 28), comprising measuring peak serum levels of IFN-γ, IL-6, and/or IL-2 after treatment and comparing the level to a reference standard, wherein peak serum levels of IFN-γ, IL-6, and/or IL-2 associate positively with being MRD negative at one month.

Embodiment 32. The method of any one of embodiments 20 through 24, 26, 27, and 30 through 31, wherein CRS and NE are graded by the method described in Lee et al., Blood 2014; 124: 188-195.

Embodiment 33. The method of embodiment 31, wherein the reference standard is established by any method generally used in the biomarker arts, such as quartile analysis of patient populations with known responses, grades of toxicity, and MRD levels.

Embodiment 34. The method of embodiment 31, wherein CAR T cell levels are measured by CAR gene copies per microgram of DNA in blood.

Embodiment 35. The method of any one of embodiments 1 through 43, further comprising reducing the levels/activity of the cytokines that associate positively with grade ≥3 CRS and/or grade ≥3 NE post CAR T cell infusion to reduce grade ≥3 CRS and/or grade ≥3 NE.

Embodiment 36. A method of improving the effectiveness of CAR T cell treatment (e.g., of classical, blastoid, and pleomorphic MCL, and B cell ALL), in a subject in need thereof, comprising manipulating the T cell phenotype of the T cell product administered to the subject, optionally wherein the manipulation comprises increasing the number of CD3+ T cells, decreasing the number of CD3− cells, increasing the number/percentage of CDRA45+ CCR7+ (naïve-like) T cells and/or decreasing the number/percentage of differentiated cells in the T cell product during production, decreasing the levels of IFN-gamma production by the T cells, wherein the improvement is observed relative to the effectiveness of a T cell product that is prepared without any intentional manipulation of the number/percentage of CDRA45+ CCR7+ (naïve-like) T cells and/or the number/percentage of differentiated cells in the T cell product.

BRIEF DESCRIPTIONS OF DRAWINGS

FIGS. 1A-1F: Comparable pharmacodynamic profile in prognostic groups defined by Ki-67 proliferation index, and trend for increased cytokine levels in patients with mutated TP53.

FIGS. 2A-2I: Increased peak levels of select cytokines in serum among patients who achieved MRD-negative status.

Figure 3:
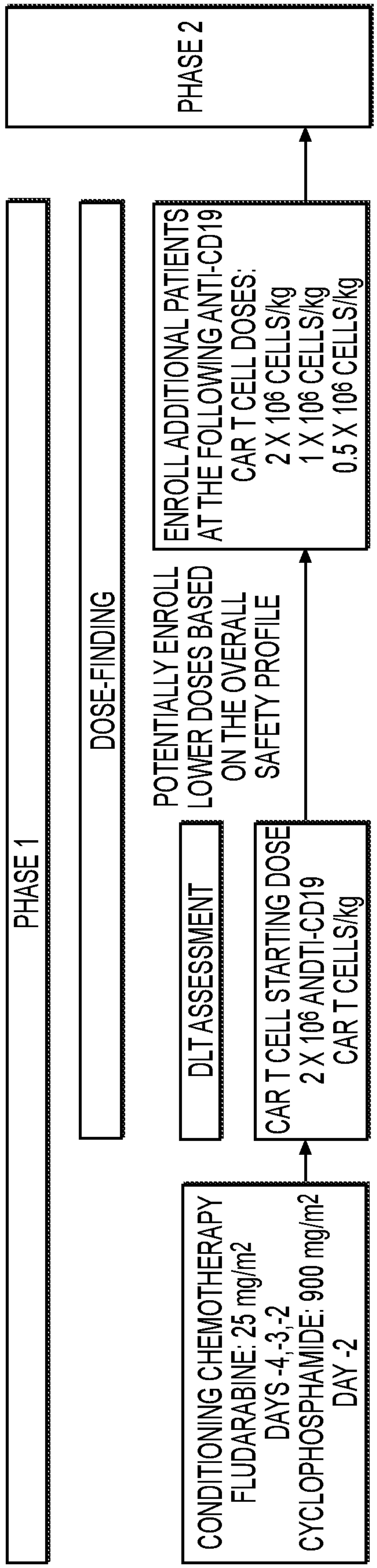

FIG. 3: ZUMA-3 Study Design. CAR, chimeric antigen receptor; DLT, dose-limiting toxicity.

Figure 4:
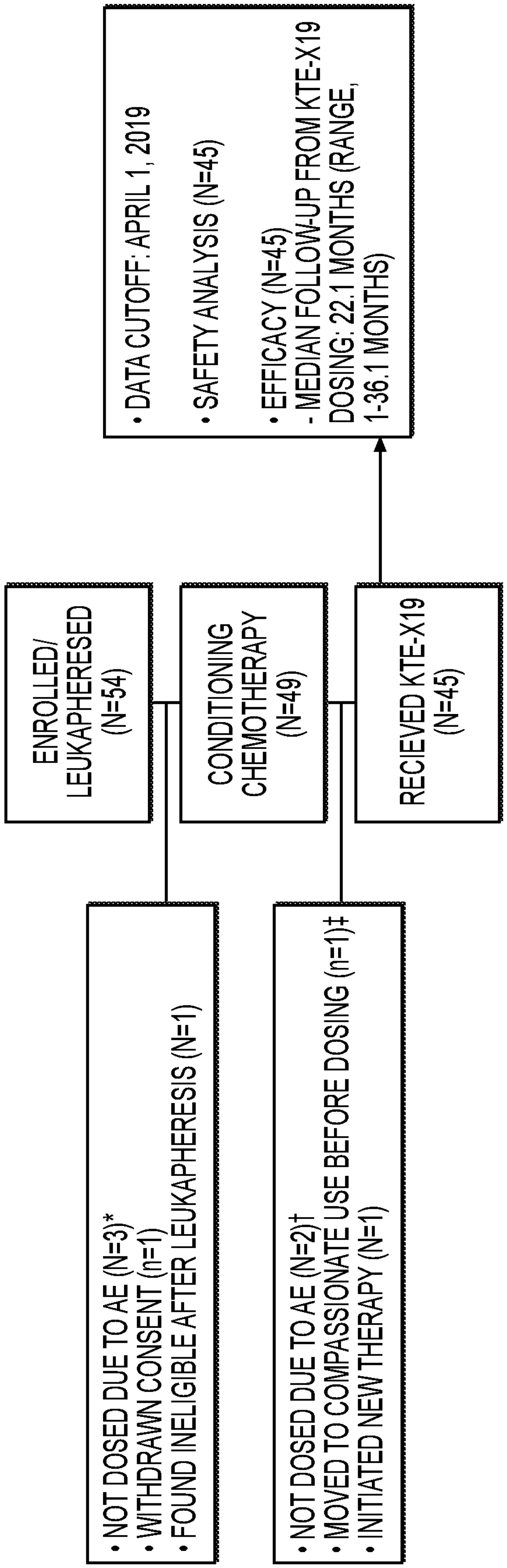

FIG. 4: ZUMA-3 CONSORT Diagram. * AEs were grade 3 pulmonary mass (n=1), grade 1 subdural hematoma (n=1), and grade 3 febrile neutropenia (n=1); † AEs were grade 4 sepsis (n=1) and grade 5 sepsis (n=1); ‡ One patient did receive KTE-X19 under compassionate use due to deep vein thrombosis, a study exclusion criterion. AE, adverse event.

Figure 5:
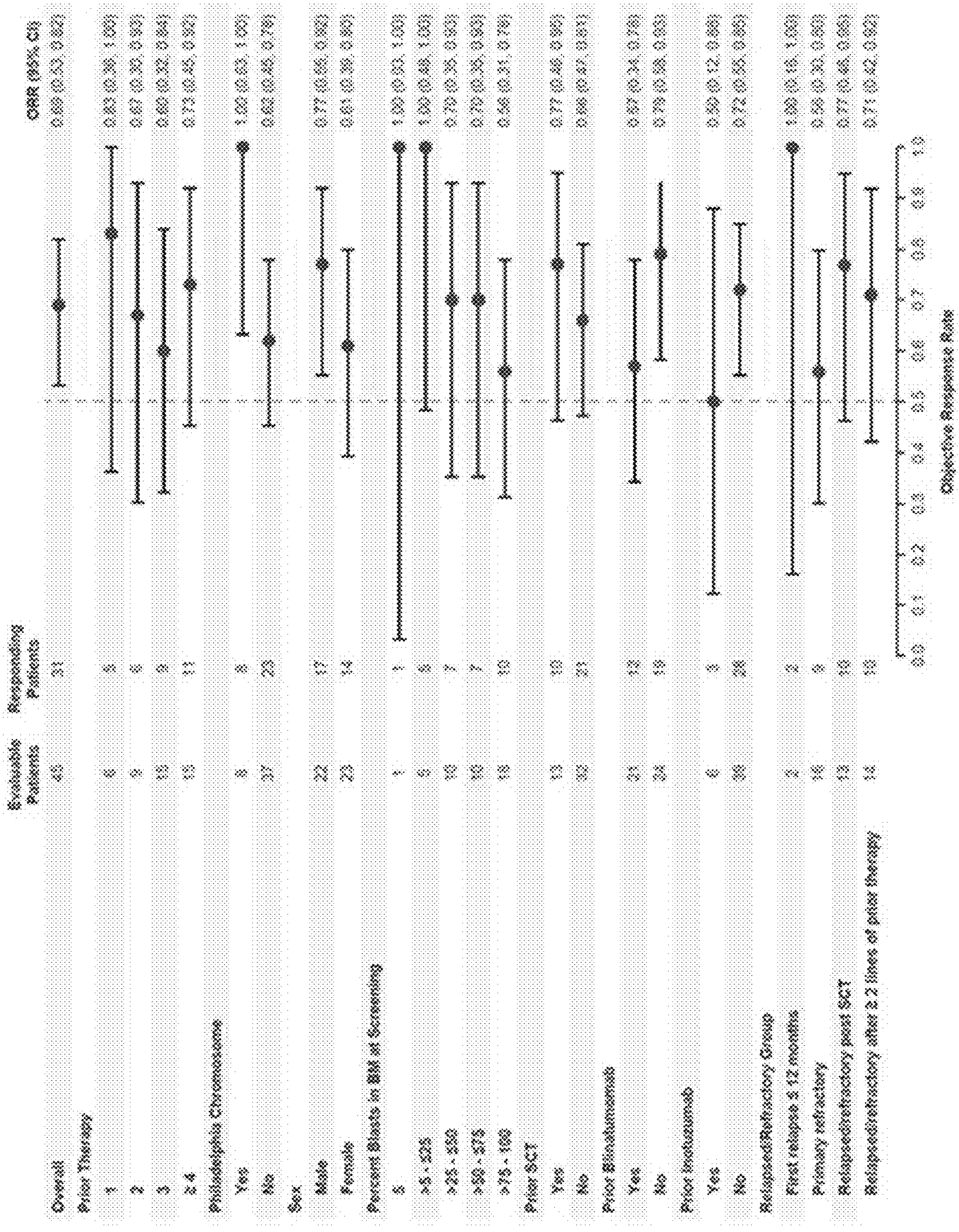

FIG. 5: Subgroup analysis of complete response rate. BM, bone marrow; ORR, overall remission rate; SCT, stem cell transplant.

FIGS. 6A, 6B, 6C, and 6D: Duration of response, censored at SCT; Duration of response, not censored at SCT; relapse-free survival; and overall survival by dose level, respectively.

Figure 7A:
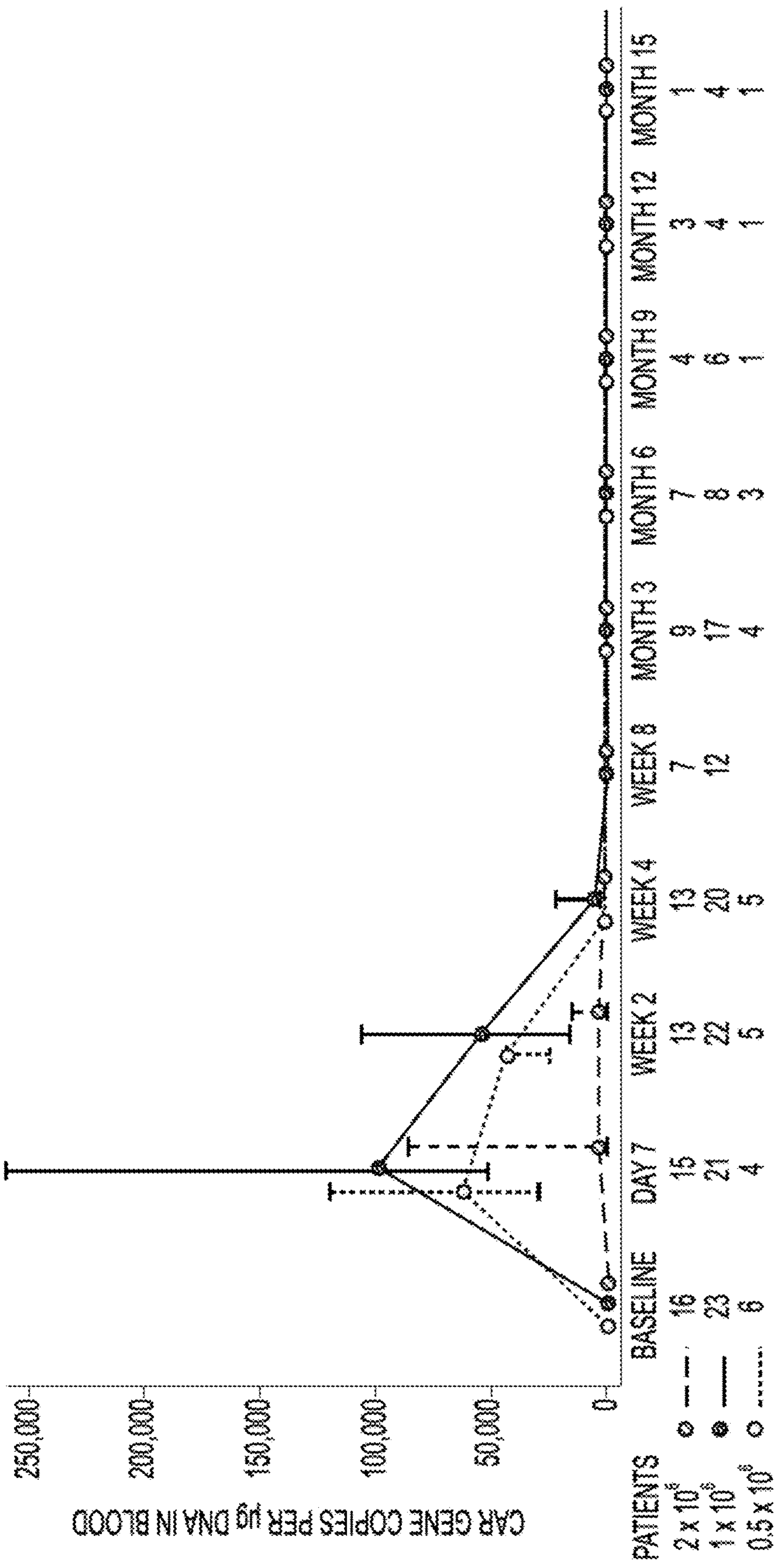
Figure 7B:
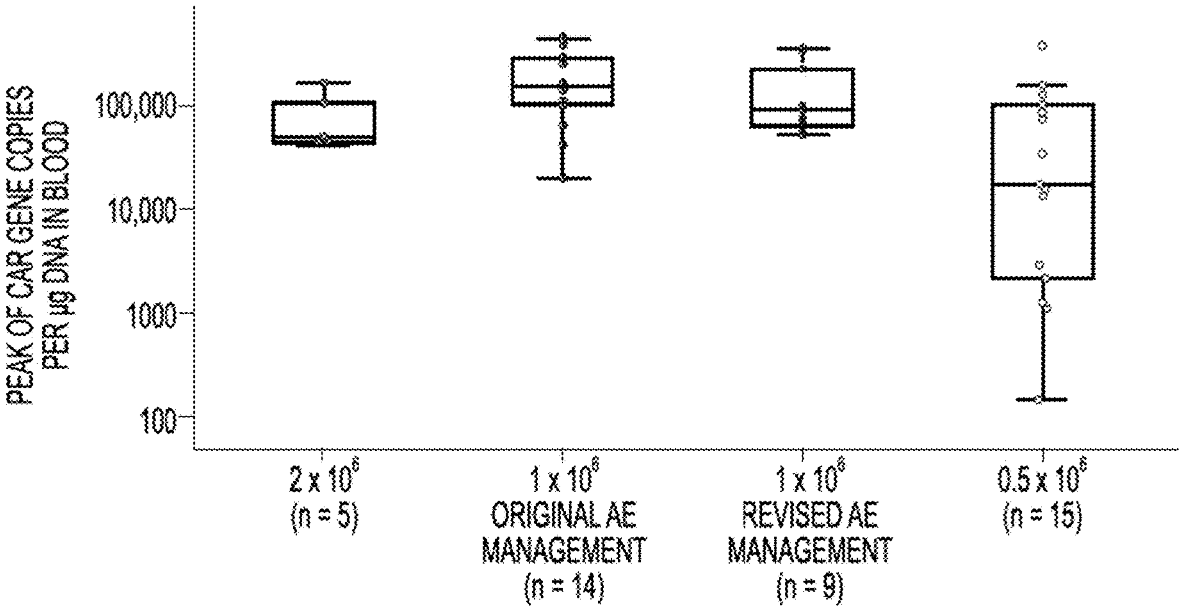
Figure 7C:
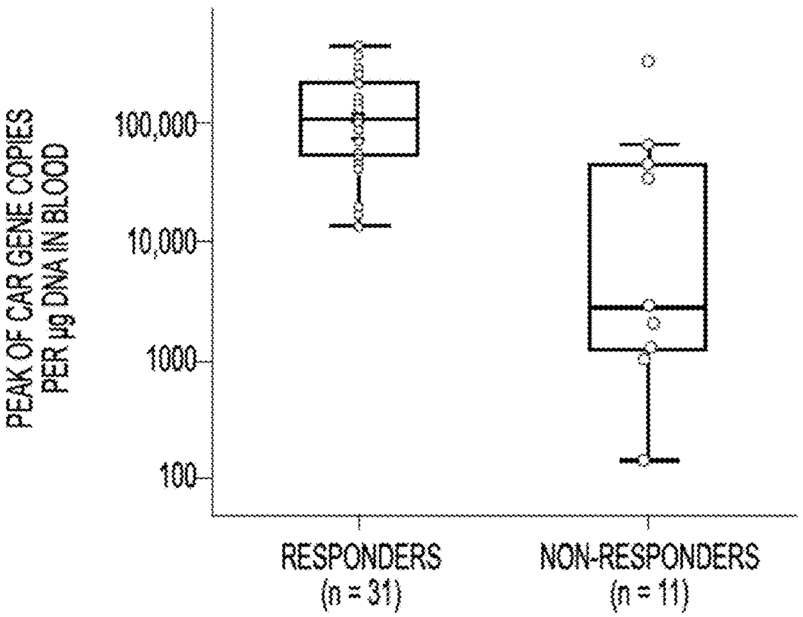
Figure 7F:
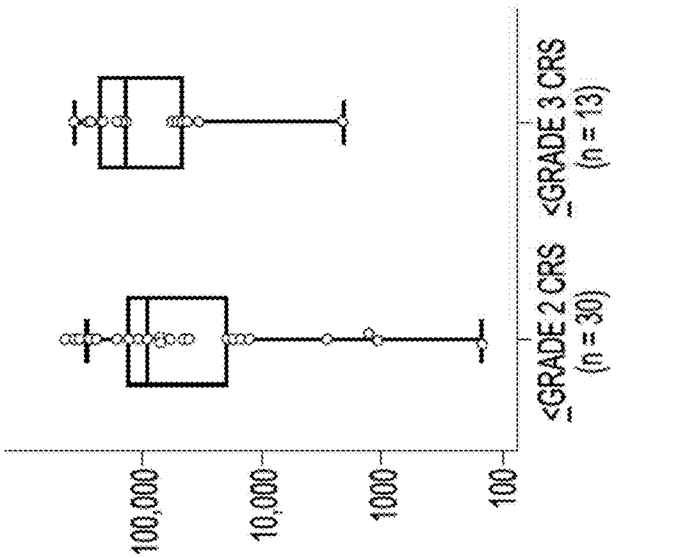
Figure 7E:
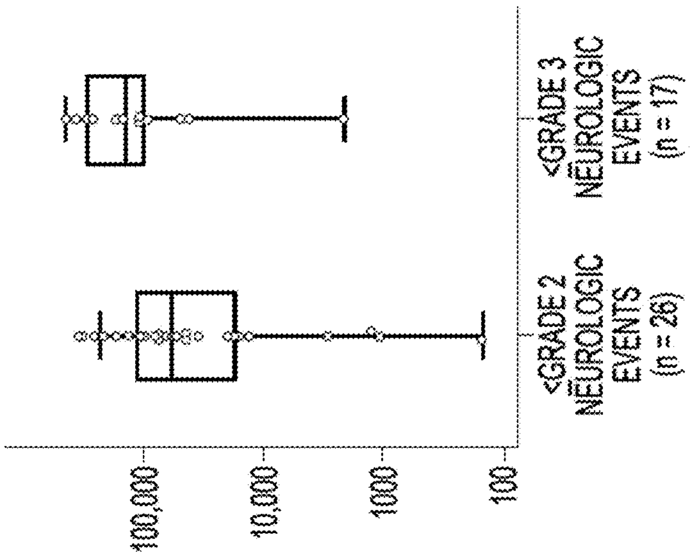
Figure 7D:
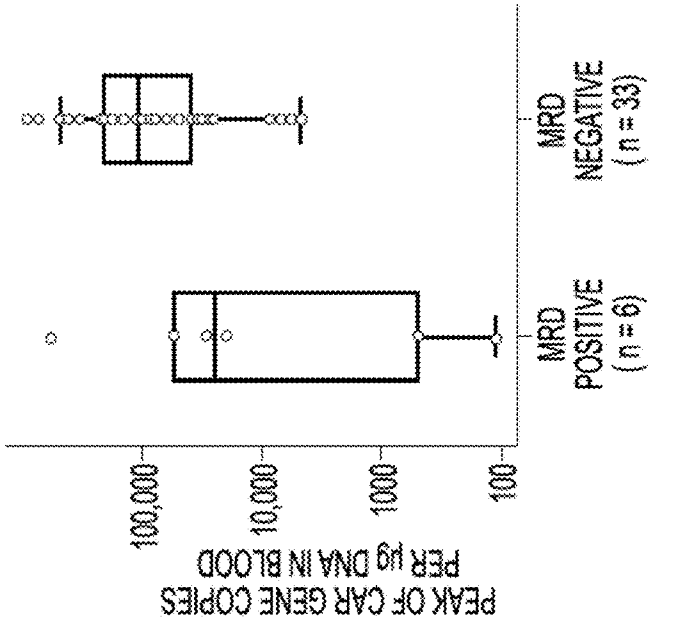

FIGS. 7A, 7B, and 7C: Peak CAR T-cell expansion and associations with response (FIG. 7C), minimal residual disease (FIGS. 7A and 7D), and toxicity (FIGS. 7B, 7E, and 7F)

Figure 8A:
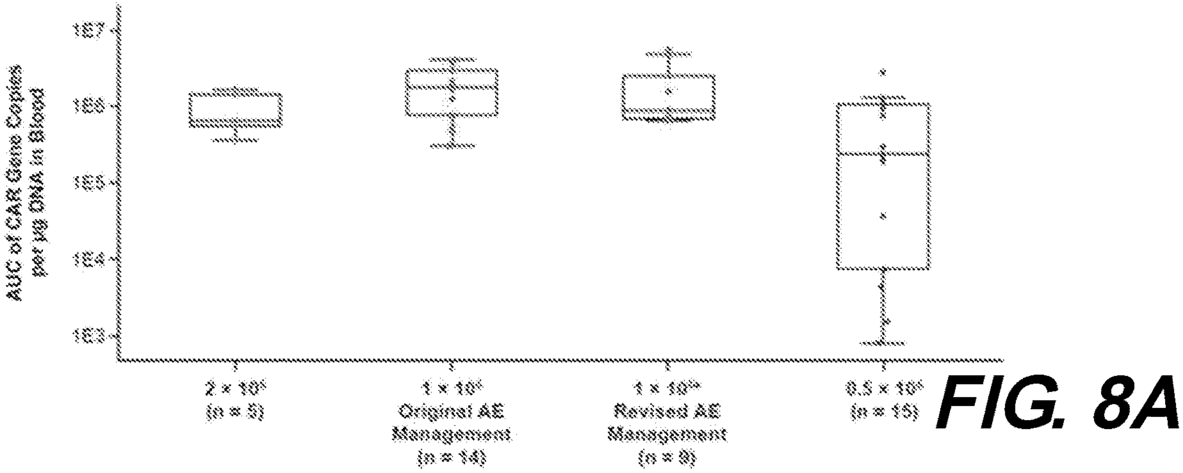
Figure 8B:
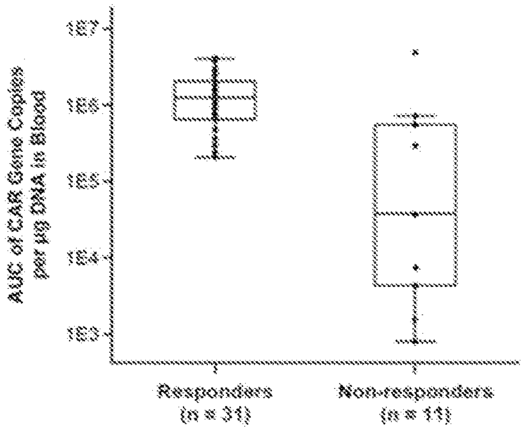
Figure 8C:
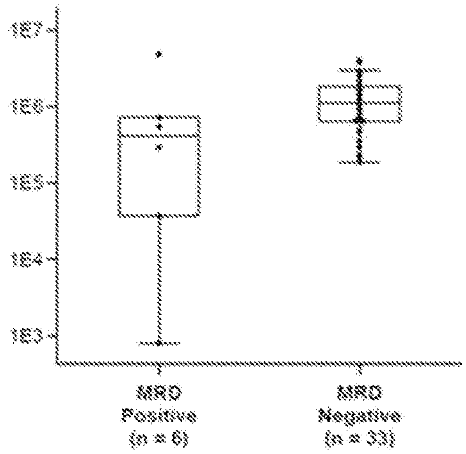
Figure 8D:
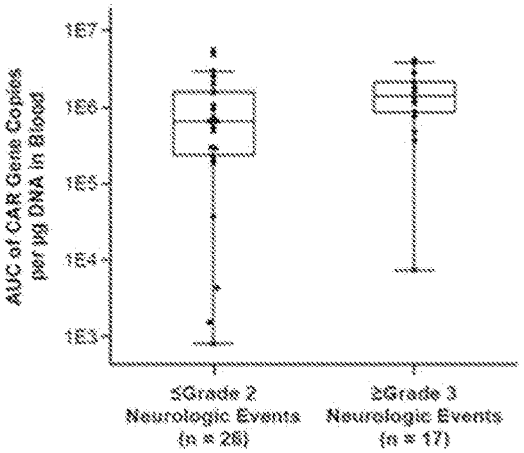
Figure 8E:
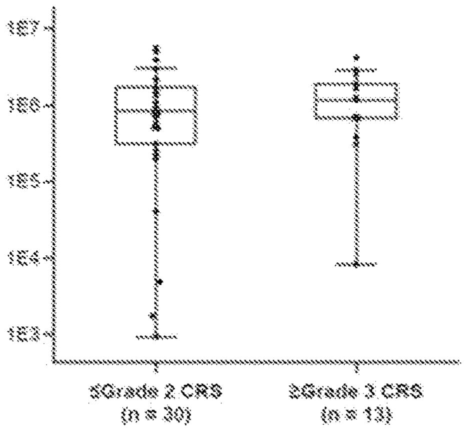

FIG. 8A-8E: CAR T-cell area under the curve associations with response (FIG. 8B), minimal residual disease (FIG. 8C), and toxicity (FIGS. 8A, 8D, and 8E). AE, adverse event; AUC, area under the curve; CAR, chimeric antigen receptor; CRS, cytokine release syndrome; MRD, minimal residual disease.

Figure 9A:
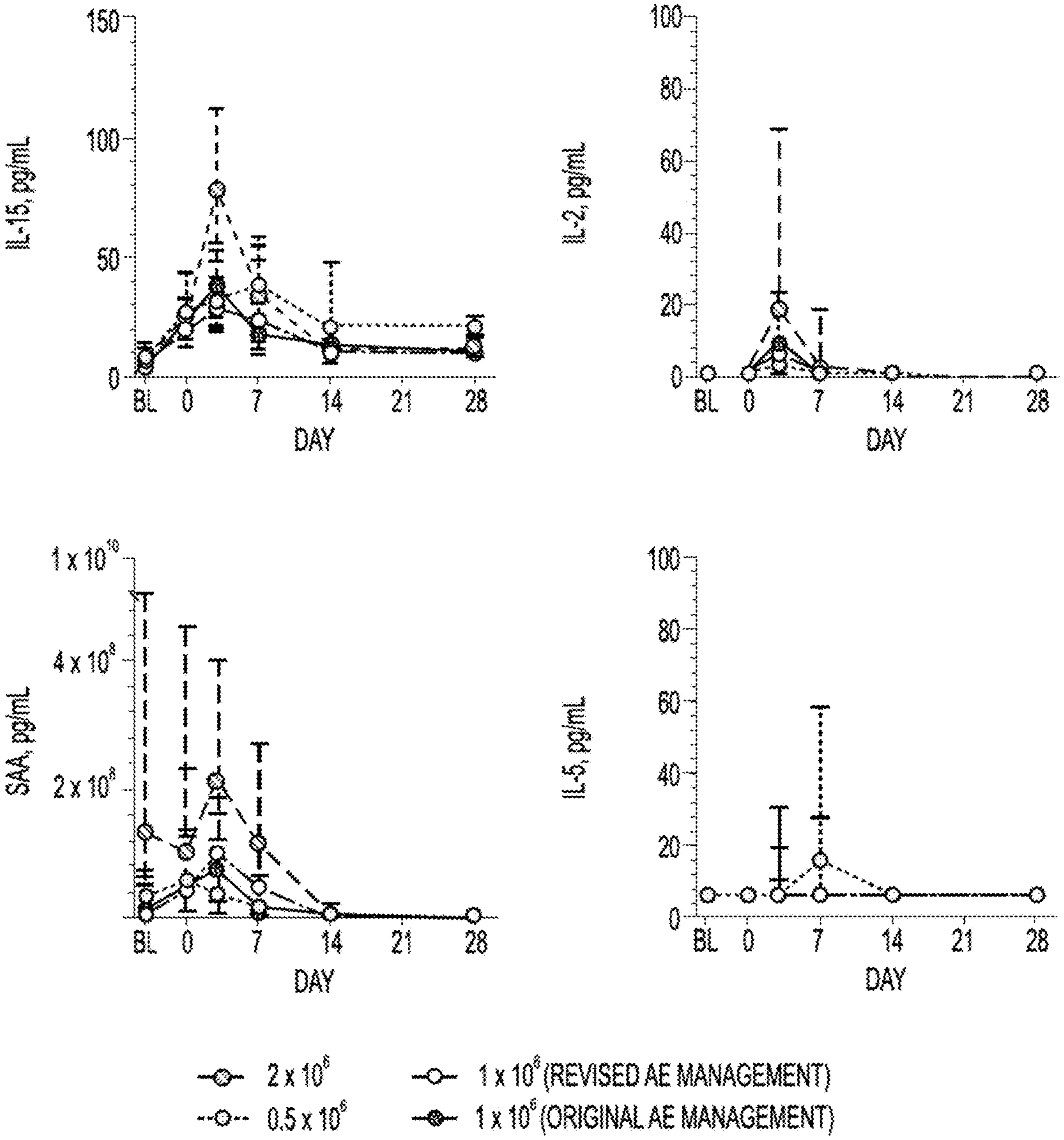
Figure 9B:
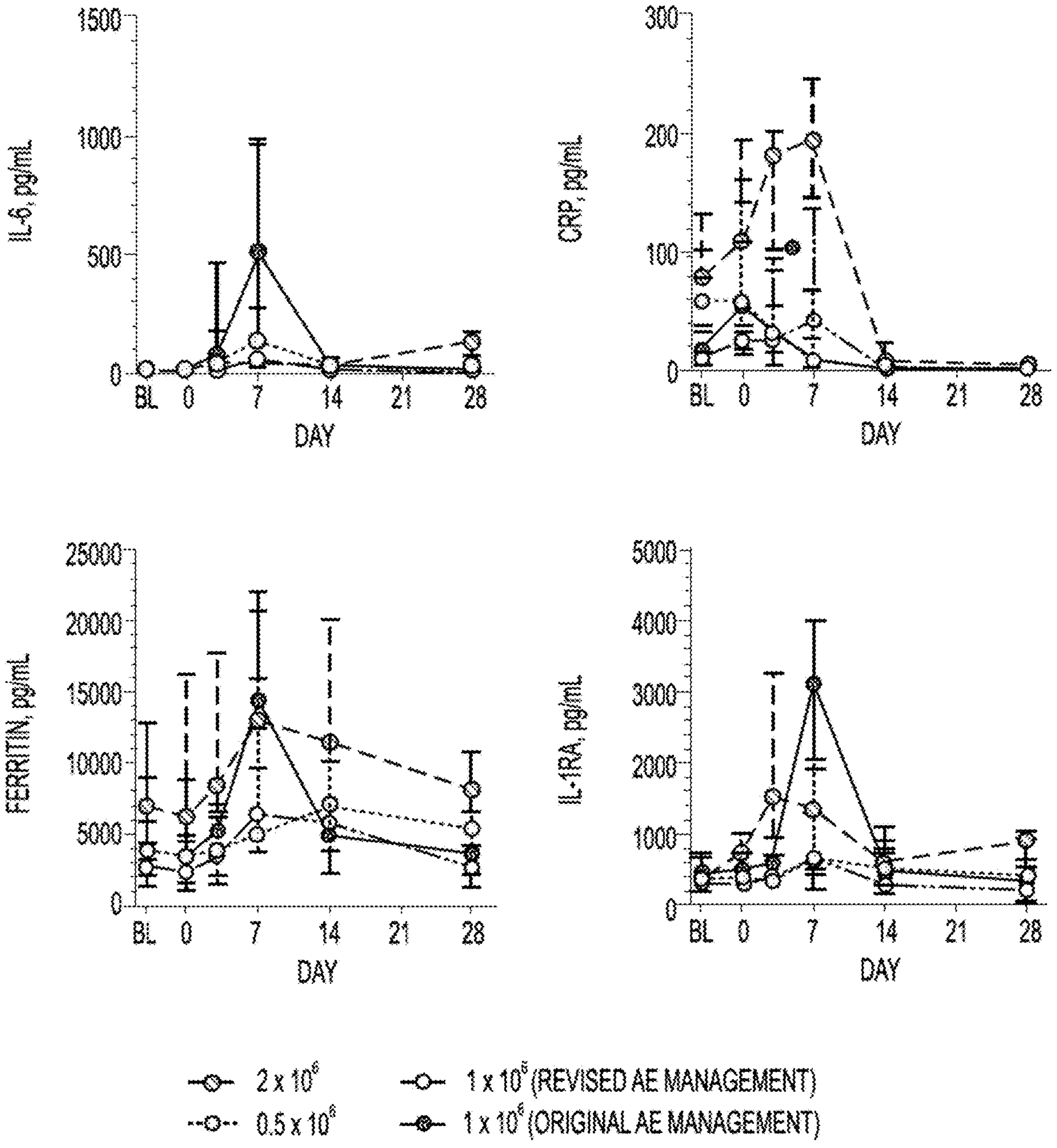
Figure 9C:
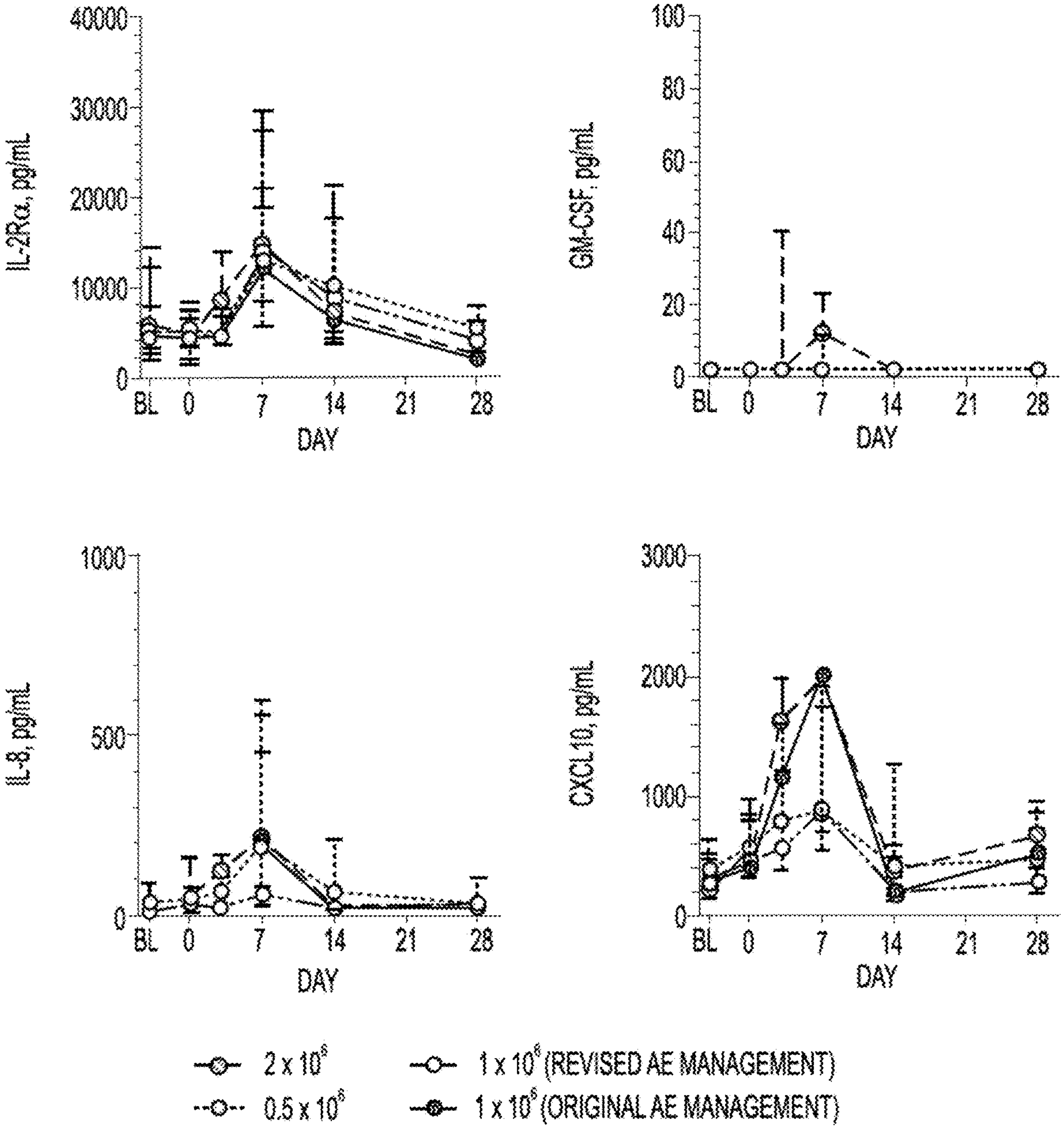
Figure 9D:
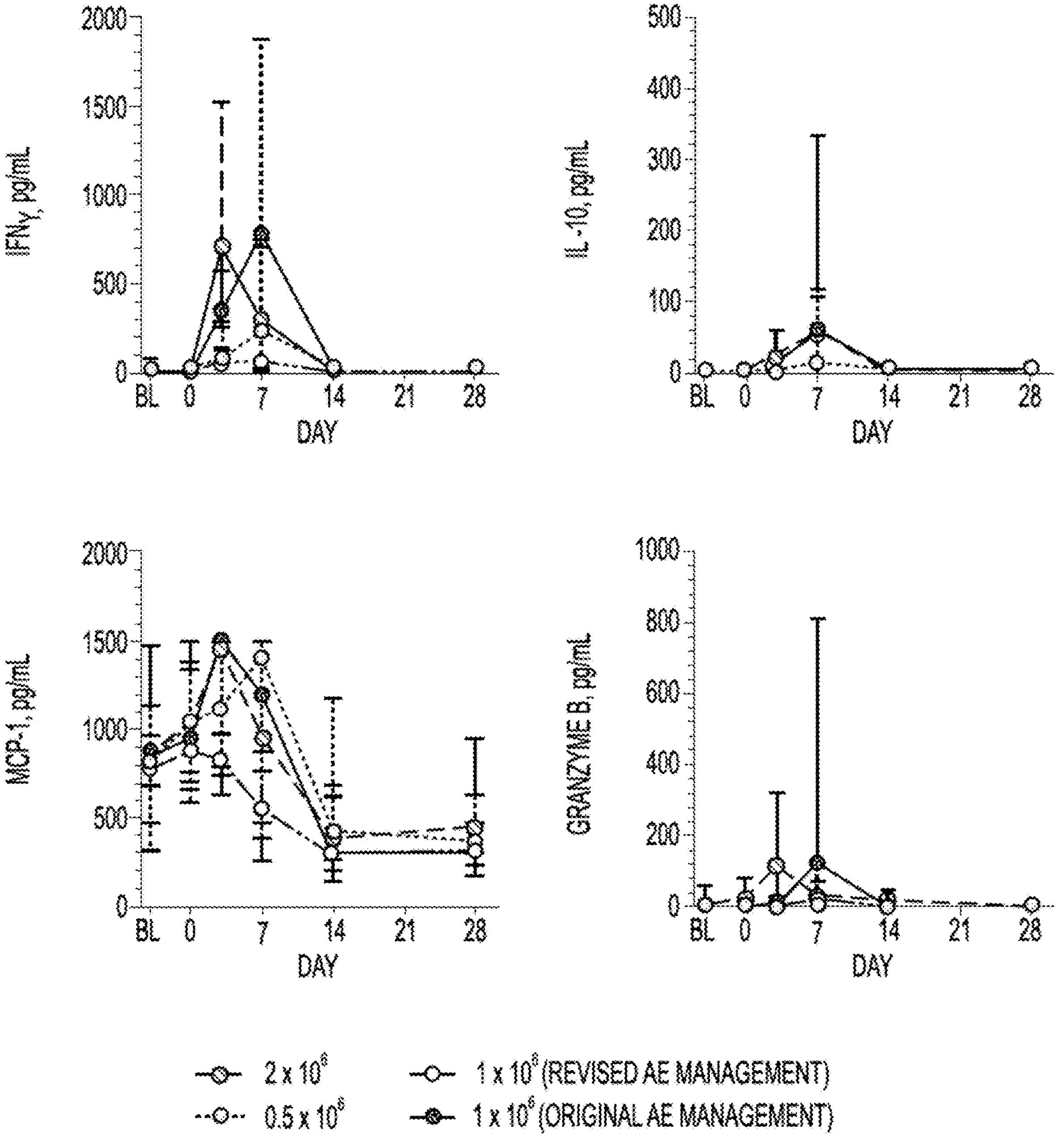

FIG. 9A-9D: Peak cytokine levels over time: IL-15, IL-2, SAA, and IL-5 (FIG. 9A); IL-6, CRP, FERRITIN, and IL-1RA (FIG. 9B); IL-2Rα, GM-CSF, IL-8, and CXCL10 (FIG. 9C); and IFNγ, IL-10, MCP-1, and GRANZYME B (FIG. 9D).

FIG. 10A-10E: Inflammatory markers in blood serum samples at baseline and at post-infusion peak. * Value represents lower limit of quantification in assay used. † Value represents upper limit of quantification in assay used. AE, adverse event; CAR, chimeric antigen receptor; CCL, C-C motif ligand; CRP, C-reactive protein; CXCL, C—X—C motif chemokine ligand; FGFBF, fibroblast growth factor basic form; FLT-1, fms related receptor tyrosine kinase 1; GM-CSF, granulocyte-macrophage colony-stimulating factor; ICAM-1, intercellular adhesion molecule 1; IFN, interferon; IL, interleukin; MCP, monocyte chemoattractant protein-1; MDC, macrophage-derived chemokine; MIP, macrophage inflammatory protein; PDL1, programmed death ligand 1; PLGF, placental growth factor; Rα, receptor alpha; RA, receptor antagonist; SAA, serum amyloid A; SFASL, soluble Fas ligand; TARC, thymus and activation-regulated cytokine; TNF, tumor necrosis factor; VCAM, vascular cell adhesion protein; VEGF, vascular endothelial growth factor; VEGFC, vascular endothelial growth factor C; VEGFD, vascular endothelial growth factor D.

FIGS. 11A and 11B: Association of Serum Biomarkers with Cytokine Release Syndrome and Neurologic Events. * Value represents lower limit of quantification in assay used.

† Value represents upper limit of quantification in assay used. CRP, C-reactive protein; CXCL, C—X—C motif chemokine ligand; GM-CSF, granulocyte-macrophage colony-stimulating factor; IFNγ, interferon gamma; IL, interleukin; IP, interferon γ-induced protein; MCP, monocyte attractant protein; Ra, receptor alpha; RA, receptor antagonist; SAA, serum amyloid A.

Figure 12:
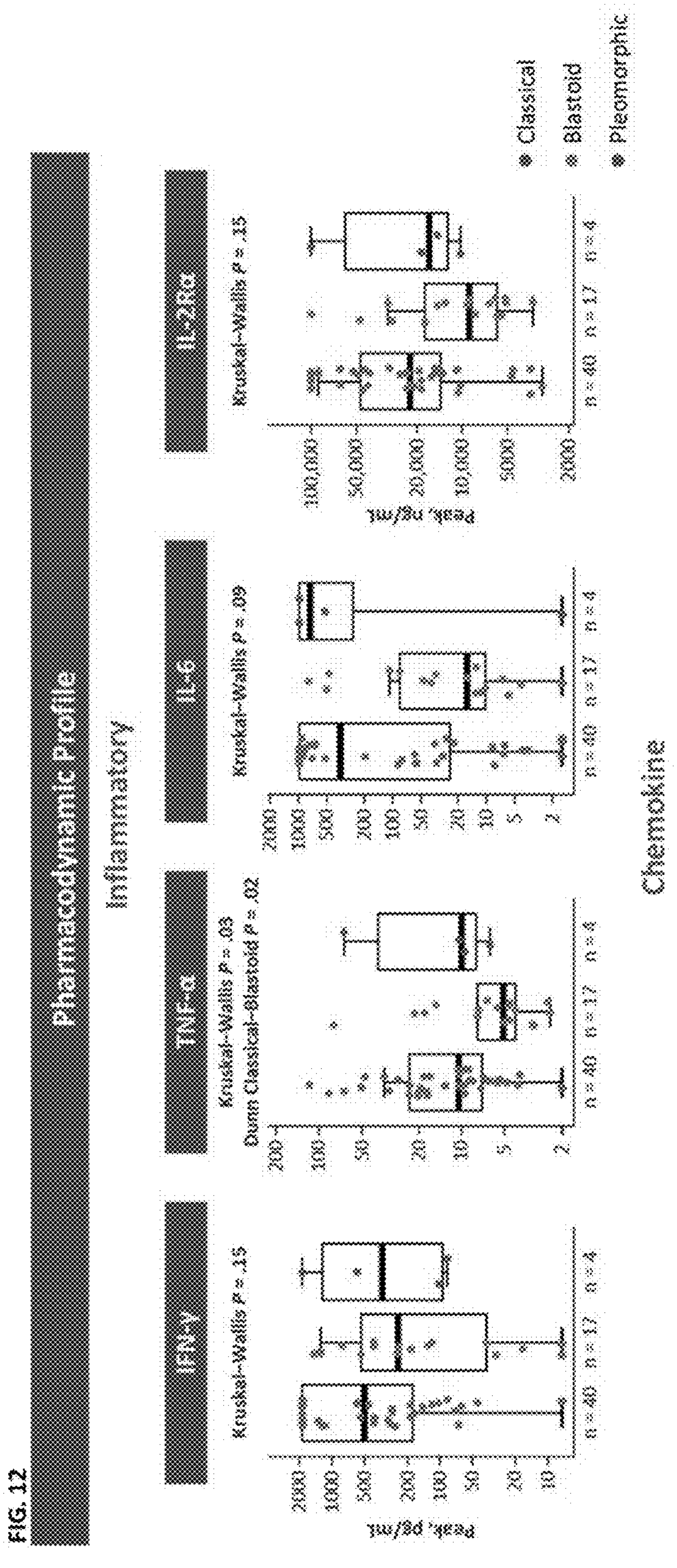

FIG. 12: Pharmacodynamic profile of KTE-X19 across MCL morphology subgroups. AUC, area under the curve; CAR, chimeric antigen receptor; CXCL10, C—X—C motif chemokine ligand 10; IFN-g, interferon gamma; IL, interleukin; MCL, mantle cell lymphoma; MCP-1, monocyte chemoattractant protein-1; MIP-1β, macrophage inflammatory protein-1 beta; PD-L1, programmed death-ligand 1; PRF, perforin; Rα, receptor alpha; TNF-α, tumor necrosis factor alpha.

Figure 13:
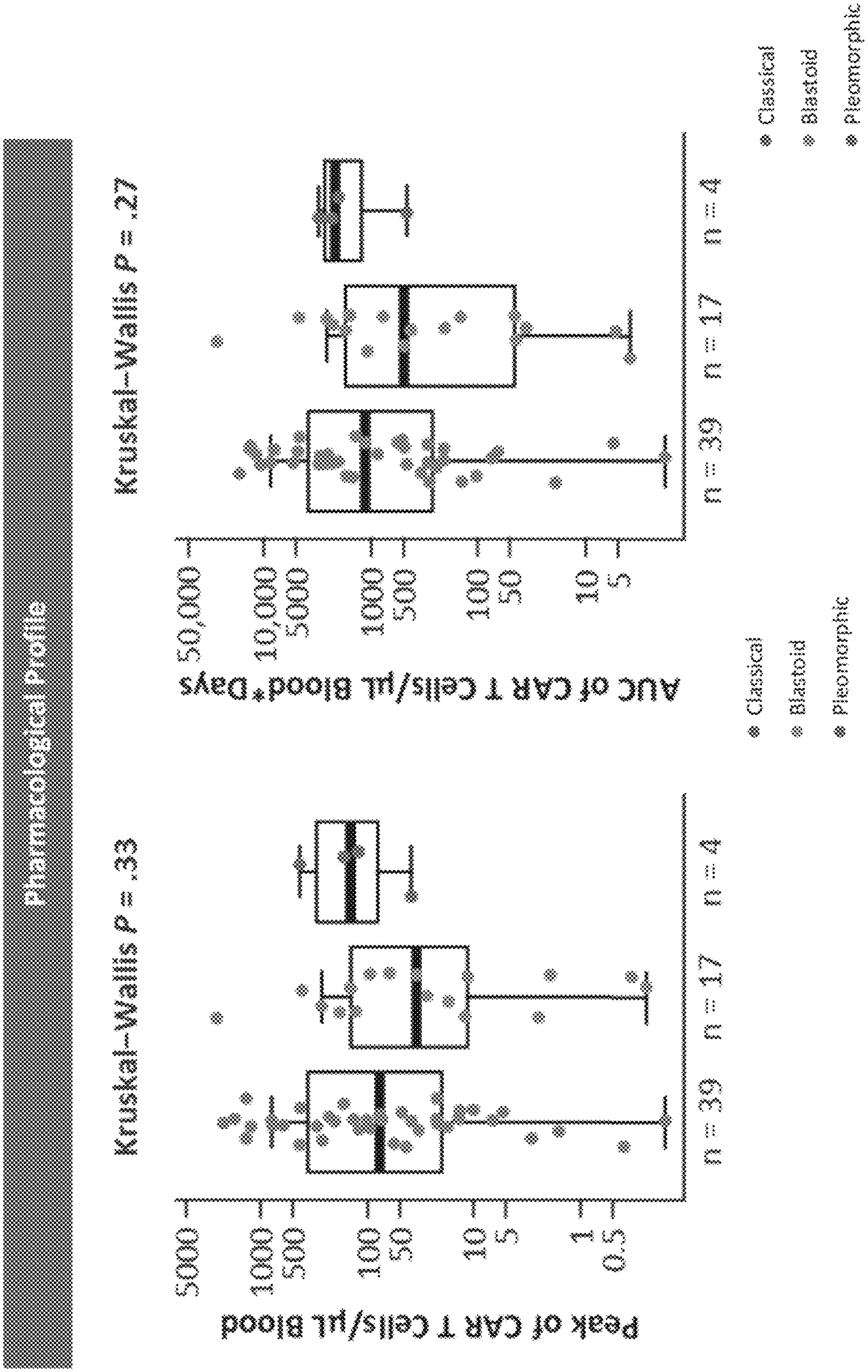

FIG. 13: Pharmacological profile of KTE-X19 across MCL morphology subgroups.

Figure 14:
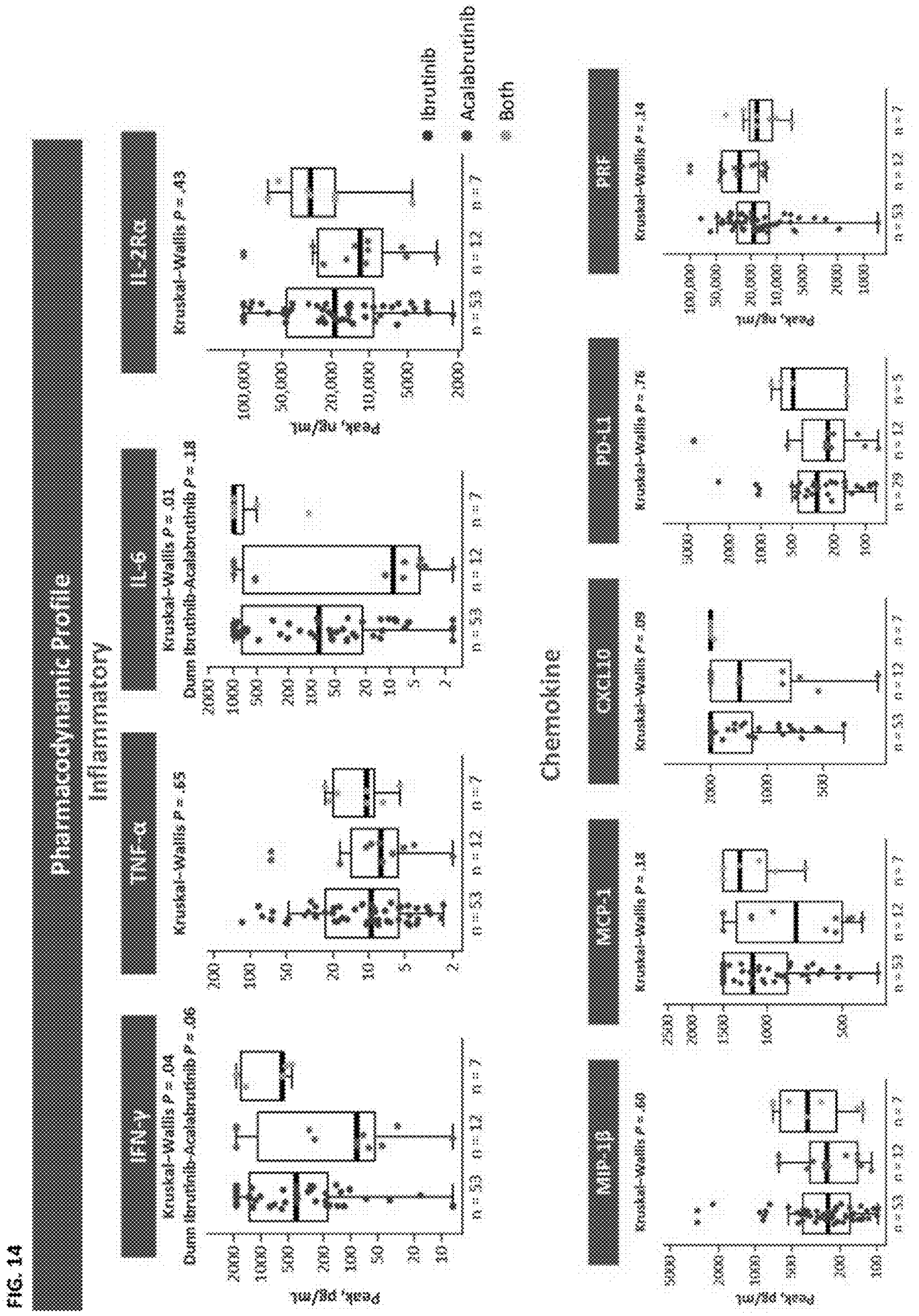

FIG. 14: Pharmacodynamic profile of KTE-X19 across prior BTKi subgroups. AUC, area under the curve; CAR, chimeric antigen receptor; CXCL10, C—X—C motif chemokine ligand 10; IFN-g, interferon gamma; IL, interleukin; MCL, mantle cell lymphoma; MCP-1, monocyte chemoattractant protein-1; MIP-1β, macrophage inflammatory protein-1 beta; PD-L1, programmed death-ligand 1; PRF, perforin; Rα, receptor alpha; TNF-α, tumor necrosis factor alpha.

Figure 15:
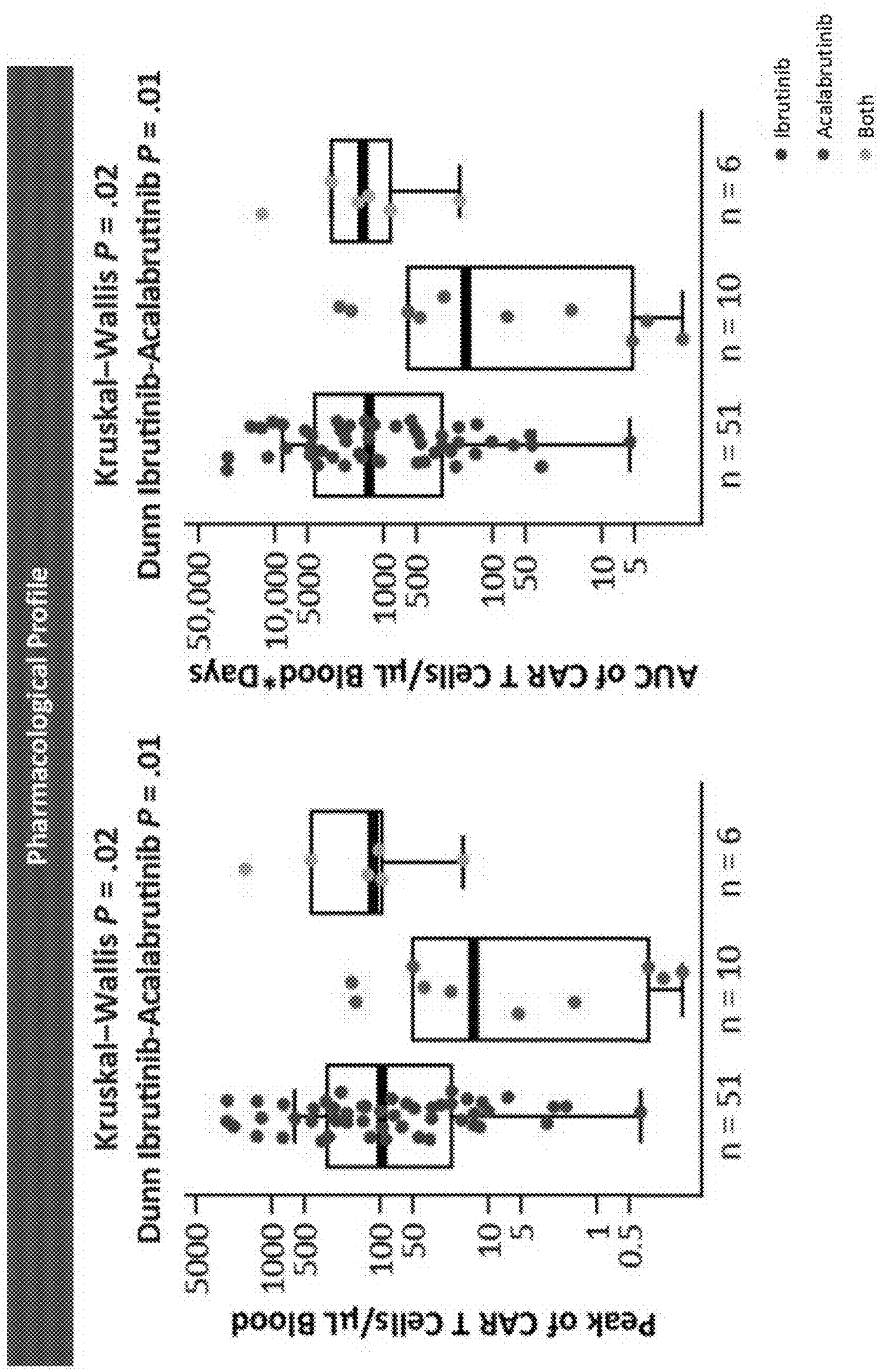

FIG. 15: Pharmacological profile of KTE-X19 across prior BTKi subgroups.

Figure 16:
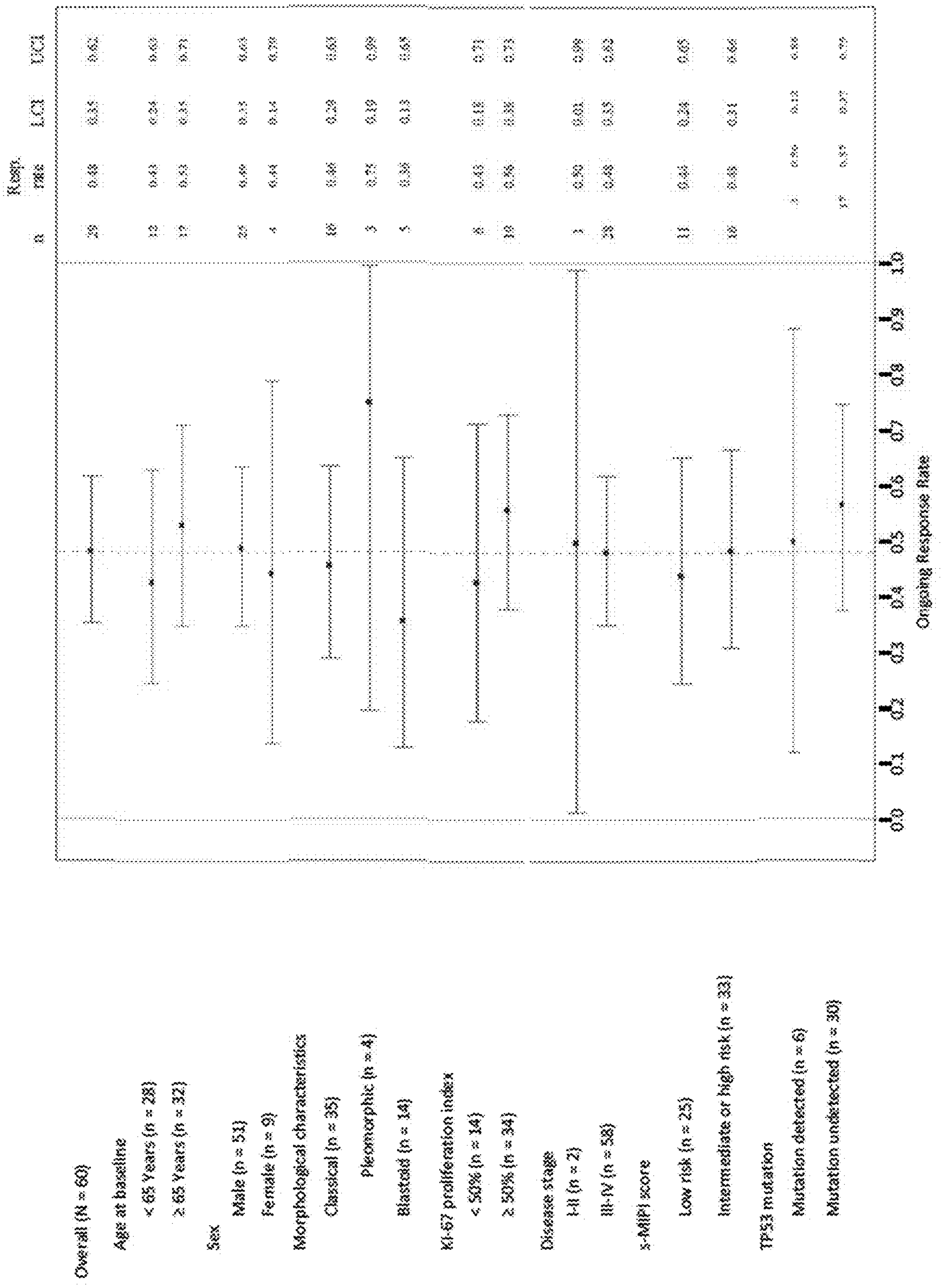

FIG. 16: Ongoing response rate across subgroups.

Figure 17A:
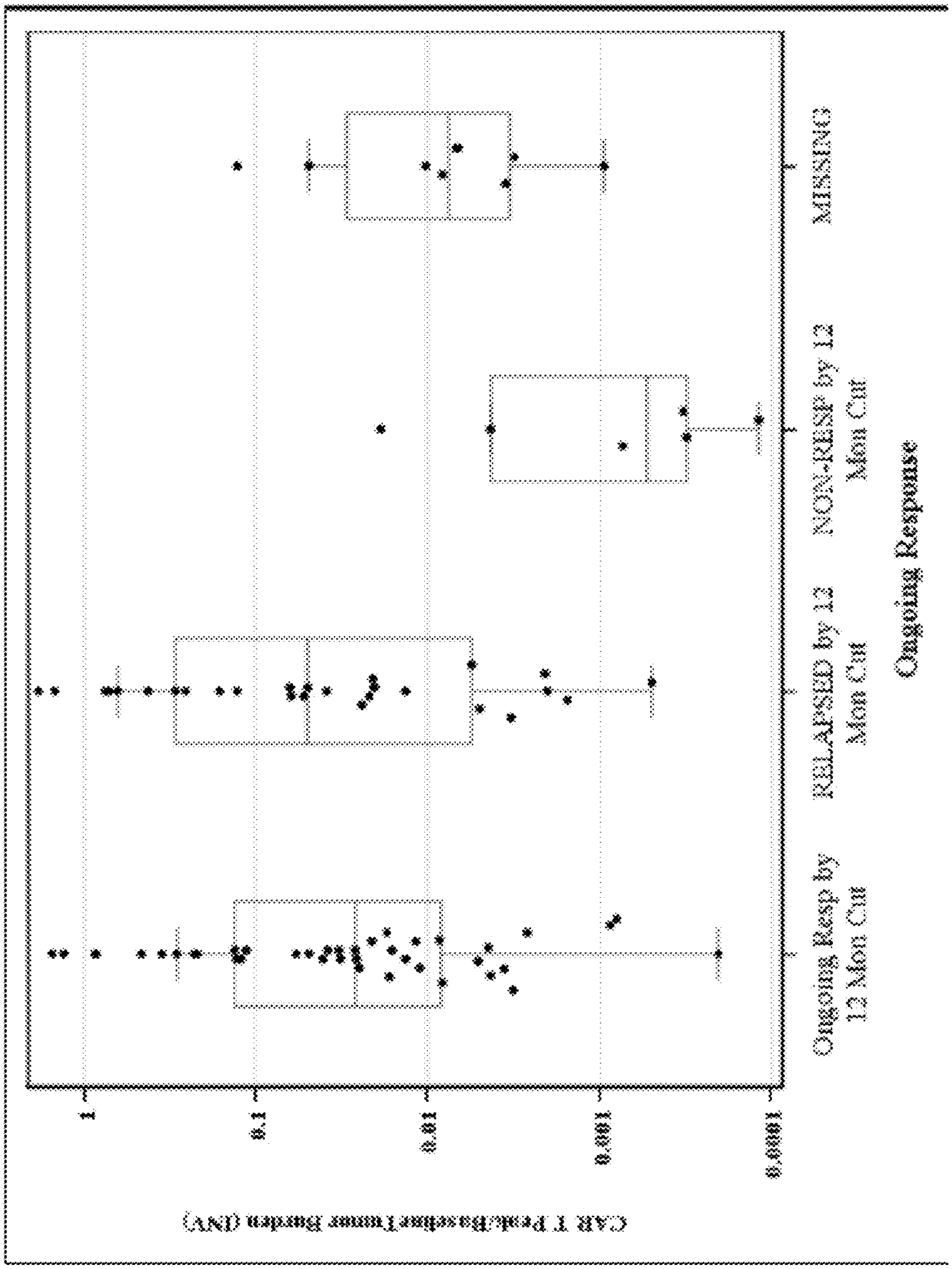
Figure 17B:
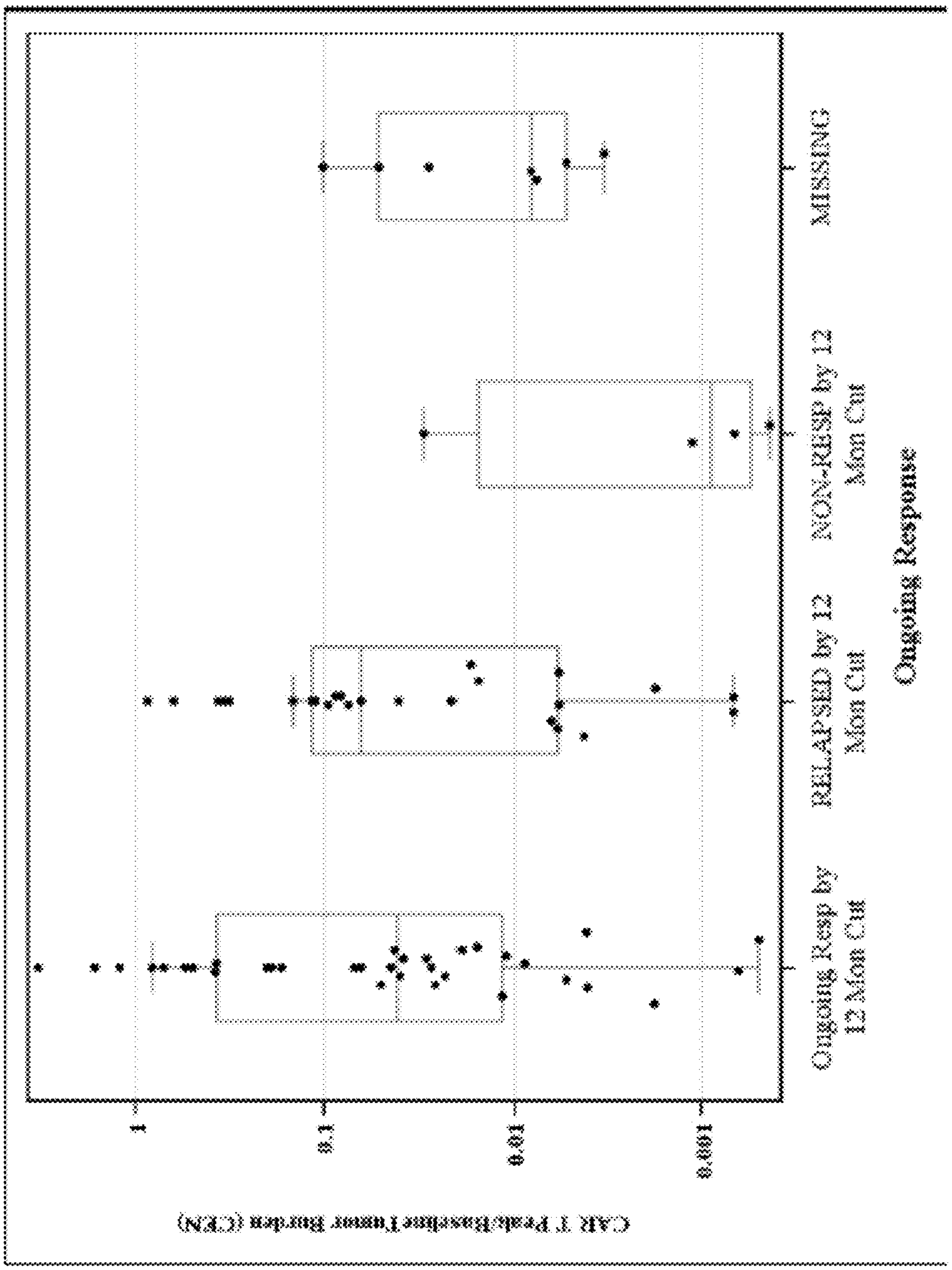

FIG. 17A, Peak CAR T level/baseline tumor burden and ongoing response, INV; FIG. 17B, Peak CAR T level/baseline tumor burden and ongoing response, CEN

DETAILED DESCRIPTION

Except as otherwise expressly provided herein, each of the following terms shall have the meaning set forth below. Additional definitions are set forth throughout the application. Unless defined otherwise, all technical and scientific terms used herein have the meaning as commonly understood by one of ordinary skill in the art. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this application.

Units, prefixes, and symbols are denoted in their Systeme International de Unites (SI) accepted form. Numeric ranges are inclusive of the numbers defining the range. The disclosure provided herein are not limitations of the various aspects of the application, which may be by reference to the specification as a whole. Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

The articles "a" or "an" refer to "one or more" of any recited or enumerated component.

The terms "about" or "comprising essentially of" refer to a value or composition that is within an acceptable error range for certain value or composition as determined by one of ordinary skill in the art, which will depend in part on how the value or composition is measured or determined, i.e., the limitations of the measurement system. For example, "about" or "comprising essentially of" may mean within 1 or more than 1 standard deviation per the practice in the art. Alternatively, "about" or "comprising essentially of" may mean a range of up to 10% (i.e., ±10%). For example, about 3 mg may include any number between 2.7 mg and 3.3 mg (for 10%). With respect to biological systems or processes, the terms may mean up to an order of magnitude or up to 5-fold of a value. When certain values or compositions are provided in the application and claims, unless otherwise stated, the meaning of "about" or "comprising essentially of" include an acceptable error range for that value or composition. Any concentration range, percentage range, ratio range, or integer range includes the value of any integer within the recited range and, when appropriate, fractions thereof (such as one-tenth and one-hundredth of an integer), unless otherwise indicated.

Unless specifically stated or obvious from context, as used herein, the term "or" is understood to be inclusive and covers both "or" and "and". The term "and/or" refer to each of the two specified features or components with or without the other. Thus, the term "and/or" as used in a phrase such as "A and/or B" herein is intended to include "A and B," "A or B," "A" (alone), and "B" (alone). Similarly, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." are used merely by way of example, without limitation intended, and not be construed as referring only those items explicitly enumerated in the specification.

The terms "or more", "at least", "more than", and the like, e.g., "at least one" include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or150, 200, 300, 400, 500, 600, 700, 800, 900, 1000, 2000, 3000, 4000, 5000 or more than the stated value. Also included is any greater number or fraction in between. The term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," is understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided. The term "consisting of" excludes any element, step, or ingredient not specified in the claim. In re Gray, 53 F.2d 520, 11 USPQ 255 (CCPA 1931); Ex parte Davis, 80 USPQ 448, 450 (Bd. App. 1948) ("consisting of" defined as "closing the claim to the inclusion of materials other than those recited except for impurities ordinarily associated therewith"). The term "consisting essentially of" limits the scope of a claim to the specified materials or steps "and those that do not materially affect the basic and novel characteristic(s)" of the claimed invention.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" may mean within one or more than one standard deviation per the practice in the art. "About" or "approximately" may mean a range of up to 10% (i.e., 10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

The term "activation," "activated," or the like refers to the state of a cell, including and not be limited to an immune cell (e.g., a T cell), that has been sufficiently stimulated to induce detectable cellular proliferation. Activation may be associated with induced cytokine production and detectable effector functions. The term "activated T cells" refers to, among other things, T cells that are undergoing cell division. T cell activation may be characterized by increased T cell expression of one or more biomarker, including, but not limited to, CD57, PD1, CD107a, CD25, CD137, CD69, and/or CD71. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. In general, such methods include contacting cells (such as T cells) with an activating, stimulatory, or costimulatory agent (such as anti-CD3 and/or anti-CD28 antibodies) which may be attached, coated, or bound to a bead or other surface, in a solution (such as feeding, culture, and/or growth medium) with certain cytokines (such as IL-2, IL-7, and/or IL-15). The activation agent (such as anti-CD3 and/or anti-CD28 antibodies) attached to the same bead serve as a "surrogate" antigen presenting cell (APC). One example is The Dynabeads® system, a CD3/CD28 activator/stimulator system for physiological activation of human T cells. In one embodiment, the T cells are activated and stimulated to proliferate with certain antibodies and/or cytokines using the methods described in U.S. Pat. Nos. 6,040,177 and 5,827,642 and PCT Publication No. WO 2012/129514, the contents of which are hereby incorporated by reference in their entirety.

The terms "administration," "Administering" or the like refer to physical introduction of an agent to a subject, using any of the various methods and delivery systems known to those skilled in the art. Exemplary routes of administration for the immune cells prepared by the methods disclosed herein include intravenous (i.v. or IV), intramuscular, subcutaneous, intraperitoneal, spinal or other parenteral routes of administration, for example by injection or infusion. Parenteral route of administration refer to modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In one embodiment, the immune cells (e.g., T cells) prepared by the present methods are administered via injection or infusion. Non-parenteral routes include a topical, epidermal or mucosal route of administration, for example, intranasally, vaginally, rectally, sublingually or topically. Administering may also be once, twice, or a plurality of times over one or more extended periods. Where one or more therapeutic agents (e.g., cells) are administered, the administration may be done concomitantly or sequentially. Sequential administration comprises administration of one agent only after administration of the other agent or agents has been completed.

The term "antibody" (Ab) includes, without limitation, an immunoglobulin which binds specifically to an antigen. In general, an antibody may comprise at least two heavy (H) chains and two light (L) chains interconnected by disulfide bonds. Each H chain comprises a heavy chain variable region (abbreviated herein as VH) and a heavy chain constant region. The heavy chain constant region may comprise three or four constant domains, CH1, CH2 CH3, and/or CH4. Each light chain comprises a light chain variable region (abbreviated herein as VL) and a light chain constant region. The light chain constant region may comprise one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, a monovalent and a divalent fragment or portion, and a single chain Ab.

An "antigen binding molecule," "antibody fragment" or the like refer to any portion of an antibody less than the whole. An antigen binding molecule may include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. In one aspect, the CD19 CAR construct comprises an anti-CD 19 single-chain FV. A "Single-chain Fv" or "scFv" antibody binding fragment comprises the variably heavy (VH) and variable light (VL) domains of an antibody, where these domains are present in a single polypeptide chain. Generally, the Fv polypeptide further comprises a polypeptide linker between the VH and VL domains, which enables the scFv to form the desired structure for antigen binding. All antibody-related terms used herein take the customary meaning in the art and are well understood by one of ordinary skill in the art.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function The term "autologous" refers to any material derived from the same individual to which it is later to be re-introduced. For example, the engineered autologous cell therapy method described herein involves a collection of lymphocytes from an individual (such as a donor or a patient), which are then engineered to express a CAR construct and then administered back to the same individual.

The term "allogeneic" refers to any material derived from one individual which is then introduced to another individual of the same species, e.g., allogeneic T cell transplantation.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor at various stages. In one embodiment, the cancer or tumor is stage 0, such that, e.g., the cancer or tumor is very early in development and has not metastasized. In another embodiment, the cancer or tumor is stage I, such that, e.g., the cancer or tumor is relatively small in size, has not spread into nearby tissue, and has not metastasized. In other embodiment, the cancer or tumor is stage II or stage III, such that, e.g., the cancer or tumor is larger than in stage 0 or stage I, and it has grown into neighboring tissues but it has not metastasized, except potentially to the lymph nodes. In additional embodiment, the cancer or tumor is stage IV, such that, e.g., the cancer or tumor has metastasized. Stage IV may also be referred to as advanced or metastatic cancer.

An "anti-tumor effect" as used herein, refers to a biological effect that may present, and not being limited to, as a decrease in tumor volume, an inhibition of tumor growth, a decrease in the number of tumor cells, a decrease in tumor cell proliferation, a decrease in the number/extent of metastases, an increase in overall or progression-free survival, an increase in life expectancy, and/or amelioration of various physiological symptoms associated with the tumor. An anti-tumor effect may also refer to the prevention of the occurrence of a tumor, e.g., a vaccine.

The term "progression-free survival" (PFS) refers to the time from the treatment date to the date of disease progression (per general guidelines, such as revised IWG Response Criteria for Malignant Lymphoma) or death from any cause. The term "Disease progression" may be assessed by measurement of malignant lesions on radiographs or other methods should not be reported as adverse events. Death due to disease progression in the absence of signs and symptoms may be reported as the primary tumor type (e.g., DLBCL). The term "duration of response" (DOR) refers to the period of time between a subject's first objective response to the date of confirmed disease progression (per general guidelines, such as the revised IWG Response Criteria for Malignant Lymphoma) or death. The term "overall survival" (OS) refers to the time from the date of treatment to the date of death.

A "cytokine" refers to a non-antibody protein that may be released by immune cells, including macrophages, B cells, T cells, and mast cells to propagate an immune response. In one embodiment, one or more cytokines are released in response to the therapy. In other embodiment, those cytokines secreted in response to the therapy may indicate or suggest an effective therapy. In one embodiment, "cytokine" refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

A "therapeutically effective amount," "therapeutically effective dosage," or the like refers to an amount of the cells (such as immune cells or engineered T cells) that are produced by the present methods (resulting in a T cell product) and that, when used alone or in combination with another therapeutic agent, protects or treats a subject against the onset of a disease or promotes disease regression as evidenced by a decrease in severity of disease symptoms, an increase in frequency and duration of disease symptom-free periods, and/or prevention of impairment or disability due to disease affliction. The ability to promote disease regression may be evaluated using a variety of methods known to the skilled practitioner, such as in subjects during clinical trials, in animal model systems predictive of efficacy in humans, or by assaying the activity of the agent in in vitro assays. In some embodiments, the donor T cells for use in the T cell therapy are obtained from the patient (e.g., for an autologous T cell therapy). In other embodiments, the donor T cells for use in the T cell therapy are obtained from a subject that is not the patient. The T cells may be administered at a therapeutically effective amount. For example, a therapeutically effective amount of the T cells may be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In some embodiments, the therapeutically effective amount of the CAR-positive viable T cells is between about $1\times10^6$ and about $2\times10^6$ CAR-positive viable T cells per kg body weight up to a maximum dose of about $1\times10^8$ CAR-positive viable T cells. In some embodiments, the therapeutically effective amount of the CAR-positive viable T cells is between about $0.4\times10^8$ and about $2\times10^8$ CAR-positive viable T cells. In some embodiments, the therapeutically effective amount of the CAR-positive viable T cells is about $0.4\times10^8$, about $0.5\times10^8$, about $0.6\times10^8$, about $0.7\times10^8$, about $0.8\times10^8$, about $0.9\times10^8$, about $1.0\times10^8$, about $1.1\times10^8$, about $1.2\times10^8$, about $1.3\times10^8$, about $1.4\times10^8$, about $1.5\times10^8$, about $1.6\times10^8$, about $1.7\times10^8$, about $1.8\times10^8$, about $1.9\times10^8$, or about $2.0\times10^8$ CAR-positive viable T cells The term "lymphocyte" as used herein may include natural killer (NK) cells, T cells, NK-T cells, or B cells. NK cells are a type of cytotoxic (cell toxic) lymphocyte that represent a major component of the inherent immune system. NK cells reject tumors and cells infected by viruses, through the process of apoptosis or programmed cell death. They were termed "natural killers" because they do not require activation to kill cells. T-cells playa major role in cell-mediated immunity (no antibody involvement). The T-cell receptors (TCR) differentiate themselves from other lymphocyte types. The thymus, a specialized organ of the immune system, is primarily responsible for the T cell's maturation.

There are several types of "immune cells," including, without limitation, macrophages (e.g, tumor associated macrophages) neutrophils, basophils, eosinophils, granulocytes, natural killer cells (NK cells), B cells, T cells, NK-T cells, mast cells, tumor infiltrating lymphocytes (TILs), myeloid derived suppressor cells (MDSCs), and dendritic cells. The term also includes precursors of these immune cells. Hematopoietic stem and/or progenitor cells may be derived from bone marrow, umbilical cord blood, adult peripheral blood after cytokine mobilization, and the like, by methods known in the art. Some precursor cells are those that may differentiate into the lymphoid lineage, for example, hematopoietic stem cells or progenitor cells of the lymphoid lineage. Additional examples of immune cells that may be used for immune therapy are described in US Publication No. 20180273601, incorporated herein by reference in its entirety.

There are also several types of T-cells, namely: Helper T-cells (e.g., CD4+ cells, effector $T_{EFF}$ cells), Cytotoxic T-cells (also known as TC, cytotoxic T lymphocyte, CTL, T-killer cell, cytolytic T cell, CD8+ T-cells or killer T cell), Memory T-cells ((i) stem memory TSCM cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and are $CCR7^+$ and $CD45RO^+$ and they secrete IL-2, but not IFNγ or IL-4, and (iii) effector memory $T_{EM}$ cells, however, do not express L-selectin or CCR7 but do express CD45RO and produce effector cytokines like IFNγ and IL-4), Regulatory T-cells (Tregs, suppressor T cells, or CD4+CD25+ regulatory T cells), Natural Killer T-cells (NKT), and Gamma Delta T-cells. T cells found within tumors are referred to as "tumor infiltrating lymphocytes" (TIL). B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

A "naïve" T cell refers to a mature T cell that remains immunologically undifferentiated. Following positive and negative selection in the thymus, T cells emerge as either $CD4^+$ or $CD8^+$ naïve T cells. In their naïve state, T cells express L-selectin ($CD62L^+$), IL-7 receptor-α (IL-7R-α), and CD132, but they do not express CD25, CD44, CD69, or CD45RO. As used herein, "immature" may also refers to a T cell which exhibits a phenotype characteristic of either a naïve T cell or an immature T cell, such as a $T_{SCM}$ cell or a $T_{CM}$ cell. For example, an immature T cell may express one or more of L-selectin ($CD62L^+$), IL-7Rα, CD132, CCR7, CD45RA, CD45RO, CD27, CD28, CD95, IL-2Rβ, CXCR3, and LFA-1. Naïve or immature T cells may be contrasted with terminal differentiated effector T cells, such as $T_{EM}$ cells and $T_{EFF}$ cells.

"T cell function," as referred to herein, refers to normal characteristics of healthy T cells. T cell function may comprise T cell proliferation, T cell activity, and/or cytolytic activity. In one embodiment, the methods of the present application of preparing T cells under certain oxygen and/or pressure condition would increase one or more T cell function, thereby making the T cells more fit and/or more potent for therapeutic purpose. In some embodiment, T cells that are prepared according to the present methods have increased T cell function as compared to those under conditions lacking certain oxygen and/or pressure. In other embodiment, T cells that are prepared according to the present methods would have increased T cell proliferation as compared to T cells cultured under conditions lacking certain oxygen and/or pressure. In additional embodiment, T cells that are prepared according to the present methods have increased T cell activity as compared to T cells cultured under conditions lacking certain oxygen and/or pressure. In further embodiment, T cells that are prepared according to the present methods have increased cytolytic activity as compared to T cells cultured under conditions lacking certain oxygen and/or pressure.

The terms cell "proliferation," "proliferating" or the like refer to the ability of cells to grow in numbers through cell division. Proliferation may be measured by staining cells with carboxyfluorescein succinimidyl ester (CFSE). Cell proliferation may occur in vitro, e.g., during T cell culture, or in vivo, e.g., following administration of a immune cell therapy (e.g., T cell therapy). The cell proliferation may be measured or determined by the methods described herein or known in the field. For example, cell proliferation may be measured or determined by viable cell density (VCD) or total viable cell (TVC). VCD or TVC may be theoretical (an aliquot or sample is removed from a culture at certain timepoint to determine the cell number, then the cell number multiples with the culture volume at the beginning of the study) or actual (an aliquot or sample is removed from a culture at certain timepoint to determine the cell number, then the cell number multiples with the actual culture volume at the certain timepoint). The term "T cell activity" refers to any activity common to healthy T cells. In one embodiment, the T cell activity comprises cytokine production (such as INFγ, IL-2, and/or TNFα). In other embodiment, the T cell activity comprises production of one or more cytokine selected from interferon gamma (IFNγ or IFN-γ), tissue necrosis factor alpha (TNFα or IFNα), and both. The terms "cytolytic activity," "cytotoxicity" or the like refer to the ability of a T cell to destroy a target cell. In one embodiment, the target cell is a cancer cell, e.g., a tumor cell. In other embodiment, the T cell expresses a chimeric antigen receptor (CAR) or a T cell receptor (TCR), and the target cell expresses a target antigen.

The term "genetically engineered," "gene editing," or "engineered" refers to a method of modifying the genome of a cell, including, but not being limited to, deleting a coding or non-coding region or a portion thereof or inserting a coding region or a portion thereof. In one embodiment, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof "Chimeric antigen receptors" (CARs or CAR-Ts) and the T cell receptors (TCRs) of the application are genetically engineered receptors. These engineered receptors may be readily inserted into and expressed by immune cells, including T cells, in accordance with techniques known in the art. With a CAR, a single receptor may be programmed to both recognize a specific antigen and, when bound to that antigen, activate the immune cell to attack and destroy the cell bearing or expressing that antigen. When these antigens exist on tumor cells, an immune cell that expresses the CAR may target and kill the tumor cell. In one embodiment, the cell that are prepared according to the present application is a cell having a chimeric antigen receptor (CAR), or a T cell receptor, comprising an antigen binding molecule, a costimulatory domain, and an activating domain. The costimulatory domain may comprise an extracellular domain, a transmembrane domain, and an intracellular domain. In one embodiment, the extracellular domain comprises a hinge or a truncated hinge domain.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The terms "immunotherapy" "immune therapy" or the like refer to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell and NK cell therapies. T cell therapy may include adoptive T cell therapy, tumor-infiltrating lymphocyte (TIL) immunotherapy, autologous cell therapy, engineered autologous cell therapy and allogeneic T cell transplantation. One of skill in the art would recognize that the methods of preparing immune cells disclosed herein would enhance the effectiveness of any cancer or transplanted T cell therapy. Examples of T cell therapies are described in U.S. Patent Publication Nos. 2014/0154228 and 2002/0006409; U.S. Pat. Nos.

7,741,465; 6,319,494; and 5,728,388; and PCT Publication No. WO 2008/081035, which are incorporated by reference in their entirety.

The term "engineered Autologous Cell Therapy," which may be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells may be engineered to express, for example, chimeric antigen receptors (CAR) or T cell receptor (TCR). CAR positive (+) T cells are engineered to express an extracellular single chain variable fragment (scFv) with specificity for certain tumor antigen linked to an intracellular signaling part comprising a costimulatory domain and an activating domain. The costimulatory domain may be a signaling region derived from, e.g., CD28, CTLA4, CD16, OX-40, 4-1BB/CD137, CD2, CD7, CD27, CD30, CD40, programmed death-1 (PD-1), programmed death ligand-1 (PD-L1), inducible T cell costimulator (ICOS), ICOS-L, lymphocyte function-associated antigen-1 (LFA-1 (CDl la/CD18), CD3 gamma, CD3 delta, CD3 epsilon, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. The activating domain may be derived from, e.g., CD3, such as CD3 zeta, epsilon, delta, gamma, or the like. In one embodiment, the CAR is designed to have two, three, four, or more costimulatory domains. The CAR scFv may be designed to target, for example, CD19, which is a transmembrane protein expressed by cells in the B cell lineage, including all normal B cells and B cell malignances, including but not limited to NHL, CLL, and non-T cell ALL. Example CAR+ T cell therapies and constructs are described in U.S. Patent Publication Nos. 2013/0287748, 2014/0227237, 2014/0099309, and 2014/0050708, which are hereby incorporated by reference in their entirety.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CDl-la, CDl-lb, CDl-lc, CDl-ld, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSFi4), LTBR, Ly9 (CD229), lymphocyte function-associated antigen-1 (LFA-1 (CDl la/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof In some aspect, the cells of the present application may be obtained through T cells obtained from a subject. In one aspect, the T cells may be obtained from, e.g., peripheral blood mononuclear cells (PBMC), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. In some aspect, the cells collected by apheresis are washed to remove the plasma fraction and placed in an appropriate buffer or media for subsequent processing. In some aspect, the cells are washed with any solution (e.g. a solution with neutralized PH value or PBS) or culture medium. As will be appreciated, a washing step may be used, such as by using a semiautomated flow through centrifuge, e.g., the Cobe™ 2991 cell processor, the Baxter CytoMate™ or the like. In some aspect, the washed cells are resuspended in one or more biocompatible buffers, or other saline solution with or without buffer. In some aspect, the undesired components of the apheresis sample are removed. Additional methods of isolating T cells for a T cell therapy are disclosed in U.S. Patent Pub. No. 2013/0287748, which are hereby incorporated by references in their entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection may be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected may be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In one embodiment, CD3+ T cells are isolated from PBMCs using Dynabeads coated with anti-CD3 antibody. CD8+ and CD4+ T cells are further separately isolated by positive selection using CD8 microbeads (e.g., Miltenyi Biotec) or CD4 microbeads (e.g., Miltenyi Biotec).

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion The one or more immune cells described herein may be obtained from any source, including, for example, a human donor. The donor may be a subject in need of an anti-cancer treatment, e.g., treatment with one immune cells generated by the methods described herein (i.e., an autologous donor), or may be an individual that donates a lymphocyte sample that, upon generation of the population of cells generated by the methods described herein, will be used to treat a different individual or cancer patient (i.e., an allogeneic donor). immune cells may be differentiated in vitro from a hematopoietic stem cell population, or immune cells may be obtained from a donor. The population of immune cells may be obtained from the donor by any suitable method used in the art. For example, the population of lymphocytes may be obtained by any suitable extracorporeal method, venipuncture, or other blood collection method by which a sample of blood with or without lymphocytes is obtained. The population of lymphocytes is obtained by apheresis. The one or more immune cells may be collected from any tissue that comprises one or more immune cells, including, but not limited to, a tumor. A tumor or a portion thereof is collected from a subject, and one or more immune cells are isolated from the tumor tissue. Any T cell may be used in the methods disclosed herein, including any immune cells suitable for a T cell therapy. For example, the one or more cells useful for the application may be selected from the group consisting of tumor infiltrating lymphocytes (TIL), cytotoxic T cells, CAR T cells, engineered TCR T cells, natural killer T cells, Dendritic cells, and peripheral blood lymphocytes. T cells may be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. T cells may also be obtained from an artificial thymic organoid (ATO) cell culture system, which replicates the human thymic environment to support efficient ex vivo differentiation of T-cells from primary and reprogrammed pluripotent stem cells. Additional methods of isolating T cells for a T cell therapy are disclosed in U.S. Patent Publication No. 2013/0287748, in PCT Publication Nos. WO2015/120096 and WO2017/070395, all of which are herein incorporated by reference in their totality for the purposes of describing these methods and in their entirety. In one embodiment, T cells are tumor infiltrating leukocytes. In certain embodiment, the one or more T cells express CD8, e.g., are $CD8^+$ T cells. In other embodiment, the one or more T cells express CD4, e.g., are $CD4^+$ T cells. Additional methods of isolating T cells for a T cell therapy are disclosed in U.S. Patent Publication No. 2013/0287748, in PCT Publication Nos. WO2015/120096 and WO2017/070395, all of which are herein incorporated by reference in their totality for the purposes of describing these methods and in their entirety.

The immune cells and their precursor cells may be isolated by available methods (see, for example, Rowland-Jones et al., Lymphocytes: A Practical Approach, Oxford University Press, New York (1999)). The sources for the immune cells or precursor cells thereof include, but are not limited to, peripheral blood, umbilical cord blood, bone marrow, or other sources of hematopoietic cells. Negative selection methods may be used to remove cells that are not the desired immune cells. Additionally, positive selection methods may isolate or enrich for desired immune cells or precursor cells thereof, or a combination of positive and negative selection methods may be employed. Monoclonal antibodies (MAbs) are useful for identifying markers associated with certain cell lineages and/or stages of differentiation for both positive and negative selections. If certain type of cell is to be isolated, for example, certain type of T cell, various cell surface markers or combinations of markers, including but not limited to, CD3, CD4, CD8, CD34 (for hematopoietic stem and progenitor cells) and the like, may be used to separate the cells, as is well known in the art (see Kearse, T Cell Protocols: Development and Activation, Humana Press, Totowa N.J. (2000); De Libero, T Cell Protocols, Vol. 514 of Methods in Molecular Biology, Humana Press, Totowa N.J. (2009))

PBMCs may be used directly for genetic modification with the immune cells (such as CARs). After isolating the PBMCs, T lymphocytes are further isolated, and both cytotoxic and helper T lymphocytes are sorted into naive, memory, and effector T cell subpopulations either before or after genetic modification and/or expansion. In one embodiment, CD8+ cells may be further sorted into naive, central memory, and effector cells by identifying cell surface antigens that are associated with each of these types of CD8+ cells. In other embodiment, the expression of phenotypic markers of central memory T cells includes CCR7, CD3, CD28, CD45RO, CD62L, and CD127 and are negative for granzyme B. In some embodiment, central memory T cells are CD8+, CD45RO+, and CD62L+ T cells. In certain embodiment, effector T cells are negative for CCR7, CD28, CD62L, and CD127 and positive for granzyme B and perforin. In additional embodiment, CD4+ T cells may be further sorted into subpopulations. For example, CD4+T helper cells may be sorted into naive, central memory, and effector cells by identifying cell populations that have cell surface antigens.

The methods described herein further comprise enriching or preparing a population of immune cells obtained from a donor, between harvesting from the donor and exposing one or more cells obtained from a donor subject. Enrichment of a population of immune cells, e.g., the one or more T cells, may be accomplished by any suitable separation method including, but not limited to, the use of a separation medium (e.g., FICOLL-PAQUE™, ROSETTESEP™ HLA Total Lymphocyte enrichment cocktail, Lymphocyte Separation Medium (LSA) (MP Biomedical Cat. No. 0850494X), or the like), cell size, shape or density separation by filtration or elutriation, immunomagnetic separation (e.g., magnetic-activated cell sorting system, MACS), fluorescent separation (e.g., fluorescence activated cell sorting system, FACS), or bead-based column separation.

In one embodiment, the T cells are obtained from a donor subject. In other embodiment, the donor subject is human patient afflicted with a cancer or a tumor. In additional embodiment, the donor subject is a human patient not afflicted with a cancer or a tumor. The present application also provides a composition or formulation comprises a pharmaceutically acceptable carrier, diluent, solubilizer, emulsifier, preservative and/or adjuvant. In certain embodiment, the composition or formulation comprises an excipient. The terms composition and formulation are used interchangeably herein. The terms composition, a therapeutic composition, a therapeutically effective composition, pharmaceutical composition, pharmaceutically effective composition, and a pharmaceutically acceptable composition are used interchangeably herein. The composition may be selected for parenteral delivery, inhalation, or delivery through the digestive tract, such as orally. The composition may be prepared by known methods by one skilled person in the art. Buffers are used to maintain the composition at physiological pH or at a slightly lower pH, typically within a pH range of from about 5 to about 8. When parenteral administration is contemplated, the composition is in the form of a pyrogen-free, parenterally acceptable aqueous solution comprising a composition described herein, with or without additional therapeutic agents, in a pharmaceutically acceptable vehicle. By way of example, the vehicle for parenteral injection is sterile distilled water in which composition described herein, with or without at least one additional therapeutic agent, is formulated as a sterile, isotonic solution, properly preserved. The preparation involves the formulation of the desired agent with polymeric compounds (such as polylactic acid or polyglycolic acid), beads or liposomes, that provide for the controlled or sustained release of the product, which are then be delivered via a depot injection. In addition, implantable drug delivery devices may be used to introduce the desired therapeutic agent.

In some embodiments, the donor T cells for use in the T cell therapy are obtained from the patient (e.g., for an autologous T cell therapy). In other embodiments, the donor T cells for use in the T cell therapy are obtained from a subject that is not the patient. The T cells may be administered at a therapeutically effective amount. For example, a therapeutically effective amount of the T cells may be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In some embodiments, the therapeutically effective amount of the CAR-positive viable T cells is between about $1\times10^6$ and about $2\times10^6$ CAR-positive viable T cells per kg body weight up to a maximum dose of about 1x108 CAR-positive viable T cells A "patient" as used herein includes any human who is afflicted with a disease or disorder, including cancer (e.g., a lymphoma or a leukemia). The terms "subject" and "patient" are used interchangeably herein. The term "donor subject" refers to herein a subject whose cells are being obtained for further in vitro engineering. The donor subject may be a cancer patient that is to be treated with a population of cells generated by the methods described herein (i.e., an autologous donor), or may be an individual who donates a lymphocyte sample that, upon generation of the population of cells generated by the methods described herein, will be used to treat a different individual or cancer patient (i.e., an allogeneic donor). Those subjects who receive the cells that were prepared by the present methods may be referred to as "recipient subject."

The terms "stimulation," "stimulating," or the like refer to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an artificial antigen presenting cell (aAPC), a dendritic cell, a B-cell, and the like) may specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class I molecule loaded with a peptide, an anti-CD3 antibody, a superagonist anti-CD28 antibody, and a superagonist anti-CD2 antibody. An "activated" or "active," as used herein, refers to a T cell that has been stimulated. An active T cell may be characterized by expression of one or more marker selected form CD137, CD25, CD71, CD26, CD27, CD28, CD30, CD154, CD40L, and CD134.

The term "exogenous activation materials" refers to any activation substance derived from an external source. For example, exogenous anti-CD3 antibody, anti-CD28 antibody, IL-2, exogenous IL-7, or exogenous IL-15 may be obtained commercially or produced recombinantly. "Exogenous IL-2," "Exogenous IL-7," or "exogenous IL-15" when added in or contacted with one or more T cells, indicates that such IL-2, IL-7 and/or IL-15 are not produced by the T cells. The T cells prior to being mixed with "Exogenous" IL-2, IL-7 or IL-15 may contain a trace amount that were produced by the T cells or isolated from the subject with the T cells (i.e., endogenous "Exogenous" IL-2, IL-7 or IL-15). The one or more T cells described herein may be contacted with exogenous anti-CD3 antibody, anti-CD28 antibody, "Exogenous" IL-2, IL-7 and/or IL-15 through any means known in the art, including addition of isolated "Exogenous" IL-2, IL-7 and/or IL-15 to the culture, inclusion of anti-CD3 antibody, anti-CD28 antibody, "Exogenous" IL-2, IL-7 and/or IL-15 in the culture medium, or expression of "Exogenous" IL-2, IL-7 and/or IL-15 by one or more cells in the culture other than the one or more T cells, such as by a feeder layer.

As used herein, the term "in vitro cell" refers to any cell which is cultured ex vivo. In one embodiment, an in vitro cell includes a T cell.

The term "persistence" refers to the ability of, e.g., one or more transplanted immune cells administered to a subject or their progenies (e.g., differentiated or matured T cells) to remain in the subject at a detectable level for a period of time. As used herein, increasing the persistence of one or more transplanted immune cells or their progenies (e.g., differentiated or matured T cells) refers to increasing the amount of time the transplanted immune cells are detectable in a subject after administration. For example, the in vivo persistence of one or more transplanted immune cells may be increased by at least about at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 1 month, at least about 2 months, at least about 3 months, at least about 4 months, at least about 5 months, or at least about 6 months. In addition, the in vivo persistence of one or more transplanted immune cells may be increased by at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold compared to the one or more transplanted immune cells that were not prepared by the present methods disclosed herein.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions. The term "modulating" T cell maturation, as used herein, refers to the use of any intervention described herein to control the maturation and/or differentiation of one or more cells such as T cells. For example, modulating refers to inactivating, delaying or inhibiting T cell maturation. In another example, modulating refers to accelerating or promoting T cell maturation. The term "delaying or inhibiting T cell maturation" refers to maintaining one or more T cells in an immature or undifferentiated state. For example, "delaying or inhibiting T cell maturation" may refer to maintaining T cells in a naïve or $T_{CM}$ state, as opposed to progressing to a $T_{EM}$ or $T_{EFF}$ state. In addition, "delaying or inhibiting T cell maturation" may refer to increasing or enriching the overall percentage of immature or undifferentiated T cells (e.g., naïve T cells and/or $T_{CM}$ cells) within a mixed population of T cells. The state of a T cell (e.g., as mature or immature) may be determined, e.g., by screening for the expression of various genes and the presence of various proteins expressed on the surface of the T cells. For example, the presence of one or more marker selected from the group consisting of L-selectin (CD62L+), IL-7R-α, CD132, CR7, CD45RA, CD45RO, CD27, CD28, CD95, IL-2Rβ, CXCR3, LFA-1, and any combination thereof may be indicative of less mature, undifferentiated T cells.

"Treatment" or "treating" of a subject/patient refers to any type of intervention or process performed on, or the administration of one or more T cells prepared by the present application to, the subject/patient with the objective of reversing, alleviating, ameliorating, inhibiting, slowing down or preventing the onset, progression, development, severity or recurrence of a symptom, complication or condition, or biochemical indicia associated with a disease. In one aspect, "treatment" or "treating" includes a partial remission. In another aspect, "treatment" or "treating" includes a complete remission.

Various aspects of the application are described in further detail in the following subsections.

Patients with B-cell malignancies bearing high levels of circulating CD19-expressing tumor cells represent a population with very high unmet need. For example, Mantle Cell Lymphoma (MCL) is challenging to treat in the relapsed or refractory setting and remains incurable. No standard-of-care exists for second-line and higher chemotherapy. Treatment options include cytotoxic chemotherapy, proteasome inhibitors, immunomodulatory drugs, tyrosine kinase inhibitors, and stem cell transplant (both autologous [ASCT] and allogenic stem cell transplant [allo-SCT]). The choice of regimen is influenced by prior therapy, comorbidities and tumor chemosensitivity. Despite the high initial response rates observed with Bruton's tyrosine kinase inhibitor (BTK inhibitors), most patients will eventually develop progressive disease. New therapeutic strategies are needed to improve the dismal prognosis of patients with r/r MCL whose disease has not been effectively controlled with chemo-immunotherapy, stem cell transplant and the BTK inhibitors.

The anti-CD19 CAR T-cell therapy or product used in CD19 CAR-T may be manufactured from the patient's own T cells, via leukapheresis suitable for B-cell malignancies with circulating tumor cell burden to minimize the CD19-expressing tumor cells in the final product. The T cells from the harvested leukocytes from the leukapheresis product may be enriched by selection for CD4+/CD8+ T cells, activated with anti-CD3 and anti-CD28 antibodies, and/or transduced with a viral vector containing an anti-CD19 CAR gene. More details of the method may be found in PCT/US2015/014520 published as WO2015/120096 and in PCT/US2016/057983 published as WO2017/070395. In one embodiment, the cells are not treated with AKT inhibitors, IL-7, and IL-15. These engineered T cells may be propagated to generate a sufficient number of cells to achieve a therapeutic effect. Such process removes CD19-expressing malignant and normal B cells, which may reduce activation, expansion, and exhaustion of the anti-CD19 CAR T cells.

The activation, transduction, and/or expansion of immune cells may be conducted at any suitable time which allows for the production of (i) a sufficient number of cells in the population of engineered immune cells for at least one dose for administering to a patient, (ii) a population of engineered immune cells with a favorable proportion of juvenile cells compared to a typical longer process, or (iii) both (i) and (ii). The suitable time may factor several parameters, including the population of one or more cells, the cell surface receptor expressed by the immune cells, the vector used, the dose that is needed to have a therapeutic effect, and/or other variables. The time for activation may be 0 day, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or more than 21 days. The time for activation according to the method of present application would be reduced compared to expansion methods known in the art. For example, the time for activation may be shorter by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, or may be shorter by more than 75%. Further, the time for expansion may be 0 day, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or more than 21 days. The time for expansion according to the method of present application would be reduced compared to expansion methods known in the art. For example, the time for expansion may be shorter by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, or may be shorter by more than 75%. In one embodiment, the time for cell expansion is about 3 days, and the time from enrichment of the population of cells to producing the engineered immune cells is about 6 days.

The delay or inhibition of the maturation or differentiation of the one or more T cells or DC cells may be measured by any methods known in the art. For example, the delay or inhibition of the maturation or differentiation of the one or more T cells or DC cells may be measured by detecting the presence of one or biomarker. The presence of the one or more biomarker may be detected by any method known in the art, including, but not limited to, immunohistochemistry and/or fluorescence-activated cell sorting (FACS). The one or more biomarker is selected from the group consisting of L-selectin (CD62L), IL-7Rα, CD132, CCR7, CD45RA, CD45RO, CD27, CD28, CD95, IL-2Rβ, CXCR3, LFA-1, or any combination thereof. In certain aspects, the delay or inhibition of the maturation or differentiation of the one or more T cells or DC cell) may be measured by detecting the presence of one or more of L-selectin (CD62L+), IL-7Rα, and CD132. One of skill in the art would recognize that though the present methods may increase the relative proportion of immature and undifferentiated T cells or DC cells in a population of collected cells, some mature and differentiated cells may still be present. As a result, the delay or inhibition of the maturation or differentiation of the one or more T cells or DC cells may be measured by calculating the total percent of immature and undifferentiated cells in a cell population before and after exposing one or more cells obtained from a donor subject to hypoxic culture conditions with or without pressures above atmospheric pressure. The methods disclosed herein may increase the percentage of immature and undifferentiated T cells in a T cell population.

The methods described herein further comprise stimulating the population of cells such as lymphocytes with one or more T-cell stimulating agents to produce a population of activated T cells under a suitable condition. Any combination of one or more suitable T-cell stimulating agents may be used to produce a population of activated T cells including, including, but not limited to, an antibody or functional fragment thereof which targets a T-cell stimulatory or co-stimulatory molecule (e.g., anti-CD2 antibody, anti-CD3 antibody (such as OKT-3), anti-CD28 antibody, or a functional fragment thereof), or any other suitable mitogen (e.g., tetradecanoyl phorbol acetate (TPA), phytohaemagglutinin (PHA), concanavalin A (conA), lipopolysaccharide (LPS), pokeweed mitogen (PWM)), or a natural ligand to a T-cell stimulatory or co-stimulatory molecule.

The suitable condition for stimulating or activating the population of immune cells as described herein further include a temperature, for an amount of time, and/or in the presence of a level of $CO_2$. The temperature for stimulation may be about 34° C., about 35° C., about 36° C., about 37° C., or about 38° C., about 34-38° C., about 35-37° C., about 36-38° C., about 36-37° C. or about 37° C.

Another condition for stimulating or activating the population of immune cells as described herein may further include a time for stimulation or activation. The time for stimulation is about 24-72 hours, about 24-36 hours, about 30-42 hours, about 36-48 hours, about 40-52 hours, about 42-54 hours, about 44-56 hours, about 46-58 hours, about 48-60 hours, about 54-66 hours, or about 60-72 hours, about 44-52 hours, about 40-44 hours, about 40-48 hours, about 40-52 hours, or about 40-56 hours. In one embodiment, the time for stimulation is about 48 hours or at least about 48 hours.

Other conditions for stimulating or activating the population of immune cells as described herein may further include a $CO_2$. Level. The level of $CO_2$ for stimulation is about 1.0-10% $CO_2$, about 1.0%, about 2.0%, about 3.0%, about 4.0%, about 5.0%, about 6.0%, about 7.0%, about 8.0%, about 9.0%, or about 10.0% $CO_2$, about 3-7% $CO_2$, about 4-6% $CO_2$, about 4.5-5.5% $CO_2$. In one embodiment, the level of $CO_2$ for stimulation is about 5% $CO_2$.

The conditions for stimulating or activating the population of immune cells may further comprise a temperature, for an amount of time for stimulation, and/or in the presence of a level of $CO_2$ in any combination. For example, the step of stimulating the population of immune cells may comprise stimulating the population of immune cells with one or more immune cell stimulating agents at a temperature of about 36-38° C., for an amount of time of about 44-52 hours, and in the presence of a level of $CO_2$ of about 4.5-5.5% $CO_2$. The one or more immune cells of the present application may be administered to a subject for use in immune or cell therapy. Accordingly, the one or more immune cells may be collected from a subject in need of a immune or cell therapy. Once collected, the one or more immune cells may be processed for any suitable period of time before being administered to a subject.

The concentration, amount, or population of lymphocytes or resulting product made by the methods herein is about 1.0-10.0×$10^6$ cells/mL. In certain aspects, the concentration is about 1.0-2.0×$10^6$ cells/mL, about 1.0-3.0×$10^6$ cells/mL, about 1.0-4.0×$10^6$ cells/mL, about 1.0-5.0×$10^6$ cells/mL, about 1.0-6.0×$10^6$ cells/mL, about 1.0-7.0×$10^6$ cells/mL, about 1.0-8.0×$10^6$ cells/mL, 1.0-9.0×$10^6$ cells/mL, about 1.0-10.0×$10^6$ cells/mL, about 1.0-1.2×$10^6$ cells/mL, about 1.0-1.4×$10^6$ cells/mL, about 1.0-1.6×$10^6$ cells/mL, about 1.0-1.8×$10^6$ cells/mL, about 1.0-2.0×$10^6$ cells/mL, at least about 1.0×$10^6$ cells/mL, at least about 1.1×$10^6$ cells/mL, at least about 1.2×$10^6$ cells/mL, at least about 1.3×$10^6$ cells/mL, at least about 1.4×$10^6$ cells/mL, at least about 1.5×$10^6$ cells/mL, at least about 1.6×$10^6$ cells/mL, at least about 1.7×$10^6$ cells/mL, at least about 1.8×$10^6$ cells/mL, at least about $1.9\times10^6$ cells/mL, at least about $2.0\times10^6$ cells/mL, at least about $4.0\times10^6$ cells/mL, at least about $6.0\times10^6$ cells/mL, at least about $8.0\times10^6$ cells/mL, or at least about $10.0\times10^6$ cells/mL.

An anti-CD3 antibody (or functional fragment thereof), an anti-CD28 antibody (or functional fragment thereof), or a combination of anti-CD3 and anti-CD28 antibodies may be used in accordance with the step of stimulating the population of lymphocytes, together or independently of exposing one or more cells obtained from a donor subject to hypoxic culture conditions with or without pressures above atmospheric pressure. Any soluble or immobilized anti-CD2, anti-CD3 and/or anti-CD28 antibody or functional fragment thereof may be used (e.g., clone OKT3 (anti-CD3), clone 145-2C11 (anti-CD3), clone UCHT1 (anti-CD3), clone L293 (anti-CD28), clone 15E8 (anti-CD28)). In some aspects, the antibodies may be purchased commercially from vendors known in the art including, but not limited to, Miltenyi Biotec, BD Biosciences (e.g., MACS GMP CD3 pure 1 mg/mL, Part No. 170-076-116), and eBioscience, Inc. Further, one skilled in the art would understand how to produce an anti-CD3 and/or anti-CD28 antibody by standard methods. In some aspect, the one or more T cell stimulating agents that are used in accordance with the step of stimulating the population of lymphocytes include an antibody or functional fragment thereof which targets a T-cell stimulatory or co-stimulatory molecule in the presence of a T cell cytokine. In one embodiment, the one or more T cell stimulating agents include an anti-CD3 antibody and IL-2. In certain embodiment, the T cell stimulating agent includes an anti-CD3 antibody at a concentration of 50 ng/mL. The concentration of anti-CD3 antibody is about 20 ng/mL-100 ng/mL, about 20 ng/mL, about 30 ng/mL, about 40 ng/mL, about 50 ng/mL, about 60 ng/mL, about 70 ng/mL, about 80 ng/mL, about 90 ng/mL, or about 100 ng/mL. In an alternative aspect, T cell activation is not needed.

The methods described herein further comprise transducing the population of activated immune cells with a viral vector comprising a nucleic acid molecule which encodes the cell surface receptor, using a single cycle or more of viral transduction to produce a population of transduced immune cells. Several recombinant viruses have been used as viral vectors to deliver genetic material to a cell. Viral vectors that may be used in accordance with the transduction step may be any ecotropic or amphotropic viral vector including, but not limited to, recombinant retroviral vectors, recombinant lentiviral vectors, recombinant adenoviral vectors, and recombinant adeno-associated viral (AAV) vectors. The method further comprises transducing the one or more immune cells with a retrovirus. In one aspect, the viral vector used to transduce the population of activated immune cells is an MSGV1 gamma retroviral vector. In one embodiment, the viral vector used to transduce the population of activated immune cells is the PG13-CD19-H3 Vector described by Kochenderfer, *J. Immunother.* 32(7): 689-702 (2009). According to one aspect of this aspect, the viral vector is grown in a suspension culture in a medium which is specific for viral vector manufacturing referred to herein as a viral vector inoculum. Any suitable growth media and/or supplements for growing viral vectors may be used in the viral vector inoculum in accordance with the methods described herein. According to some aspects, the viral vector inoculum is then added to the serum-free culture media described below during the transduction step. In some aspect, the one or more immune cells may be transduced with a retrovirus. In one embodiment, the retrovirus comprises a heterologous gene encoding a cell surface receptor. In another embodiment, the cell surface receptor may bind an antigen on the surface of a target cell, e.g., on the surface of a tumor cell. In addition to optionally exposing one or more cells obtained from a donor subject to hypoxic culture conditions with or without pressures above atmospheric pressure, the conditions for transducing the population of activated immune cells as described herein may comprise a specific time, at a specific temperature and/or in the presence of a specific level of $CO_2$. The temperature for transduction is about 34° C., about 35° C., about 36° C., about 37° C., or about 38° C., about 34-38° C., about 35-37° C., about 36-38° C., about 36-37° C. In one embodiment, the temperature for transduction is about 37° C. The predetermined temperature for transduction may be about 34° C., about 35° C., about 36° C., about 37° C., about 38° C., or about 39° C., about 34-39° C., about 35-37° C. In one embodiment, the predetermined temperature for transduction may be from about 36-38° C., about 36-37° C. or about 37° C. The time for transduction is about 12-36 hours, about 12-16 hours, about 12-20 hours, about 12-24 hours, about 12-28 hours, about 12-32 hours, about 20 hours or at least about 20 hours, is about 16-24 hours, about 14 hours, at least about 16 hours, at least about 18 hours, at least about 20 hours, at least about 22 hours, at least about 24 hours, or at least about 26 hours. The level of $CO_2$ for transduction is about 1.0-10% $CO_2$, about 1.0%, about 2.0%, about 3.0%, about 4.0%, about 5.0%, about 6.0%, about 7.0%, about 8.0%, about 9.0%, about 10.0% $CO_2$, about 3-7% $CO_2$, about 4-6% $CO_2$, about 4.5-5.5% $CO_2$, or about 5% $CO_2$.

Transducing the population of activated immune cells as described herein may be performed for a period of time, at certain temperature and/or in the presence of a specific level of $CO_2$ in any combination: a temperature of about 36-38° C., for an amount of time of about 16-24 hours, and in the presence of a level of $CO_2$ of about 4.5-5.5% $CO_2$. The immune cells may be prepared by the combination of any one of the methods of the application with any manufacturing method of preparing T cells for immunotherapy, including, without limitation, those described in PCT Publications Nos. WO2015/120096 and WO2017/070395, which are herein incorporated by reference in their totality for the purposes of describing these methods; any and all methods used in the preparation of Axicabtagene ciloleucel or Yescarta®; any and all methods used in the preparation of Tisagenlecleucel/Kymriah™; any and all methods used in the preparation of "off-the-shelf" T cells for immunotherapy; and any other methods of preparing lymphocytes for administration to humans. The manufacturing process may be adapted to remove circulating tumor cells from the cells obtained from the patient.

CAR-T cells may be engineered to express other molecules and may be of any one of the following exemplary types or others available in the art: first, second, third, fourth, fifth, or more CAR-T cells; Armored CAR-T cells, Motile CAR-T cells, TRUCK T-cells, Switch receptor CAR-T cells; Gene edited CAR T-cells; dual receptor CAR T-cells; suicide CAR T-cells, drug-inducible CAR-T cells, synNotch inducible CAR T-cells; and inhibitory CAR T-cells. In one aspect, the T cells are autologous T-cells. In one aspect, the T cells are autologous stem cells (for autologous stem cell therapy or ASCT). In one aspect, the T cells are non-autologous T-cells.

The cells (such as immune cells or T cells) are genetically modified following isolation or selection using known methods or activated and/or expanded (or differentiated in the case of progenitors) in vitro prior to being genetically modified. The immune cells, e.g., T cells, are genetically modified with the chimeric antigen receptors described herein (e.g., transduced with a viral vector comprising one or more nucleotide sequences encoding a CAR) and activated and/or expanded in vitro. Methods for activating and expanding T cells may be found in U.S. Pat. Nos. 6,905,874; 6,867,041; and 6,797,514; and PCT Publication No. WO 2012/079000, which are hereby incorporated by reference in their entirety. Generally, such methods may include contacting PBMC or isolated T cells with a stimulatory agent and costimulatory agent, such as anti-CD3 and/or anti-CD28 antibodies, that may be attached to a bead or other surface, in a culture medium with certain cytokines, such as IL-2. The Dynabeads® system, a CD3/CD28 activator/stimulator system for physiological activation of human T cells may be used. The T cells may be activated and stimulated to proliferate with suitable feeder cells, antibodies and/or cytokines as described in U.S. Pat. Nos. 6,040,177 and 5,827,642 and PCT Publication No. WO 2012/129514, which are hereby incorporated by reference in their entirety.

The cell surface receptor that is expressed by the engineered immune cells may be any antigen or molecule to be targeted by CAR, such as an anti-CD19 CAR, FMC63-28Z CAR, or FMC63-CD828BBZ CAR (Kochenderfer et al., *J Immunother.* 2009, 32(7): 689; Locke et al., *Blood* 2010, 116(20):4099, the subject matter of both of which is hereby incorporated by reference. In certain aspects, the predetermined dose of engineered immune cells may be more than about 1 million to less than about 3 million transduced engineered T cells/kg. In one embodiment, the predetermined dose of engineered T cells may be more than about 1 million to about 2 million transduced engineered T cells per kilogram of body weight (cells/kg). The predetermined dose of engineered T cells may be more than 1 million to about 2 million, at least about 2 million to less than about 3 million transduced engineered T cells per kilogram of body weight (cells/kg). In one embodiment, the predetermined dose of engineered T cells may be about 2 million transduced engineered T cells/kg. In another embodiment, the predetermined dose of engineered T cells may be at least about 2 million transduced engineered T cells/kg. Examples of the predetermined dose of engineered T cells may be about 2.0 million, about 2.1 million, about 2.2 million, about 2.3 million, about 2.4 million, about 2.5 million, about 2.6 million, about 2.7 million, about 2.8 million, or about 2.9 million transduced engineered T cells/kg.

The methods described herein comprise increasing or enriching the population of transduced one or more immune cells for a period of time to produce a population of engineered immune cells. The time for expansion may be any suitable time which allows for production of (i) a sufficient number of cells in the population of engineered immune cells for at least one dose for administering to a patient, (ii) a population of engineered immune cells with a favorable proportion of juvenile cells compared to a typical longer process, or (iii) both (i) and (ii). This time will depend on the cell surface receptor expressed by the immune cells, the vector used, the dose that is needed to have a therapeutic effect, and other variables. The predetermined time for expansion may be 0 day, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or more than 21 days. In one embodiment, the time for expansion of the present method is reduced compared to those known in the art. For example, the predetermined time for expansion may be shorter by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, or may be shorter by more than 75%. In one example, the time for expansion is about 3 days, and the time from enrichment of the population of lymphocytes to producing the engineered immune cells is about 6 days.

The conditions for expanding the population of transduced immune cells may include a temperature and/or in the presence of a level of $CO_2$. In certain aspects, the temperature is about 34° C., about 35° C., about 36° C., about 37° C., or about 38° C., about 35-37° C., about 36-37° C., or about 37° C. The level of $CO_2$ is 1.0-10% $CO_2$, about 1.0%, about 2.0%, about 3.0%, about 4.0%, about 5.0%, about 6.0%, about 7.0%, about 8.0%, about 9.0%, about 10.0% $CO_2$, about 4.5-5.5% $CO_2$, about 5% $CO_2$, about 3.5%, about 4.0%, about 4.5%, about 5.0%, about 5.5%, or about 6.5% $CO_2$.

Each step of the methods described herein may be performed in a closed system. The closed system may be a closed bag culture system, using any suitable cell culture bags (e.g., Miltenyi Biotec MACS® GMP Cell Differentiation Bags, Origen Biomedical PermaLife Cell Culture bags). The cell culture bags used in the closed bag culture system may be coated with a recombinant human fibronectin fragment during the transduction step. The recombinant human fibronectin fragment may include three functional domains: a central cell-binding domain, heparin-binding domain II, and a CS1-sequence. The recombinant human fibronectin fragment may be used to increase gene efficiency of retroviral transduction of immune cells by aiding co-localization of target cells and viral vector. In one embodiment, the recombinant human fibronectin fragment is RETRONECTIN® (Takara Bio, Japan). The cell culture bags are coated with recombinant human fibronectin fragment at a concentration of about 1-60 μg/mL or about 1-40 μg/mL, about 1-20 μg/mL, 20-40 μg/mL, 40-60 μg/mL, about 1 μg/mL, about 2 μg/mL, about 3 μg/mL, about 4 μg/mL, about 5 μg/mL, about 6 μg/mL, about 7 μg/mL, about 8 μg/mL, about 9 μg/mL, about 10 μg/mL, about 11 μg/mL, about 12 μg/mL, about 13 μg/mL, about 14 μg/mL, about 15 μg/mL, about 16 μg/mL, about 17 μg/mL, about 18 μg/mL, about 19 μg/mL, about 20 μg/mL, about 2-5 μg/mL, about 2-10 μg/mL, about 2-20 μg/mL, about 2-25 μg/mL, about 2-30 μg/mL, about 2-35 μg/mL, about 2-40 μg/mL, about 2-50 μg/mL, about 2-60 μg/mL, at least about 2 μg/mL, at least about 5 μg/mL, at least about 10 μg/mL, at least about 15 μg/mL, at least about 20 μg/mL, at least about 25 μg/mL, at least about 30 μg/mL, at least about 40 μg/mL, at least about 50 μg/mL, or at least about 60 μg/mL recombinant human fibronectin fragment. In one embodiment, the cell culture bags are coated with at least about 10 μg/mL recombinant human fibronectin fragment. The cell culture bags used in the closed bag culture system may optionally be blocked with human albumin serum (HSA) during the transduction step. In another embodiment, the cell culture bags are not blocked with HSA during the transduction step.

The population of engineered immune cells produced by the methods described above may optionally be cryopreserved so that the cells may be used later. A method for cryopreservation of a population of engineered immune cells also is provided herein. Such a method may include a step of washing and concentrating the population of engineered immune cells with a diluent solution. For example, the diluent solution is normal saline, 0.9% saline, PlasmaLyte A (PL), 5% dextrose/0.45% NaCl saline solution (D5), human serum albumin (HSA), or a combination thereof. Also, HSA may be added to the washed and concentrated cells for improved cell viability and cell recovery after thawing. In another aspect, the washing solution is normal saline and washed and concentrated cells are supplemented with HSA (5%). The method may also include a step of generating a cryopreservation mixture, wherein the cryopreservation mixture includes the diluted population of cells in the diluent solution and a suitable cryopreservative solution. The cryopreservative solution may be any suitable cryopreservative solution including, but not limited to, CryoStor10 (BioLife Solution), mixed with the diluent solution of engineered immune cells at a ratio of 1:1 or 2:1. HSA may be added to provide a final concentration of about 1.0-10%, about 1.0%, about 2.0%, about 3.0%, about 4.0%, about 5.0%, about 6.0%, about 7.0%, about 8.0%, about 9.0%, about 10.0%, about 1-3% HSA, about 1-4% HSA, about 1-5% HSA, about 1-7% HSA, about 2-4% HSA, about 2-5% HSA, about 2-6% HSA, about 2-7% HAS or about 2.5% HSA in the cryopreserved mixture. Cryopreservation of a population of engineered immune cells may comprise washing cells with 0.9% normal saline, adding HSA at a final concentration of 5% to the washed cells, and diluting the cells 1:1 with CryoStor™ CS10 (for a final concentration of 2.5% HSA in the final cryopreservation mixture). In some aspect, the method also includes a step of freezing the cryopreservation mixture. Also, the cryopreservation mixture is frozen in a controlled rate freezer using a defined freeze cycle at a cell concentration of between about $1\times10^6$ to about $1.5\times10^7$ cells/mL of cryopreservation mixture. The method may also include a step of storing the cryopreservation mixture in vapor phase liquid nitrogen.

The population of engineered immune cells produced by the methods described herein may be cryopreserved at a predetermined dose. The predetermined dose may be a therapeutically effective dose, which may be any therapeutically effective dose as provided below. The predetermined dose of engineered immune cells may depend on the cell surface receptor that is expressed by the immune cells (e.g., the affinity and density of the cell surface receptors expressed on the cell), the type of target cell, the nature of the disease or pathological condition being treated, or a combination of both.

In one embodiment, the population of engineered T cells may be cryopreserved at a predetermined dose of about 1 million engineered T cells per kilogram of body weight (cells/kg). In certain embodiment, the population of engineered T cells may be cryopreserved at a predetermined dose of from about 500,000 to about 1 million engineered T cells/kg. In certain embodiment, the population of engineered T cells may be cryopreserved at a predetermined dose of at least about 1 million, at least about 2 million, at least about 3 million, at least about 4 million, at least about 5 million, at least about 6 million, at least about 7 million, at least about 8 million, at least about 9 million, at least about 10 million engineered T cells/kg. In other aspects, the population of engineered T cells may be cryopreserved at a predetermined dose of less than 1 million cells/kg, 1 million cells/kg, 2 million cells/kg, 3 million cells/kg, 4 million cells/kg, 5 million cells/kg, 6 million cells/kg, 7 million cells/kg, 8 million cells/kg, 9 million cells/kg, 10 million cells/kg, more than 10 million cells/kg, more than 20 million cells/kg, more than 30 million cells/kg, more than 40 million cells/kg, more than 50 million cells/kg, more than 60 million cells/kg, more than 70 million cells/kg, more than 80 million cells/kg, more than 90 million cells/kg, or more than 100 million cells/kg. In certain aspects, the population of engineered T cells may be cryopreserved at a predetermined dose of from about 1 million to about 2 million engineered T cells/kg. The population of engineered T cells may be cryopreserved at a predetermined dose between about 1 million cells to about 2 million cells/kg, about 1 million cells to about 3 million cells/kg, about 1 million cells to about 4 million cells/kg, about 1 million cells to about 5 million cells/kg, about 1 million cells to about 6 million cells/kg, about 1 million cells to about 7 million cells/kg, about 1 million cells to about 8 million cells/kg, about 1 million cells to about 9 million cells/kg, about 1 million cells to about 10 million cells/kg. The predetermined dose of the population of engineered T cells may be calculated based on a subject's body weight. In one example, the population of engineered T cells may be cryopreserved in about 0.5-200 mL of cryopreservation media. Additionally, the population of engineered T cells may be cryopreserved in about 0.5 mL, about 1.0 mL, about 5.0 mL, about 10.0 mL, about 20 mL, about 30 mL, about 40 mL, about 50 mL, about 60 mL, about 70 mL, about 80 mL, about 90 mL, or about 100 mL, about 10-30 mL, about 10-50 mL, about 10-70 mL, about 10-90 mL, about 50-70 mL, about 50-90 mL, about 50-110 mL, about 50-150 mL, or about 100-200 mL of cryopreservation media. In certain aspects, the population of engineered T cells may be preferably cryopreserved in about 50-70 mL of cryopreservation media.

In one embodiment, at least one of (a) contacting the population of immune cells with exogenous IL-2, exogenous IL-7, exogenous IL-15, and/or other cytokine(s), (b) stimulating the population of immune cells (c) transducing the population of activated immune cells, and (d) expanding the population of transduced immune cells is performed using a serum-free culture medium which is free from added serum. In some aspect, each of (a) to (d) is performed using a serum-free culture medium which is free from added serum. As referred to herein, the term "serum-free media" or "serum-free culture medium" means that the growth media used is not supplemented with serum (e.g., human serum or bovine serum). In other words, no serum is added to the culture medium as an individually separate and distinct ingredient for the purpose of supporting the viability, activation and grown of the cultured cells. Any suitable immune cell growth media may be used for culturing the cells in suspension in accordance with the methods described herein. For example, an immune cell growth media may include, but is not limited to, a sterile, low glucose solution that includes a suitable amount of buffer, magnesium, calcium, sodium pyruvate, and sodium bicarbonate. In one aspect, the T cell growth media is OPTMIZER™ (Life Technologies). In contrast to typical methods for producing engineered immune cells, the methods described herein may use culture medium that is not supplemented with serum (e.g., human or bovine).

The application provides various methods of treatment of cancer with T cells. In one aspect, the T cells are CAR-T cells against CD19, which may be prepared by the combination of any one of the methods of the application with any step of the manufacturing method of preparing T cells for immunotherapy, including, without limitation, those described in PCT Publication Nos. WO2015/120096 and WO2017/070395, both of which are herein incorporated by reference in their totality for the purposes of describing these methods; any and all methods used in the preparation of Axicabtagene ciloleucel or Yescarta®; any and all methods used in the preparation of Tisagenlecleucel/Kymriah™; any and all methods used in the preparation of "off-the-shelf" T cells for immunotherapy; and any other methods of preparing lymphocytes for administration to humans. In some aspect, the manufacturing process is adapted to specifically remove circulating tumor cells from the cells obtained from the patient.

In one aspect, the T cells are the CD19 CAR-T cells, prepared by the method described in PCT/US2016/057983. In one embodiment, a population of T cells that is depleted of circulating tumor cells is prepared from leukapheresis products. These cells may be prepared as described in PCT/US2016/057983 and are further described herein as CD19 CAR-T cells. Briefly, CD19 CAR-T is an autologous CAR T-cell product in which a subject's T cells are engineered to express receptors consisting of a single-chain antibody fragment against CD19 linked to CD28 and CD3ζ activating domains that result in elimination of CD19-expressing cells. Following CAR engagement with $CD19^+$ target cells, the CD3ζ domain activates the downstream signaling cascade that leads to T-cell activation, proliferation, and acquisition of effector functions, such as cytotoxicity. The intracellular signaling domain of CD28 provides a costimulatory signal that function with the primary CD3ζ signal to augment T-cell function, including interleukin (IL)-2 production. Together, these signals may stimulate proliferation of the CAR T cells and direct killing of target cells. In addition, activated T cells may secrete cytokines, chemokines, and other molecules that may recruit and activate additional antitumor immune cells. The anti-CD19 CAR in the CD19 CAR-T cells may comprise FMC63-28Z.

Due to the presence of circulating tumor cells in certain cancers, the manufacture of CD19 CAR-T includes a $CD4^+$ and $CD8^+$ T-cell enrichment step. The T-cell enrichment or isolation step may reduce circulating CD19-expressing tumor cells in leukapheresis material, and may relate to the activation, expansion, and exhaustion of the anti-CD19 CAR T cells during manufacturing.

The methods described herein may enhance the treatment outcome or effectiveness of a immune or cell therapy), which may be an adoptive T cell therapy selected from the group consisting of tumor-infiltrating lymphocyte (TIL) immunotherapy, autologous cell therapy, engineered autologous cell therapy (eACT™), allogeneic T cell transplantation, non-T cell transplantation, and any combination thereof. Adoptive T cell therapy broadly includes any method of selecting, enriching in vitro, and administering to a patient autologous or allogeneic T cells that recognize and are capable of binding tumor cells. TIL immunotherapy is a type of adoptive T cell therapy, wherein lymphocytes capable of infiltrating tumor tissue are isolated, enriched in vitro, and administered to a patient. The TIL cells may be either autologous or allogeneic. Autologous cell therapy is an adoptive T cell therapy that involves isolating T cells capable of targeting tumor cells from a patient, enriching the T cells in vitro, and administering the T cells back to the same patient. Allogeneic T cell transplantation may include transplant of naturally occurring T cells expanded ex vivo or genetically engineered T cells. Engineered autologous cell therapy, as described in more detail above, is an adoptive T cell therapy wherein a patient's own lymphocytes are isolated, genetically modified to express a tumor targeting molecule, expanded in vitro, and administered back to the patient. Non-T cell transplantation may include autologous or allogeneic therapies with non-T cells such as, but not limited to, natural killer (NK) cells.

The immune cell therapy of the present application is engineered Autologous Cell Therapy (eACT™). According to this aspect, the method may include collecting immune cells from a donor. The isolated immune cells may then be contacted with an exogenous activation reagent (e.g., cytokine), expanded, and engineered to express a chimeric antigen receptor ("engineered CAR T cells") or T cell receptor ("engineered TCR T cells"). In some aspect, the engineered immune cells treat a tumor in the subject. For example, the one or more immune cells are transduced with a retrovirus comprising a heterologous gene encoding a cell surface receptor. In one embodiment×, the cell surface receptor is capable of binding an antigen on the surface of a target cell, e.g., on the surface of a tumor cell. In some embodiment, the cell surface receptor is a chimeric antigen receptor or a T cell receptor. In another embodiment, the one or more immune cells may be engineered to express a chimeric antigen receptor. The chimeric antigen receptor may comprise a binding molecule to a tumor antigen. The binding molecule may be an antibody or an antigen binding molecule thereof. For example, the antigen binding molecule may be selected from scFv, Fab, Fab', Fv, F(ab')2, and dAb, and any fragments or combinations thereof. The chimeric antigen receptor may further comprise a hinge region. The hinge region may be derived from the hinge region of IgG1, IgG2, IgG3, IgG4, IgA, IgD, IgE, IgM, CD28, or CD8 alpha. In one embodiment, the hinge region is derived from the hinge region of IgG4. The chimeric antigen receptor may also comprise a transmembrane domain. The transmembrane domain may be a transmembrane domain of any transmembrane molecule that is a co-receptor on immune cells or a transmembrane domain of a member of the immunoglobulin superfamily. In certain embodiment, the transmembrane domain is derived from a transmembrane domain of CD28, CD28T, CD8 alpha, CD4, or CD19. In another embodiment, the transmembrane domain comprises a domain derived from a CD28 transmembrane domain. In another embodiment, the transmembrane domain comprises a domain derived from a CD28T transmembrane domain. The chimeric antigen receptor may further comprise one or more costimulatory signaling regions. For example, the costimulatory signaling region may be a signaling region of CD28, CD28T, OX-40, 41BB, CD27, inducible T cell costimulator (ICOS), CD3 gamma, CD3 delta, CD3 epsilon, CD247, Ig alpha (CD79a), or Fc gamma receptor. In further embodiment, the costimulatory signaling region is a CD28 signaling region. In another embodiment, the costimulatory signaling region is a CD28T signaling region. In additional embodiment, the chimeric antigen receptor further comprises a CD3 zeta signaling domain.

In some aspects, the tumor antigen is selected from 707-AP (707 alanine proline), AFP (alpha (a)-fetoprotein), ART-4 (adenocarcinoma antigen recognized by T4 cells), BAGE (B antigen; b-catenin/m, b-catenin/mutated), BCMA (B cell maturation antigen), Bcr-abl (breakpoint cluster region-Abelson), CAIX (carbonic anhydrase IX), CD19 (cluster of differentiation 19), CD20 (cluster of differentiation 20), CD22 (cluster of differentiation 22), CD30 (cluster of differentiation 30), CD33 (cluster of differentiation 33), CD44v7/8 (cluster of differentiation 44, exons 7/8), CAMEL (CTL-recognized antigen on melanoma), CAP-1 (carcinoembryonic antigen peptide—1), CASP-8 (caspase-8), CDCl27m (cell-division cycle 27 mutated), CDK4/m (cycline-dependent kinase 4 mutated), CEA (carcinoembryonic antigen), CT (cancer/testis (antigen)), Cyp-B (cyclophilin B), DAM (differentiation antigen melanoma), EGFR (epidermal growth factor receptor), EGFRvIII (epidermal growth factor receptor, variant III), EGP-2 (epithelial glycoprotein 2), EGP-40 (epithelial glycoprotein 40), Erbb2, 3, 4 (erythroblastic leukemia viral oncogene homolog-2, -3, 4), ELF2M (elongation factor 2 mutated), ETV6-AML1 (Ets variant gene 6/acute myeloid leukemia 1 gene ETS), FBP (folate binding protein), fAchR (Fetal acetylcholine receptor), G250 (glycoprotein 250), GAGE (G antigen), GD2 (disialoganglioside 2), GD3 (disialoganglioside 3), GnT-V (N-acetylglucosaminyltransferase V), Gp100 (glycoprotein 100 kD), HAGE (helicose antigen), HER-2/neu (human epidermal receptor-2/neurological; also known as EGFR2), HLA-A (human leukocyte antigen-A) HPV (human papilloma virus), HSP70-2M (heat shock protein 70-2 mutated), HST-2 (human signet ring tumor—2), hTERT or hTRT (human telomerase reverse transcriptase), iCE (intestinal carboxyl esterase), IL-13R-a2 (Interleukin-13 receptor subunit alpha-2), KIAA0205, KDR (kinase insert domain receptor), κ-light chain, LAGE (L antigen), LDLR/FUT (low density lipid receptor/GDP-L-fucose: b-D-galactosidase 2-a-Lfucosyltransferase), LeY (Lewis-Y antibody), L1CAM (L1 cell adhesion molecule), MAGE (melanoma antigen), MAGE-A1 (Melanoma-associated antigen 1), MAGE-A3, MAGE-A6, mesothelin, Murine CMV infected cells, MART-1/Melan-A (melanoma antigen recognized by T cells-1/Melanoma antigen A), MC1R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NKG2D (Natural killer group 2, member D) ligands, NY-BR-1 (New York breast differentiation antigen 1), NY-ESO-1 (New York esophageal squamous cell carcinoma-1), oncofetal antigen (h5T4), P15 (protein 15), p190 minor bcr-abl (protein of 190KD bcr-abl), Pml/RARa (promyelocytic leukaemia/retinoic acid receptor a), PRAME (preferentially expressed antigen of melanoma), PSA (prostate-specific antigen), PSCA (Prostate stem cell antigen), PSMA (prostate-specific membrane antigen), RAGE (renal antigen), RU or RU2 (renal ubiquitous 1 or 2), SAGE (sarcoma antigen), SART-1 or SART-3 (squamous antigen rejecting tumor 1 or 3), SSX1, -2, -3, 4 (synovial sarcoma X1, -2, -3, -4), TAA (tumor-associated antigen), TAG-72 (Tumor-associated glycoprotein 72), TEL/AML1 (translocation Ets-family leukemia/acute myeloid leukemia 1), TPI/m (triosephosphate isomerase mutated), TRP-1 (tyrosinase related protein 1, or gp75), TRP-2 (tyrosinase related protein 2), TRP-2/INT2 (TRP-2/intron 2), VEGF-R2 (vascular endothelial growth factor receptor 2), WTi (Wilms' tumor gene), and any combination thereof. In one embodiment, the tumor antigen is CD19.

The T cell therapy comprises administering to the patient engineered T cells expressing T cell receptor ("engineered TCR T cells"). The T cell receptor (TCR) may comprise a binding molecule to a tumor antigen. In some aspects, the tumor antigen is selected from the group consisting of 707-AP, AFP, ART-4, BAGE, BCMA, Bcr-abl, CAIX, CD19, CD20, CD22, CD30, CD33, CD44v7/8, CAMEL, CAP-1, CASP-8, CDCl27m, CDK4/m, CEA, CT, Cyp-B, DAM, EGFR, EGFRvIII, EGP-2, EGP-40, Erbb2, 3, 4, ELF2M, ETV6-AML1, FBP, fAchR, G250, GAGE, GD2, GD3, GnT-V, Gp100, HAGE, HER-2/neu, HLA-A, HPV, HSP70-2M, HST-2, hTERT or hTRT, iCE, IL-13R-a2, KIAA0205, KDR, K-light chain, LAGE, LDLR/FUT, LeY, L1CAM, MAGE, MAGE-A1, mesothelin, Murine CMV infected cells, MART-1/Melan-A, MC1R, Myosin/m, MUC1, MUM-1, -2, -3, NA88-A, NKG2D ligands, NY-BR-1, NY-ESO-1, oncofetal antigen, P15, p190 minor bcr-abl, Pml/RARa, PRAME, PSA, PSCA, PSMA, RAGE, RU1 or RU2, SAGE, SART-1 or SART-3, SSX1, -2, -3, 4, TAA, TAG-72, TEL/AML 1, TPI/m, TRP-1, TRP-2, TRP-2/INT2, VEGF-R2, WT 1, and any combination thereof.

"CD19-directed genetically modified autologous T cell immunotherapy" refers to a suspension of chimeric antigen receptor (CAR)-positive immune cells. An example of such immunotherapy is Clear CAR-T therapy, which uses CAR-T cells that are free of circulating tumor cells and enriched in CD4+/CD8+ T cells. Another example is axicabtagene ciloleucel (also known as Axi-cel™, YESCARTA®). See Kochenderfer, et al., (J Immunother 2009; 32:689 702). Other non-limiting examples include JCAR017, JCAR015, JCAR014, Kymriah (tisagenlecleucel), Uppsala U. anti-CD19 CAR (NCT02132624), and UCART19 (Celectis). See Sadelain et al. Nature Rev. Cancer Vol. 3 (2003), Ruella et al., Curr Hematol Malig Rep., Springer, NY (2016) and Sadelain et al. Cancer Discovery (April 2013) To prepare CD19-directed genetically modified autologous T cell immunotherapy, a patient's own T cells may be harvested and genetically modified ex vivo by retroviral transduction to express a chimeric antigen receptor (CAR) comprising a murine anti-CD19 single chain variable fragment (scFv) linked to CD28 and CD3-zeta co-stimulatory domains. In some embodiments, the CAR comprises a murine anti-CD19 single chain variable fragment (scFv) linked to 4-1BB and CD3-zeta co-stimulatory domain. The anti-CD19 CAR T cells may be expanded and infused back into the patient, where they may recognize and eliminate CD19-expressing target cells.

In one aspect, the TCR comprises a binding molecule to a viral oncogene. In one embodiment, the viral oncogene is selected from human papilloma virus (HPV), Epstein-Barr virus (EBV), and human T-lymphotropic virus (HTLV). In other embodiment, the TCR comprises a binding molecule to a testicular, placental, or fetal tumor antigen. In one embodiment, the testicular, placental, or fetal tumor antigen is selected from the group consisting of NY-ESO-1, synovial sarcoma X breakpoint 2 (SSX2), melanoma antigen (MAGE), and any combination thereof. In another embodiment, the TCR comprises a binding molecule to a lineage specific antigen. In additional embodiment, the lineage specific antigen is selected from the group consisting of melanoma antigen recognized by T cells 1 (MART-1), gp100, prostate specific antigen (PSA), prostate specific membrane antigen (PSMA), prostate stem cell antigen (PSCA), and any combination thereof. In certain embodiment, the T cell therapy comprises administering to the patient engineered CAR T cells expressing a chimeric antigen receptor that binds to CD19 and further comprises a CD28 costimulatory domain and a CD3-zeta signaling region. In additional embodiment, the T cell therapy comprises administering to a patient KTE-C19. In one aspect, the antigenic moieties also include, but are not limited to, an Epstein-Barr virus (EBV) antigen (e.g., EBNA-1, EBNA-2, EBNA-3, LMP-1, LMP-2), a hepatitis A virus antigen (e.g., VP1, VP2, VP3), a hepatitis B virus antigen (e.g., HBsAg, HBcAg, HBeAg), a hepatitis C viral antigen (e.g., envelope glycoproteins E1 and E2), a herpes simplex virus type 1, type 2, or type 8 (HSV1, HSV2, or HSV8) viral antigen (e.g., glycoproteins gB, gC, gC, gE, gG, gH, gI, gJ, gK, gL. gM, UL20, UL32, US43, UL45, UL49A), a cytomegalovirus (CMV) viral antigen (e.g., glycoproteins gB, gC, gC, gE, gG, gH, gI, gJ, gK, gL. gM or other envelope proteins), a human immunodeficiency virus (HIV) viral antigen (glycoproteins gp120, gp41, or p24), an influenza viral antigen (e.g., hemagglutinin (HA) or neuraminidase (NA)), a measles or mumps viral antigen, a human papillomavirus (HPV) viral antigen (e.g., L1, L2), a parainfluenza virus viral antigen, a rubella virus viral antigen, a respiratory syncytial virus (RSV) viral antigen, or a varicella-zostser virus viral antigen. In such aspects, the cell surface receptor may be any TCR, or any CAR which recognizes any of the aforementioned viral antigens on a target virally infected cell. In other aspects, the antigenic moiety is associated with cells having an immune or inflammatory dysfunction. Such antigenic moieties may include, but are not limited to, myelin basic protein (MBP) myelin proteolipid protein (PLP), myelin oligodendrocyte glycoprotein (MOG), carcinoembryonic antigen (CEA), pro-insulin, glutamine decarboxylase (GAD65, GAD67), heat shock proteins (HSPs), or any other tissue specific antigen that is involved in or associated with a pathogenic autoimmune process.

The methods disclosed herein may involve a T cell therapy comprising the transfer of one or more T cells to a patient. The T cells may be administered at a therapeutically effective amount. For example, a therapeutically effective amount of T cells, e.g., engineered CAR+ T cells or engineered TCR+ T cells, may be at least about $10^4$ cells, at least about $10^5$ cells, at least about $10^6$ cells, at least about $10^7$ cells, at least about $10^8$ cells, at least about $10^9$, or at least about $10^{10}$. In another aspect, the therapeutically effective amount of the T cells, e.g., engineered CAR+ T cells or engineered TCR+ T cells, is about $10^4$ cells, about $10^5$ cells, about $10^6$ cells, about $10^7$ cells, or about $10^8$ cells. In one embodiment, the therapeutically effective amount of the T cells, e.g., engineered CAR+ T cells or engineered TCR+ T cells, is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In one embodiment, the amount of CD19 CAR-T cells is $2\times10^6$ cells/kg, with a maximum dose of $2\times10^8$ cells for subjects ≥100 kg. In another embodiment, the amount of CD19 CAR-T cells is $0.5\times10^6$ cells/kg, with a maximum dose of $0.5\times10^8$ cells for subjects ≥100 kg.

The patients may be preconditioned or lymphodepleted prior to administration of the T cell therapy. The patient may be preconditioned according to any methods known in the art, including, but not limited to, treatment with one or more chemotherapy drug and/or radiotherapy. In some aspects, the preconditioning may include any treatment that reduces the number of endogenous lymphocytes, removes a cytokine sink, increases a serum level of one or more homeostatic cytokines or pro-inflammatory factors, enhances an effector function of T cells administered after the conditioning, enhances antigen presenting cell activation and/or availability, or any combination thereof prior to a T cell therapy. The preconditioning may comprise increasing a serum level of one or more cytokines in the subject. The methods further comprise administering a chemotherapeutic. The chemotherapeutic may be a lymphodepleting (preconditioning) chemotherapeutic. Beneficial preconditioning treatment regimens, along with correlative beneficial biomarkers are described in U.S. Pat. No. 9,855,298, which is hereby incorporated by reference in its entirety herein. These describe, e.g., methods of conditioning a patient in need of a T cell therapy comprising administering to the patient specified beneficial doses of cyclophosphamide (between 200 $mg/m^2$/day and 2000 $mg/m^2$/day) and specified doses of fludarabine (between 20 $mg/m^2$/day and 900 $mg/m^2$/day). One such dose regimen involves treating a patient comprising administering daily to the patient about 500 $mg/m^2$/day of cyclophosphamide and about 60 $mg/m^2$/day of fludarabine for three days prior to administration of a therapeutically effective amount of engineered T cells to the patient. In one aspect, the conditioning regimen comprises cyclophosphamide 500 $mg/m^2$+fludarabine 30 $mg/m^2$ for 3 days. They may be administered at days −4, −3, and −2 or at days −5, −4, and −3 (day 0 being the day of administration of the cells). In one embodiment, the conditioning regimen comprises cyclophosphamide 200 $mg/m^2$, 250 $mg/m^2$, 300 $mg/m^2$, 400v, 500 $mg/m^2$ daily for 2, 3, or 4 days and fludarabine 20 $mg/m^2$, 25 $mg/m^2$, or 30 $mg/m^2$ for 2, 3, or 4 days. In one embodiment, and after leukapheresis, conditioning chemotherapy (fludarabine 30 $mg/m^2$/day and cyclophosphamide 500 $mg/m^2$/day) is administered on days −5, −4, and −3 prior to an intravenous infusion of a suspension of CD19 CAR-T cells. In some embodiments, the intravenous infusion time is between 15 and 120 minutes. In one embodiment, the intravenous infusion time is between 1 and 240 minutes. In some embodiments, the intravenous infusion time is up to 30 minutes. In some embodiments, the intravenous infusion time is up to 5, 10, 15, 20, 25, 30, 35, 40, 45, 50, 55, 60, 65, 70, 75, 80, 85, 90, 95, or up to 100 minutes. In some embodiments, the infusion volume is between 50 and 100 mL. In some embodiments, the infusion volume is between 20 and 100 ml. In some embodiments, the infusion volume is about 30, 35, 40, 45, 50, 55, 60, or about 65 ml. In some embodiments, the infusion volume is about 68 mL. In some embodiments, the suspension has been frozen and is used within 6, 5, 4, 3, 2, 1 hour of thawing. In some embodiments, the suspension has not been frozen. In some embodiments, the immunotherapy is infused from an infusion bag. In some embodiments, the infusion bag is agitated during the infusion. In some embodiments, the immunotherapy is administered within 3 hours after thawing. In some embodiments, the suspension further comprises albumin. In some embodiments, albumin is present in an amount of about 2-3% (v/v). In some embodiments, albumin is present in an amount of about 2.5% (v/v). In some embodiments, the albumin is present in an amount of about 1%, 2%, 3%, 4%, or 5% (v/v). In some embodiments, albumin is human albumin. In some embodiments, the suspension further comprises DMSO. In some embodiments, DMSO is present in an amount of about 4-6% (v/v). In some embodiments, DMSO is present in an amount of about 5% (v/v). In some embodiments, the DMSO is present in an amount of 1%, 2%, 3%, 4%, 5%, 6%, 7%, 8%, 9%, or 10% (v/v).

The methods disclosed herein may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain aspects, the methods may induce a complete response. In other aspects, the methods may induce a partial response.

Cancers that may be treated include tumors that are not vascularized, not yet substantially vascularized, or vascularized. The cancer may also include solid or non-solid tumors.

In one embodiment, the method may be used to treat a B-cell malignancy bearing high levels of circulating CD19-expressing tumor cells and will be indicated for a distinct patient population with high unmet need.

Exemplary Treatment of MCL

In some embodiments, the malignancy may be mantle cell lymphoma (MCL). MCL is an aggressive subtype of non-Hodgkin lymphoma (NHL). MCL accounts for approximately 6% of all new cases of NHL in the United States (US) and 5% to 7% of malignant lymphoma in Western Europe The estimated annual incidence of MCL is approximately 1 to 2 per 100,000 persons in the US and Europe. MCL is more likely to affect men than women, and the median age at diagnosis is 68 years. In some embodiments, the r/r MCL is r/r to treatment with allogeneic stem cell transplant (allo-SCT), which itself can result in durable remission for approximately 25% of patients with relapsed or refractory (r/r) MCL if their disease was shown to be chemosensitive prior to transplant, but allo-SCT is also associated with treatment-related mortality rates of up to 40%.

In some embodiments, the r/r MCL is r/r to treatment with bortezomib, lenalidomide, and temsirolimus, which itself results in ORRs ranging from 22% to 32%. Bruton's tyrosine kinase (BTK) inhibitors such as ibrutinib and acalabrutinib result in ORRs of 68% and 81%, respectively, in patients with r/r MCL. However, most patients progress following BTK inhibitor treatment and have poor outcomes in response to salvage therapies, with ORRs ranging from 20% to 42%, median durations of response (DORs) ranging from 3 to 5.4 months, and median OS ranging from 2.5 to 9 months. In some embodiments, the disclosure provides that CAR T cell intervention can be used to treat cancers with poor prognostic factors such as high Ki67 tumor proliferation index expression (≥30% or ≥50%) and mutated TP53. In some embodiments, the cancer is MCL. In some embodiments, the MCL morphology is classical, pleomorphic, or blastoid. In some embodiments, the Ki-67 index may be between 5% and 80%. In some embodiments, the Ki-67 index is about 38%. In some embodiments, high-risk patients have a Ki-67≥50% and/or TP53 mutation by next generations sequencing. In some embodiments, the patient is aged ≥18 years old. In some embodiments, MCL is pathologically confirmed with documentation of either cyclin D1 overexpression and/or presence of t(11:14).

In some embodiments, the CAR T cell intervention comprises T cells which are expanded from a T cell population depleted of circulating lymphoma cells and enriched for CD4+/CD8+ T cells by positive selection of mononuclear cells from a leukapheresis sample that is activated with anti-CD3 and anti-CD28 antibodies in the presence of IL-2, and then transduced with a replication-incompetent viral vector containing an anti-CD19 CAR construct. In some embodiments, the CAR construct is FMC63-28Z CAR. The CAR T cell generated using this method may be referred to as KTE-X19. In some embodiments, the cells are autologous. In some embodiments, the cells are heterologous. In some embodiments, the dose of CAR-positive T cells is $2\times10^6$ anti-CD19 CAR T cells/kg. In some embodiments, the dose of CAR-positive T cells is $1\times10^6$ anti-CD19 CAR T cells/kg. In some embodiments, the dose of CAR-positive T cells is $1.6\times10^6$ anti-CD19 CAR T cells/kg, $1.8\times10^6$ anti-CD19 CAR T cells/kg, or $1.9\times10^6$ anti-CD19 CAR T cells/kg. In some embodiments, the CD19 CAR construct contains a CD3ζ T cell activation domain and CD28 signaling domain.

In some embodiments, the CAR T cells are administered as a single infusion on Day 0 following conditioning therapy with 25 mg/m$^2$/day of fludarabine on Days −5, −4, and −3 and 900 mg/m$^2$/day of cyclophosphamide on Day −2, after leukapheresis. In some embodiments, the conditioning therapy comprises 300 mg/m$^2$/day of cyclophosphamide and 30 mg/m$^2$/day of fludarabine for 3 days. In some embodiments, the conditioning chemotherapy comprises 30 mg/m$^2$/day of fludarabine and 500 mg/m$^2$/day of cyclophosphamide on Days −5, −4, and −3. In some embodiments, the patient may also have received acetaminophen and diphenhydramine or another H1-antihistamine approximately 30 to 60 minutes prior to infusion of anti-CD19 CAR T cells. In some embodiments, the patients receive one or more additional doses of anti-CD19 CAR T cells.

In some embodiments, the MCL cancer is relapsed/refractory MCL (r/r MCL). In some embodiments, the patient has received one or more prior treatments. In some embodiments, the patient has received 1-5 prior treatments. In some embodiments, the prior treatments may have included autologous SCT, anti-CD20 antibody, anthracycline- or bendamustine-containing chemotherapy, and/or a Bruton Tyrosine Kinase inhibitor (BTKi). In some embodiments, the BTKi is ibrutinib (Ibr). In some embodiments, the BTKi is acalabrutinib (Acala). In some embodiments, the disclosure provides that MCL patients who were previously treated with ibrutinib had a more pronounced response to anti-CD19 CAR T cell therapy as compared to patients previously treated with acalabrutinib. Accordingly, the disclosure provides a method of treating r/r MCL with anti-CD19 CAR T cell therapy wherein the patient has been previously treated with ibrutinib or acalabrutinib and whose cancer is, preferably, relapsed/refractory to the same. In some embodiments, the BTKi is tirabrutinib (ONO-4059), zanubrutinib (BGB-3111), CGI-1746 or spebrutinib (AVL-292, CC-292).

In some embodiments, the disclosure provides that for patients with prior Ibr, Acala, or both, median (range) peak CAR T cell levels were 95.9 (0.4-2589.5), 13.7 (0.2-182.4), or 115.9 (17.2-1753.6), respectively. In some embodiments, ORR/CR rates to anti-CD19 CAR T cell therapy in patients with MCL were 94%/65% in patients with prior Ibr, 80%/40% in patients with prior Acala, and 100%/100% inpatients with both BTKis. In some embodiments, the 12-month survival rates in patients with prior Ibr, Acala, or both were 81%, 80%, or 100%, respectively. In some embodiments, CAR T cell expansion is associated with ORR/CR rate in patients previously treated with Ibr and/or Acala. Accordingly, in one embodiment, the patient is treated with both Ibr and Acala. In one embodiment, the disclosure provides a method of predicting ORR/CR in an MCL patient previously treated with Ibr and/or Acala by measuring peak CAR T cell levels and comparing them to a reference standard. In one embodiment, the disclosure provides a method of predicting ongoing response based on the measurement of CAR T cell peak levels/baseline tumor burden (CEN and INV). In one embodiment, the higher the ratio, the higher the likelihood of ongoing response at/by 12 months. In one embodiment, a ratio between 0.00001 and 0.005 is predictive of non-response at/by 12 months. In one embodiment, a ratio between 0.006 and 0.3 is predictive of relapse at/by 12 months. In one embodiment, a ration between 0.4 and 1 is predictive of ongoing response at/by 12 months. In one embodiment, the ratios may be determined by one of ordinary skill in the art from the average populations.

In some embodiments, additional inclusion criteria include those listed in EXAMPLE 2. In some embodiments, additional exclusion criteria include those listed in EXAMPLE 2.

In some embodiments, the patient may have received bridging therapy (after leukapheresis and before chemotherapy) with dexamethasone (e.g., 20-40 mg or equivalent PO or IV daily for 1-4 days), methylprednisolone, ibrutinib (e.g., 560 mg PO daily), and/or acalabrutinib (e.g, 100 mg PO twice daily) after leukapheresis and completed, for example, in 5 days or less before conditioning chemotherapy. In some embodiments, such patient may have had high disease burden. In some embodiments, the bridging therapy is selected from an immunomodulator, R-CHOP, bendamustine, alkylating agents, and/or platinum-based agents.

In some embodiments, the disclosure provides that all MCL patients who responded to CAR T cell infusion achieved T cell expansion, whereas no expansion was observed in non-responding patients. In some embodiments, response is objective response (complete response+partial response). The disclosure provides that CAR T cell levels correlated with ORR in the first 28 days, where the area under the curve on days 0 to 28 ($AUC_{0-28}$) and peak levels were >200-fold higher in responders versus non-responders, suggesting that higher expansion led to better and perhaps deeper response as also indicated by the >80-fold higher peak/AUC CAR T cell levels in minimal residual disease (MRD, $10^{-5}$ sensitivity) negative compared with MRD positive patients (at week 4). Accordingly, the disclosure provides a method of predicting patient response and MRD to CAR T cell treatment of MCL comprising measuring peak/AUC CAR T cell levels and comparing them to a reference standard. In some embodiments, peak CAR T cell expansion is observed between Days 8 and 15 after CAR T cell administration. In some embodiments, CAR T cells levels are measured by qPCR. In some embodiments, the peak CAR T cell levels, $AUC_{0-28}$, and/or MRD are monitored by next-generation sequencing. In some examples, the CAR T cell numbers are measured in cells/microliter of blood. In some examples, the CAR T cell numbers are measured by the number of CAR gene copies/μg of host DNA. In some examples, the CAR T cell numbers are measured as described in Kochenderfer J. N et al. *J. Clin. Oncol.* 2015; 33:540-549. In one embodiment, CAR T cell levels are measured as described in Locke F L et al. *Mol Ther.* 2017; 25(1):285-295.

In some embodiments, the disclosure provides that there is a difference between T cell expansion of responders and nonresponders. In some embodiments, the disclosure provides that the median peak anti-CD19 CAR T cell level in responders (those with complete remission and partial remission) was 102.4 cells/μL (range: 0.2 to 2589.5 cells/μL; n=51), and in nonresponders was 12.0 cells/μL (range: 0.2 to 1364.0 cells/μL, n=8). In some embodiments, the disclosure provides that the median AUC Day 0-28 ($AUC_{0-28}$) in patients with an objective response was 1487.0 cells/μL·days (range: 3.8 to $2.77\times10^4$ cells/μL·days; n=51) and 169.5 cells/μL·days in nonresponders (range: 1.8 to 1.17 $10\times10^4$ cells/μL·days; n=8). The median peak (24.7 cells/μL) anti-CD19 CAR T cell (peak: and $AUC_{0-28}$ levels (360.4 cells/μL·days) in patients (n=18) who received neither corticosteroids nor tocilizumab was similar to those of patients (n=2) who received only corticosteroids (peak: 24.2 cells/μL; $AUC_{0-28}$: 367.8 cells/μL·days). In the patients who received only tocilizumab (n=10), the mean peak anti-CD19 CAR T cells was 86.5 cells/μL and $AUC_{0-28}$ was 1188.9 cells/μL·days. In the patients who received both corticosteroids and tocilizumab (n=37), the mean peak was 167.2 cells/μL and $AUC_{0-28}$ was 1996.0 cells/μL·days. The median peak anti-CD19 CAR T-cell values were 74.1 cells/μL in patients ≥65 years of age (n=39) and 112.5 cells/μL in patients <65 years of age (n=28). Median anti-CD19 CAR T-cell $AUC_{0-28}$ values were 876.5 cells/μL·day in patients ≥65 years of age and 1640.2 cells/μL·day in patients <65 years of age. Gender had no significant impact on $AUC_{0-28}$ and $C_{max}$ of anti-CD19 CAR T cells. Accordingly, the disclosure provides a method of predicting response in MCL comprising measuring T cell expansion after anti-CD19 CAR T treatment and comparing the level to a reference standard.

In some embodiments, the disclosure provides that CAR T cell expansion was greater in MCL patients with grade ≥3 than in those with grade ≤3 CRS and NE events. Accordingly, the disclosure provides a method of predicting grade ≥3 CRS and NE events comprising measuring CAR T cell expansion after CAR T cell treatment and comparing the levels to a reference value, wherein the higher the CAR T cell expansion, the higher the chance for grade ≥3 CRS and NE events.

In some embodiments, the cytokine levels are measured by and are protein or mRNA levels (which ones). In some embodiments, the cytokine levels are measured as described in Locke F L et al. *Mol Ther.* 2017; 25(1):285-295.

In some embodiments, the disclosure provides that serum GM-CSF and IL-6 peak levels (reached about 8 days post CAR T cell administration) were positively associated with grade ≥3 CRS and grade ≥3 NE in MCL patients. Accordingly, the disclosure provides a method of predicting grade ≥3 CRS and grade ≥3 NE comprising measuring the peak levels of GM-CSF and IL-6 post-CAR T cell administration and comparing them to a reference level, wherein the higher the peak level of these cytokines, the higher the chance for grade ≥3 CRS and NE.

In some embodiments, the disclosure provides that serum ferritin was positively associated with grade ≥3 CRS in MCL patients. Accordingly, the disclosure provides a method of predicting grade ≥3 CRS comprising measuring the peak levels of serum ferritin post-CAR T cell administration and comparing them to a reference level, wherein the higher the peak level of ferritin, the higher the chance for grade ≥3 CRS.

In some embodiments, the disclosure provides that serum IL-2 and IFN-gamma were positively associated with grade ≥3 NE in MCL patients. Accordingly, the disclosure provides a method of predicting grade ≥3 CRS comprising measuring the peak levels of serum IL-2 and IFN-gamma post-CAR T cell administration and comparing them to a reference level, wherein the higher the peak level of IL-2 and IFN-gamma, the higher the chance for grade ≥3 NE.

In some embodiments, the disclosure provides that cerebrospinal fluid levels of C-reactive protein, ferritin, IL-6, IL-8, and vascular cell adhesion molecule (VCAM) were positively associated with grade ≥3 NE in MCL patients. Accordingly, the disclosure provides a method of predicting grade ≥3 CRS comprising measuring the cerebrospinal fluid levels of C-reactive protein, ferritin, IL-6, IL-8, and/or vascular cell adhesion molecule (VCAM) post-CAR T cell administration and comparing them to a reference level, wherein the higher the cerebrospinal fluid levels of C-reactive protein, ferritin, IL-6, IL-8, and/or vascular cell adhesion molecule (VCAM), the higher the chance for grade ≥3 NE. In some embodiments, one or more adverse events were managed according to Table 13 and/or Table 14.

In some embodiments, the disclosure provides that peak serum levels of cytokines associated positively with Grade ≥3 CRS included IL-15, IL-2 Rα, IL-6, TNFα, GM-CSF, ferritin, IL-10, IL-8, MIP-1a, MIP-1b, granzyme A, granzyme B, and perforin. In some embodiments, the disclosure provides that peak serum levels of cytokines associated with Grade ≥3 NE included IL-2, IL-1 Rα, IL-6, TNFα, GM-CSF, IL-12p40, IFN-γ, IL-10, MCP-4, MIP-1b, and granzyme B. In some embodiments, the disclosure provides that cytokines associated with both Grade ≥3 CRS and NE included IL-6, TNFα, GM-CSF, IL-10, MIP-1b, and granzyme B. In some embodiments, cytokine serum levels peak within 7 days of CAR T cell administration. Accordingly, the disclosure provides a method of predicting grade ≥3 CRS post-CAR T cell administration comprising measuring peak serum levels of IL-15, IL-2 Rα, IL-6, TNFα, GM-CSF, ferritin, IL-10, IL-8, MIP-1a, MIP-1b, granzyme A, granzyme B, and/or perforin after anti-CD19 CAR T treatment and comparing the levels to a reference standard. Accordingly, the disclosure also provides a method of predicting grade ≥3 CRS and grade ≥3 NE in MCL comprising measuring peak serum levels of IL-6, TNFα, GM-CSF, IL-10, MIP-1b, and granzyme B after anti-CD19 CAR T treatment and comparing the levels to a reference standard.

In some embodiments, the disclosure provides that there was a trend for increased proliferative (IL-15, IL-2) and inflammatory (IL-6, IL-2Rα, sPD-L1 and VCAM-1) peak cytokine levels in patients with MCL with mutated TP53 vs wild-type TP53. Accordingly, in some embodiments, the disclosure provides a method of improving response to CAR T cell treatment in MCL comprising manipulating the levels of proliferative and/or inflammatory cytokines after CAR T cell administration.

In some embodiments, the disclosure provides that for patients that were MRD negative at one month post CAR T cell administration, there was an increase in peak levels of IFN-gamma and IL-6, and a trend towards increased IL-2, relative to patients that were MRD positive at one month. Accordingly, the disclosure provides a method of predicting whether a patient is MRD negative in MCL comprising measuring peak serum levels of IFN-gamma, IL-6, and/or IL-2 after anti-CD19 CAR T treatment and comparing the level to a reference standard.

In some embodiments, the disclosure provides that the T cell product phenotype varied among types of MCL. In some embodiments, the disclosure provides that, in the manufactured anti-CD19 CAR T product, median (range) CD4+/CD8+ T cell ratios for patients with classical, blastoid, or pleomorphic MCL were 0.7 (0.04-2.8), 0.6 (0.2-1.1), or 0.7 (0.5-2.0), respectively. Product T cell phenotypes (median [range]) included less differentiated CCR7+ T cells (classical 40.0% [2.6-88.8]; blastoid 35.3% [14.3-73.4]; pleomorphic 80.8% [57.3-88.8]) and effector and effector memory CCR7− T cells (classical 59.9% [11.1-97.4]; blastoid 64.8% [26.6-85.7]; pleomorphic 19.2% [11.1-42.7]). In some embodiments, the disclosure provides that the 12-mo survival rates in patients with classical, blastoid, or pleomorphic MCL were 86.7%, 67.9%, or 100%, respectively. Accordingly, the disclosure provides a method of improving treatment of classical, blastoid, or pleomorphic MCL by manipulating the T cell product phenotype administered to the patient.

Exemplary Treatment of B Cell ALL

B-ALL cells typically express CD19, and CAR T-cell therapies targeting CD19 are a treatment approach in R/R B-ALL. Pehlivan K. C. et al. *Curr Hematol Malig Rep.* 2018; 13(5):396-406 An anti-CD19 CAR T-cell therapy containing a CD3ζ and CD28 co-stimulatory domain developed at the National Cancer Institute (Kochenderfer I N et al. *J Immunother.* 2009; 32(7):689-702; Kochenderfer J N et al. *Blood.* 2010; 116(19):3875-3886) showed an overall remission rate of 70% after a median 10-month follow-up in a phase 1 trial in children and adults ≤30 years of age with R/R B-ALL. Lee D W et al. *Lancet.* 2015; 385(9967):517-528. A similar CAR construct evaluated in a phase 1 trial in adults with R/R B-ALL provided an 83% complete remission (CR) rate and median 12.9-month OS at a median 29-months follow-up. Park J H et al. *N Engl J Med.* 2018; 378(5):449-459. In these studies, the CAR T cells were prepared from leukapheresis samples that were not enriched for CD4+/CD8+ T cells.

In some embodiments, the disclosure is directed to a T cells product whereby the T cells are expanded from a T cell population depleted of circulating lymphoma cells and enriched for CD4+/CD8+ T cells by positive selection of mononuclear cells from a leukapheresis sample that is activated with anti-CD3 and anti-CD28 antibodies in the presence of IL-2, and then transduced with a replication-incompetent viral vector containing an anti-CD19 CAR construct. In some embodiments, such T cell product may be used to treat ALL, CLL, AML. In some embodiments, the CAR construct is FMC63-28Z CAR. In some embodiments, the cells are autologous. In some embodiments, the cells are heterologous. In some embodiments, the dose of CAR-positive T cells is $2\times10^6$ anti-CD19 CAR T cells/kg. In some embodiments, the dose of CAR-positive T cells is $1\times10^6$ anti-CD19 CAR T cells/kg. In some embodiments, the dose of CAR-positive T cells is $1.6\times10^6$ anti-CD19 CAR T cells/kg, $1.8\times10^6$ anti-CD19 CAR T cells/kg, or $1.9\times10^6$ anti-CD19 CAR T cells/kg. In some embodiments, the CD19 CAR construct contains a CD3ζ T cell activation domain and CD28 signaling domain. In some embodiments, the T cell product is KTE-X19. In some embodiments, the disclosure provides that the anti-CAR T cell product prepared as described in the preceding paragraph may be used in B cell ALL and B cell NHL. In one embodiment, the T cell product has the characteristics of the products of Table 23. In some embodiments, the product characteristics may be selected from percentage of T cells of specific subsets (naïve, central memory, effector, and effector memory), percentage of CD4+ cells, percentage of CD8+ cells and CD4/CD8 ratio. In some embodiments, the product characteristic is the level of IFNγ production in co-culture (pg/mL) with target CD19-expressing cancer cells (e.g. Toledo) cells mixed in a 1:1 ratio with the anti-CD19 CAR T product cells. In one embodiment, IFNγ may be measured in cell culture media 24 h post-incubation using a qualified ELISA. In some embodiments, one or more of these product characteristics is superior than those of anti-CAR T cells prepared from leukapheresis without CD4+/CD8+ positive cell enrichment. In some embodiments, the superior product characteristic may be selected from increased percentage of cells with naïve phenotype (CD45RA+ CCR7+), decreased percentage of cells with differentiated phenotype (CCR7−), decreased level of IFNγ-producing cells, and increased level of CD8+ cells. In some embodiments, the anti-CD19 T cell product comprises $T_{CM}$, central memory T cells (CD45RA-CCR7+); $T_{EFF}$, effector T cells (CD45RA+ CCR7−); $T_{EM}$, effector memory T cells (CD45RA-CCR7−); and/or $T_N$, naïve-like T cells (CD45RA+ CCR7+). In some embodiments, the product comprises $T_N$ naïve-like T cells means T cells that are CD45RA+ CCR7+ and comprises stem-like memory cells. In some embodiments, the T cell product is KTE-X19. In some embodiments, KTE-X19 has ≥190 μg/mL IFN-γ production. In certain embodiment, KTE-X19 has ≥90% of CD3+ cells. In some other embodiments, the percentage of NK cells in KTE-X19 is 0.1% (range 0.0%-2.8%). In some additional embodiments, the percentage of $CD3^-$ cellular impurities in KTE-X19 is 0.5% (range 0.3%-3.9%).

In some embodiments, the cancer is relapsed/refractory B cell ALL. In some embodiments, the patient is ≤21 years-old. In some embodiments, the patient is ≤21 years-old, weighs ≥10 kg, and has B cell ALL that is primary refractory, relapsed within 18 months of first diagnosis, R/R after ≥2 lines of systemic therapy, or R/R after allogeneic stem cell transplantation at least 100 days prior to enrollment. In one embodiment, the cancer is indolent lymphoma or leukemia. In one embodiment, the cancer is an aggressive B-cell lymphoma, which include many types, subtypes and variants of diffuse large B-cell lymphoma (DLBCL), Burkitt lymphoma (BL), mantle cell lymphoma and its blastoid variant, and B lymphoblastic lymphoma. DLBCL may be DLBCL NOS, T-cell/histiocyte-rich large B-cell lymphoma, Primary DLBCL of the CNS, Primary cutaneous DLBCL, leg type, EBV-positive DLBCL of the elderly. Other lymphomas of large B cells include Primary mediastinal (thymic) LBCL, DLBCL associated with chronic inflammation, Lymphomatoid granulomatosis, ALK-positive LBCL, Plasmablastic lymphoma, Large B-cell lymphoma arising in HHV8-associated multicentric Castleman disease, and Primary effusion lymphoma. Other types of lymphomas include B-cell lymphoma, unclassifiable, with features intermediate between DLBCL, and Burkitt's lymphoma and B-cell lymphoma, unclassifiable, with features intermediate between DLBCL and classical Hodgkin lymphoma, Splenic marginal zone B-cell lymphoma, Extranodal marginal zone B-cell lymphoma of MALT, Nodal marginal zone B-cell lymphoma, Hairy cell leukemia, Lymphoplasmacytic lymphoma (Waldenstrom macroglobulinemia), and Primary effusion lymphoma. The cancer may be at any stage, from stage 1 through stage 4.

ALL is a common childhood malignancy, constituting approximately 80% of childhood leukemias and approximately 25% of all childhood cancers. Approximately 20% of pediatric patients do not achieve long-term remission after initial therapy, with a 5-year OS rate of approximately 55%. Hunger S P, et al. *N Engl J Med.* 2015; 373:1541-1552; Sun W, et al. *Leukemia.* 2018; 32:2316-2325; Rheingold S R, et al. *J Clin Oncol.* 2019; 37 (suppl, abstr): 10008 and Oskarsson T, et al. *Haematologica.* 2016; 101:68-76. Outcomes are poor for patients who relapse early or have primary refractory disease after initial treatment; patients with R/R disease after stem cell transplantation; and multiply relapsed patients. Sun W, et al. *Leukemia.* 2018; 32:2316-2325; Rheingold S R, et al. *J Clin Oncol.* 2019; 37 (suppl, abstr):10008; Oskarsson T, et al. *Haematologica.* 2016; 101:68-76; Nguyen K, et al. *Leukemia.* 2008; 22:2142-2150; Crotta A, et al. *Curr Med Res Opin.* 2018; 34:435-440; Schrappe M, et al. *N Engl J Med.* 2012; 366:1371-1381. Patients who relapse within 18 months of initial diagnosis generally have a 5-year OS rate of 21%-28%. Rheingold S R, et al. *J Clin Oncol.* 2019; 37 (suppl, abstr):10008; Nguyen K, et al. *Leukemia.* 2008; 22:2142-2150. The likelihood of achieving remission and the duration of EFS decrease with each subsequent line of salvage therapy. Sun W, et al. *Leukemia.* 2018; 32:2316-2325. Outcomes remain poor in pediatric and adolescent patients with R/R ALL after treatment with the novel therapies blinatumomab and inotuzumab ozogamicin, with a 1-year OS rate of approximately 36%, highlighting the need for more effective therapeutic options. von Stackelberg A, et al. *J Clin Oncol.* 2016; 34:4381-4389. 10; Bhojwani D, et al. *Leukemia.* 2019; 33:884-892.

In some embodiments, the cancer is B cell NHL and key enrollment criteria include age <18 years, weight ≥10 kg, histologically confirmed diffuse large B cell lymphoma not otherwise specified (DLBCL NOS), primary mediastinal large B cell lymphoma, Burkitt lymphoma (BL), Burkitt-like lymphoma or unclassified B cell lymphomas intermediate between DLBCL and BL, with ≥1 measurable lesion. In one embodiment, for NHL treatment, the disease may have been primary refractory, R/R after ≥2 lines of systemic therapy, or R/R after autologous or allogeneic stem cell transplantation ≥100 days prior to enrollment. Patients with acute graft-versus-host disease or chronic graft-versus-host disease requiring treatment within 4 weeks of enrollment may not be eligible.

In some embodiments, these B cell ALL and/or the B cell NHL patients receive conditioning chemotherapy with fludarabine 25 $mg/m^2$/day on Days −4, −3, and −2 and cyclophosphamide 900 $mg/m^2$/day on Day −2 followed by a single infusion of CD4+/CD8+-enriched anti-CD19 CAR T cells (prepared as described immediately above) at a target dose of $1\times10^6$ anti-CD19 CAR T cells/kg on Day 0.

In some embodiments, the disclosure provides the use of CD4+/CD8+ enriched/cancer cell depleted anti-CD19 CAR T cells to successfully treat B cell ALL, where the patient is ≥18 years of age with R/R B cell ALL, defined as refractory to first-line therapy (i.e., primary refractory), relapse ≤12 months after first remission, relapsed or refractory after ≥2 prior lines of systemic therapy, or relapsed after allogeneic stem cell transplant (SCT). In some embodiments, patients were required to have ≥5% bone marrow blasts, an Eastern Cooperative Oncology Group performance status of 0 or 1, and adequate renal, hepatic, and cardiac function. For patients who received prior blinatumomab, leukemic blasts with CD19 expression ≥90% was required. Patients with Philadelphia chromosome-positive (Ph+) disease, concomitant extramedullary disease, central nervous system (CNS)-2 disease (cerebrospinal fluid [CSF] blast cells with <5 white blood cells/$mm^3$) without neurological changes and patients with Down syndrome were eligible. CNS-3 disease (CSF blast cells with ≥5 white blood cells/$mm^3$) independent of neurologic changes and a history of CNS disorder were exclusions. In some embodiments, additional inclusion and exclusion criteria are described in EXAMPLE 9.

In some embodiments, the patient may have a cancer that is primary refractory. In some embodiments, the patient may have a cancer that has relapsed after SCT. In some embodiments, the patient may have received prior blinatumomab, which may have been the last therapy used prior to anti-CD19 CAR T cell therapy. In some embodiments, the patient baseline characteristics are those of any one of the patients described in Table 18.

In some embodiments, these B cell ALL patients are administered $2\times10^6$, $1\times10^6$, or $0.5\times10^6$ CAR T cells/kg. In some embodiments, the $0.5\times10^6$ CAR T cells/kg are administered in a formulation with a total volume of 40 mL. In another embodiment, the $0.5\times10^6$ CAR T cells/kg are administered in a formulation with a total volume of 68 mL. In some embodiments, the CAR T cell product is formulated in a total volume of 20, 25, 30, 35, 40, 45, 50, 55, 60, 65, 70, 75, 80, 85, 90, 95, 100, 200, 300, 400, 500, 500, 700, 800, 900, or 1000 mL. In some embodiments, the 40 mL formulation is intended to maintain cell density and cell viability during the freezing/thawing process. In some embodiments, the treatment is associated with adverse events. In some embodiments, one or more adverse events is managed in accordance with any one of Tables 13, 14, 16, or combinations thereof. In some embodiments, the one or more adverse events is managed in accordance with the Original Management Guidelines of Table 16. In some embodiments, one or more adverse events is managed in accordance with the Revised Management Guidelines of Table 16. In some embodiments, vasopressors may be administered to treat CRS. In some embodiments, signs or symptoms associated with CRS, include fever, chills, fatigue, tachycardia, nausea, hypoxia, and hypotension. In some embodiments, signs or symptoms associated with neurologic events, including encephalopathy, seizures, changes in level of consciousness, speech disorders, tremors, and confusion.

In some embodiments, the patient may have a high disease burden at baseline, which is defined as having (>25% leukemic blasts in bone marrow or ≥1,000 blasts/

$mm^3$ in peripheral circulation by local review. In some embodiments, the patients may receive bridging chemotherapy after leukapheresis and before conditioning chemotherapy. In some embodiments, the bridging chemotherapy follows one of the predefined bridging chemotherapy regimens of Table 17.

In some embodiments, the conditioning chemotherapy/lymphodepleting regimen is administered after ≥7 days or 5 half-lives (if shorter) washout from bridging chemotherapy. In some embodiments, the conditioning chemotherapy/lymphodepleting regimen consists of fludarabine intravenous (IV) 25 $mg/m^2$/day on days −4, −3, and −2, and cyclophosphamide IV 900 $mg/m^2$/day on day −2. On day 0, a single infusion of anti-CD19 CAR T cells may be administered. In some embodiments, additional infusions of anti-CD19 CAR T cells may be administered at a later time. In some embodiments, patients achieving complete response to the first infusion may receive a second infusion of anti-CD19 CAR T cells, if progressing following >3 months of remission, provided CD19 expression has been retained and neutralizing antibodies against the CAR are not suspected.

In some embodiments, droplet digital polymerase chain reaction may be used to measure the presence, expansion, and persistence of transduced anti-CD19 CAR+ T cells in the blood. In some embodiments, the procedure is as described in Locke F. L. et al. *Mol Ther.* 2017; 25(1):285-295. In some embodiments, the disclosure provides a method of treatment whereby the CAR T cell levels are as described in Table 22. In some embodiments, the disclosure provides that CAR T cells may be undetectable at relapse. Median peak CAR T-cell levels may be highest with $1\times10^6$ CAR T cells/kg and may be similar between patients who received original vs. revised AE management. In some embodiments, patients achieving CR/CRi had greater median peak expansion than non-responders, as did patients with undetectable vs. detectable MRD. Higher median peak expansion was also observed in patients with grade ≥3 NE vs. those with grade ≤2 NE. Some patients who relapse may have detectable CD19-positive cells at relapse or may have no detectable CD19-postive cells. In some embodiments, undetectable MRD, defined as <1 leukemia cell per 10,000 viable cells, may be assessed using flow cytometry (NeoGenomics, Fort Myers, FL) as per the methods described in Borowitz M J, Wood B L, Devidas M, et al. *Blood.* 2015; 126(8):964-971; Bruggemann M. et al. *Blood Adv.* 2017; 1(25):2456-2466; or Gupta S. et al. *Leukemia.* 2018; 32(6): 1370-1379.

In some embodiments, the disclosure provides that peak levels of some cytokines, chemokines, and pro-inflammatory markers occurred by day 7. In some embodiments, some of these trended higher in patients dosed with $2\times10^6$ compared with $1\times10^6$ CAR T cells/kg (IL-15, CRP, SAA, CXCL10, IFNγ), or lower in those with revised AE management vs those with original AE management (IL-6, Ferritin, IL-1RA, IFNγ, IL-8, CXCL10, MCP-1). In some embodiments, the levels of these proteins/biomarkers change as described in FIG. 9; FIG. 10; and FIG. 11). Accordingly, in some embodiments, the disclosure provides methods for using these protein levels as biomarkers for Grade ≥3 and/or Grade 0-2 CRS. In some embodiments, the disclosure provides methods for using these protein levels as biomarkers for Grade ≥3 and/or Grade 0-2 CRS, according to their values in FIG. 11.

In some embodiments, the disclosure provides that peak IL-15 serum levels are lower in patients with grade ≥3 CRS. In some embodiments, the disclosure provides that median peak levels of several pro-inflammatory markers trended higher in patients with grade ≥3 CRS and those with grade ≥3 NE (IFNγ, IL-8, GM-CSF, IL-1RA, CXCL10, MCP-1, Granzyme B, as described in FIG. 11. Accordingly, in some embodiments, the disclosure provides a method for predicting whether a patient is going to have grade ≥3 CRS by measuring the peak levels of serum IL-15 and comparing to a reference standard. In some embodiments, the disclosure provides a method for predicting whether a patient is going to have grade ≥3 CRS and/or grade ≥3 NE by measuring the peak levels of IFNγ, IL-8, GM-CSF, IL-1RA, CXCL10, MCP-1, and/or Granzyme B and comparing to a reference standard. In some embodiments, the disclosure provides a method for improving anti-CD19 CAR T cell therapy by administering agents that decrease the levels of one or more of these biomarkers.

The reference levels/standards may be established by any method known by one of ordinary skill in the art. They serve to identify thresholds or groups of values (e.g., quartiles) from which a comparison may be made to determine in which group, or above or below which threshold does the measured value (cytokine level, CAR T cell number, etc.) for each subject fall. These groups are established from comparisons of different populations chosen as is typical in the art. Depending on where the measured value falls, one can predict a number of treatment characteristics such as objective response, CRS grade, NE grade, and the like.

In certain embodiments, the cancer may be selected from a tumor derived from acute lymphoblastic leukemia (ALL), acute myeloid leukemia (AML), adenoid cystic carcinoma, adrenocortical, carcinoma, AIDS-related cancers, anal cancer, appendix cancer, astrocytomas, atypical teratoid/rhabdoid tumor, central nervous system, B-cell leukemia, lymphoma or other B cell malignancies, basal cell carcinoma, bile duct cancer, bladder cancer, bone cancer, osteosarcoma and malignant fibrous histiocytoma, brain stem glioma, brain tumors, breast cancer, bronchial tumors, burkitt lymphoma, carcinoid tumors, central nervous system cancers, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, embryonal tumors, central nervous system, endometrial cancer, ependymoblastoma, ependymoma, esophageal cancer, esthesioneuroblastoma, ewing sarcoma family of tumors extracranial germ cell tumor, extragonadal germ cell tumor extrahepatic bile duct cancer, eye cancer fibrous histiocytoma of bone, malignant, and osteosarcoma, gallbladder cancer, gastric (stomach) cancer, gastrointestinal carcinoid tumor, gastrointestinal stromal tumors (GIST), soft tissue sarcoma, germ cell tumor, gestational trophoblastic tumor, glioma, hairy cell leukemia, head and neck cancer, heart cancer, hepatocellular (liver) cancer, histiocytosis, hodgkin lymphoma, hypopharyngeal cancer, intraocular melanoma, islet cell tumors (endocrine pancreas), kaposi sarcoma, kidney cancer, langerhans cell histiocytosis, laryngeal cancer, leukemia, lip and oral cavity cancer, liver cancer (primary), lobular carcinoma in situ (LCIS), lung cancer, lymphoma, macroglobulinemia, male breast cancer, malignant fibrous histiocytoma of bone and osteosarcoma, medulloblastoma, medulloepithelioma, melanoma, merkel cell carcinoma, mesothelioma, metastatic squamous neck cancer with occult primary midline tract carcinoma involving NUT gene, mouth cancer, multiple endocrine neoplasia syndromes, multiple myeloma/plasma cell neoplasm, mycosis fungoides, myelodysplastic syndromes, myelodysplastic/myeloproliferative neoplasms, myelogenous leukemia, chronic (CML), Myeloid leukemia, acute (AML), myeloma, multiple, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma of bone, ovarian cancer, pancreatic cancer, papillomatosis, paraganglioma, paranasal sinus and nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, pregnancy and breast cancer, primary central nervous system (CNS) lymphoma, prostate cancer, rectal cancer, renal cell (kidney) cancer, renal pelvis and ureter, transitional cell cancer, retinoblastoma, rhabdomyosarcoma, salivary gland cancer, sarcoma, sezary syndrome, small cell lung cancer, small intestine cancer, soft tissue sarcoma, squamous cell carcinoma, squamous neck cancer, stomach (gastric) cancer, supratentorial primitive neuroectodermal tumors, t-cell lymphoma, cutaneous, testicular cancer, throat cancer, thymoma and thymic carcinoma, thyroid cancer, transitional cell cancer of the renal pelvis and ureter, trophoblastic tumor, ureter and renal pelvis cancer, urethral cancer, uterine cancer, uterine sarcoma, vaginal cancer, vulvar cancer, Waldenström macroglobulinemia, Wilms Tumor. In certain embodiments, the cancer is treated with KTE-X19.

In one embodiment, the method may be used to treat a tumor, wherein the tumor is a lymphoma or a leukemia. Lymphoma and leukemia are cancers of the blood that specifically affect lymphocytes. All leukocytes in the blood originate from a single type of multipotent hematopoietic stem cell found in the bone marrow. This stem cell produces both myeloid progenitor cells and lymphoid progenitor cell, which then give rise to the various types of leukocytes found in the body. Leukocytes arising from the myeloid progenitor cells include T lymphocytes (T cells), B lymphocytes (B cells), natural killer cells, and plasma cells. Leukocytes arising from the lymphoid progenitor cells include megakaryocytes, mast cells, basophils, neutrophils, eosinophils, monocytes, and macrophages. Lymphomas and leukemias may affect one or more of these cell types in a patient. In certain embodiments, the tumor is treated with KTE-X19.

In general, lymphomas may be divided into at least two sub-groups: Hodgkin lymphoma and non-Hodgkin lymphoma. Non-Hodgkin Lymphoma (NHL) is a heterogeneous group of cancers originating in B lymphocytes, T lymphocytes or natural killer cells. In the United States, B cell lymphomas represent 80-85% of cases reported. In 2013 approximately 69,740 new cases of NHL and over 19,000 deaths related to the disease were estimated to occur. Non-Hodgkin lymphoma is the most prevalent hematological malignancy and is the seventh leading site of new cancers among men and women and account for 4% of all new cancer cases and 3% of deaths related to cancer. In certain embodiments, the lymphoma is treated with KTE-X19.

Diffuse large B cell lymphoma (DLBCL) is the most common subtype of NHL, accounting for approximately 30% of NHL cases. There are approximately 22,000 new diagnoses of DLBCL in the United States each year. It is classified as an aggressive lymphoma with the majority of patients cured with conventional chemotherapy (NCCN guidelines NHL 2014). First line therapy for DLBCL typically includes an anthracycline-containing regimen with rituximab, such as R-CHOP (rituximab, cyclophosphamide, doxorubicin, vincristine, and prednisone), which has an objective response rate of about 80% and a complete response rate of about 50%, with about one-third of patients have refractory disease to initial therapy or relapse after R-CHOP. For those patients who relapse after response to first line therapy, approximately 40-60% of patients may achieve a second response with additional chemotherapy. The standard of care for second-line therapy for autologous stem cell transplant (ASCT) eligible patients includes rituximab and combination chemotherapy such as R-ICE (rituximab, ifosfamide, carboplatin, and etoposide) and R-DHAP (rituximab, dexamethasone, cytarabine, and cisplatin), which each have an objective response rate of about 63% and a complete response rate of about 26%. Patients who respond to second line therapy and who are considered fit enough for transplant receive consolidation with high-dose chemotherapy and ASCT, which is curative in about half of transplanted patients Patients who failed ASCT have a very poor prognosis and no curative options. Primary mediastinal large B cell lymphoma (PMBCL) has distinct clinical, pathological, and molecular characteristics compared to DLBCL. PMBCL is thought to arise from thymic (medullary) B cells and represents approximately 3% of patients diagnosed with DLBCL. PMBCL is typically identified in the younger adult population in the fourth decade of life with a slight female predominance. Gene expression profiling suggests deregulated pathways in PMBCL overlap with Hodgkin lymphoma. Initial therapy of PMBCL generally includes anthracycline-containing regimens with rituximab, such as infusional dose-adjusted etoposide, doxorubicin, and cyclophosphamide with vincristine, prednisone, and rituximab (DA-EPOCH-R), with or without involved field radiotherapy. Follicular lymphoma (FL), a B cell lymphoma, is the most common indolent (slow-growing) form of NHL, accounting for approximately 20% to 30% of all NHLs. Some patients with FL will transform (TFL) histologically to DLBCL which is more aggressive and associated with a poor outcome. Histological transformation to DLBCL occurs at an annual rate of approximately 3% for 15 years with the risk of transformation continuing to drop in subsequent years. The biologic mechanism of histologic transformation is unknown. Initial treatment of TFL is influenced by prior therapies for follicular lymphoma but generally includes anthracycline-containing regimens with rituximab to eliminate the aggressive component of the disease. Treatment options for relapsed/refractory PMBCL and TFL are similar to those in DLBCL. Given the low prevalence of these diseases, no large prospective randomized studies in these patient populations have been conducted. Patients with chemotherapy refractory disease have a similar or worse prognosis to those with refractory DLBCL. As an example, subjects who have refractory, aggressive NHL (e.g., DLBCL, PMBCL and TFL) have a major unmet medical need and further research with novel treatments are warranted in these populations. In certain embodiments, the DLBCL is treated with KTE-X19.

The CAR T cell treatment of the disclosure may be administered as a first line of treatment or a second or later line of treatment. In some embodiments, the CAR T cell treatment is administered as a third line, fourth line, fifth line and so on and so forth. The lines of prior therapy may be any prior anti-cancer therapy, including, but not limited to Bruton Tyrosine Kinase inhibitor (BTKi), check-point inhibitors (e.g., anti-PD1 antibodies, pembrolizumab (Keytruda), Cemiplimab (Libtayo), nivolumab (Opdivo); anti-PD-L1 antibodies, Atezolizumab (Tecentriq), Avelumab (Bavencio), Durvalumab (Imfinzi); anti-CTLA-4 antibodies, Ipilimumab (Yervoy)), anti-CD19 antibodies (e.g. blinatumomab), anti-CD52 antibodies (e.g. alentuzumab); allogeneic stem cell transplantation, anti-CD20 antibodies (e.g., rituximab), systemic chemotherapy, rituximab, anthracycline, ofatumumab, and combination thereof. The prior therapies may also be used in combination with the CD19 CAR T therapies of the application. In one aspect, the eligible patients may have refractory disease to the most recent therapy or relapse within 1 year after autologous hematopoietic stem cell transplantation (HSCT/ASCT). The CAR T cell treatment may be administered to patients that have or suspect to have cancers that are refractory and/or that relapsed to one or more lines of previous therapy. The cancer may be refractory to first-line therapy (i.e., primary refractory) or refractory to one or more lines of therapy. The cancer may have relapsed at twelve months after first remission, relapsed or refractory after two or more lines of prior therapy, or relapsed after HSCT/ASCT. In some embodiments, the cancer is refractory to ibrutinib or acalabrutinib. In some embodiments, the cancer is NHL, and the disease must have been primary refractory, R/R after two or more lines of systemic therapy, or R/R after autologous or allogeneic stem cell transplantation ≥100 days prior to enrollment in CAR T cell therapy and off immunosuppressive medications for ≥4 weeks. In certain embodiments, the CAR T cell therapy is KTE-X19.

Accordingly, the method may be used to treat a lymphoma or a leukemia, wherein the lymphoma or leukemia is a B cell malignancy. Examples of B cell malignancies include, but are not limited to, Non-Hodgkin's Lymphomas (NHL), Small lymphocytic lymphoma (SLL/CLL), Mantle cell lymphoma (MCL), FL, Marginal zone lymphoma (MZL), Extranodal (MALT lymphoma), Nodal (Monocytoid B-cell lymphoma), Splenic, Diffuse large cell lymphoma, B cell chronic lymphocytic leukemia/lymphoma, Burkitt's lymphoma, and Lymphoblastic lymphoma. In some aspects, the lymphoma or leukemia is selected from B-cell chronic lymphocytic leukemia/small cell lymphoma, B-cell prolymphocytic leukemia, lymphoplasmacytic lymphoma (e.g., Waldenstrom macroglobulinemia), splenic marginal zone lymphoma, hairy cell leukemia, plasma cell neoplasms (e.g., plasma cell myeloma (i.e., multiple myeloma), or plasmacytoma), extranodal marginal zone B cell lymphoma (e.g., MALT lymphoma), nodal marginal zone B cell lymphoma, follicular lymphoma (FL), transformed follicular lymphoma (TFL), primary cutaneous follicle center lymphoma, mantle cell lymphoma, diffuse large B cell lymphoma (DLBCL), Epstein-Barr virus-positive DLBCL, lymphomatoid granulomatosis, primary mediastinal (thymic) large B-cell lymphoma (PMBCL), Intravascular large B-cell lymphoma, ALK+ large B-cell lymphoma, plasmablastic lymphoma, primary effusion lymphoma, large B-cell lymphoma arising in HHV8-associated multicentric Castleman's disease, Burkitt lymphoma/leukemia, T-cell prolymphocytic leukemia, T-cell large granular lymphocyte leukemia, aggressive NK cell leukemia, adult T-cell leukemia/lymphoma, extranodal NK/T-cell lymphoma, enteropathy-associated T-cell lymphoma, Hepatosplenic T-cell lymphoma, blastic NK cell lymphoma, Mycosis fungoides/Sezary syndrome, Primary cutaneous anaplastic large cell lymphoma, Lymphomatoid papulosis, Peripheral T-cell lymphoma, Angioimmunoblastic T cell lymphoma, Anaplastic large cell lymphoma, B-lymphoblastic leukemia/lymphoma, B-lymphoblastic leukemia/lymphoma with recurrent genetic abnormalities, T-lymphoblastic leukemia/lymphoma, and Hodgkin lymphoma. In some aspect, the cancer is refractory to one or more prior treatments, and/or the cancer has relapsed after one or more prior treatments. In certain embodiments, the leukemia or lymphoma is treated with KTE-X19.

In one embodiment, the cancer is selected from follicular lymphoma, transformed follicular lymphoma, diffuse large B cell lymphoma, and primary mediastinal (thymic) large B-cell lymphoma. In another embodiment, the cancer is diffuse large B cell lymphoma. In some embodiment, the cancer is refractory to or the cancer has relapsed following one or more of chemotherapy, radiotherapy, immunotherapy (including a T cell therapy and/or treatment with an antibody or antibody-drug conjugate), an autologous stem cell transplant, or any combination thereof. In one embodiment, the cancer is refractory diffuse large B cell lymphoma. In certain embodiments, the cancer is treated with KTE-X19.

In some embodiments, the CAR T cell treatment is KTE-X19 and the cancer is selected from MCL, ALL, CLL, and SLL. In some embodiments, the CAR T cell treatment is KTE-X19 and the cancer is NHL. In some embodiments, the cancer is selected from diffuse large B cell lymphoma not otherwise specified (DLBCL NOS), primary mediastinal large B cell lymphoma, Burkitt lymphoma (BL), Burkitt-like lymphoma or unclassified B cell lymphomas intermediate between DLBCL and BL. In some embodiments, the cancer is relapsed/refractory. In some embodiments, the KTE-X19 treatment is administered as first line, second line, or after 1 or more prior lines of therapy. In some embodiments, the patient is a pediatric patient, an adolescent patient, an adult patient, less than 65 years old, more than 65 years old, or any other age group.

In some embodiment, compositions comprising immune cells disclosed herein may be administered in conjunction with any number of additional therapeutic agents. In one embodiment, the additional therapeutic agent is administered concurrently with the T cell therapy. In one embodiment, the additional therapeutic agent is administered prior to, during, and/or after T cell therapy. In one embodiment, the one or more additional therapeutic agents is administered prophylactically. In one aspect, the compositions comprising the immune cells are administered in conjunction with agents for management of adverse events (many of which are described elsewhere in this application, including the Examples section). These agents may manage one or more of the signs and symptoms of adverse reactions, such as fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

Examples of such agents include, without limitation, tocilizumab, steroids (e.g., methylprednisolone), rabbit anti-thymocyte globulin. In some aspect, Vancomycin and aztreonam (each 1 gm IV twice daily) may be administered for non-neutropenic fever. In some aspects, the method further comprises administering a non-sedating, anti-seizure medicine for seizure prophylaxis; administering at least one of erythropoietin, darbepoetin alfa, platelet transfusion, filgrastim, or pegfilgrastim; and/or administering tocilizumab, siltuximab. In one aspect, the agent is a CSF family member such as GM-CSF (Granulocyte-macrophage colony-stimulating factor, also known as CSF2). GM-CSF may be produced by a number of haemopoietic and nonhaemopoietic cell types upon stimulation, and it may activate/'prime' myeloid populations to produce inflammatory mediators, such as TNF and interleukin 1 (IL13). In some embodiments, the GM-CSF inhibitor is an antibody that binds to and neutralizes circulating GM-CSF. In some embodiments, the antibody is selected from Lenzilumab; namilumab (AMG203); GSK3196165/MOR103/Otilimab (GSK/MorphoSys), KB002 and KB003 (KaloBios), MT203 (Micromet and Nycomed), and MORAb-022/gimsilumab (Morphotek). In some embodiments, the antibody is a biosimilar of the same. In some embodiments, the antagonist is E21R, a modified form of GM-CSF that antagonizes the function of GM-CSF. In some embodiments, the inhibitor/antagonist is a small molecule. In one embodiment, the CSF family member is M-CSF (also known as macrophage colony-stimulating factor or CSF1). Non-limiting examples of agents that inhibit or antagonize CSF1 include small molecules, antibodies, chimeric antigen receptors, fusion proteins, and other agents. In one embodiment, the CSF1 inhibitor or antagonist is an anti-CSF1 antibody. In one embodiment, the anti-CSF1 antibody is selected from those made by Roche (e.g., RG7155), Pfizer (PD-0360324), Novartis (MCS110/lacnotuzumab), or a biosimilar version of any one of the same. In some embodiments, the inhibitor or antagonist inactivates the activity of either the GM-CSF-R-alpha (aka CSF2R) or CSF1R receptors. In some embodiments, the inhibitor is selected from Mavrilimumab (formerly CAM-3001), a fully human GM-CSF Receptor α monoclonal antibody currently being developed by MedImmune, Inc.; cabiralizumab (Five Prime Therapeutics); LY3022855 (IMC-CS4)(Eli Lilly), Emactuzumab, also known as RG7155 or RO5509554; FPA008, a humanized mAb (Five Prime/BMS); AMG820 (Amgen); ARRY-382 (Array Biopharma); MCS110 (Novartis); PLX3397 (Plexxikon); ELB041/AFS98/TG3003 (ElsaLys Bio, Transgene), SNDX-6352 (Syndax). In some embodiments, the inhibitor or antagonist is expressed in CAR-T cells. In some embodiments, the inhibitor is a small molecule (e.g. heteroaryl amides, quinolinone series, pyrido-pyrimide series); BLZ945 (Novartis), PLX7486, ARRY-382, Pexidrtinib (also known as PLX3397) or 5-((5-chloro-1H-pyrrolo[2,3-b]pyridin-3-yl)methyl)-N-06-(trifluoromethyl)pyridin-3-yl) methyl)pyridin-2-amine; GW 2580 (CAS 870483-87-7), KÏ20227 (CAS 623142-96-1), AC708 by Ambit Biosciences, or any CSF1R inhibitor listed in Cannarile et al. *Journal for Immuno Therapy of Cancer* 2017, 5:53 and US20180371093, incorporated herein by reference for the inhibitors they disclose. Additional neutralizing antibodies to GM-CSF or its receptor have been described in the art, including in, for example, "GM-CSF as a target in inflammatory/autoimmune disease: current evidence and future therapeutic potential" Hamilton, J. A. Expert Rev. Clin. Immunol., 2015; and "Targeting GM-CSF in inflammatory diseases" Wicks, I. P., Roberts, A. W. Nat. Rev. Rheumatol., 2016. In other embodiments, the agent is an anti-IL6 or anti-IL-6 receptor blocking agent, including tocilizumab and siltuximab.

In one aspect, the therapeutic agent is a chemotherapeutic agent. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some aspects, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

The (chemo)therapeutic agent may be administered at the same time or within one week after the administration of the engineered cell or nucleic acid. In other aspects, the (chemo) therapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some aspects, the (chemo)therapeutic agent is administered at least 1 month before administering the cell or nucleic acid. In some aspects, the methods further comprise administering two or more chemotherapeutic agents.

A variety of additional therapeutic agents may be used in conjunction/combination with the compositions or agents/treatments described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche), tocilizumab (with and without corticosteroids), inhibitors of GM-CSF, CSF1, GM-CSFR, or CSF1R GM-CSF, CSF1, GM-CSFR, or CSF1R (anti-CSF1 antibody is selected from those made by Roche (e.g., RG7155), Pfizer (PD-0360324), Novartis (MCS110/lacnotuzumab), Mavrilimumab (formerly CAM-3001), a fully human GM-CSF Receptor a monoclonal antibody currently being developed by MedImmune, Inc.; cabiralizumab (Five Prime Therapeutics); LY3022855 (IMC-CS4)(Eli Lilly), Emactuzumab, also known as RG7155 or R05509554; FPA008, a humanized mAb (Five Prime/BMS); AMG820 (Amgen); ARRY-382 (Array Biopharma); MCS110 (Novartis); PLX3397 (Plexxikon); ELB041/AFS98/TG3003 (EsaLys Bio, Transgene), SNDX-6352 (Syndax). In some aspects, the inhibitor or antagonist is expressed in CAR-T cells. In some aspects, the inhibitor is a small molecule (e.g. heteroaryl amides, quinolinone series, pyrido-pyrimide series); BLZ945 (Novartis), PLX7486, ARRY-382, Pexidrtinib (also known as PLX3397) or 5-((5-chloro-1H-pyrrolo[2,3-b]pyridin-3-yl) methyl)-N-06-(trifluoromethyl)pyridin-3-yl)methyl)pyridin-2-amine; GW 2580 (CAS 870483-87-7), KĬ20227 (CAS 623142-96-1), AC708 by Ambit Siosciences, or any CSF1R inhibitor listed in Cannarile et al. *Journal for Immuno Therapy of Cancer* 2017, 5:53 and US20180371093, incorporated herein by reference for the inhibitors they disclose. Additional neutralizing antibodies to GM-CSF or its receptor have been described in the art). Additional therapeutic agents suitable for use in combination with the compositions or agents/treatments and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, lenalidomide, axitinib, masitinib, pazopanib, sunitinib, sorafenib, tocilizumab, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

The composition or agents/treatments comprising immune cells are, or may be, administered with an anti-inflammatory agent. Anti-inflammatory agents or drugs may include, but are not limited to, steroids and glucocorticoids (including betamethasone, budesonide, dexamethasone, hydrocortisone acetate, corticosteroid, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

The compositions or agents/treatments described herein may be administered in conjunction with a cytokine and/or a cytokine modulator as an additional therapeutic agent. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO, Epogen, Procrit®); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. In one embodiment, the compositions described herein are administered in conjunction with a steroid or corticosteroid.

Corticosteroid treatment may be used for treatment of adverse events. Corticosteroids (or any other steroids, as well as any other treatment for adverse events) may be used prophylactically, before any symptoms of adverse events are detected and/or after detection of adverse events. They may be administered one or more days prior to T cell administration, on the day of T cell administration (before, after, and/or during T cell administration), and/or after T cell administration. They may be administered prior to, during, or after conditioning therapy. Any corticosteroid may be appropriate for this use. In one embodiment, the corticosteroid is dexamethasone. In some embodiments, the corticosteroid is methylprednisolone. In some embodiments, the two are administered in combination. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17 valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, flupredni solones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylpredni solones (methylprednisolone aceponate, methylprednisolone acetate, methylprednisolone hemisuccinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemisuccinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21 palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980) and Remington: The Science and Practice of Pharmacy, 22nd Edition, Lippincott Williams & Wilkins, Philadelphia, Pa. (2013) and any other editions, which are hereby incorporated by reference. In some embodiments, the glucocorticoid is selected from among cortisones, dexamethasones, hydrocortisones, methylprednisolones, prednisolones and prednisones. In an embodiment, the glucocorticoid is dexamethasone. In other embodiments, the steroid is a mineralcorticoid. Any other steroid may be used in the methods provided herein.

The one or more corticosteroids may be administered at any dose and frequency of administration, which may be adjusted to the severity/grade of the adverse event (e.g., CRS and NE). Tables 13, 14 and 16 provide examples of dosage regimens for management of CRS and NE. In another embodiment, corticosteroid administration comprises oral or IV dexamethasone 10 mg, 1-4 times per day. Another embodiment, sometimes referred to as "high-dose" corticosteroids, comprises administration of IV methylprednisone 1 g per day alone, or in combination with dexamethasone. In some embodiments, the one or more cortico steroids are administered at doses of 1-2 mg/kg per day.

The corticosteroid may be administered in any amount that is effective to ameliorate one or more symptoms associated with the adverse events, such as with the CRS or neurotoxicity. The corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid may be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Equivalence in terms of potency for various glucocorticoids and routes of administration. is well known. Information relating to equivalent steroid dosing (in a non-chronotherapeutic manner) may be found in the British National Formulary (BNF) 37, March 1999.

In some embodiments, the adverse events/reactions may be chosen from one or more of the following:

| Adverse Event/Reaction |
|---|
| Blood and Lymphatic System Disorders |
| Coagulopathy [a] |
| Cardiac Disorders |
| Tachycardias [b] |
| Bradycardias [c] |
| Non-ventricular Arrhythmias [d] |
| Gastrointestinal Disorders |
| Nausea |
| Constipation |
| Diarrhea |
| Abdominal pain [e] |
| Oral pain [f] |
| Vomiting [g] |
| Dysphagia |
| Pyrexia |
| Fatigue [h] |
| Chills |
| Edema [i] |
| Dry mouth |

-continued

| Adverse Event/Reaction |
|---|
| Pain [j] |
| Immune System Disorders |
| Cytokine release syndrome |
| Hypogammaglobulinemia [k] |
| Infections and Infestations |
| Infection - pathogen unspecified |
| Viral infections |
| Bacterial infections |
| Metabolism and nutrition disorders |
| Decreased appetite |
| Musculoskeletal pain [l] |
| Motor dysfunction [m] |
| Psychiatric Disorders |
| Nervous System Disorders |
| Encephalopathy [n] |
| Tremor |
| Headache [o] |
| Aphasia [p] |
| Dizziness [q] |
| Neuropathy [r] |
| Insomnia |
| Delirium [s] |
| Anxiety |
| Immune System Disorders |
| Cytokine release syndrome |
| Hypogammaglobulinemia [k] |
| Infections and Infestations |
| Infection - pathogen unspecified |
| Viral infections |
| Bacterial infections |
| Metabolism and nutrition disorders |
| Decreased appetite |
| Musculoskeletal pain [l] |
| Motor dysfunction [m] |
| Psychiatric Disorders |
| Nervous System Disorders |
| Encephalopathy [n] |
| Tremor |
| Headache [o] |
| Aphasia [p] |
| Dizziness [q] |
| Neuropathy [r] |
| Insomnia |
| Delirium [s] |
| Anxiety |
| Renal and Urinary Disorders |
| Renal insufficiency [t] |
| Urine output decreased [u] |
| Hypoxia |
| Cough [v] |
| Dyspnea [w] |
| Pleural effusion |
| Skin and Subcutaneous Tissue Disorders |
| Rash [x] |
| Vascular Disorders |
| Hypotension [y] |
| Hypertension |
| Thrombosis [z] |
| Hemorrage |

Other adverse reactions include; Gastrointestinal disorders: dry mouth; Infections and infestations disorders: fungal infection; Metabolism and nutrition disorders: dehydration; Nervous system disorders: ataxia, seizure, increased intracranial pressure; Respiratory, thoracic and mediastinal disorders: respiratory failure, pulmonary edema; Skin and subcutaneous tissue disorders: rash; Vascular disorders: hemorrhage.

In one embodiment, cytokine release syndrome symptoms include but are not limited to, fever, rigors, fatigue, anorexia, myalgias, arthalgias, nausea, vomiting, headache, rash, diarrhoea, tachypnea, hypoxemia, tachycardia, hypotension, widened pulse pressure, early increased cardiac output, late diminished cardiac output, hallucinations, tremor, altered gait, seizures and death. In one embodiment, a method for grading CRS is described in Neelapu et al., Nat Rev Clin Oncol. 15(1):47-62 (2018) and Lee, et al., Blood 2014; 124:188-195. In one embodiment, Neurotoxicity/Neurologic events may be graded by the method described in Lee, et al, Blood 2014; 124: 188-195.

In some embodiments, the adverse events are managed with tocilizumab (or another anti-IL6/IL6R agent/antagonist), a corticosteroid therapy, or an anti-seizure medicine for toxicity prophylaxis. In some embodiments, the adverse events are managed by one or more agent(s) selected from inhibitors of GM-CSF, CSF1, GM-CSFR, or CSF1R, anti-thymocyte globulin, lenzilumab, mavrilimumab, cytokines, and anti-inflammatory agents.

In some embodiments, the present disclosure provides methods of preventing the development or reducing the severity of adverse reactions to the T cell treatments of the disclosure. In some embodiments, the cell therapy is administered in with one or more agents that prevents, delays the onset of, reduces the symptoms of, treats the adverse events, which include cytokine release syndromes and neurologic toxicity. In one embodiment, the agent has been described above. In other embodiments, the agent is described below. In some embodiments, the agent is administered by one of the methods and doses described elsewhere in the specification, before, after, or concurrently with the administration of the cells. In one embodiment, the agent(s) are administered to a subject that may be predisposed to the disease but has not yet been diagnosed with the disease.

In this respect, the disclosed method may comprise administering a "prophylactically effective amount" of tocilizumab, of a corticosteroid therapy, and/or of an anti-seizure medicine for toxicity prophylaxis. In some embodiments, the method comprises administering inhibitors of GM-CSF, CSF1, GM-CSFR, or CSF1R, lenzilumab, mavrilimumab, cytokines, and/or anti-inflammatory agents. The pharmacologic and/or physiologic effect may be prophylactic, i.e., the effect completely or partially prevents a disease or symptom thereof. A "prophylactically effective amount" may refer to an amount effective, at dosages and for periods of time necessary, to achieve a desired prophylactic result (e.g., prevention of onset of adverse reactions).

In some embodiments, the method comprises management of adverse reactions in any subject. In some embodiments, the adverse reaction is selected from the group consisting of cytokine release syndrome (CRS), a neurologic toxicity, a hypersensitivity reaction, a serious infection, a cytopenia and hypogammaglobulinemia. In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia. In some embodiments, the patient has been identified and selected based on one or more of the biomarkers of adverse events. In some embodiments, the patient has been identified and selected simply by the clinical presentation (e.g., presence and grade of toxicity symptom). In some embodiments, the adverse events are managed by any one of the protocols of Tables 13, 14, 16, and 17.

In some embodiments, the method comprises preventing or reducing the severity of CRS in a chimeric receptor treatment. In some embodiments, the engineered CAR T cells are deactivated after administration to the patient. In some embodiments, the method comprises identifying CRS based on clinical presentation. In some embodiments, the method comprises evaluating for and treating other causes of fever, hypoxia, and hypotension. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered. In some embodiments, the method comprises monitoring patients at least daily for 7 days at the certified healthcare facility following infusion for signs and symptoms of CRS. In some embodiments, the method comprises monitoring patients for signs or symptoms of CRS for 4 weeks after infusion. In some embodiments, the method comprises counseling patients to seek immediate medical attention should signs or symptoms of CRS occur at any time. In some embodiments, the method comprises instituting treatment with supportive care, tocilizumab or tocilizumab and corticosteroids as indicated at the first sign of CRS.

In some embodiments, the method comprises monitoring patients for signs and symptoms of neurologic toxicities. In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life-threatening neurologic toxicities. In some embodiments, the symptom of neurologic toxicity is selected from encephalopathy, headache, tremor, dizziness, aphasia, delirium, insomnia, and anxiety.

In some embodiments, the cell treatment is administered before, during/concurrently, and/or after the administration of one or more agents (e.g., steroids) or treatments (e.g., debulking) that treat and or prevent (are prophylactic) one or more symptoms of adverse events. A "prophylactically effective amount" refers to an amount effective, at dosages and for periods of time necessary, to achieve the desired prophylactic result. In one embodiment, a prophylactically effective amount is used in subjects prior to or at an earlier stage of disease. In one embodiment, the prophylactically effective amount will be less than the therapeutically effective amount. In one embodiment, the adverse event treatment or prophylaxis is administered to any patient that will receive, is receiving, or has received cell therapy. In some embodiments, the method of managing adverse events comprises monitoring patients at least daily for 7 days at the certified healthcare facility following infusion for signs and symptoms of neurologic toxicities. In some embodiments, the method comprises monitoring patients for signs or symptoms of neurologic toxicities and/or CRS for 4 weeks after infusion.

In some embodiments, the disclosure provides two methods of managing adverse events in subjects receiving CAR T cell treatment with steroids and anti-IL6/anti-IL-6R antibody/ies. In one embodiment, the disclosure provides a method of adverse event management whereby corticosteroid therapy is initiated for management of all cases of grade 1 CRS if there was no improvement after 3 days and for all grade ≥1 neurologic events. In one embodiment, tocilizumab is initiated for all cases of grade 1 CRS if there is no improvement after 3 days and for all grade ≥2 neurologic events. In one embodiment, the disclosure provides a method of reducing overall steroid exposure in patients receiving adverse event management after CAR T cell administration, the method comprising initiation of corticosteroid therapy for management of all cases of grade 1 CRS if there was no improvement after 3 days and for all grade ≥1 neurologic events and/or initiation of tocilizumab for all cases of grade 1 CRS if there is no improvement after 3 days and for all grade ≥2 neurologic events. In one embodiment, the corticosteroid and tocilizumab are administering in a regimen selected from those exemplified the Examples section. In one embodiment, the disclosure provides that earlier steroid use is not associated with increased risk for severe infection, decreased CAR T-cell expansion, or decreased tumor response.

In one embodiment, the disclosure supports the safety of levetiracetam prophylaxis in CAR T cell cancer treatment. In one embodiment, the cancer is NHL. In one embodiment, the cancer is R/R LBCL and the patients receive KTE-X19. Accordingly, in one embodiment, the disclosure provides a method of managing adverse events in patients treated with CAR T cells comprising administering to the patient a prophylactic dosage of an anti-seizure medication. In some embodiments, the patients receive levetiracetam (for example, 750 mg orally or intravenous twice daily) starting on day 0 of the CAR T cell treatment (after conditioning) and also at the onset of grade ≥2 neurologic toxicities, if neurologic events occur after the discontinuation of prophylactic levetiracetam. In one embodiment, if a patient does not experience any grade ≥2 neurologic toxicities, levetiracetam is tapered and discontinued as clinically indicated. In one embodiment, levetiracetam prophylaxis is combined with any other adverse event management protocol.

In one embodiment, patients may receive levetiracetam (750 mg oral or intravenous twice daily) starting on day 0. At the onset of grade ≥2 neurologic events, levetiracetam dose is increased to 1000 mg twice daily. If a patient did not experience any grade ≥2 neurologic event, levetiracetam is tapered and discontinued as clinically indicated. Patients also receive tocilizumab (8 mg/kg IV over 1 hour [not to exceed 800 mg]) on day 2. Further tocilizumab (±corticosteroids) may be recommended at the onset of grade 2 CRS in patients with comorbidities or older age, or otherwise in case of grade ≥3 CRS. For patients experiencing grade ≥2 neurologic events, tocilizumab is initiated, and corticosteroids are added for patients with comorbidities or older age, or if there is any occurrence of a grade ≥3 neurologic event with worsening symptoms despite tocilizumab use.

In one embodiment, the disclosure provides that prophylactic steroid use appears to reduce the rate of severe CRS and NEs to a similar extent as early steroid use administration. Accordingly, the disclosure provides a method for adverse event management in CAR T-cell therapy wherein patients receive dexamethasone 10 mg PO on Days 0 (prior to infusion), 1, and 2. Steroids may also administered starting at Grade 1 NE, and for Grade 1 CRS when no improvement is observed after 3 days of supportive care. Tocilizumab may also administered for Grade ≥1 CRS if no improvement is observed after 24 hours of supportive care. In one embodiment, the disclosure provides that adverse event management of CAR T-cell therapy with an antibody that neutralizes and/or depletes GM-CSF prevents or reduces treatment-related CRS and/or NEs in treated patients. In one embodiment, the antibody is lenzilumab.

In some embodiments, the adverse events are managed by the administration of an agent/agents that is/are an antagonist or inhibitor of IL-6 or the IL-6 receptor (IL-6R). In some embodiments, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-TL-6 antibody, such as siltuximab, elsilimomab, ALD518/BMS-945429, sirukumab (CNTO 136), CPSI-2634, ARGX 109, FE301, FM101, or olokizumab (CDP6038), and combinations thereof. In some embodiments, the agent may neutralize IL-6 activity by inhibiting the ligand-receptor interactions. In some embodiments, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, other agents that may be used to manage adverse reactions and their symptoms include an antagonist or inhibitor of a cytokine receptor or cytokine. In some embodiments, the cytokine or receptor is IL-10, TL-6, TL-6 receptor, IFNy, IFNGR, IL-2, IL-2R/CD25, MCP-1, CCR2, CCR4, MIP13, CCR5, TNFalpha, TNFR1, such as TL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1P receptor (e.g., CCR5), TNF alpha receptor (e.g., TNFR1), IL-1 receptor (IL1-Ra/IL-1RP), or IL-10 receptor (IL-10R), IL-1, and IL-1Ralpha/IL-1beta. In some embodiments, the agent comprises situximab, sarilumab, olokizumab (CDP6038), elsilimomab, ALD518/BMS-945429, sirukumab (CNTO 136), CPSI-2634, ARGX 109, FE301, or FM101. In some embodiments, the agent, is an antagonist or inhibitor of a cytokine, such as transforming growth factor beta (TGF-beta), interleukin 6 (TL-6), interleukin 10 (IL-10), IL-2, MIP13 (CCL4), TNF alpha, IL-1, interferon gamma (IFN-gamma), or monocyte chemoattractant protein-I (MCP-1). In some embodiments, the is one that targets (e.g. Inhibits or is an antagonist of) a cytokine receptor, such as TL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1P receptor (e.g., CCR5), TNF alpha receptor (e.g., TNFR1), IL-1 receptor (IL1-Ra/IL-1RP), or IL-10 receptor (IL-10R) and combinations thereof. In some embodiments, the agent is administered by one of the methods and doses described elsewhere in the specification, before, after, or concurrently with the administration of the cells.

In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the agent is administered in a dosage amount of at least or at least about or about 2 mg/kg, 4 mg/kg, 6 mg/kg or 8 mg/kg. In some embodiments, is administered in a dosage amount from about 1 mg/kg to 12 mg/kg, such as at or about 10 mg/kg. In some embodiments, the agent is administered by intravenous infusion. In one embodiment, the agent is tocilizumab. In some embodiments, the (agent(s), e.g, specifically tocilizumab) is/are administered by one of the methods and doses described elsewhere in the specification, before, after, or concurrently with the administration of the cells.

In some embodiments, the method comprises identifying CRS based on clinical presentation. In some embodiments, the method comprises evaluating for and treating other causes of fever, hypoxia, and hypotension. If CRS is observed or suspected, it may be managed according to the recommendations in protocol A, which may also be used in combination with the other treatments of this disclosure, including Neutralization or Reduction of the CSF/CSFR1 Axis. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered. In some embodiments, a biosimilar or equivalent of tocilizumab may be used instead of tocilizumab in the methods disclosed herein. In other embodiments, another anti-IL6R may be used instead of tocilizumab.

In some embodiments, adverse events are managed according to the following protocol (protocol A):

| CRS Grade (a) | Tocilizumab | Corticosteroids |
|---|---|---|
| Grade 1<br>Symptoms require symptomatic treatment only (e.g., fever, nausea, fatigue, headache, myalgia, malaise). | N/A | N/A |
| Grade 2<br>Symptoms require and respond to moderate intervention.<br>Oxygen requirement less than 40% $FiO_2$ or hypotension responsive to fluids or low-dose of one vasopressor or Grade 2 organ toxicity (b). | Administer tocilizumab (c) 8 mg/kg IV over 1 hour (not to exceed 800 mg).<br>Repeat tocilizumab every 8 hours as needed if not responsive to IV fluids or increasing supplemental oxygen.<br>Limit to a maximum of 3 doses in a 24-hour period; maximum total of 4 doses if no clinical improvement in the signs and symptoms of CRS. | Manage per Grade 3 if no improvement within 24 hours after starting tocilizumab. |
| Grade 3<br>Symptoms require and respond to aggressive intervention.<br>Oxygen requirement greater than or equal to 40% $FiO_2$ or | Per Grade 2 | Administer methylprednisolone 1 mg/kg IV twice daily or equivalent dexamethasone (e.g., 10 mg IV every 6 hours).<br>Continue corticosteroids use |

-continued

| CRS Grade (a) | Tocilizumab | Corticosteroids |
|---|---|---|
| hypotension requiring high-dose or multiple vasopressors or Grade 3 organ toxicity or Grade 4 transaminitis. | | until the event is Grade 1 or less, then taper over 3 days. If not improving, manage as Grade 4. |
| Grade 4 Life-threatening symptoms. Requirements for ventilator support, continuous veno-venous hemodialysis (CVVHD) or Grade 4 organ toxicity (excluding transaminitis). | Per Grade 2 | Administer methylprednisolone 1000 mg IV per day for 3 days; if improves, then manage as above. Consider alternate immunosuppressants if no improvement or if condition worsens. |

(a) Lee D W et al., (2014). Current concepts in the diagnosis and management of cytokine release syndrome. Blood. 2014 Jul. 10; 124(2): 188-195.
(b) Refer to Table 2 for management of neurologic toxicity.
(c) Refer to ACEMTRA ® (tocilizumab) Prescribing Information for details, https://www.gene.com/download/pdf/actemra_prescribing.pdf (last accessed Oct. 18, 2017). Initial U.S. approval is indicated to be in 2010.

Neurologic Toxicity

In some embodiments, the method comprises monitoring patients for signs and symptoms of neurologic toxicities. In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life-threatening neurologic toxicities. Consider non-sedating, anti-seizure medicines (e.g., levetiracetam) for seizure prophylaxis for any ≥Grade 2 neurologic toxicities. The following treatments may be used in combination with the other treatments of this disclosure, including Neutralization or Reduction of the CSF/CSFR1 Axis.

In some embodiments, adverse events are managed according to the following protocol (protocol B):

| Grading Assessment | Concurrent CRS | No concurrent CRS |
|---|---|---|
| Grade 2 | Administer tocilizumab per table above (protocol A) for management of Grade 2 CRS. If no improvement within 24 hours after starting tocilizumab, administer dexamethasone 10 mg IV every 6 hours if not already taking other steroids. Continue dexamethasone use until the event is Grade 1 or less, then taper over 3 days. | Administer dexamethasone 10 mg IV every 6 hours. Continue dexamethasone use until the event is Grade 1 or less, then taper over 3 days. |
| | Consider non-sedating, anti-seizure medicines (e.g., levetiracetam) for seizure prophylaxis. | |
| Grade 3 | Administer tocilizumab per (protocol A) for management of Grade 2 CRS. In addition, administer dexamethasone 10 mg IV with the first dose of tocilizumab and repeat dose every 6 hours. Continue dexamethasone use until the event is Grade 1 or less, then taper over 3 days. | Administer dexamethasone 10 mg IV every 6 hours. Continue dexamethasone use until the event is Grade 1 or less, then taper over 3 days. |
| | Consider non-sedating, anti-seizure medicines (e.g., levetiracetam) for seizure prophylaxis. | |
| Grade 4 | Administer tocilizumab per (protocol A) for management of Grade 2 CRS. Administer methylprednisolone 1000 mg IV per day with first dose of tocilizumab and continue methylprednisolone 1000 mg IV per day for 2 more days; if improves, then manage as above. | Administer methylprednisolone 1000 mg IV per day for 3 days; if improves, then manage as above. |
| | Consider non-sedating, anti-seizure medicines (e.g., levetiracetam) for seizure prophylaxis. | |

Additional Safety Management Strategies with Corticosteroids

Administration of corticosteroids and/or tocilizumab at Grade 1 may be considered prophylactic. Supportive care may be provided in all protocols at all CRS and NE severity grades. In one embodiment of a protocol for management of adverse events related to CRS, tocilizumab and/or corticosteroids are administered as follows: Grade 1 CRS: no tocilizumab; no corticosteroids; Grade 2 CRS: tocilizumab (only in case of comorbidities or older age); and/or corticosteroids (only in case of comorbidities or older age); Grade 3 CRS: tocilizumab; and/or corticosteroids; Grade 4 CRS: tocilizumab; and/or corticosteroids. In another embodiment of a protocol for management of adverse events related to CRS, tocilizumab and/or corticosteroids are administered as follows: Grade 1 CRS: tocilizumab (if no improvement after 3 days); and/or corticosteroids (if no improvement after 3 days); Grade 2 CRS: tocilizumab; and/or corticosteroids; Grade 3 CRS: tocilizumab; and/or corticosteroids; Grade 4 CRS: tocilizumab; and/or corticosteroids, high dose.

In one embodiment of a protocol for management of adverse events related to NE, tocilizumab and/or corticosteroids are administered as follows: Grade 1 NE: no tocilizumab; no corticosteroids; Grade 2 NE: no tocilizumab; no corticosteroids; Grade 3 NE: tocilizumab; and/or corticosteroids (only if no improvement to tocilizumab, standard dose); Grade 4 NE: tocilizumab; and/or corticosteroids. In another embodiment of a protocol for management of adverse events related to NE, tocilizumab and/or corticosteroids are administered as follows: Grade 1 NE: no tocilizumab; and/or corticosteroids; Grade 2 NE: tocilizumab; and/or corticosteroids; Grade 3 NE: tocilizumab; and/or corticosteroids, high dose; Grade 4 NE: tocilizumab; and/or corticosteroids, high dose. In one embodiment, corticosteroid treatment is initiated at CRS grade ≥2 and tocilizumab is initiated at CRS grade ≥2. In one embodiment, corticosteroid treatment is initiated at CRS grade ≥1 and tocilizumab is initiated at CRS grade ≥1. In one embodiment, corticosteroid treatment is initiated at NE grade ≥3 and tocilizumab is initiated at CRS grade ≥3. In one embodiment, corticosteroid treatment is initiated at CRS grade ≥1 and tocilizumab is initiated at CRS grade ≥2. In some embodiments, prophylactic use of tocilizumab administered on Day 2 may decrease the rates of Grade ≥3 CRS. The one or more corticosteroids may be administered at any dose and frequency of administration, which may be adjusted to the severity/grade of the adverse event (e.g., CRS and NE). Tables 1 and 2 provide examples of dosage regimens for management of CRS and NE, respectively. In another embodiment, corticosteroid administration comprises oral or IV dexamethasone 10 mg, 1-4 times per day. Another embodiment, sometimes referred to as "high-dose" corticosteroids, comprises administration of IV methylprednisone 1 g per day alone, or in combination with dexamethasone. In some embodiments, the one or more corticosteroids are administered at doses of 1-2 mg/kg per day. Generally, the dose of corticosteroid administered is dependent upon the specific corticosteroid, as a difference in potency exists between different corticosteroids. It is typically understood that drugs vary in potency, and that doses may therefore vary, in order to obtain equivalent effects. Equivalence in terms of potency for various glucocorticoids and routes of administration. is well known. Information relating to equivalent steroid dosing (in a non-chronotherapeutic manner) may be found in the British National Formulary (BNF) 37, March 1999. The application also provides dosages and administrations of cells prepared by the methods of the application, for example, an infusion bag of CD19-directed genetically modified autologous T cell immunotherapy, comprises a suspension of chimeric antigen receptor (CAR)-positive T cells in approximately 68 mL for infusion. In some embodiments, the CAR T cells are formulated in approximately 40 mL for infusion In some embodiments, the CAR T cell product is formulated in a total volume of 35, 40, 45, 50, 55, 60, 65, 70, 75, 80, 85, 90, 95, 100, 200, 300, 400, 500, 500, 700, 800, 900, 1000 mL. In one aspect, the dosage and administration of cells prepared by the methods of the application, for example, an infusion bag of CD19-directed genetically modified autologous T cell immunotherapy, comprises a suspension of $1\times10^6$ CAR-T positive cells in approximately 40 mL. The target dose may be between about $1\times10^6$ and about $2\times10^6$ CAR-positive viable T cells per kg body weight, with a maximum of $2\times10^8$ CAR-positive viable T cells.

In some embodiments, the dosage form comprises a cell suspension for infusion in a single-use, patient-specific infusion bag; the route of administration is intravenous; the entire contents of each single-use, patient-specific bag is infused by gravity or a peristaltic pump over 30 minutes. In one embodiment, the dosing regimen is a single infusion consisting of $2.0\times10^6$ anti-CD19 CAR T cells/kg of body weight (20%), with a maximum dose of $2\times10^8$ anti-CD19 CAR T cells (for subjects ≥100 kg). In some embodiments, the T cells that make up the dose are CD19 CAR-T cells.

In some embodiments, the CD19-directed T cell immunotherapy is KTE-X19, which is prepared as described elsewhere in this application. In one embodiment, KTE-X19 may be used for treatment of MCL, ALL, CLL, SLL, and any other B cell malignancy. In some embodiment, the CD19-directed genetically modified autologous T cell immunotherapy is Axi-ce™ (YESCARTA®, axicabtagene ciloleucel) prepared by one of the methods of the application. Amounts of CAR T cells, dosage regimens, methods of administration, subjects, cancers, that fall within the scope of these methods are described elsewhere in this application, alone or in combination with another chemotherapeutic agent, with or without preconditioning, and to any of the patients described elsewhere in the application The following examples are intended to illustrate various aspects of the application. As such, the specific aspects discussed are not to be construed as limitations on the scope of the application. For example, although the Examples below are directed to T cells transduced with an anti-CD19 chimeric antigen receptor (CAR), one skilled in the art would understand that the methods described herein may apply to immune cells transduced with any CAR. It will be apparent to one skilled in the art that various equivalents, changes, and modifications may be made without departing from the scope of application, and it is understood that such equivalent aspects are to be included herein. Further, all references cited in the application are hereby incorporated by reference in their entirety, as if fully set forth herein.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, dictionaries, documents, manuscripts, genomic database sequences, and scientific literature cited herein are hereby incorporated by reference.

Other features and advantages of the disclosure will be apparent from the Drawings and the following Detailed Description, including the Examples.

EXAMPLES

Example 1

In this study, patients with R/R MCL who received 1-5 prior therapies, including a Bruton Tyrosine Kinase Inhibitor (BTKi), were treated with autologous anti-CD19 CAR-T cells.

Eligible patients (aged ≥18 years) with R/R MCL had an ECOG score of 0-1 and ≤5 prior therapies, including chemotherapy, an anti-CD20 antibody, and a BTK inhibitor (BTKi). Patients underwent leukapheresis and chemotherapy (cyclophosphamide 300 mg/$m^2$/d and fludarabine 30 mg/$m^2$/d for 3 days) followed by an infusion of CD19 CAR-T at a target dose of $2\times10^6$ CAR T cells/kg. Patients may have received bridging therapy with dexamethasone, ibrutinib, or acalabrutinib after leukapheresis and before chemotherapy. The primary endpoint was objective response rate (ORR [complete response (CR)+partial response (PR)]) according to the Lugano Classification. Interim efficacy endpoints were investigator-assessed using the revised IWG Response Criteria for Malignant Lymphoma. Key secondary endpoints were duration of response (DOR), progression-free survival (PFS), OS, frequency of adverse events (AEs), levels of CAR T cells in blood, and levels of cytokines in serum.

28 patients received CD19 CAR-T cells with ≥1 year of follow-up (median 13.2 months [range, 11.5-18.5]). Forty-three percent of patients had ECOG score of 1, 21% had blastoid morphology, 82% had stage IV disease, 50% had intermediate/high-risk MIPI, 86% received a median of 4 (range, 1-5) prior therapies, and 57% were refractory to last prior therapy. In 20/28 patients, the median Ki-67 index was 38% (range, 5%-80%). Eight patients received bridging therapy; all had disease present post-bridging. ORR was 86% (95% CI, 67%-96%) with a CR rate of 57% (95% CI, 37%-76%). 75% of responders remained in response and 64% of treated patients had ongoing responses. The 12-month estimates of DOR, PFS and OS were 83% (95% CI, 60%-93%), 71% (95% CI, 50%-84%), 86% (95% CI, 66%-94%), respectively and the medians were not reached. Grade ≥3 AEs (≥20% of patients) were anemia (54%), platelet count decreased (39%), neutropenia (36%), neutrophil count decreased (32%), white blood cell count decreased (29%), encephalopathy (25%), and hypertension (21%). Grade 3/4 cytokine release syndrome (CRS) assessed by Lee D W, et al. *Blood* 2014; 124:188 was reported in 18% of patients, manifesting as hypotension (14%), hypoxia (14%), and pyrexia (11%). Grade 3/4 neurologic events (NE) were reported in 46% of patients and included encephalopathy (25%), confusional state (14%), and aphasia (11%). No Grade 5 CRS or NE occurred. All CRS events and most NE (15/17 patients) were reversible. Median time to onset and resolution of CRS was 2 days (range, 1-7) and 13 days (range, 4-60), respectively. Median time to onset of NE was 6 days (range, 1-15) and median time to resolution was 20 days (range, 9-99). Median CAR T cell levels as measured by peak and area under the curve were 99 cells/μL (range, 0.4-2589) and 1542 cells/μL (range, 5.5-27239), respectively. Peak CAR T cell expansion was observed between Days 8 and 15 and declined over time.

Example 2

This example provided additional analysis to the studies described above. Eligible patients were aged ≥18 years with pathologically confirmed MCL with documentation of either cyclin D1 overexpression or presence of t(11;14), and were relapsed/refractory to 1-5 prior regimens for MCL. Prior therapy must have included anthracycline or bendamustine-containing chemotherapy, an anti-CD20 monoclonal antibody, and ibrutinib or acalabrutinib. All patients received prior BTKi. Although patients must have had prior BTKi therapy, it was not required as the last line of therapy before study entry, and patients were not required to be refractory to BTKi therapy. Eligible patients had an absolute lymphocyte count ≥100/μL Patients who underwent autologous SCT within 6 weeks of CD19 CAR-T infusion or had previous CD19-targeted therapy or allogeneic SCT were excluded.

Additional inclusion criteria included: at least 1 measurable lesion. Lesions that had been previously irradiated were considered measurable only if progression had been documented following completion of radiation therapy; If the only measurable disease was lymph node disease, at least 1 lymph node should have been ≥2 cm; Magnetic resonance imaging (MRI) of the brain showing no evidence of central nervous system (CNS) lymphoma; At least 2 weeks or 5 half-lives, whichever is shorter, must have elapsed since any prior systemic therapy or BTKi (ibrutinib or acalabrutinib) at the time the patient was planned for leukapheresis, except for systemic inhibitory/stimulatory immune checkpoint therapy; At least 3 half-lives must have elapsed from any prior systemic inhibitory/stimulatory immune checkpoint molecule therapy at the time the patient was planned for leukapheresis (eg, ipilimumab, nivolumab, pembrolizumab, atezolizumab, OX40 agonists, 4-1BB agonists); Toxicities due to prior therapy must have been stable and recovered to ≤Grade 1 (except for clinically non-relevant toxicities such as alopecia); Eastern Cooperative Oncology Group (ECOG) performance status of 0 or 1; Absolute neutrophil count (ANC)≥1 000/uL; Platelet count ≥75 000/uL; Absolute lymphocyte count ≥100/uL; Adequate renal, hepatic, pulmonary, and cardiac function defined as: Creatinine clearance (as estimated by Cockcroft Gault)≥60 cc/min; Serum alanine aminotransferase/aspartate aminotransferase ≤2.5 upper limit of normal (ULN); Total bilirubin ≤1.5 mg/dl, except in patients with Gilbert's syndrome; Cardiac ejection fraction ≥50%, no evidence of pericardial effusion as determined by an echocardiogram (ECHO), and no clinically relevant electrocardiogram (ECG) findings; No clinically relevant pleural effusion; Baseline oxygen saturation >92% on room air; and Females of childbearing potential must have had a negative serum or urine pregnancy test. Females who had undergone surgical sterilization or who had been postmenopausal for at least 2 years were not considered to be of childbearing potential.

Additional exclusion criteria included: History of malignancy other than nonmelanomatous skin cancer or carcinoma in situ (eg, cervix, bladder, breast) unless disease-free for at least 3 years; History of allogeneic stem cell transplantation; Prior CAR therapy or other genetically modified T-cell therapy; History of severe, immediate hypersensitivity reaction attributed to aminoglycosides; Presence of fungal, bacterial, viral, or other infection that was uncontrolled or requiring intravenous (IV) antimicrobials for management. Simple urinary tract infection (UTI) and uncomplicated bacterial pharyngitis were permitted if responding to active treatment and after consultation with the medical monitor; History of human immunodeficiency virus (HIV) infection or acute or chronic active hepatitis B or C infection. Patients with a history of hepatitis infection must have had cleared their infection as determined by standard serological and genetic testing; Presence of any in-dwelling line or drain (eg, percutaneous nephrostomy tube, in-dwelling Foley catheter, biliary drain, or pleural/peritoneal/pericardial catheter). Ommaya reservoirs and dedicated central venous access catheters, such as a Port-a-Cath or Hickman catheter, were permitted; Patients with detectable cerebrospinal fluid malignant cells or brain metastases or with a history of CNS lymphoma, cerebrospinal fluid malignant cells, or brain metastases; History or presence of CNS disorder, such as seizure disorder, cerebrovascular ischemia/hemorrhage, dementia, cerebellar disease, cerebral edema, posterior reversible encephalopathy syndrome, or any autoimmune disease with CNS involvement; History of myocardial infarction, cardiac angioplasty or stenting, unstable angina, active arrhythmias, or other clinically relevant cardiac disease within 12 months of enrollment; Patients with cardiac atrial or cardiac ventricular lymphoma involvement; History of symptomatic deep vein thrombosis or pulmonary embolism within the last 6 months of enrollment; Possible requirement for urgent therapy due to ongoing or impending oncologic emergency (eg, tumor mass effect, tumor lysis syndrome); Primary immunodeficiency; Any medical condition likely to interfere with assessment of safety or efficacy of study treatment; History of severe immediate hypersensitivity reaction to any of the agents used in this study; Live vaccine ≤6 weeks prior to planned start of conditioning regimen; Women of childbearing potential who were pregnant or breastfeeding because of the potentially dangerous effects of the preparative chemotherapy on the fetus or infant; Patients of both genders who were not willing to practice birth control from the time of consent through 6 months after the completion of the CD19 CAR-T cell treatment; In the investigator's judgment, the patient was unlikely to complete all protocol-required study visits or procedures, including follow-up visits, or comply with the study requirements for participation; and History of autoimmune disease (eg Crohn's disease, rheumatoid arthritis, systemic lupus) resulting in end organ injury or requiring systemic immunosuppression/systemic disease modifying agents within the last 2 years.

All patients underwent leukapheresis to obtain cells for CD19 CAR-T cell treatment manufacturing. The manufacturing process was modified relative to that of axicabtagene ciloleucel to remove circulating lymphoma cells through positive enrichment for CD4+/CD8+ cells. Conditioning chemotherapy with fludarabine (30 $mg/m^2$/day) and cyclophosphamide (500 $mg/m^2$/day) was administered on days −5, −4, and −3 prior to a single intravenous infusion of $2\times10^6$ CAR T cells/kg of CD19 CAR-T cells on day 0. The dose was informed from studies of axicabtagene ciloleucel in large B-cell lymphoma and CD19 CAR-T cells in acute lymphoblastic leukemia. Neelapu S S et al. *The New England journal of medicine* 2017; 377:2531; Locke F L et al. *Mol Ther* 2017; 25:285; Shah B D et al. *Journal of Clinical Oncology* 2019; 37:(suppl; abstr 7006); and Lee D W et al. *Annals of oncology: official journal of the European Society for Medical Oncology/ESMO* 2017; 28:1008PD, all of which are incorporated herein by reference in their entirety. Following leukapheresis and before conditioning therapy, patients with high disease burden were allowed to receive bridging therapy with dexamethasone or equivalent corticosteroid, ibrutinib, or acalabrutinib at the investigator's discretion, after which a repeat baseline positron emission tomography-computed tomography (PET-CT) scan was performed. The goal of bridging therapy was not to be curative but to keep patients stable through the manufacturing period. Hospitalization post-CD19 CAR-T cell infusion was required through day 7.

The primary end point was the objective response rate (ORR [complete response (CR)+partial response] (PR)) as assessed by the Independent Radiology Review Committee (IRRC) using the Lugano classification. Cheson et al., *J Cin Oncol* 2014; 32:3059-68. In order to confirm a CR, bone marrow evaluation in addition to PET-CT was required. Secondary end points included duration of response (DOR), progression-free survival (PFS), OS, investigator-assessed ORR according to Cheson, et al, *J Clin Oncol* 2007; 25:579-86, incidence of adverse events (AEs), levels of CAR T cells in blood and cytokines in serum, and change in scores over time in the European Quality of Life-5 Dimensions with 5 levels per dimension (EQ-5D-5L). CAR T-cell presence, expansion, and persistence and serum cytokines, as well as their associations with clinical outcomes, were assessed as previously reported. Kochenderfer J N et al. *J Cin Oncol* 2017; 35:1803-13; Locke F L et al. *Mol Ther* 2017; 25:285-95, both of which are incorporate herein by reference in their entirety.

Changes in EQ-5D-5L scores from baseline to month 6 were assessed. Cytokine release syndrome (CRS) was graded according to Lee et al. *Blood* 2014; 124:188, incorporate herein by reference in its entirety. Severity of AEs, including neurologic events and symptoms of CRS, was graded using the National Cancer Institute Common Terminology Criteria for Adverse Events, version 4.03. Minimal residual disease (MRD; $10^{-5}$ sensitivity) was an exploratory analysis assessed in cryopreserved peripheral blood mononuclear cells at baseline and months 1, 3, and 6, and was analyzed by next-generation sequencing using the clonoSEQ assay (Adaptive Biotechnologies, Seattle, WA.

For all patients, positron emission tomography-computed tomography (PET-CT) scans of disease-specific sites were required at baseline, 4 weeks post-infusion, and at regular intervals during the posttreatment period. A bone marrow aspirate/biopsy was required to confirm a complete response in patients with bone marrow disease involvement at baseline and in patients with indeterminate bone marrow involvement at baseline, or if no baseline bone marrow biopsy was done or the results were unavailable. Patients with symptoms of CNS malignancy had lumbar puncture performed at screening for examination of cerebral spinal fluid (CSF). Lumbar puncture was also performed as applicable for patients with new onset of Grade ≥2 neurologic toxicities after anti-CD19 CAR T-cell infusion. In addition, for patients who sign an optional portion of the consent form, lumbar puncture for CSF collection was performed at baseline prior to anti-CD19 CAR T-cell infusion and after anti-CD19 CAR T-cell infusion (Day 5±3 days); samples were submitted to the central laboratory and analyzed for changes in cytokine levels.

The primary analysis for efficacy was conducted after 60 patients were enrolled, treated, and evaluated for response 6 months after the week 4 disease assessment, as required by the protocol. This analysis had a power of ≥96% to distinguish between an active therapy with a 50% true response rate and a therapy with a response rate of ≤25% with a one-sided alpha level of 0.025. An exact binomial test was used to analyze ORR. All efficacy endpoints, including time-to-event endpoints as assessed using Kaplan-Meier estimates, were analyzed in the 60 efficacy-evaluable patients described above. Safety analyses were conducted in all treated patients (n=68). Associations between outcomes and CAR T-cell and cytokine levels were measured using the Wilcoxon rank-sum test; P values were adjusted using Holm's procedure. Full analysis set (N=74): Consisted of all enrolled/leukapheresed patients and was used for the summary of patient disposition. Safety analysis set (n=68): Defined as all patients treated with any dose of anti-CD19 CAR T cells. This analysis set was used for the summary of demographics and baseline characteristics and all analysis of safety. Inferential analysis (efficacy evaluable) set (n=60): Consisted of the first 60 treated CD19 CAR-T cell patients. This analysis set was used for the hypothesis testing of the primary endpoint of objective response rate at the time of the primary analysis, as well as all other efficacy analyses. The hypothesis for the primary endpoint was that the ORR to CD19 CAR-T cells using central assessment would be greater than the prespecified historical control rate of 25% at the 1-sided significance level of 0.025 using an exact binomial test. This hypothesis was to be tested in the inferential analysis set. The historical control rate for ORR was determined a priori based on 2 retrospective studies that were published at the time of the study protocol development. In these 2 studies, outcomes after salvage therapy were evaluated in patients with relapsed/refractory MCL who had progressed following treatment with a BTKi (a required prior therapy for study eligibility). These studies showed that patients with relapsed/refractory MCL who had ≥3 prior lines before receiving the BTKi had ORRs to salvage therapy of approximately 25%. Wang M et al. *Lancet* 2018; 391:659; Martin P et al. *Blood* 2016; 127:1559, both of which are incorporated herein by reference in their entirety.

Seventy-four patients were enrolled; CD19 CAR-T cells were manufactured for 71 and administered to 68. Primary efficacy analysis conducted after 60 patients were treated exhibited an ORR of 93% (67% complete responses). At a median follow-up of 12.3 months (range, 7.0-32.3), 57% of patients remained in remission and median duration of response was not reached. The estimated 12-month progression-free survival and overall survival rates were 61% and 83%, respectively. Common grade ≥3 adverse events were cytopenias (94%) and infections (32%). Grade ≥3 cytokine release syndrome and neurologic events occurred in 15% and 31% of patients, respectively; none were fatal. Two grade 5 infectious adverse events occurred.

CD19 CAR-T cells were manufactured for 71 patients (96%) and administered to 68 (92%). The median time from leukapheresis to delivery of CD19 CAR-T cells to the study site was 16 days (range, 11-128). One patient who had CD19 CAR-T cells manufactured was treated with bendamustine-rituximab due to rapid PD following leukapheresis, making the patient ineligible for the study. After later developing PD, the patient's original product was shipped from the manufacturing facility 127 days after the initial leukapheresis date, arriving at the treating site 1 day later. Three patients with manufacturing issues did not proceed to an additional apheresis due to AE (n=1; deep vein thrombosis), death due to progressive disease (PD; n=1), or consent withdrawal (n=1). Two additional patients discontinued prior to conditioning chemotherapy due to death from PD. After receiving conditioning chemotherapy, 1 patient with ongoing atrial fibrillation, an exclusion criterion, was deemed ineligible for CD19 CAR-T cells infusion. The median follow-up for efficacy-evaluable patients was 12.3 months (range, 7.0-32.3); 28 patients had ≥24 months of follow-up.

The median age was 65 years (range, 38-79) and 57 (84%) of patients were male. (Table 1) 65% had an ECOG performance status score of 0 and 35% of 1. Patients had high-risk features at baseline, including stage IV disease (85%), blastoid or pleomorphic morphology (31%), Ki-67 proliferation index ≥30% (40/49 [82%]) (Wang M L et al. *The Lancet Oncology* 2016; 17:48), and TP53 mutation (6/36 [17%]). Eighty-one percent of patients had received ≥3 prior lines of therapy (median, 3 [range 1-5]).

TABLE 1

Baseline patient characteristics

| Characteristic | N = 68 |
|---|---|
| Age, median (range), y | 65 (38-79) |
| ≥65 years, n (%) | 39 (57) |
| Male, n (%) | 57 (84) |
| ECOG performance status score, n (%) | |
| 0 | 44 (65) |
| 1 | 24 (35) |
| Stage IV disease, n (%) | 58 (85) |
| Bone marrow involvement, n (%) | 37 (54) |
| Splenic involvement, n (%) | 23 (34) |
| Extranodal disease, n (%)* | 38 (56) |
| Bulky disease (≥10 cm), n (%) | 7 (10) |
| Simplified MIPI, n (%)† | |
| Low risk | 28 (41) |
| Intermediate risk | 29 (43) |
| High risk | 9 (13) |
| Missing | 2 (3) |
| MCL morphology, n (%) | |
| Classical | 40 (59) |
| Pleomorphic | 17 (25) |
| Blastoid | 4 (6) |
| Other/Unknown†† | 11 (16) |
| Ki-67 proliferation index, median (range), %§ | 65 (1-95) |
| ≥30%, n/n (%) | 40/49 (82) |
| ≥50%, n/n (%) | 34/49 (69) |
| TP53 mutation, n (%) | 6/36 (17%) |
| CD19 status, n/n (%) | |
| Positive | 47/51 (92) |
| Negative | 4/51 (8) |
| Number of prior therapies, median (range) | 3 (1-5) |
| ≥3 prior lines of therapy, n (%) | 55 (81) |
| Prior therapy,¶ n (%) | |
| Anti-CD20 | 68 (100) |
| BTKi | 68 (100) |
| Ibrutinib | 58 (85) |
| Acalabrutinib | 16 (24) |
| Both | 6 (9) |
| Anthracycline or bendamustine | 67 (99) |
| Anthracycline | 49 (72) |
| Bendamustine | 37 (54) |
| Autologous SCT | 29 (43) |
| Bortezomib | 24 (35) |
| Lenalidomide | 19 (28) |
| Other investigational agent | 11 (16) |
| Venetoclax | 6 (9) |
| Relapsed/refractory subgroup, n (%) | |
| Relapsed after autologous SCT | 29 (43) |
| Refractory to last prior therapy | 27 (40) |
| Relapsed after last prior therapy | 12 (18) |
| Refractory to ibrutinib, n (%) | 38 (56) |
| Refractory to acalabrutinib, n (%) | 8 (12) |

*Excludes bone marrow and splenic involvement.
†At diagnosis.
††One patient was reported by the investigator to have kappa light chain restricted MCL at diagnosis. Morphology was reported as unknown for 10 patients.
§Ki-67 data was available for 49 patients at diagnosis.
¶Induction plus consolidation/maintenance and/or all treatments occurring between sequential complete responses was counted as 1 regimen.
BTKi, Bruton tyrosine kinase inhibitor;
ECOG, Eastern Cooperative Oncology Group;
MCL, mantle cell lymphoma;
MIPI, Mantle Cell Lymphoma International Prognostic Index;
SCT, stem cell transplant.

All patients had progressed on a BTKi (ibrutinib n=58; acalabrutinib n=16; both n=6), and 43% had prior autologous SCT (Table 2). Median time from end of last BTKi therapy excluding bridging to CD19 CAR-T cell infusion was 88 days (range, 25-1047). Forty percent of patients were refractory to last therapy, including 3 ibrutinib-intolerant patients with confirmed progression after last therapy.

Twenty-five patients (37%) received bridging therapy with ibrutinib (n=14), acalabrutinib (n=5), dexamethasone (n=12), and/or methylprednisolone (n=2). Post-bridging scans showed that most patients had tumor burden higher than the median at screening.

TABLE 2

Bridging Therapies

| Characteristic | N = 68 |
|---|---|
| Any bridging therapy, n (%) | 25 (37) |
| Ibrutinib | 14 (21) |
| Acalabrutinib | 5 (7) |
| Dexamethasone | 12 (18) |
| Methylprednisolone | 2 (3) |
| Both BTKi and steroids, n (%) | 6 (9) |
| Ibrutinib + steroid | 4 (6) |
| Acalabrutinib + steroid | 2 (3) |

BTKi, Bruton tyrosine kinase inhibitor.

The IRRC-assessed ORR among the protocol-specified 60 patients treated with CD19 CAR-T with a minimum follow-up of 7 months was 93% (95% CI, 84-98), with a 67% CR rate and 27% PR rate. High concordance (95%) was observed between IRRC-assessed and investigator-assessed ORR (Table 3).

TABLE 3

Response in Efficacy-Evaluable Patients Based on Investigator Assessment According to Cheson B D et al. *J Clin Oncol* 2007; 25: 57 and in Intent-to-Treat Patients by IRRC Review per the Lugano Classification (2014).

| n (%) | Investigator-Assessed Efficacy Evaluable N = 60 | IRRC-Assessed Intent-to-Treat N = 74 |
|---|---|---|
| Objective response rate | 53 (88) | 63 (85) |
| Complete response | 42 (70) | 44 (59) |
| Partial response | 11 (18) | 19 (26) |
| Stable disease | 5 (8) | 3 (4) |
| Disease Progression | 2 (3) | 2 (3) |
| Not Assessed* | 0 (0) | 6 (8) |
| Concordance with IRRC-assessed ORR, %† | 95 | N/A |
| Kappa coefficient (95% CI) | 0.7 (0.4-1.0) | N/A |
| Concordance with IRRC-assessed CR rate, %† | 90 | N/A |
| Kappa coefficient (95% CI) | 0.8 (0.6-0.9) | N/A |

*No assessment at the time of analysis.

†Concordance is the percentage of subjects whose IRRC-assessed read matches investigator-assessed read.

CR, complete response;

IRRC, Independent Radiology Review Committee;

N/A, not applicable;

ORR, objective response rate.

The IRRC-assessed ORR for all enrolled patients (n=74) was 85% (95% CI, 75-92), with a 59% CR rate. ORR was consistent across key subgroups, including age, relapsed/refractory subgroup, number of prior therapies, MCL morphology, disease stage, extranodal disease, bone marrow involvement, simplified MIPI, CD19 positive, tumor burden, serum lactate dehydrogenase levels, TP53 mutational status, Ki-67 index, use of tocilizumab or steroids for AE management, and use of bridging therapy. The median time to initial response was 1.0 month (range, 0.8-3.1), and the median time to CR was 3.0 months (range, 0.9-9.3). Of the 42 patients who initially achieved PR or SD, 24 patients (57%), including 21 with initial response of PR and 3 with initial response of SD, subsequently converted to a CR after a median of 2.2 months (range, 1.8-8.3) following the initial response; 18 of these 24 patients remain in remission. MRD analysis was conducted in 29/60 patients (48%); 24/29 patients (83% % [19 CR; 5PR]) were MRD negative at week 4, and 15/19 patients (79%) with available data remained MRD negative at month 6. MRD was unable to be assessed in all patients due to the lack of availability of a formalin-fixed paraffin-embedded tumor biopsy sample for calibration, which was required by the methodology and used to establish dominant rearranged IgH (VDJ or DJ), IgK, or IgL receptor gene sequences tracked over time in blood. Two patients who progressed after responding to CD19 CAR-T cells received a second infusion approximately 1 year and 2.6 years after the initial infusion; analysis of these patients is ongoing.

The median DOR has not been reached after a median follow-up of 12.3 months (Median (95% CI); Not reached (8.6, NE). The median progression free survival (95% CI) was not reached (9.2, NE). The median overall survival (95% CI) was also not reached (24.0, NE). Fifty-seven percent of all patients and 78% CR patients remain in remission. However, the first 28 patients treated had a median follow-up of 27.0 months (range; 25.3-32.3), with 43% in continued remission without additional therapy. Ongoing response rates were consistent across key covariates, including age, MCL morphology, relapsed/refractory subgroup, Ki-67 index, disease stage, extranodal disease, bone marrow involvement, simplified MIPI, TP53 mutation, CD19 positive, bridging therapy, tumor burden, and use of tocilizumab or steroids. The 3 patients with CD19− tumors at baseline achieved CR and remain in ongoing responses as of the data cutoff. The median PFS and OS were not reached, with estimated 12-month rates of 61% (95% CI, 45-74) and 83% (95% CI, 71-91), respectively. Although limited in sample size, subgroup analysis of PFS showed that the 6-month PFS rate was consistent among patients with blastoid or pleomorphic morphology, TP53 mutation, or Ki-67 index ≥50%. At the time of this analysis, 76% of all patients remain alive. Of the patients who had a response, 14 had PD. One patient who had a PR underwent allogeneic SCT.

This study showed an ORR of 93% in the protocol-specified 60 patients with relapsed/refractory MCL, all of whom had relapsed after or were refractory to BTKi therapy. This ORR included a 67% CR rate, after a single infusion. After a median follow-up of 12.3 months, the median DOR had not been reached; 57% of all patients and 78% of CR patients remained in response. Twenty-eight (28) patients treated with CD19 CAR-T cells have had a longer median follow-up of 27 months (range, 25.3-32.3), and 43% continued to be in remission without additional therapy. Response rates, including ongoing responses, were generally similar among key subgroups including patients with high-risk features. Patients with Ki-67≥50%, as well as patients with blastoid/pleomorphic morphology or TP53 mutation had high ORR and 6-month PFS rates similar to the overall population, suggesting that CD19 CAR-T cell treatment benefited patients with typically worse prognosis.

All patients who responded after CAR T-cell infusion achieved T-cell expansion. This expansion was not observed in non-responding patients, suggesting that response may have been related to sufficient CAR T cell expansion. Similar to prior studies, CAR T-cell levels correlated with ORR in the first 28 days, suggesting that higher expansion led to better and perhaps deeper responses as indicated by the >80-fold higher peak/AUC CAR T-cell levels in MRD negative compared with positive patients. Response rates were also similar regardless of whether bridging therapy was administered, and most patients with post-bridging scans (87%) had an increase in SPD compared with pre-bridging scans.

All treated patients experienced >1 AE of any grade, with grade ≥3 AEs in 99% (Table 2). The most common AEs of any grade were pyrexia (94%), neutropenia (87%), thrombocytopenia (74%), and anemia (68%). The most common grade ≥3 AEs were neutropenia (85%), thrombocytopenia (51%), anemia (50%), and infections (32%). Twenty-six percent of patients had grade 3 cytopenias present >90 days post-CD19 CAR-T cells, including neutropenia (16%), thrombocytopenia (16%), and anemia (12%). CRS occurred in 91% of patients (Table 4). No patient died due to CRS. Most cases were grade 1/2 (76%), with grade ≥3 CRS occurring in 15% of patients. The most common grade ≥3 symptoms of CRS were hypotension (22%), hypoxia (18%), and pyrexia (11%). For CRS management, 59% of patients received tocilizumab, 22% received steroids, and 16% required vasopressors. The median time after infusion to the onset of any grade and grade ≥3 CRS was 2 days (range, 1-13) and 4 days (range, 1-9), respectively; all events resolved within a median of 11 days.

TABLE 4

Adverse events, cytokine release syndrome, and neurologic events

| | N = 68 | | | | | |
|---|---|---|---|---|---|---|
| n (%)* | Any Grade | Grade 1 | Grade 2 | Grade 3 | Grade 4 | Grade 5 |
| Any adverse event | 68 (100) | 0 (0) | 1 (1) | 11 (16) | 52 (76) | 2 (3) |
| Pyrexia | 64 (94) | 14 (21) | 41 (60) | 9 (13) | 0 | 0 |
| Neutropenia | 59 (87) | 0 (0) | 1 (1) | 11 (16) | 47 (69) | 0 (0) |
| Thrombocytopenia | 50 (74) | 9 (13) | 6 (9) | 11 (16) | 24 (35) | 0 (0) |
| Anemia | 46 (68) | 0 | 12 (18) | 34 (50) | 0 | 0 |
| Hypotension | 35 (51) | 4 (6) | 16 (24) | 13 (19) | 2 (3) | 0 |
| Chills | 28 (41) | 17 (25) | 11 (16) | 0 | 0 | 0 |
| Hypoxia | 26 (38) | 2 (3) | 10 (15) | 8 (12) | 6 (9) | 0 |
| Cough | 25 (37) | 14 (21) | 11 (16) | 0 | 0 | 0 |
| Hypophosphatemia | 25 (37) | 2 (3) | 8 (12) | 15 (22) | 0 | 0 |
| Fatigue | 24 (35) | 10 (15) | 13 (19) | 1 (1) | 0 | 0 |
| Headache | 24 (35) | 15 (22) | 8 (12) | 1 (1) | 0 | 0 |
| Tremor | 24 (35) | 19 (28) | 5 (7) | 0 | 0 | 0 |
| Hypoalbuminemia | 23 (34) | 5 (7) | 17 (25) | 1 (1) | 0 | 0 |
| Hyponatremia | 22 (32) | 15 (22) | 0 | 7 (10) | 0 | 0 |
| Nausea | 22 (32) | 11 (16) | 10 (15) | 1 (1) | 0 | 0 |
| Alanine aminotransferase increased | 21 (31) | 13 (19) | 2 (3) | 5 (7) | 1 (1) | 0 |
| Encephalopathy | 21 (31) | 5 (7) | 3 (4) | 7 (10) | 6 (9) | 0 |
| Hypokalemia | 21 (31) | 12 (18) | 4 (6) | 3 (4) | 2 (3) | 0 |
| Tachycardia | 21 (31) | 14 (21) | 7 (10) | 0 | 0 | 0 |
| CRS† | 62 (91) | 20 (29) | 32 (47) | 8 (12) | 2 (3) | 0 |
| Symptoms | | | | | | |
| Pyrexia | 62 (100) | 15 (24) | 40 (65) | 7 (11) | 0 | 0 |
| Hypotension | 35 (56) | 4 (6) | 16 (26) | 14 (23) | 1 (2) | 0 |
| Hypoxia | 23 (37) | 1 (2) | 10 (16) | 8 (13) | 4 (6) | 0 |
| Chills | 21 (34) | 12 (19) | 9 (15) | 0 | 0 | 0 |
| Tachycardia | 16 (26) | 11 (18) | 5 (8) | 0 | 0 | 0 |
| Headache | 15 (24) | 7 (11) | 8 (13) | 0 | 0 | 0 |
| Alanine aminotransferase increased | 10 (16) | 5 (8) | 1 (2) | 3 (5) | 1 (2) | 0 |
| Aspartate aminotransferase increased | 9 (15) | 4 (6) | 0 (0) | 5 (8) | 0 | 0 |
| Fatigue | 9 (15) | 6 (10) | 2 (3) | 1 (2) | 0 | 0 |
| Nausea | 9 (15) | 5 (8) | 4 (6) | 0 | 0 | 0 |
| Any neurologic event | 43 (63) | 13 (19) | 9 (13) | 15 (22) | 6 (9) | 0 |
| Tremor | 24 (35) | 19 (28) | 5 (7) | 0 | 0 | 0 |
| Encephalopathy | 21 (31) | 5 (7) | 3 (4) | 7 (10) | 6 (9) | 0 |
| Confusional state | 14 (21) | 3 (4) | 3 (4) | 8 (12) | 0 | 0 |
| Aphasia | 10 (15) | 3 (4) | 4 (6) | 3 (4) | 0 | 0 |

*Included are adverse events occurring in ≥30% of patients, and symptoms of CRS and neurologic events occurring in ≥15% of patients.
†Percentages in the CRS rows were calculated out the 62 patients who experienced CRS.

Sixty-three percent of patients experienced NE (Table 4). No patient died from NE. Grade 1/2 NE occurred in 32% of patients and grade ≥3NE in 310%. Common grade ≥3NE were encephalopathy (190%), confusional state (120%), and aphasia (40%). One patient developed grade 4 cerebral edema and fully recovered with aggressive multimodality therapy including ventriculostomy. Tocilizumab and steroids were used to treat NE in 26% and 38% of patients, respectively. The median time to onset of any grade and grade ≥3 NE was 7 days (range, 1-32) and 8 days (range, 5-24), respectively. The median duration of NE was 12 days with events fully resolving in 37/43 patients (860%). As of this analysis, 4 patients had ongoing events, including grade 1 tremor (n=3), grade 2 concentration impairment (n=1), and grade 1 dysesthesia (n=1). Serious AEs occurred in 68% of patients (Table 5).

TABLE 5

| Serious Adverse Events Occurring in at Least 3 Patients | | | | | | |
|---|---|---|---|---|---|---|
| Serious adverse | N = 68 | | | | | |
| event, n (%) | Any Grade | Grade 1 | Grade 2 | Grade 3 | Grade 4 | Grade 5 |
| Any | 46 (68) | 2 (3) | 7 (10) | 20 (29) | 13 (19) | 2 (3) |
| Encephalopathy | 15 (22) | 2 (3) | 1 (1) | 6 (9) | 6 (9) | 0 |
| Pyrexia | 15 (22) | 7 (10) | 5 (7) | 3 (4) | 0 | 0 |
| Hypotension | 11 (16) | 0 | 3 (4) | 6 (9) | 2 (3) | 0 |
| Hypoxia | 8 (12) | 0 | 0 | 4 (6) | 4 (6) | 0 |
| Acute kidney injury | 5 (7) | 0 | 0 | 1 (1) | 4 (6) | 0 |
| Confusional state | 5 (7) | 0 | 0 | 5 (7) | 0 | 0 |
| Pneumonia | 5 (7) | 0 | 0 | 5 (7) | 0 | 0 |
| Anemia | 4 (6) | 0 | 0 | 4 (6) | 0 | 0 |
| Respiratory failure | 4 (6) | 0 | 0 | 0 | 4 (6) | 0 |
| Sepsis | 4 (6) | 0 | 0 | 1 (1) | 3 (4) | 0 |
| Aphasia | 3 (4) | 0 | 0 | 3 (4) | 0 | 0 |
| Pleural effusion | 3 (4) | 0 | 1 (1) | 1 (1) | 1 (1) | 0 |
| Tachycardia | 3 (4) | 0 | 3 (4) | 0 | 0 | 0 |

Thirty-two percent of patients experienced grade ≥3 infections. The most common was pneumonia (90%)(Table 6).

TABLE 6

| Infections Occurring in at Least 2 Patients | | | | | | |
|---|---|---|---|---|---|---|
| | N = 68 | | | | | |
| Infection, n (%) | Any Grade | Grade 1 | Grade 2 | Grade 3 | Grade 4 | Grade 5 |
| Any | 38 (56) | 1 (1) | 15 (22) | 17 (25) | 4 (6) | 2 (2)* |
| Upper respiratory tract infection | 9 (13) | 0 (0) | 8 (12) | 1 (1) | 0 (0) | 0 (0) |
| Pneumonia | 7 (10) | 0 (0) | 1 (1) | 6 (9) | 0 (0) | 0 (0) |
| Sinusitis | 5 (7) | 0 (0) | 5 (7) | 0 (0) | 0 (0) | 0 (0) |
| Sepsis | 4 (6) | 0 (0) | 0 (0) | 1 (1) | 3 (4) | 0 (0) |
| Oral candidiasis | 4 (6) | 0 (0) | 4 (6) | 0 (0) | 0 (0) | 0 (0) |
| Herpes zoster | 3 (4) | 0 (0) | 3 (4) | 0 (0) | 0 (0) | 0 (0) |
| Influenza | 3 (4) | 0 (0) | 3 (4) | 0 (0) | 0 (0) | 0 (0) |
| Staphylococcal bacteremia | 3 (4) | 0 (0) | 0 (0) | 2 (3) | 0 (0) | 1 (1) |
| Cytomegalovirus infection | 2 (3) | 0 (0) | 2 (3) | 0 (0) | 0 (0) | 0 (0) |
| Fungal skin infection | 2 (3) | 1 (1) | 1 (1) | 0 (0) | 0 (0) | 0 (0) |
| Cellulitis | 2 (3) | 0 (0) | 2 (3) | 0 (0) | 0 (0) | 0 (0) |
| Bronchitis | 2 (3) | 0 (0) | 1 (1) | 1 (1) | 0 (0) | 0 (0) |
| Nasopharyngitis | 2 (3) | 2 (3) | 0 (0) | 0 (0) | 0 (0) | 0 (0) |
| Tooth infection | 2 (3) | 0 (0) | 0 (0) | 2 (3) | 0 (0) | 0 (0) |

*One patient died from staphylococcus bacteremia. One patient died from organizing pneumonia (developed acute kidney injury in the setting of infection and during autopsy was found to have a previously undiagnosed pulmonary embolism in addition to organizing pneumonia).

Two cases of grade 2 cytomegalovirus infection occurred (3). Grade 3 hypogammaglobulinemia and grade 3 tumor lysis syndrome occurred in 1 patient each (1%). Twenty-two patients (320%) received intravenous immunoglobulin therapy. No cases of replication-competent retrovirus, EBV-associated lymphoproliferation, hemophagocytic lymphohistiocytosis, or CD19 CAR-T cells-related secondary cancers were reported. EQ-5D scores revealed decrements from baseline in patient-reported health-related quality of life at week 4, yet improvements in mobility, self-care, usual activities, and overall health (EQ-5D visual analogue scale) were observed by month 3, with overall health returning to baseline or better in most patients by month 6 (Table 7).

TABLE 7

| EQ-5D Summary by Visit | | | | |
|---|---|---|---|---|
| EQ-5D | Screening | Week 4 | Month 3 | Month 6 |
| Mobility, n/n (%) | | | | |
| Patients reporting no problems | 53/62 (85) | 25/51 (49) | 37/54 (69) | 30/40 (75) |
| Patients with deterioration from screening | N/A | 21/51 (41) | 13/54 (24) | 8/40 (20) |

TABLE 7-continued

EQ-5D Summary by Visit

| EQ-5D | Screening | Week 4 | Month 3 | Month 6 |
|---|---|---|---|---|
| Self-care, n/n (%) | | | | |
| Patients reporting no problems | 59/62 (95) | 35/52 (67) | 45/54 (83) | 37/40 (93) |
| Patients with deterioration from screening | N/A | 16/52 (31) | 9/54 (17) | 3/40 (8) |
| Usual activity, n/n (%) | | | | |
| Patients reporting no problems | 53/65 (82) | 22/51 (43) | 38/55 (69) | 30/41 (73) |
| Patients with deterioration from screening | N/A | 25/51 (49) | 13/55 (24) | 8/41 (20) |
| Pain/Discomfort, n/n (%) | | | | |
| Patients reporting no problems | 43/65 (66) | 34/54 (63) | 33/55 (60) | 28/42 (67) |
| Patients with deterioration from screening | N/A | 9/54 (17) | 13/55 (24) | 5/42 (12) |
| Anxiety/Depression, n/n (%) | | | | |
| Patients reporting no problems | 49/65 (75) | 36/54 (67) | 38/55 (69) | 26/42 (62) |
| Patients with deterioration from screening | N/A | 11/54 (20) | 12/55 (22) | 10/42 (24) |
| EQ-5D VAS* | | | | |
| n | 65 | 52 | 55 | 42 |
| Mean (SD) | 82.0 (15.4) | 74.5 (15.6) | 80.1 (15.6) | 84.8 (17.5) |
| Median (range) | 85 (75-95) | 78 (60-89) | 83 (70-92) | 90 (80-95) |
| VAS reduced by ≥10 from screening, n/n (%) | N/A | 26/52 (50) | 16/55 (29) | 5/42 (12) |

*EQ-5D visual analogue scale (VAS) assesses overall health on a scale from 0 to 100, with higher scores indicating better health status.
EQ-5D, European Quality of Life-5 Dimensions;
N/A, not applicable;
SD, standard deviation Sixteen patients (24%) who received CD19 CAR-T cells died, primarily from PD (n=14 [21%]). Two patients had grade 5 AEs (3%), including 1 patient with organizing pneumonia related to conditioning chemotherapy, and 1 patient with *staphylococcus* bacteremia that was related to conditioning chemotherapy and CD19 CAR-T cell treatment.

The median time to peak anti-CD19 CAR T-cell levels was 15 days (range, 8-31) after CD19 CAR-T cell infusion and cells were still detectable at 24 months in some patients with evaluable samples at the time of data cutoff (6/10 [60%]) in the presence of normal median B-cell levels. CAR T cell persistence in blood over time as measured by qPCR showed a decline over time in patients with ongoing response and those who relapsed.

The rapid expansion, resolution to baseline, and clearance over time are consistent with the known mechanism of action of anti-CD19 CAR T cells harboring CD28 and CD3ζ costimulatory domains. All 4 patients with no response to CD19 CAR-T cell treatment had detectable B-cells at baseline; none experienced B-cell aplasia at any point on study. While there was no association with baseline tumor burden, expansion was associated with response (P=0.0036), with an area under the curve (AUC) and peak that were >200-fold higher among responders vs non-responders, with a similar trend among MRD-negative vs -positive patients at week 4. For both CRS and NE, expansion was greater in patients with grade ≥3 vs those with grade ≤2 events and the highest peak and AUC were noted in patients who received tocilizumab±steroids post-CD19 CAR-T cell infusion. Median time to peak for evaluated cytokines was 8 days; most resolved to baseline levels by 28 days. Serum granulocyte-macrophage colony-stimulating factor and interleukin (IL)-6 were associated with grade ≥3 CRS and NE. Serum ferritin was associated only with grade 3 CRS, whereas serum IL-2 and interferon-γ were associated only with grade ≥3 NE. In addition, cerebrospinal fluid cytokine analysis revealed higher levels of C-reactive protein, ferritin, IL-6, IL-8, and vascular cell adhesion molecule 1 in patients with grade ≥3 NE. Induction of anti-CAR antibodies was not observed in any patient.

Rates of grade ≥3 CRS and NE were similar to those previously reported with anti-CD19 CAR T-cell therapies in aggressive NHL. Neelapu S S et al. *The New England journal of medicine* 2017; 377:2531; Schuster S J et al. *The New England journal of medicine* 2019; 380:45. There were no deaths due to CRS or NE, and most symptoms occurred early in treatment and were generally reversible, with no long-term clinical sequelae impairing activities of daily living. The associations observed between peak serum cytokines and Grade ≥3 CRS and/or Grade ≥3 neurologic events suggeste a role for CD19 CAR-T cells in these toxicities, given that they were observed commensurate with rising and peak levels of CAR T cells in blood. Associations of peak levels of CAR and myeloid-cell-related serum cytokines, chemokines, and effector molecules with toxicity are consistent with previously published data using a similar CAR construct in the setting of NHL.[10,13] One case of grade 4 cerebral edema occurred, but the patient fully recovered and remains in CR at 24-months follow-up with no unresolved neurological sequelae. Patient-reported outcomes similarly suggest no long-term quality-of-life deficits following CD19 CAR-T cells therapy.

Example 3

This example provided additional analysis to the studies described above. Eligible patients (aged ≥18 years) with R/R MCL had an ECOG score of 0-1 and ≤5 prior therapies, including chemotherapy, an anti-CD20 antibody, and a BTKi. Patients underwent leukapheresis and conditioning chemotherapy (cyclophosphamide 300 mg/m2/d and fludarabine 30 mg/m2/d for 3 days, on Days −5, −4, −3) followed by a single infusion of CD19 CAR-T cells at a target dose of $2\times10^6$ CAR T cells/kg, by single IV infusion on Day 0. The CD19 CAR construct contains a CD3ζ T cell activation domain and CD28 signaling domain. The manufacturing process removed circulating CD19-expressing leukemia cells from the leukapheresis product. Sabatino M, et al. *Blood* 2016; 128:1227.

Some patients received bridging therapy with dexamethasone (20-40 mg or equivalent PO or IV daily for 1-4 days), ibrutinib (560 mg PO daily), or acalabrutinib (100 mg PO twice daily), administered after leukapheresis and completed ≤5 days before initiating conditioning chemotherapy; PET-CT was required post-bridging. The primary endpoint was objective response rate (ORR [complete response (CR)+ partial response]). Key secondary endpoints were duration of response (DOR), progression-free survival (PFS), OS, frequency of adverse events (AEs), levels of CAR T cells in blood, and levels of cytokines in serum. Efficacy and safety analyses included all patients who received CD19 CAR-T cell therapy.

The key inclusion criteria included R/R MCL defined as disease progression after last regimen or failure to exhibit a CR or PR to the last regimen; one to five prior therapies that must have included an anthracycline- or bendamustine-containing chemotherapy and anti-CD20 monoclonal antibody therapy and Ibrutinib or acalabrutinib; ≥1 measurable lesion; age ≥18 years; ECOG of 0 or 1; and adequate bone marrow, renal, hepatic, pulmonary, and cardiac function. Key exclusion criteria included prior autologous stem cell transplant (alloSCT); prior CD19-targeted therapy; prior CAR T cell therapy; clinically relevant infection; and history of or current CNS involvement by MCL or other CNS disorders.

A total of 68 patients received CD19 CAR-T cell therapy. Presented here are the updated safety (68 patients) and efficacy (60 patients) results, with median follow-up of 12.3 months [range 7.0-32.3]). A total of 28 patients (47%) had ≥24 months follow-up. The median time to initial response was 1.0 months [range 0.8-3.1] and to complete response was 3.0 months [range 0.9-9.3]. A total of 24 patients (40%) converted from PR/SD to CR, with 21 (35%) converting from PR to CR and 3 patients (5%) converting from SD to CR.

The median age was 65 years (range, 38-79) and 39 (57%) of patients were male. One hundred percent (100%) of patients had ECOG score of 0/1, 25% had blastoid morphology, 85% had stage IV disease, 56% had intermediate/high-risk MIPI, 81% received 3 or more prior therapies, with a median of 3 (range, 1-5) prior therapies, 99% received prior anthracycline or bendamustine, 100% received prior anti-CD20 monoclonal antibody, and 100% received prior BTKi (85% ibrutinib, 24% acalabrutinib, and 9% both). Forty-three (43%) of the patients had relapsed after autoSCT, 56% were refractory to ibrutinib, and 12% were refractory to acalabrutinib. In 34/49 of the patients with available data, the Ki-67 index was ≥50%. Twenty-five (37%) of the patients received bridging therapy (21% ibrutinib, 7% acalabrutinib, 18% dexamethasone, 3% methylprednisolone, 9% both BTKi and steroids, 6% ibrutinib and steroid, 3% acalabrutinib and steroid); 23/25 patients had post-bridging PET-CT to document measurable disease before CD19 CAR-T cell infusion (20/23 had an increase in SPD $mm^2$ from screening; 3/23 had a slight decrease in SPD $mm^2$ from screening).

A high ORR was observed in both efficacy-evaluable and ITT patients. 95% concordance for ORR; 90% concordance for CR. The investigator-assessed ORR in 60 efficacy-evaluable patients was 88% (95% CI, 77%-95%) with a CR rate of 70% (95% CI, 57%-81%) and a PR rate of 18% (95% CI, 10%-30%). ORR in 60 efficacy-evaluable patients by IRRC assessment was 93% (95% CI, 84%-98%) with a CR rate of 67% (95% CI, 53%-78%), and a PR rate of 27% (95% CI, 16%-40%). ORR was consistent across key subgroups (age, MCL morphology, Ki-67 index, disease stage, simplified MIPI, steroid use for AE management, tocilizumab use, and bridging therapy use). The investigator-assessed ORR in ITT patients was 80% (95% CI, 69%-88%) with a CR rate of 59% (95% CI, 47%-71%) and a PR rate of 20% (95% CI, 12%-31%). ORR in ITT patients by IRRC assessment was 85% (95% CI, 75%-92%) with a CR rate of 59% (95% CI, 47%-71%), and a PR rate of 26% (95% CI, 16%-37%).

The median DOR had not been reached after a median follow-up of 12.3 months. Fifty-seven percent (57%) of all patients and 78% of patients with a CR remained in remission. The first 28 patients treated had a median follow-up of 27.0 months (range, 25.3-32.3), 43% of which remained in continued remission without additional therapy. Median PFS and median OS were not reached after a median follow-up of 12.3 months. The 12-month PFS rate (95% CI) was 61% (45%-74%). The 12-month OS rate (95% CI) was 83% (71%-91%).

More than 35% of the patients had treatment-emergent adverse events (0% Grade 1; 1% Grade 2; 16% Grade 3; 76% Grade 4, and 3% Grade 5). The most common Grade ≥3 AEs (≥20% of patients) were neutropenia (69%, grade 4), thrombocytopenia (35%, grade 4), anemia (50%, grade 3), hypophosphatemia (22%, grade 3). No patient died from cytokine release syndrome (CRS). Grade ≥3 CRS, assessed by Lee D W, et al. *Blood.* 2014, 124:188, was reported in 15% of patients. Most common symptoms of any grade of CRS were hypotension (51%), hypoxia (34%), and pyrexia (91%). Adverse event management included tocilizumab (59%) and corticosteroids (22%). The median time to onset was 2 days (range 1-13), the median duration was 11 days, and 62/62 (100%) of the patients with any grade CRS had resolved events.

Neurologic events (NE) of any grade were reported in 63% of patients (31% had Grade ≥3 NE) and included encephalopathy (31%), confusional state (21%), and tremor (35%). No patient died from neurologic events. One patient had Grade 4 cerebral edema that fully resolved with aggressive multimodality therapy including ventriculostomy and IV rabbit, anti-thymocyte globulin (ATG). All CRS events and most NE (37/43 patients) were reversible. Median time to onset and duration of NE was 7 days (range, 1-32) and 12 days, respectively.

A higher peak level of CAR T cells was associated with responders than with non-responders (Objective Response). A higher peak level of CAR T cells was associated with negative than with positive MRD at week 4. The median time to peak anti-CD19 CAR T cell levels after CD19 CAR-T cell infusion was 15 days (range, 8-31). Anti-CD19 CAR T cells were detectable at 24 months in most patients with evaluable samples (6/10 [60%]). Expansion was associated with response and MRD status. Expansion was greater in patients with Grade ≥3 vs ≤2 CRS and neurologic events.

Several associations were observed between peak serum biomarker levels and toxicity. Analytes associated with Grade ≥3 CRS included IL-15, IL-2 Rα, IL-6, TNFα, GM-CSF, ferritin, IL-10, IL-8, MIP-1a, MIP-1b, granzyme A, granzyme B, and perforin. Analytes associated with Grade ≥3 neurologic events included IL-2, IL-1 Rα, IL-6, TNFα, GM-CSF, IL-12p40, IFN-γ, IL-10, MCP-4, MIP-1b, and granzyme B. And the analytes associated with both Grade ≥3 CRS and neurologic events included IL-6, TNFα, GM-CSF, IL-10, MIP-1b, and granzyme B.

The CD19 CAR-T cell treatment described herein, administered in a single infusion, showed high rates of durable responses in R/R MCL. The 93% ORR, which included a 67% CR rate, is the highest reported rate of disease control in patients with prior BTKi failure. Of the initial 28 patients treated, 43% remained in remission after ≥24 months of follow-up. The safety profile is consistent with that reported in prior studies of anti-CD19 CAR T cell therapies in aggressive NHL No deaths due to CRS or neurologic events; most symptoms occurred early in treatment and were generally reversible. The efficacy, reliable and rapid manufacturing, and manageable toxicities identify a role for the CD19 CAR-T cell treatment described herein in treating patients with R/R MCL who have an unmet medical need.

Example 4

This example provides additional analysis of the clinical studies described above. Eligible patients were aged ≥18 years with pathologically confirmed MCL with documentation of either cyclin D1 overexpression or presence of t(11;14), and were relapsed/refractory to 1-5 prior regimens for MCL. Prior therapy must have included anthracycline or bendamustine-containing chemotherapy, an anti-CD20 monoclonal antibody, and ibrutinib or acalabrutinib. All patients received prior BTKi. Although patients must have had prior BTKi therapy, it was not required as the last line of therapy before study entry, and patients were not required to be refractory to BTKi therapy. Eligible patients had an absolute lymphocyte count ≥100/μL Patients who underwent autologous SCT within 6 weeks of CD19 CAR-T infusion or had previous CD19-targeted therapy or allogeneic SCT were excluded. All patients underwent leukapheresis to obtain cells for CD19 CAR-T cell treatment manufacturing. Patients received optional bridging therapy, which included dexamethasone (20-40 mg or equivalent PO or IV daily for 1-4 days), ibrutinib (560 mg by mouth (PO) daily), or acalabrutinib (100 mg PO twice daily). The manufacturing process was modified relative to that of axicabtagene ciloleucel to remove circulating lymphoma cells through positive enrichment for $CD4^+/CD8^+$ cells. This product is referred to herein as "the CAR T cells." This product may also be identified as KTE-X19. Conditioning chemotherapy with fludarabine (30 mg/$m^2$/day) and cyclophosphamide (500 mg/$m^2$/day) was administered on days −5, −4, and −3 prior to a single intravenous infusion of $2\times10^6$ CAR T cells/kg of CD19 CAR-T cells on day 0. More details about patient treatment can be found in Example 2.

The goals of this study were two-fold. First, to compare the pharmacological profile of the CAR T product in lower- and higher-risk patients in the clinical trial ZUMA-2, defined by TP53, (tumor protein p53) gene mutation status and Ki-67 tumor proliferation index. Patients with high-risk MCL characteristics, including tumor protein p53 gene (TP53) mutation and high Ki-67 proliferation index, typically have a poor prognosis with current standard therapies. Cheah C Y, et al. *J Clin Oncol.* 2016; 34:1256-1269. Lower-risk patients in this analysis had a Ki-67 proliferation index <50% (by central evaluation) or wild-type TP53; higher-risk patients had Ki-67≥50% or TP53 mutation by next generation sequencing. In the primary efficacy analysis of ZUMA-2 (N=60), the ORR was 93% (67% CR) after a median follow-up of 12.3 months. 57% of all patients and 78% of patients in CR had ongoing responses. The ORR was generally comparable between lower- and higher-risk patients in ZUMA-2, including in patients with Ki-67 proliferation index < or ≥50% and unmutated vs mutated TP53. Wang M, et al. *New Engl J Med.* 2020; 382:1331-1342.

The second goal was to characterize the pharmacodynamic profile in patients who achieved early (Day 28) Minimal residual disease (MRD)-negative status and those with Grade 4 neurotoxicity. In a previous analysis of ZUMA-2 results, CAR T cell levels in blood by peak and area under the curve (AUC) on Days 0-28 were associated with ORR (including undetectable MRD) and Grade ≥3 CRS and neurologic events. Wang M, et al. *New Engl J Med.* 2020; 382:1331-1342. In that analysis, CRS and neurologic events were mostly reversible (N=68 treated patients): 15% had Grade ≥3 CRS; 31% had Grade ≥3 neurologic events; and two had Grade 5 AEs (one of which was CAR T product-related). MRD ($10^{-5}$ sensitivity) was assessed by next-generation sequencing, as previously reported. Wang M, et al. *New Engl J Med.* 2020; 382:1331-1342.

This update reports pharmacology data for all 68 patients in ZUMA-2 who were treated with the CAR T cells Product attributes, CAR T cell levels in blood, and cytokine levels in serum, and their associations with clinical outcomes, were analyzed by using previously described methods. Locke F L, et al. *Mol Ther.* 2017; 25:285-295. Wilcoxon rank-sum test was used to measure associations between subgroup outcomes and CAR T cell and cytokine levels. P values were not adjusted for multiple testing.

CAR T cell product attributes were generally comparable across prognostic groups defined by Ki-67 proliferation index and TP53 mutation status. There was a trend toward more differentiated phenotypes in the high-Ki-67 subgroup, and CD4-based phenotypes in patients with TP53 mutation. (Table 8).

TABLE 8

| | Treated | Ki-67 Proliferation Index | | TP53 | |
|---|---|---|---|---|---|
| Median (range) | Patients[a] (n = 65) | <50% (n = 14) | ≥50% (n = 34) | Mutation (n = 6) | Nonmutation (n = 30) |
| CD4/CD8 Ratio | 0.7 (0.04, 3.7) | 0.8 (0.4, 1.7) | 0.7 (0.04, 3.7) | 1.2 (0.7, 3.7) | 0.7 (0.04, 1.9) |
| Naive T cells, % | 24.5 (0.3, 80.7) | 30.4 (11.0, 57.0) | 20.1 (0.3, 68.8) | 23.0 (11.8, 46.5) | 25.2 (0.3, 78.1) |
| Central memory T cells, % | 12.8 (2.3, 51.6) | 10.1 (8.4, 45.0) | 12.0 (2.3, 51.6) | 13.2 (6.0, 51.6) | 10.2 (2.3, 45.0) |

TABLE 8-continued

| Median (range) | Treated Patients[a] (n = 65) | Ki-67 Proliferation Index <50% (n = 14) | ≥50% (n = 34) | TP53 Mutation (n = 6) | Nonmutation (n = 30) |
|---|---|---|---|---|---|
| Effector memory T cells, % | 24.5 (0.8, 70.3) | 19.4 (6.3, 56.1) | 29.1 (5.8, 70.3) | 25.9 (7.0, 38.2) | 29.4 (2.2, 70.3 |
| Effector T cells, % | 28.7 (2.8, 65.2) | 23.7 (11.5, 49.30) | 32.4 (2.8, 65.2) | 29.1 (2.8, 44.7) | 29.1 (8.4, 54.5) |

[a]Of all 68 treated patients, product characteristic data were available for 65 total patients. Product characteristic data were available for 48/49 total patients with Ki-67 data available and for all 36 patients with TP53 mutation data available.
TP53, tumor protein p53 gene There was also comparable CAR T cell expansion in groups with different prognostic factors defined by Ki-67 proliferation index and TP53 mutation status. Both peak levels and AUC of CAR T cells in the blood after administration were comparable in patients with wild-type vs mutated TP53 or Ki-67 proliferation index <50% vs ≥50%, which was consistent with the comparable efficacy in these subgroups. The primary endpoint of objective response rate (ORR) in patients was shown in Table 9. The median time to response was 28 days (range: 24 to 92 days) with a median follow-up time of 12.3 months. 28 patients had potential follow-up for ≥24 months and 12 of these patients remained in remission. Efficacy was established based on complete response and duration of response (DOR).

The ORR was 100% vs 94% in patients with Ki-67 proliferation index <50% vs ≥50% whereas the CR rate was 64% vs 78% in patients Ki-67 proliferation index <50% vs ≥50%. Table 9. The number of patients with available data for Ki-67 proliferation index was 49.

TABLE 9

| | ORR (95% CI), % | CR Rate (95% CI), % |
|---|---|---|
| Ki-67 PI < 50% | 100 (77-100) | 64 (35-87) |
| Ki-67 PI ≥ 50% | 94 (79-99) | 78 (60-91) |

The ORR was 100% for both in patients with wild-type vs mutated TP53 whereas the CR rate was 67% vs 100% in wild-type vs mutated TP53. Table 10. The number of patients with available data for TP53 was 36. All six patients with TP53 mutation and all 30 patients with no mutation responded. Among the six patients with TP53 mutation, three had Grade ≥3 neurotoxicity and two had Grade ≥3 CRS

TABLE 10

| | ORR (95% CI), % | CR Rate (95% CI), % |
|---|---|---|
| TP53 mutation | 100 (54-100) | 100 (54-100) |
| TP53 nonmutation | 100 (88-100) | 67 (47-83) |

Up to 44 biomarkers in serum were measured pretreatment, at Day 0, and at various time points through Day 28 post CAR T cell infusion, including IL (interleukins); INF-γ (interferon gamma), MCP-1 (monocyte chemoattractant protein-1), IL-2Rα (IL-2 receptor alpha), sPD-L1 (soluble programmed death-ligand 1) and sVCAM (soluble vascular cell adhesion molecule). The pharmacodynamic profile for the two prognostic groups with Ki-67 proliferation index <50% vs ≥50% was comparable with regard to proliferative (IL-15, IL-2), inflammatory (IL-6, L-2Rα, sPD-L1 and VCAM-1), immune-modulating (IFN-γ, IL-10), chemokine (IL-8 and MCP-1)), and effector cytokines (Granzyme B). In addition, there was a trend for increased proliferative (IL-15, IL-2) and inflammatory (IL-6, IL-2Rα, sPD-L1 and VCAM-1) cytokine levels in patients with mutated TP53 vs wild-type TP53. FIGS. 1A-1F.

There was also an increase in the peak levels of select cytokines in serum among patients who achieved MRD-negative status. MRD was analyzed in 29 of 68 patients (43%); 24 of these patients (83% [19 patients with a complete response and 5 with a partial response]) were MRD negative at one month post CAR T cell administration. At one month post CAR T cell administration, MRD negative (n=24/29) vs -positive patients (n=5/29) had increased median peak levels of interferon (IFN)-γ and interleukin (IL)-6 and a trend towards increased IL-2. Cytokine levels peaked in serum within 7 days of treatment. Consistent trends were seen for PD-L1 and Granzyme B. Increased peak CAR T cell levels, measured within 14 days posttreatment, were also seen in patients who were MRD negative at 1 month. FIGS. 2A-2I.

Six patients developed Grade 4 neurologic events, including one with cerebral edema. Three patients had concurrent Grade 4 CRS. Patients with Grade 4 neurologic events showed increased peak levels of proinflammatory serum biomarkers (e.g., IFNγ, MCP-1, TNF-α, IL-2 and IL-6) compared to patients without neurologic events.

The cerebral edema was completely resolved following aggressive multimodality therapy. Wang M, et al. *New Engl J Med.* 2020; 382:1331-1342. Expansion of CAR T cells and peak serum levels of IL-2 were highest in this patient; the rise in multiple cytokines was several-fold higher in this patient compared with the median of other study/ZUMA-2 patients. Table 11.

TABLE 11

| | Patient With Cerebral Edema | | Other ZUMA-2 Patients (n = 67), Median (IQR) | |
|---|---|---|---|---|
| | Baseline (Day 0) | Peak (Post CAR T cell administration) | Baseline (Day 0) | Peak (Post CAR T cell administration) |
| CAR T cell levels, cells/μL | 0 | 431.3 | 0 | 83.1 (17.2-264.3)[a] |
| IFN-γ, pg/mL | 7.5 | 584.4 | 7.5 (7.5-17.7) | 411.2 (144.8-1876) |
| MCP-1, pg/mL | 462.6 | 1500 | 882.9 (557.2-1164.8) | 1084.3 (804.2-1500) |
| TNFα, pg/mL | 1.9 | 10.4 | 5.7 (3.2-10.6) | 9.5 (5.5-23.2) |
| sVCAM-1, ng/mL | 527.5 | 1659.7 | 1195.9 (791.7-2533.1) | 1900.7 (1032.4-3646.7) |
| IL-2, ng/mL | 0.9 | 16.7 | 0.9 (0.9-0.9) | 6.0 (3.0-14.4) |
| IL-6, pg/mL | 1.6 | 159.5 | 1.6 (1.6-6.4) | 87.9 (12.9-879.1) |
| CRP, mg/L | 6.8 | 18.2 | 30.5 (15.1-63.0) | 119.4 (54.6-173.8) |
| Ferritin, ng/mL | 606.3 | 824.2 | 502.4 (273.5-877.7) | 1265 (597.8-2970.1) |
| IL-15, ng/mL | 29.1 | 56.1 | 33.2 (25.4-48) | 38.4 (29.7-61.7) |

[a]Out of 66 patients with available data.

CAR T cell pharmacokinetic and pharmacodynamic profiles were comparable across MCL patient groups with different prognostic marker status associated with lower and higher risk (defined by Ki-67 and mutated TP53), consistent with comparable clinical response rates. There was a trend toward higher levels of proinflammatory markers in patients with mutated TP53.

The pharmacodynamic profile of CAR T cell administration was associated with efficacy (MRD status at 1 month) and Grade 4 treatment-emergent neurologic events. The patient who developed cerebral edema had the highest peak CAR T cell levels and serum L-2, as well as elevated proinflammatory markers posttreatment.

Example 5

A Phase 2 single-arm clinical study was conducted for a CD19-directed genetically modified autologous T cell immunotherapy treating patients with relapsed or refractory mantle cell lymphoma (MCL) who had received one or more prior treatment (which may have included an anti-CD20 antibody, anthracycline- or bendamustine-containing chemotherapy, and/or a Bruton tyrosine kinase inhibitor (BTKi) such as ibrutinib or acalabrutinib). Eligible patients also had disease progression after their last treatment or refractory disease to their most recent treatment. The study excluded patients with active or serious infections, prior allogeneic hematopoietic stem cell transplant (HSCT), detectable cerebrospinal fluid malignant cells or brain metastases, and any history of central nervous system (CNS) lymphoma or CNS disorders.

Patient's peripheral blood mononuclear cells were obtained via a leukapheresis procedure. The mononuclear cells were enriched for T cells by selection for CD4+ and CD8+ cells, activated with anti-CD3 and anti-CD28 antibodies in the presence of IL-2, then transduced with a replication-incompetent viral vector containing FMC63-28Z CAR, a chimeric antigen receptor (CAR) comprising an anti-CD19 single-chain variable fragment (scFv), CD28 and CD3-zeta domains. Without being bound to any hypothesis, selection for CD4+ and CD8+ cells may have reduced potential circulating CD19-expressing tumor cells in patients' leukapheresis material to be included during the ex vivo manufacturing process. The T cell product of this process may be identified as KTE-X19. The anti-CD19 CAR T cells were expanded, washed, formulated into a suspension, and cryopreserved. Prior to receiving the anti-CD19 CAR T cell therapy, patients were treated with a lymphodepleting chemotherapy regimen of cyclophosphamide 500 mg/m$^2$ intravenously and fludarabine 30 mg/m$^2$ intravenously on each of the fifth, fourth, and third days before infusion of CAR T-cells; patients may also have received acetaminophen and diphenhydramine or another H1-antihistamine approximately 30 to 60 minutes prior to infusion of anti-CD19 CAR T cells. Prophylactic use of systemic corticosteroids was avoided as it may interfere with the activity of CAR T cells.

The target dose was $2\times10^6$ CAR positive viable T cells or anti-CD19 CAR T cells per kg body weight, with a maximum of $2\times10^8$ anti-CD19 CAR T cells (for patients 100 kg and above) cells. 68 patients received a single infusion (by either gravity or a peristaltic pump for approximately 30 minute) of anti-CD19 CAR T cells, and 60 of these patients were followed for at least 6 months after their Week 4 disease assessment, qualifying them as efficacy-evaluable. 56 patients received $2\times10^6$ anti-CD19 CAR T cells/kg; 1 patient received a dose of $1\times10^6$ anti-CD19 CAR T cells/kg, 1 patient received a dose of $1.6\times10^6$ anti-CD19 CAR T cells/kg, 2 patients received a dose of $1.8\times10^6$ anti-CD19 CAR T cells/kg, and −2 patients received a dose of $1.9\times10^6$ anti-CD19 CAR T cells/kg. Of these 60 patients, the median age was 65 years (range: 38 to 79 years), 51 were male, and 56 were white. 50 patients had stage IV disease. Based on the simplified Mantle Cell Lymphoma International Prognostic Index (s-MIPI), 25 patients were classified as low risk, 25 patients were classified as intermediate risk, 8 patients was classified as high risk, and 2 patients had an unknown risk status. 20 patients had baseline bone marrow examinations performed per protocol; of these, 10 were negative, 8 were positive, and 2 were indeterminate. The median number of prior therapies among all 60 efficacy-evaluable patients was 3 (range: two to five). 26 patients had relapsed after or were refractory to autologous HSCT. 21 patients had relapsed after their last therapy for MCL, while 36 patients were refractory to their last therapy for MCL. 14 patients had blastoid MCL. Following leukapheuresis and prior to infusion of anti-CD19 CAR T cells, 21 patients received bridging therapy. 19 were treated with a BTKi, 14 patients were treated with corticosteroid, and 6 patients were treated with both a BTKi and a corticosteroid. 53 patients received a lymphodepleting chemotherapy regimen of cyclophosphamide 500 mg/m$^2$ intravenously and fludarabine 30 mg/m$^2$ intravenously, both given on each of the fifth, fourth, and third days prior to anti-CD19 CAR T therapy (day 0). The remaining 7 patients received the same dosage of lymphodepleting chemotherapy over 4 or more days prior to CAR T therapy. The primary endpoint of objective response rate (ORR) in patients was shown in Table 12. The median time to response was 28 days (range: 24 to 92 days) with a median follow-up time of 12.3 months. Twenty-eight patients had potential follow-up for ≥24 months and twelve of these patients remained in remission. Efficacy was established based on complete response and duration of response (DOR).

TABLE 12

| | Efficacy-Evaluable Patients N = 60 | Leukapheresed Patients N = 74 |
|---|---|---|
| Response Rate | | |
| Objective Response Rate (ORR) [95% CI] | 52 [75, 94] | 59 [69, 88] |
| Complete Remission (CR) Rate [95% CI] | 37 [48, 74] | 41 [43, 67] |
| Partial Remission (PR) Rate [95% CI] | 15 [15, 38] | 18 [15, 36] |
| Duration of Response (DOR) [a] | | |
| Median in months [95% CI] Range in months | NR [8.6, NE] $0.0^b$, $29.2^b$ | NR [11.8, NE] $0.0^b$, $29.2^b$ |
| DOR, if best response is CR, median in months [95% CI] Range in months | NR [13.6, NE] $1.9^b$, $29.2^b$ | NR [13.6, NE] $0.0^b$, $29.2^b$ |
| DOR, if best response is PR, median in days [95% CI] Range in months | 2.2 [1.5, 5.1] $0.0^b$, $22.1^b$ | 4.2 [1.5, 5.1] $0.0^b$, $22.1^b$ |
| Median Follow-up for DOR in months | 8.6 | 8.1 |

CI, confidence interval; NE, not estimable; NR, not reached; PR, partial remission.
[a] Among all responders. DOR is measured from the date of first objective response to the date of progression or death.
[b] A censored value.

CRS (cytokine release syndrome) was observed in 75 out of 82 patients, including ≥Grade 3 (Lee grading system1) CRS in 15 out of 82 patients. The median time to onset of CRS was 3 days (range: 1 to 13 days) and the median duration of CRS was 10 days (range: 1 to 50 days). Among patients with CRS, key manifestations (i.e., manifestations that occurred in >10% of the patients) included fever (99% of the patients), hypotension (60% of the patients), hypoxia (37% of the patients), chills (33% of the patients), tachycardia (37% of the patients), headache (24% of the patients), fatigue (19% of the patients), nausea (13% of the patients), alanine aminotransferase increased (13% of the patients), aspartate aminotransferase increased (12% of the patients), and diarrhea (11% of the patients). Serious events associated with CRS included hypotension, fever, hypoxia, acute kidney injury, and tachycardia. In response to CRS, patients may have received tocilizumab and/or corticosteroids per the indications in Table 13.

TABLE 13

| CRS Grade[a] | Tocilizumab | Corticosteroids |
|---|---|---|
| Grade 1<br>Symptoms require symptomatic treatment only (e.g., fever, nausea, fatigue, headache, myalgia, malaise). | If not improving after 24 hours, administer tocilizumab[c] 8 mg/kg intravenously over 1 hour (not to exceed 800 mg). (for other cancers, this may be not applicable) | Not applicable. |
| Grade 2<br>Symptoms require and respond to moderate intervention.<br>Oxygen requirement less than 40% $FiO_2$ or hypotension responsive to fluids or low dose of one vasopressor or Grade 2 organ toxicity[b]. | Administer tocilizumab 8 mg/kg intravenously over 1 hour (not to exceed 800 mg).<br>Repeat tocilizumab every 8 hours as needed if not responsive to intravenous fluids or increasing supplemental oxygen. Limit to a maximum of 3 doses in a 24-hour period; maximum total of 4 doses if no clinical improvement in the signs and symptoms of CRS.<br>If improving, discontinue tocilizumab. | Manage per Grade 3 if no improvement within 24 hours after starting tocilizumab.<br>If improving, taper corticosteroids. |
| Grade 3<br>Symptoms require and respond to aggressive intervention.<br>Oxygen requirement greater than or equal to 40% $FiO_2$ or hypotension requiring high-dose or multiple vasopressors or Grade 3 organ toxicity or Grade 4 transaminitis. | Per Grade 2 | Administer methylprednisolone 1 mg/kg intravenously twice daily or equivalent dexamethasone (e.g., 10 mg intravenously every 6 hours) until Grade 1, then taper corticosteroids.<br>If improving, manage as Grade 2.<br>If not improving, manage as Grade 4. |
| Grade 4<br>Life-threatening symptoms.<br>Requirements for ventilator support or continuous veno- | Per Grade 2 | Administer methylprednisolone 1000 mg intravenously per day for 3 days. |

TABLE 13-continued

| CRS Grade[a] | Tocilizumab | Corticosteroids |
|---|---|---|
| venous hemodialysis (CVVHD), or Grade 4 organ toxicity (excluding transaminitis). | | If improving, taper corticosteroids, and manage as Grade 3. If not improving, consider alternate immunosuppressants. |

[a]Lee D W et al (2014). Current concepts in the diagnosis and management of cytokine release syndrome. Blood. 2014 Jul. 10; 124(2): 188-195.
[b]Refer to Table 14 for management of neurologic toxicity.
[c]Refer to tocilizumab Prescribing Information for details Neurologic events were observed in 53 patients, 20 of whom experienced Grade 3 or higher (severe or life-threatening) adverse reactions. The median time to onset for neurologic events was 6 days (range: 1 to 32 days). Neurologic events were resolved for 52 out of 66 patients with a median duration of 21 days (range: 2 to 454 days). 3 patients had ongoing neurologic events at the time of death, including 1 patient with serious encephalopathy. The remaining unresolved neurologic events were either Grade 1 or Grade 2. 54 patients experienced CRS by the onset of neurological events. 5 patients did not experience CRS with neurologic events and 8 patients developed neurological events after the resolution of CRS. 56 patients experienced the first CRS or neurological event within the 7 seven days after infusion of anti-CD19 CAR T cells.

The most common neurologic events (occurring in >10% of the patients) included encephalopathy (51% of the patients), headache (35% of the patients), tremor (38 of the patients aphasia (23% of the patients), and delirium (16% of the patients). Serious events including encephalopathy, aphasia, and seizures occurred after treatment. Some adverse reactions observed in at least ten percent of treated patients included: Blood and Lymphatic System Disorders (Coagulopathy, Cardiac Disorders, Tachycardias, Bradycardias, Non-ventricular Arrhythmias); Gastrointestinal Disorders (Nausea, Constipation, Diarrhea, Abdominal pain, Oral pain, Vomiting, Dysphagia); General Disorders and Administration Site Conditions (Pyrexia, Fatigue, Chills, Edema, Pain); Immune System Disorders (Cytokine release syndrome, Hypogammaglobulinemia); Infections and Infestations (Infection—pathogen unspecified, Viral infections, Bacterial infections); Metabolism and nutrition disorders (Decreased appetite), Musculoskeletal and Connective Tissue Disorders (Musculoskeletal pain, Motor dysfunction); Nervous System Disorders (Encephalopathy, Tremor; Headache, Aphasia, Dizziness, Neuropathy); Psychiatric Disorders (Insomnia, Delirium, Anxiety); Renal and Urinary Disorders (Renal insufficiency, Urine output decreased); Respiratory, Thoracic and Mediastinal Disorders (Hypoxia, Cough, Dyspnea, Pleural effusion); Skin and Subcutaneous Tissue Disorders (Rash); and Vascular Disorders (Hypotension, Hypertension, Thrombosis). Patients who experience Grade 2 or higher neurologic toxicities may have been treated per the indications shown in Table 14.

TABLE 14

| Grading Assessment[a] | Concurrent CRS | No Concurrent CRS |
|---|---|---|
| Grade 2 | Administer tocilizumab per Table 13 for management of Grade 2 CRS. If not improving within 24 hours after starting tocilizumab, administer dexamethasone 10 mg intravenously every 6 hours until the event is Grade 1 or less, then taper corticosteroids. If still not improving, manage as Grade 3. | Administer dexamethasone 10 mg intravenously every 6 hours until the event is Grade 1 or less, then taper corticosteroids. |
| | Consider non-sedating anti-seizure medicines (e.g., levetiracetam) for seizure prophylaxis. | |
| Grade 3 | Administer tocilizumab per Table 13 for management of Grade 2 CRS. In addition, administer dexamethasone 10 mg intravenously with the first dose of tocilizumab and repeat dexamethasone dose every 6 hours. Continue dexamethasone use until the event is Grade 1 or less, then taper corticosteroids. If improving, discontinue tocilizumab and manage as Grade 2. If still not improving, manage as Grade 4 (below). | Administer dexamethasone 10 mg intravenously every 6 hours. Continue dexamethasone use until the event is Grade 1 or less, then taper corticosteroids. If not improving, manage as Grade 4. |
| | Consider non-sedating anti-seizure medicines (e.g., levetiracetam) for seizure prophylaxis. | |
| Grade 4 | Administer tocilizumab per Table 13 for management of Grade 2 CRS. | Administer methylprednisolone 1000 mg intravenously per day for 3 |

TABLE 14-continued

| Grading Assessment[a] | Concurrent CRS | No Concurrent CRS |
|---|---|---|
| | Administer methylprednisolone 1000 mg intravenously per day with first dose of tocilizumab and continue methylprednisolone 1000 mg intravenously per day for 2 more days. If improving, then manage as Grade 3. If not improving, consider alternate immunosuppressants. | days. If improving, then manage as Grade 3. If not improving, consider alternate immunosuppressants. |
| | Consider non-sedating anti-seizure medicines (e.g., levetiracetam) for seizure prophylaxis. | |

[a]Severity based on Common Terminology Criteria for Adverse Events.

After infusion of anti-CD19 CAR T cells, pharmacodynamic responses were evaluated over a four-week interval by measuring transient elevation of cytokines, chemokines and other molecules in blood. Levels of IL-6, IL-8, IL-10, IL-15, TNF-α, IFN-γ, and/or sIL2Rα were analyzed. Peak elevation of these cytokine levels was generally observed between 4 and 8 days after infusion, and levels generally returned to baseline within 28 days. A period of B cell aplasia was expected. Following infusion, an initial expansion of anti-CD19 CAR T cells was followed by a decline to near baseline levels by 3 months. Peak levels of anti-CD19 CAR T cells occurred within the first 7 to 15 days after infusion. Results showed that the levels of anti-CD19 CAR T cells in blood were associated with objective response (i.e. complete remission (CR) or partial remission (PR)). The median peak anti-CD19 CAR T cell level in responders (those with complete remission and partial remission) was 102.4 cells/μL (range: 0.2 to 2589.5 cells/μL; n=51), and in nonresponders was 12.0 cells/μL (range: 0.2 to 1364.0 cells/μL, n=8). The median AUC Day 0-28 ($AUC_{0-28}$) in patients with an objective response was 1487.0 cells/μL·days (range: 3.8 to $2.77\times10^4$ cells/μL·days; n=51) and 169.5 cells/μL·days in nonresponders (range: 1.8 to 1.17 $10\times10^4$ cells/μL·days; n=8). The median peak (24.7 cells/μL) anti-CD19 CAR T cell (peak: and $AUC_{0-28}$ levels (360.4 cells/μL·days) in patients (n=18) who received neither corticosteroids nor tocilizumab was similar to those of patients (n=2) who received only corticosteroids (peak: 24.2 cells/μL; $AUC_{0-28}$: 367.8 cells/μL·days). In the patients who received only tocilizumab (n=10), the mean peak anti-CD19 CAR T cells was 86.5 cells/μL and $AUC_{0-28}$ was 1188.9 cells/μL·days. In the patients who received both corticosteroids and tocilizumab (n=37), the mean peak was 167.2 cells/μL and $AUC_{0-28}$ was 1996.0 cells/μL·days. The median peak anti-CD19 CAR T-cell values were 74.1 cells/μL in patients ≥65 years of age (n=39) and 112.5 cells/μL in patients <65 years of age (n=28). Median anti-CD19 CAR T-cell $AUC_{0-28}$ values were 876.5 cells/μL·day in patients ≥65 years of age and 1640.2 cells/μL·day in patients <65 years of age. Gender had no significant impact on AUC 0-28 and $C_{max}$ of anti-CD19 CAR T cells.

Example 6

Patients with MCL who progress after BTKi therapy have a median overall survival of only 5.8 months with salvage therapies. ZUMA-2 (ClinicalTrials.gov Identifier: NCT02601313) is a Phase 2, registrational, multicenter study of patients with R/R MCL after 1-5 prior therapies, including a BTKi. Patients were administered an autologous anti-CD19 chimeric antigen receptor (CAR) T cell therapy, prepared and administered as described in EXAMPLE 5. This anti-CD19 CAR T cell product may be referred to as KTE-X19. In the primary analysis of ZUMA-2 (N=60), the objective response rate (ORR) with anti-CD19 CAR T cell treatment (median follow-up 12.3 months) was 93% (67% complete response [CR] rate). This Example describes a comparative analysis of the pharmacology profile of the anti-CD19 CAR T cell treatment prepared as described in EXAMPLE 5 and outcomes by MCL morphology and prior BTKi exposure (ibrutinib [Ibr] and/or acalabrutinib [Acala]), accompanied by basic product attribute characterization.

Eligible patients with R/R MCL underwent leukapheresis and conditioning chemotherapy followed by a single infusion of $2\times10^6$ anti-CD19 CAR T cells/kg. Product attributes (e.g., IFNγ production by the anti-CD19 CAR T cells upon co-culture with CD19+ cells), CAR T cell levels in blood, and cytokine levels in serum were assessed using methods previously described (see previous EXAMPLES). Clinical outcomes are reported in the 60 efficacy-evaluable patients; product attributes and pharmacology data are reported for all 68 treated patients.

At baseline, 40 patients (59%) had classical MCL, 17 (25%) had blastoid MCL, and 4 (6%) had pleomorphic MCL, as assessed by investigator. Before study entry, 52 patients (76%) had prior Ibr, 10 (15%) had prior Acala, and 6 (9%) had both; 88% had BTKi-refractory disease. In the manufactured anti-CD19 CAR T product, median (range) CD4+/CD8+ T cell ratios for patients with classical, blastoid, or pleomorphic MCL were 0.7 (0.04-2.8), 0.6 (0.2-1.1), or 0.7 (0.5-2.0), respectively. Product T cell phenotypes (median [range]) included less differentiated CCR7+ T cells (classical 40.0% [2.6-88.8]; blastoid 35.3% [14.3-73.4]; pleomorphic 80.8% [57.3-88.8]) and effector and effector memory CCR7− T cells (classical 59.9% [11.1-97.4]; blastoid 64.8% [26.6-85.7]; pleomorphic 19.2% [11.1-42.7]). Median (range) interferon (IFN)-γ levels by coculture in patients with classical, blastoid, or pleomorphic MCL were 6309.5 μg/mL (424.0-20,000), 6510.0 μg/mL (2709.0-18,000), or 7687.5 μg/mL (424.0-12,000), respectively. In patients with classical, blastoid, or pleomorphic MCL, median (range) peak CAR T cell levels were 77.6 cells/μL (0.2-2241.6), 35.0 cells/μL (0.2-2589.5), or 144.9 cells/μL (39.2-431.3), respectively. ORR/CR rates were 93%/65% in patients with classical MCL, 88%/53% in those with blastoid MCL, and 100%/75% in those with pleomorphic MCL. The 12-mo survival rates in patients with classical, blastoid, or pleomorphic MCL were 86.7%, 67.9%, or 100%, respectively. Grade ≥3 cytokine release syndrome (CRS) and neurologic events occurred in 15% and 38% of patients with classical MCL, 6% and 8% of patients with blastoid MCL, and 25% and 50% of patients with pleomorphic MCL.

For patients who received prior Ibr, Acala, or both, median CD4+/CD8+ T cell ratios in the manufactured anti-CD19 CAR T cell product were 0.7 (range, 0.04-3.7), 0.6 (range, 0.3-1.2), or 1.0 (range, 0.7-1.9), respectively. Product T cell phenotypes (median [range]) included less differentiated CCR7+ T cells (Ibr 39.3% [2.6-86.4]; Acala 42.7% [16.3-88.8]; both 49.5% [14.3-83.0]) and CCR7− effector and effector memory T cells (Ibr 60.6 [13.7-97.4]; Acala 57.3% [11.1-83.8]; both 50.6% [17.0-85.7]). Median (range) levels of IFN-7 by coculture in patients with prior Ibr, Acala, or both was 6496.0 pg/mL (424.0-20,000), 5972.5 pg/mL (2502.0-18,000), or 7985.5 pg/mL (2709.0-12,000), respectively. For patients with prior Ibr, Acala, or both, median (range) peak CAR T cell levels were 95.9 (0.4-2589.5), 13.7 (0.2-182.4), or 115.9 (17.2-1753.6), respectively. ORR/CR rates were 94%/65% in patients with prior Ibr, 80%/40% in patients with prior Acala, and 100%/100% in patients with both BTKis. The 12-month survival rates in patients with prior Ibr, Acala, or both were 81%, 80%, or 100%, respectively. Grade ≥3 CRS and neurologic events occurred in 17% and 31% of patients with prior Ibr, 10% and 10% of patients with Acala, and 0 and 67% of patients with both BTKis. While post-treatment CAR T cell levels were lower in patients with blastoid morphology or previously treated with Acala alone, mirrored by similar trends in clinical outcomes, all subgroups defined by MCL morphology or prior BTKi drew clinical benefit from anti-CD19 CAR T cell treatment.

Example 7

This EXAMPLE provides an updated analysis of efficacy, safety, and pharmacology for all patients in ZUMA-2 with a minimum follow-up of 1 year. Eligible patients with R/R MCL underwent leukapheresis and conditioning chemotherapy followed by a single infusion of anti-CD19 CAR T cell therapy ($2\times10^6$ CAR T cells/kg) as described in the previous EXAMPLES. The primary endpoint was ORR (CR+partial response) as assessed by an Independent Review Committee according to the Lugano Classification. Efficacy data are reported for the 60 treated patients with ≥1 year of follow-up; safety data are presented for all 68 treated patients.

The median follow-up was 17.5 months (range, 12.3-37.6). The ORR was 92% (95% CI, 81.6-97.2), with a CR rate of 67% (95% CI, 53.3-78.3). Of all efficacy-evaluable patients, 48% had ongoing responses as of the data cutoff. Medians were not reached for duration of response, progression-free survival (PFS), or overall survival; 15-month estimates were 58.6% (95% CI, 42.5-71.7), 59.2% (95% CI, 44.6-71.2), or 76.0% (95% CI, 62.8-85.1), respectively. In patients who achieved a CR, the median PFS was not reached (15-month rate, 75.1% [95% CI, 56.8-86.5]); in those who achieved a partial response, the median PFS was 3.1 months (95% CI, 2.3-5.2). Median PFS was 1.1 months (95% CI, 0.9-3.0) in nonresponding patients. The first 28 patients treated had a median follow-up of 32.3 months (range, 30.6-37.6); 39.3% of these patients remained in continued remission with no further therapy.

Common grade ≥3 adverse events were neutropenia (85%), thrombocytopenia (53%), anemia (53%), and infections (34%). Grade ≥3 cytopenias were reported in 60% of patients ≥30 days post-infusion. Grade ≥3 cytokine release syndrome occurred in 15% of patients; 59% received tocilizumab for management of CRS. Grade ≥3 neurologic events (NEs) were reported in 31% of patients, and 38% received steroids for NE management. All CRS events and most NEs (37/43) resolved. There were no Grade 5 CRS events or NEs, and no new Grade 5 events occurred with additional follow-up. There were 2 cases of Grade 2 cytomegalovirus infection, 1 case each of Grade ≥3 hypogammaglobulinemia and Grade ≥3 tumor lysis syndrome, and no cases of Epstein-Barr virus-associated lymphoproliferation, replication-competent retrovirus, hemophagocytic lymphohistiocytosis, or anti-CD19 CAR T-cell-related secondary cancers.

Median peak CAR T cell levels and median area under the curve (Days 0-28) were 98.9 cells/μL (range, 0.2-2565.8) and 1394.9 cells/μL (range, 3.8-27,700) in patients with ongoing responses at 12 months, 202.6 cells/μL (range, 1.6-2589.5) and 2312.3 cells/μL (range, 19.0-27,200) in patients who were relapsed at 12 months, and 0.4 cells/μL (range, 0.2-95.9) and 5.5 cells/μL (range, 1.8-1089.1) in nonresponders. Of the 57 efficacy-evaluable patients with data available, 84% had B cells detectable by flow cytometry at baseline. Of those in ongoing responses at 12 months, 10 of 26 patients (38%) with evaluable samples had B cells detectable at 3 months, and 10 of 18 (56%) had detectable B cells at 12 months; gene-marked CAR T cells were no longer detectable at 12 months in 5 of 28 evaluable patients (17%). The ZUMA-2 study continues to show a substantial and durable clinical benefit of anti-CD19 CAR T cell therapy with manageable safety in patients with R/R MCL. Within this patient population, which lacked curative treatment options, most patients achieved durable CR, and no new safety signals were reported. Although early CAR T cell expansion was higher in patients who achieved an objective response, those who later relapsed showed elevated CAR T cell levels pointing to alternate mechanisms of secondary treatment failure in MCL.

Example 8

Although approximately 80-85% of patients with ALL achieve durable complete remissions (CRs) after initial treatment, the remaining 15-20% of patients with relapsed or refractory (R/R) ALL have unfavorable outcomes with a 2-year event-free survival of 40% in patients with relapsed disease. An anti-CD19 CAR T cell therapy prepared as described above shown high rates of complete responses, with a manageable safety profile for adult patients with R/R B cell lymphoma (see previous EXAMPLES). In particular se, e.g., Example 5). ZUMA-4 (ClinicalTrials.gov Identifier: NCT02625480) is a Phase 1/2 study evaluating this anti-CD19 CAR T cell therapy in pediatric and adolescent patients with R/R B cell ALL or NHL. End-of-Phase 1 interim analysis of ZUMA-4 showed the feasibility of anti-CD19 CAR T cell therapy with optimized dosing and adverse event (AE) management strategies for the treatment of pediatric patients with R/R ALL. The protocol for Phase 2 of ZUMA-4 has been amended to include broader B cell ALL enrollment criteria with a focus on patients with early relapse associated with poorer outcomes, and an NHL cohort was added.

Key B cell ALL enrollment criteria included age ≤21 years, weight ≥10 kg, and B cell ALL that was primary refractory, relapsed within 18 months of first diagnosis, R/R after ≥2 lines of systemic therapy, or R/R after allogeneic stem cell transplantation at least 100 days prior to enrollment. The B cell ALL was also B-precursor cell ALL R/R after autologous stem cell transplantation at least 100 days prior to enrollment and off immunosuppressive medications for ≥4 weeks. The Lansky (age <16 years) or Karnofsky (age ≥16 years) performance status was PS ≥80, weight ≥6 kg. Eligible patients included patients with CNS-1 disease, patients with CNS-2 disease without clinically evident neurological changes, and patients with ≥5% BM blasts or MRD-positive disease (threshold $10^{-4}$ by flow or PCR). CNS-1 disease was defined by no detectable lymphoblasts in CSF; CNS-2 disease was defined by detectable disease and white blood cell count <5/μL in CSF. CNS-3 disease was defined by WBC ≥5/μL in CSF. Criteria for disease burden had been amended to also include patients with minimal residual disease-positive disease at enrollment. Patients with Philadelphia chromosome-positive ALL were eligible if intolerant to tyrosine kinase inhibitor therapy or if R/R after ≥2 tyrosine kinase inhibitor therapies. Patients with prior blinatumomab were also included. Patients with chronic myelogenous leukemia lymphoid blast crisis or clinically significant infections were not eligible. Patients with Burkitt leukemia/lymphoma were also not eligible.

For B cell NHL, key enrollment criteria included age <18 years, weight ≥10 kg, histologically confirmed diffuse large B cell lymphoma not otherwise specified (DLBCL NOS), primary mediastinal large B cell lymphoma, Burkitt lymphoma (BL), Burkitt-like lymphoma or unclassified B cell lymphomas intermediate between DLBCL and BL, with ≥1 measurable lesion. For NHL, disease must have been primary refractory, R/R after ≥2 lines of systemic therapy, or R/R after autologous or allogeneic stem cell transplantation ≥100 days prior to enrollment. Patients must have been off immunosuppressive medications for ≥4 weeks. The Lansky (age <16 years) or Karnofsky (age ≥16 years) performance status was PS ≥80, weight ≥6 kg. Patients with prior blinatumomab were also included. Patients must have received adequate prior therapy, at a minimum anti-CD20 mAb and anthracycline-containing chemotherapy and have one or more measurable lesions. Patients with acute graft-versus-host disease or chronic graft-versus-host disease requiring treatment within 4 weeks of enrollment were not eligible. Patients with prior CAR T cell therapy or other genetically modified T cell therapy were excluded, though patients who received KTE-X19 in this study were eligible for re-treatment. Patients with cardiac lymphoma involvement or who required urgent therapy due to tumor mass effects were also excluded. Additional exclusion to the ALL and NHL cohorts included: patients with clinically significant infection; patients with acute or chronic GVHD requiring treatment within 4 weeks of enrollment Alemtuzumab (or other anti-CD52 antibody) within past 6 months, clofarabine or cladribine within past 3 months, PEG-asparaginase within past 3 weeks, or donor leukocyte infusion (DLI) within past 28 days.

Patients with CNS involvement and certain abnormalities were excluded. Patients with central nervous system-1 disease (no detectable lymphoblasts in cerebrospinal fluid), central nervous system-2 disease (detectable disease, but white blood cell count <5/μL in cerebrospinal fluid) with presence of lymphoblasts and with neurologic symptoms and without clinically evident neurologic changes who had prior blinatumomab treatment may have been included in the ALL and NHL cohorts. Patients with presence of lymphoblasts and with neurologic symptoms, central nervous system-3 disease (WBC ≥5/μL in CSF) disease with presence of lymphoblasts with or without neurologic symptoms, patients with any CNS tumor mass by imaging and/or parameningeal mass, history or presence of any CNS disorder such as cerebrovascular ischemia/hemorrhage, dementia, cerebellar disease, or any autoimmune disease with CNS involvement, posterior reversible encephalopathy syndrome, or cerebral edema with structural defects, history of stroke or transient ischemic attack within past 12 months, and seizure disorder requiring active anti-convulsive medication were excluded. Patients with prior CD19-directed therapy, except for blinatumomab, were excluded.

Patients received conditioning chemotherapy with fludarabine 25 mg/$m^2$ on Days −4, −3, and −2 and cyclophosphamide 900 mg/$m^2$ on Day −2 followed by a single infusion of anti-CD19 CAR T cells at a target dose of $1\times10^6$ anti-CD19 CAR T cells/kg on Day 0. For ALL, the primary Phase 2 objective was to evaluate anti-CD19 CAR T cell efficacy as assessed by overall CR rate (CR and CR with incomplete hematologic recovery). For NHL, the primary Phase 2 objective was to evaluate anti-CD19 CAR T cell therapy efficacy by objective response rate (CR+partial response). Secondary Phase 2 objectives for ALL and NHL cohorts included safety and tolerability, additional efficacy endpoints, and changes in patient-reported outcome scores.

The CAR T cell treatment used in this study was described in prior examples, such as Example 5 (also known as KTE-X19), which is an autologous anti-CD19 CAR T cell therapy for the treatment of R/R mantle cell lymphoma and other R/R hematologic malignancies. PBMCs from an apheresis product are enriched for T cells by CD4+/CD8+ positive selection which results in removal of malignant cells. The resulting T cells are activated with anti-CD3/anti-CD28 antibodies in the presence of IL-2, retrovirally transduced to introduce the anti-CAR gene construct (FMC63-28Z CAR) and expanded to the desired dose. The expanded T cells may be frozen for transport and shipped back to the patient for infusion. Axicabtagene ciloleucel is made by a different method as described in, for example, Park J. H. et al. *N Engl J Med.* 2018; 378(5):449-459; and Lee D. W. et al. *Lancet.* 2015; 385(9967):517-528. In adult patients with R/R B-ALL, KTE-X19 treatment improved CR rate, CRi rate, or safety profile in the Phase 1. Shah B D, et al. *J Clin Oncol.* 2019; 37 (suppl, abstr):7006.

During the DLT assessment in Phase 1, the starting dose was $2\times10^6$ anti-CD19 CAR T cell/kg. DLT was defined as Grade 3 nonhematologic AEs lasting >7 days and Grade 4 nonhematologic AEs regardless of duration, with protocol-specified exceptions, or Grade 4 hematologic AEs lasting >30 days. The dose of $1\times10^6$ CAR-T cells in 68-mL volume or in 40-mL volume was also examined. Patients receiving the 40-mL, $1\times10^6$ cohort received modified AE management. Based on available data, $1\times10^6$ cells/kg in 40-mL was used in Phase 2. Results of Phase 1 study showed 94% of MRD-negativity and 73% of CR+Cri were observed in pediatric and adolescent patients with R/R B-ALL. Results also showed a manageable AE profile consistent with known toxicities, and lower incidence and severity of NEs with optimized dose formulation and revised safety management. Wayne A S, et al. *Pediatr Blood Cancer.* 2019; 66 (suppl): S24.

In Phase 2, patients were screened and subject to leukapheresis followed by conditioning chemotherapy starting at Day −4. Bridging therapy may have been administered after leukapheresis at the investigator's discretion and had to be completed ≥7 days or 5 half-lives before conditioning chemotherapy. KTE-X19 was infused at Day 0. The first disease assessment occurred at Day 28. Post-treatment assessment of safety and efficacy occurred on Week 2, Week 4, Month 2, and Month 3. Patients are followed up every 3 months through Month 18 and every 6 months between Months 24 and 60. Beginning with year 6, patients return once annually for up to 15 years. A total of 50 patients with R/R ALL and 16 patients with R/R NHL were enrolled with the 40-mL formulation of $1\times10^6$ KTE-X19 cells/kg. The patients in Phase 2 of the current study included also an NHL cohort and broadened enrollment criteria for R/R B-ALL to include patients with early first relapse, which was associated with poorer outcomes, as well as patients with MRD-positive disease. Primary objective was the efficacy as assessed by overall CR rate (CR and Cri) for ALL and by ORR (CR+PR) for NHL. Secondary objectives included assessment of safety, tolerability, DOR, OS, relapse-free survival (RFS)/progression-free survival (PFS), and patient reported outcomes (PROs). For ALL, additional secondary objectives included assessment of MRD-negative rate and allo-SCT rate. For the overall CR rate (ALL cohort only), incidence and exact 2-sided 95% CIs will be determined. It will be compared with a response rate of 35% at a 1-sided α-level of 0.025 using an exact binomial test. For the MRD-negative rate (ALL cohort only), incidence and exact 2-sided 95% CIs will be determined. If statistical testing of the overall CR rate is significant, MRD-negative rate will be compared to a rate of 30% at a 1-sided α-level of 0.025 using an exact binomial test. For DOR and OS, Kaplan-Meier estimates and 2-sided 95% CIs will be determined. For the AlloSCT rate (ALL cohort only), incidence in mITT set and exact 2-sided 95% CIs will be determined. In terms of safety, incidence rates of AEs including all, serious, fatal, CTCAE version 4.03 Grade ≥3, and treatment-related AEs with onset on or after the date of infusion will be determined. No specific hypothesis will be tested for the NHL cohort. With the planned sample size in this cohort, assuming an observed ORR of 63% (10/16 patients), 69% (11/16), 75% (12/16), and 81% (13/16), the lower bound of the 95% exact CI for the estimated ORR will be 35%, 41%, 48%, and 54%, respectively.

Example 9

This Example reports on the phase 1 results for ZUMA-3 (ClinicalTrials.gov Identifier: NCT02614066), a phase 1/2 study evaluating an autologous anti-CD19 chimeric antigen receptor (CAR) T-cell therapy that includes a CD3ζ and CD28 co-stimulatory domain and is prepared as described in the previous Examples (CD4+/CD8+ enrichment/removal of malignant cells), in adults with relapsed/refractory (R/R) B cell ALL. This protocol for preparation of anti-CD19 CAR T cells with cancer cell removal reduces the likelihood of activation and exhaustion of anti-CD19 CAR T cells during ex vivo manufacturing. The presence of leukemic blasts in peripheral blood may limit the number of T cells available for the manufacture CAR T-cell products, potentially leading to manufacturing failure. Sabatino M. et al. *Blood.* 2016; 128(22):1227. The anti-CD19 CAR T cell product used in this study has been described in Wang M. et al. *N Engl J Med.* 2020; 382(14):1331-1342 for use in MCL. It is different from that used in Sabatino M. et al. *Blood.* 2016; 128(22):1227, Park J. H. et al. *N Engl J Med.* 2018; 378(5):449-459; and Lee D. W. et al. *Lancet.* 2015; 385 (9967):517-528. This anti-CD19 CAR T cell product has different product characteristics in terms of T cell phenotype than that made by previously-described methods. This anti-CD19 CAR was also referred to as KTE-X19 in this example and elsewhere in the application.

Following fludarabine/cyclophosphamide lymphodepletion, patients received anti-CD19 CAR T cells at 2, 1, or $0.5\times10^6$ cells/kg. Rate of dose-limiting toxicities (DLTs) within 28 days following CAR T cell infusion was the primary endpoint. Anti-CD19 CAR T cells were manufactured for 54 enrolled patients and administered to 45 (median age 46 years [range, 18-77]). No DLTs occurred in the DLT-evaluable cohort. Grade ≥3 cytokine release syndrome (CRS) and neurologic events (NE) occurred in 31% and 38% of patients, respectively. To optimize the benefit-risk ratio, revised adverse event (AE) management for CRS and NE (earlier steroid use for NE and tocilizumab only for CRS) was evaluated at $1\times10^6$ cells/kg anti-CD19 CAR T cells. In the 9 patients treated under revised AE management, 33% had grade 3 CRS and 11% had grade 3 NE, with no grade 4/5 NE. The overall complete remission rate correlated with CAR T cell expansion and was 83% in patients treated with $1\times10^6$ cells/kg and 69% in all patients. Minimal residual disease was undetectable in all responding patients. At 22.1 months (range, 7.1-36.1) median follow-up, the median DOR was 17.6 months (range, 5.8-17.6) in patients treated with $1\times10^6$ cells/kg and 14.5 months (range, 5.8-18.1) in all patients. Anti-CD19 CAR T cell treatment provided a high response rate and tolerable safety in adults with R/R B-ALL. Phase 2 proceeded at $1\times10^6$ cells/kg with revised AE management.

Patients

Eligible patients were ≥18 years of age with R/R B cell ALL, defined as refractory to first-line therapy (i.e., primary refractory), relapse ≤12 months after first remission, relapsed or refractory after ≥2 prior lines of systemic therapy, or relapsed after allogeneic stem cell transplant (SCT). Patients were required to have ≥5% bone marrow blasts, an Eastern Cooperative Oncology Group performance status of 0 or 1, and adequate renal, hepatic, and cardiac function. The first six patients enrolled were required to have ≥25% blasts in bone marrow. For patients who received prior blinatumomab, leukemic blasts with CD19 expression ≥90% was required. Patients with Philadelphia chromosome-positive (Ph+) disease, concomitant extramedullary disease, central nervous system (CNS)-2 disease (cerebrospinal fluid [CSF] blast cells with <5 white blood cells/$mm^3$) without neurological changes and patients with Down syndrome were eligible. CNS-3 disease (CSF blast cells with ≥5 white blood cells/$mm^3$) independent of neurologic changes and a history of CNS disorder were exclusions.

Additional eligibility criteria included: Subjects with Philadelphia chromosome (Ph)+ disease were eligible if they had disease intolerant to tyrosine kinase inhibitor (TKI) therapy, or if they had relapsed/refractory disease despite treatment with ≥2 different TKIs; Absolute neutrophil count ≥500/μL unless in the opinion of the investigator cytopenia is due to underlying leukemia and is potentially reversible with leukemia therapy; Platelet count ≥50,000/μL unless in the opinion of the investigator cytopenia is due to underlying leukemia and is potentially reversible with leukemia therapy; Absolute lymphocyte count ≥100/μL; Adequate renal, hepatic, pulmonary and cardiac function were defined [Creatinine clearance (as estimated by Cockcroft Gault)≥60 cc/min; Serum alanine aminotransferase/aspartate aminotransferase 2.5×upper limit of normal; Total bilirubin ≤1.5 mg/dL, except in subjects with Gilbert's syndrome; Left ventricular ejection fraction ≥50%, no evidence of pericardial effusion as determined by an echocardiogram, no New York Heart Association class III or class IV functional classification, and no clinically significant arrhythmias; No clinically significant pleural effusion; Baseline oxygen saturation >92% on room air]; Females of childbearing potential must have had a negative serum or urine pregnancy test; Females of childbearing potential must have had a negative serum or urine pregnancy test.

Additional exclusion criteria included: Diagnosis of Burkitt's leukemia/lymphoma according to World Health Organization classification or chronic myelogenous leukemia lymphoid blast crisis; History of malignancy other than non-melanoma skin cancer or carcinoma in situ (eg, cervix, bladder, breast) unless disease-free for ≥3 years; History of severe hypersensitivity reaction to aminoglycosides or any of the agents used in this study; Central nervous system (CNS) abnormalities [Presence of CNS-3 disease defined as detectable cerebrospinal blast cells in a sample of cerebrospinal fluid (CSF) with ≥5 white blood cells (WBCs) per $mm^3$ with or without neurological changes, and; Presence of CNS-2 disease defined as detectable cerebrospinal blast cells in a sample of CSF with <5 WBCs per $mm^3$ with neurological changes. Note: Subjects with CNS-1 (no detectable leukemia in the CSF) and those with CNS-2 without clinically evident neurological changes are eligible to participate in the study; History or presence of any CNS disorder such as a seizure disorder, cerebrovascular ischemia/hemorrhage, dementia, cerebellar disease, any autoimmune disease with CNS involvement, posterior reversible encephalopathy syndrome, or cerebral edema]; History of severe hypersensitivity reaction to aminoglycosides or any of the agents used in this study; History of concomitant genetic syndrome associated with bone marrow failure; History of clinically significant cardiac disease within 12 months of enrollment; History of symptomatic deep vein thrombosis or pulmonary embolism within 6 months of enrollment; Primary immunodeficiency; Known infection with HIV, hepatitis B, or hepatitis C virus. A history of hepatitis B or hepatitis C is permitted if the viral load is undetectable per quantitative polymerase chain reaction and/or nucleic acid testing; Simple urinary tract infection and uncomplicated bacterial pharyngitis are permitted if responding to active treatment and after consultation with the Kite Medical Monitor; Acute graft-vs-host disease (GVHD) grade II-IV by Glucksberg criteria or severity B-D by International Bone Marrow Transplant Registry index; acute or chronic GVHD requiring systemic treatment within 4 weeks prior to enrollment; Prior medication [Salvage systemic therapy (including chemotherapy, TKIs for Ph+ disease, and blinatumomab)≤1 blinatumomab; History of Common Terminology Criteria for Adverse Events grade 4 neurologic event or grade 4 cytokine release syndrome with prior CD19-directed therapy; Treatment with alemtuzumab ≤6 months prior to enrollment, clofarabine or cladribine ≤3 months prior to enrollment or PEG-asparaginase ≤3 months prior to enrollment; Donor lymphocyte infusion ≤4 weeks prior to enrollment; Treatment with any drug for GVHD and any immunosuppressive antibody 4 weeks prior to enrollment; At least 3 half-lives must have elapsed from any prior systemic inhibitory/stimulatory immune checkpoint molecular therapy prior to enrollment; Corticosteroid therapy at a pharmacologic dose (>5 mg/day of prednisone or equivalent doses of other corticosteroids) and other immunosuppressive drugs must be avoided for 1 week prior to enrollment]; Presence of any indwelling line or drain. Ommaya reservoirs and dedicated central venous access catheters are permitted; Live vaccine ≤4 weeks prior to enrollment; Women of childbearing potential who are pregnant or breastfeeding because of the potentially dangerous effects of the preparative chemotherapy on the fetus or infant; Subjects of both genders of childbearing potential who are not willing to practice birth control from the time of consent through 6 months after the completion of anti-CD19 CAR T cell therapy; Subjects who, in the investigator's judgment, are unlikely to complete all protocol-required study visits or procedures or comply with the study requirements for participation [History of autoimmune disease resulting in end organ injury or requiring systemic immunosuppression or systemic disease modifying agents within the last 2 years].

Study Design and Treatment

The phase 1 objective was to evaluate the safety of anti-CD19 CAR T cell treatment and determine the optimal phase 2 dose based on the incidence of dose-limiting toxicities (DLTs) and overall safety profile. DLTs were defined as anti-CD19 CAR T cell-related adverse events (AEs) occurring within the first 28 days following anti-CD19 CAR T cell infusion, including grade 3 non-hematologic AEs lasting >7 days, grade 4 non-hematologic AEs regardless of duration except for prespecified expected events (e.g., tumor lysis syndrome), and grade 4 hematologic AEs lasting >30 days, except lymphopenia (Table 15).

TABLE 15

| Dose-limiting toxicities |
|---|
| DLTs were defined as the following anti-CD19 CAR T cells-related events with onset within the first 28 days following anti-CD19 CAR T cells infusion: |
| Grade 4 hematologic toxicity lasting more than 30 days (except lymphopenia) if not attributable to underlying disease |
| All anti-CD19 CAR T cell-related grade 3 non-hematologic toxicities lasting for >7 days and all anti-CD19 CAR T cell-related grade 4 non-hematologic toxicities regardless of duration were considered DLTs, with the exception of the following: |
| Aphasia/dysphasia or confusion/cognitive disturbance which resolved to at least grade 1 or baseline within 2 weeks and to at least baseline within 4 weeks |
| Fever grade 3 or 4 |
| Immediate hypersensitivity reactions occurring within 2 hours of anti-CD19 CAR T cells infusion (related to anti-CD19 CAR T cells infusion) that were reversible to a grade 2 or less within 24 hours of anti-CD19 CAR T cell infusion with standard therapy |
| Renal toxicity which required dialysis for ≤7 days |
| Intubation for airway protection if ≤7 days |
| TLS including associated manifestations attributable to TLS (eg, electrolyte abnormalities, renal function, hyperuricemia) |
| Grade 3 transaminase, alkaline phosphatase, bilirubin or other liver function test elevation, provided there was resolution to ≤ grade 2 within 14 days |
| Grade 4 transient serum hepatic enzyme abnormalities provided there was resolution to ≤ grade 3 within <72 hours |
| Hypogammaglobulinemia grade 3 or 4 |
| Grade 3 nausea and/or anorexia |

TABLE 15-continued

| Dose-limiting toxicities |
|---|
| Adverse events attributed to CRS were mapped to the overall CRS grading assessment for the determination of DLT |
| All occurrences of grade 3 CRS of duration >7 days and all occurrences of grade 4 CRS were considered DLTs, other than occurrences of CRS due to the exceptions listed above |

CRS, cytokine release syndrome;
DLT, dose-limiting toxicity;
TLS, tumor lysis syndrome Initial patients were enrolled at a starting dose of $2\times10^6$ CAR T cells/kg (FIG. 3). Based on the overall safety profile, subsequent patients received $2\times10^6$, $1\times10^6$, or $0.5\times10^6$ CAR T cells/kg. At $0.5\times10^6$ CAR T cells/kg. Two formulations were explored for patients receiving the lower dose $0.5\times10^6$ CAR T cells/kg, one with a total volume of 40 mL and the other with a volume of 68 mL. The 40-mL formulation was intended to maintain cell density and cell viability during the freezing/thawing process).

To mitigate the risk of cytokine release syndrome (CRS) and neurologic events (NE), AE management guidelines were revised to limit tocilizumab to the treatment of CRS (and not isolated neurotoxicity), and to initiate corticosteroid treatment at the onset of grade 2 rather than grade 3NE (Table 16).

TABLE 16

Original and revised neurotoxicity management guidelines

| NE Grade | Original Management Guidelines | Revised Management Guidelines |
|---|---|---|
| Grade 1 | Supportive care<br>Neurological examination and additional work-up as clinically indicated | Supportive care<br>Closely monitor neurologic status<br>Consider prophylactic antiepileptic |
| Grade 2 | Supportive Care and Evaluation<br>Neurological examination, brain MRI, and evaluation of CSF; consider EEG as clinically indicated<br>Consider prophylactic antiepileptic | Supportive Care and Evaluation<br>Continuous cardiac telemetry and pulse oximetry as indicated<br>Serial neurological examinations to include fundoscopy and Glasgow Coma Score, brain MRI, evaluation of CSF, EEG; consider neurology consult<br>Administer antiepileptics for patients with seizures |
| | Tocilizumab<br>Consider tocilizumab 8 mg/kg IV over 1 hour (not to exceed 800 mg) for patients with comorbid conditions (eg, grade ≥2 CRS) | Tocilizumab<br>For patients with concurrent CRS, administer tocilizumab 8 mg/kg IV over 1 hour (not to exceed 800 mg); repeat every 4-6 hours as needed if not responsive to IV fluids or increasing supplemental oxygen, for a maximum of 3 doses in 24 hours<br>Discontinue tocilizumab if patient improves |
| | Corticosteroids<br>N/A | Corticosteroids<br>For patients without concurrent CRS, administer dexamethasone 10 mg IV every 6 hours<br>For patients with concurrent CRS, if no improvement within 24 hours after starting tocilizumab, administer dexamethasone 10 mg IV every 6 hours<br>Taper corticosteroids if patient improves |
| Grade 3 | Supportive Care and Evaluation<br>Per grade 2<br>Monitor with continuous cardiac telemetry and pulse oximetry | Supportive Care and Evaluation<br>Manage in monitored care or ICU |
| | Tocilizumab<br>Consider tocilizumab 8 mg/kg IV over 1 hour (not to exceed 800 mg); repeat every 4-6 hours if symptoms have not stabilized or improved | Tocilizumab<br>Per grade 2<br>Discontinue tocilizumab if patient improves |
| | Corticosteroids<br>Consider corticosteroids (eg, dexamethasone 10 mg IV every 6 hours or methylprednisolone 1 mg/kg BID) for worsening symptoms despite tocilizumab | Corticosteroids<br>Administer dexamethasone 10 mg IV every 6 hours<br>Taper corticosteroids if patient improves |

TABLE 16-continued

| Original and revised neurotoxicity management guidelines | | |
|---|---|---|
| NE Grade | Original Management Guidelines | Revised Management Guidelines |
| Grade 4 | Supportive Care and Evaluation<br>Per grade 2<br>Monitor with continuous cardiac telemetry and pulse oximetry | Supportive Care and Evaluation<br>Per grade 3<br>Mechanical ventilation may be required<br>Administer immunosuppresants if patient does not improve |
| | Tocilizumab<br>Administer tocilizumab per grade 3 if not previously administered | Tocilizumab<br>Per grade 2 |
| | Corticosteroids<br>Administer corticosteroids (eg, methylprednisolone 1 g/d × 3 days, followed by 250 mg BID × 2 days, then 125 mg BID × 2 days, then 60 mg BID × 2 days) | Corticosteroids<br>Administer high-dose corticosteroids (eg, methylprednisone 1 g/d × 3 days)<br>Taper corticosteroids if patient improves |

Revised AE management guidelines were implemented in an additional cohort of patients treated with $1\times10^6$ CAR T cells/kg. A safety review team (SRT) reviewed safety and efficacy data on an ongoing basis and made recommendations regarding further phase 1 enrollment and the recommended phase 2 dose (RP2D) at milestones defined in the protocol and SRT charter.

Patients underwent leukapheresis at enrollment to obtain a target of $5\text{-}10\times10^9$ mononuclear cells for anti-CD 19 CAR T cells manufacture. Predefined bridging chemotherapy (Table 17) was recommended following leukapheresis, particularly for patients with high disease burden at baseline (>25% leukemic blasts in bone marrow or ≥1,000 blasts/$mm^3$ in peripheral circulation by local review).

After ≥7 days or 5 half-lives (if shorter) washout from bridging chemotherapy, patients received a lymphodepleting regimen of fludarabine intravenous (IV) 25 mg/$m^2$/day on days −4, −3, and −2, and cyclophosphamide IV 900 mg/$m^2$/day on day −2. On day 0, a single infusion of anti-CD19 CAR T cells was administered.

Outcomes and Assessments

The primary phase 1 endpoint was the incidence of DLTs in DLT-evaluable patients. Secondary endpoints included safety, investigator-assessed overall remission rate (CR+CR with incomplete hematologic recovery [CRi]), duration of remission (DOR), relapse-free survival, OS, and rate of undetectable minimal residual disease (MRD) in bone marrow. Levels of CAR T cells and cytokines in blood were

TABLE 17

| Bridging chemotherapy<br>Predefined Bridging Chemotherapy Regimens | |
|---|---|
| Attenuated VAD | Vincristine non-liposomal (1-2 mg IV weekly) or liposomal (2.25 mg/$m^2$ IV weekly), and dexamethasone 20-40 mg IV or PO daily x 3-4 days per week. Optional doxorubicin 50 mg/$m^2$ IV x 1 (first week only) |
| Mercaptopurine (6-MP) | 50-75 mg/$m^2$/day by mouth (administer at bedtime on an empty stomach to improve absorption) |
| Hydroxyurea | Doses titrated between 15-50 mg/kg/day (rounded to the nearest 500 mg capsule and given as a single daily oral dose on a continuous basis) |
| DOMP | Dexamethasone 6 mg/$m^2$/day PO (or IV) divided BID days 1-5, vincristine 1.5 mg/$m^2$ (maximum dose 2 mg) IV on day 1, methotrexate 20 mg/$m^2$ PO weekly, 6-MP 50-75 mg/$m^2$/day PO daily |
| Attenuated FLAG/FLAG-IDA | Fludarabine 30 mg/$m^2$ IV days 1-2, cytarabine 2 g/$m^2$ IV days 1-2, G-CSF 5 μg/kg SC or IV starts on day 3 and can continue until day before the start of conditioning chemotherapy. With or without idarubicin 6 mg/$m^2$ IV days 1-2 |
| Mini-hyper CVAD (courses A and/or B) | Course A: Cyclophosphamide 150 mg/$m^2$ every 12 h x 3 days, dexamethasone 20 mg/d IV or PO daily days 1-4 and 11-14, vincristine 2 mg IV x 1<br>Course B: methotrexate 250 mg/$m^2$ IV over 24 hours on day 1, cytarabine 0.5 g/$m^2$ IV every 12 hours x 4 doses on days 2 and 3 |

BID, twice daily;
CVAD, cyclophosphamide, vincristine, doxorubicin, and dexamethasone;
DOMP, dexamethasone, 6-mercaptopurine, methotrexate, and vincristine;
FLAG, fludarabine, high-dose cytarabine, and G-CSF;
G-CSF, granulocyte-colony stimulating factor;
IDA, idarubicin; IV, intravenous;
MP, 6-mercaptopurine; PO, oral;
SC, subcutaneous;
VAD, vincristine, doxorubicin, and dexamethasone.

exploratory endpoints. AEs including symptoms of CRS and NE were graded per the Common Terminology Criteria for AEs version 4.03. CRS was graded per the criteria of Lee, et al. *Blood.* 2014; 124(2):188-195. For patients with extramedullary disease, response was assessed per the response criteria for extramedullary and CNS disease in the revised International Working Group Criteria for malignant lymphoma. Cheson B D et al. *J Clin Oncol.* 2007; 25(5): 579-586. Undetectable MRD, defined as <1 leukemia cell per 10,000 viable cells, was centrally assessed using flow cytometry (NeoGenomics, Fort Myers, FL). Borowitz M J et al *Blood.* 2015; 126(8):964-971; Bruggemann M. et al. *Blood Adv.* 2017; 1(25):2456-2466; and Gupta S. et al. *Leukemia.* 2018; 32(6):1370-1379.

Hospitalization for ≥7 days post-infusion was required. Patients were evaluated at days 14 and 28 and months 2 and 3 by physical examinations, vital sign measurements, and neurological and laboratory assessments. Bone marrow evaluations and response assessments were conducted at days 7-14 (optional) and 28 and months 2 and 3. For patients who underwent SCT post-anti-CD19 CAR T cell infusion, bone marrow evaluation was not required during the first 100 days post-SCT. Collection and analysis of CSF was required to confirm CR for patients with baseline CNS-2 disease. Patients completing month 3 post-treatment assessments were followed for survival and disease status every 3 months through month 18, every 6 months during months 24-60, and annually for up to 15 years. Patients achieving CR could receive a second infusion of anti-CD19 CAR T cells if progressing following >3 months of remission, provided CD19 expression was retained and neutralizing antibodies against the CAR were not suspected.

Biomarker analyses were performed on blood and serum samples to evaluate predictive pharmacokinetics and pharmacodynamic markers for anti-CD19 CAR T cells. As previously described, droplet digital polymerase chain reaction was used to measure the presence, expansion, and persistence of transduced CD19 CAR+ T cells in blood Locke F L et al. *Mol Ther.* 2017; 25(1):285-295. Serum was assessed for cytokines, chemokines, immune effector molecules, and markers of macrophage-activating syndrome using previously reported methods. Locke F L et al. *Mol Ther.* 2017; 25(1):285-295.

Statistical Analysis

The DLT-evaluable cohort included the first 3 patients treated at the $2\times10^6$ dose level. Safety and efficacy analyses included all patients treated with any dose of anti-CD19 CAR T cells. Kaplan-Meier estimates and 2-sided 95% confidence intervals were generated for time-to-event endpoints. DOR was defined as time from CR to relapse or death without documented relapse. The DOR for patients who underwent allogeneic SCT while in remission was censored at the date of transplant. OS was defined as time from anti-CD19 CAR T cell infusion to date of death from any cause. Data are presented as of Apr. 1, 2019. All statistical analyses were done in SAS (version 9.4).

Results

Patients

Between Mar. 9, 2016 and Jul. 12, 2018, 54 patients were enrolled and underwent leukapheresis in phase 1 (FIG. 4). The anti-CD19 CAR T cell product was successfully manufactured for all 54 patients; 1 patient required 2 leukapheresis procedures and 1 patient required 3 for procedures for product manufacturing. The median time from leukapheresis to delivery of anti-CD19 CAR T cells to the study site was 15 days. Five patients discontinued prior to lymphodepletion because of AEs (n=3; FIG. 4), withdrawal of consent (n=1), or ineligibility after leukapheresis (n=1). Four additional patients discontinued following lymphodepletion. Three received no anti-CD19 CAR T cells due to grade 4 sepsis (n=1), initiation of new therapy (n=1), and death from grade 5 sepsis (n=1). One patient discontinued prior to infusion due to deep vein thrombosis (an exclusion criterion) but received anti-CD19 CAR T cells under compassionate use. Forty-five of 54 patients (83%) received anti-CD19 CAR T cells at these dose levels: $2\times10^6$ (n=6), $1\times10^6$ (n=23), or $0.5\times10^6$ CAR T cells/kg (n=16). Nine of 23 patients in the $1\times10^6$ CAR T cells/kg cohort were treated under revised AE management guidelines requiring earlier use of steroids for NE and reserving tocilizumab only for treating CRS. Forty-four patients received their target dose of anti-CD19 CAR T cells; 1 patient enrolled to receive $1\times10^6$ anti-CD19 CAR T cells/kg and revised AE management was treated with $0.5\times10^6$ cells/kg, but was included in the analysis at the $1\times10^6$ dose level.

The median age of all treated patients was 46 years (range, 18-77), and 67 received ≥3 prior lines of therapy (Table 18). Prior to enrollment, 16 patients (40) were primary refractory, 13 (290%) relapsed after SCT, and 21 (47%) received prior blinatumomab. Blinatumomab was the last therapy used before study entry n 8 patients (18), only 1 of whom achieved a response (CR) to blinatumomab.

TABLE 18

Patient baseline characteristics

| Baseline Characteristics | N = 45 |
|---|---|
| Age, median (range), y | 46 (18-77) |
| Male, n (%) | 22 (49) |
| ECOG performance status score, n (%) | |
| 0 | 15 (33) |
| 1 | 29 (64) |
| Missing | 1 (2) |
| Philadelphia chromosome-positive, n (%) | 8 (18) |
| Extramedullary disease, n (%) | 4 (9) |
| CNS disease at screening, n (%) | |
| CNS-1 | 42 (93) |
| CNS-2 | 3 (7) |
| Prior regimens, n (%) | |
| 1 | 6 (13) |
| 2 | 9 (20) |
| ≥3 | 30 (67) |
| Prior blinatumomab, n (%) | 21 (47) |
| Prior inotuzumab ozogamicin, n (%) | 6 (13) |
| Refractory, n (%) | |
| Primary refractory | 16 (36) |
| First relapse with remission ≤12 months | 2 (4) |
| Relapsed or refractory post-allogeneic SCT | 13 (29) |
| BM blasts at screening, median (range), % | 61 (5-100) |
| BM blasts at preconditioning after bridging, median (range), % | 70 (0-97) |

BM, bone marrow;
CNS, central nervous system;
ECOG, Eastern Cooperative Oncology Group;
SCT, stem cell transplant Safety No DLTs were observed among the DLT-evaluable set (n=3). Ninety-eight percent of patients experienced grade ≥3 AEs (Table 19). The most common any-grade AEs were pyrexia (89), hypotension (69%), diarrhea (42%), and chills (42%). Common grade ≥3 AEs (≥20% of patients) were pyrexia (42%), hypotension (40%), platelet count decreased (33%), anemia (31%), hypophosphatemia (31%), hypoxia (24%), encephalopathy (22%), febrile neutropenia (22%), and neutrophil count decreased (22%). Serious AEs of any grade occurred in 84% of patients.

TABLE 19

| Adverse events | | | | | | | | |
|---|---|---|---|---|---|---|---|---|
| n (%)* | $2 \times 10^6$ (n = 6) | | $1 \times 10^6$ (n = 23) | | $0.5 \times 10^6$ (n = 16) | | All Patients (N = 45) | |
| Any adverse event | 6 (100) | 6 (100) | 23 (100) | 23 (100) | 16 (100) | 15 (94) | 45 (100) | 44 (98) |
| Pyrexia | 6 (100) | 3 (50) | 22 (96) | 11 (48) | 12 (75) | 5 (31) | 40 (89) | 19 (42) |
| Hypotension | 5 (83) | 3 (50) | 17 (74) | 11 (48) | 9 (56) | 4 (25) | 31 (69) | 18 (40) |
| Chills | 3 (50) | 0 | 13 (57) | 0 | 3 (19) | 0 | 19 (42) | 0 (0) |
| Diarrhea | 3 (50) | 0 | 10 (43) | 1 (4) | 6 (38) | 0 | 19 (42) | 1 (2) |
| Headache | 1 (17) | 0 | 10 (43) | 1 (4) | 7 (44) | 1 (6) | 18 (40) | 2 (4) |
| Anemia | 4 (67) | 4 (67) | 10 (43) | 8 (35) | 3 (19) | 2 (13) | 17 (38) | 14 (31) |
| Encephalopathy | 4 (67) | 2 (33) | 11 (48) | 6 (26) | 2 (13) | 2 (13) | 17 (38) | 10 (22) |
| Hypophosphatemia | 2 (33) | 1 (17) | 12 (52) | 10 (43) | 3 (19) | 3 (19) | 17 (38) | 14 (31) |
| Nausea | 1 (17) | 0 | 13 (57) | 1 (4) | 3 (19) | 0 | 17 (38) | 1 (2) |
| Confusional state | 2 (33) | 1 (17) | 9 (39) | 1 (4) | 5 (31) | 2 (13) | 16 (36) | 4 (9) |
| Hypoxia | 2 (33) | 1 (17) | 8 (35) | 6 (26) | 6 (38) | 4 (25) | 16 (36) | 11 (24) |
| Platelet count decreased | 3 (50) | 3 (50) | 8 (35) | 8 (35) | 5 (31) | 4 (25) | 16 (36) | 15 (33) |
| Constipation | 2 (33) | 0 | 10 (43) | 0 | 2 (13) | 0 | 14 (31) | 0 (0) |
| Fatigue | 1 (17) | 0 | 7 (30) | 1 (4) | 6 (38) | 0 | 14 (31) | 1 (2) |
| Sinus tachycardia | 2 (33) | 0 | 10 (43) | 1 (4) | 2 (13) | 0 | 14 (31) | 1 (2) |
| Hypokalemia | 1 (17) | 0 | 11 (48) | 0 | 1 (6) | 0 | 13 (29) | 0 (0) |
| Tachycardia | 1 (17) | 1 (17) | 6 (26) | 1 (4) | 6 (38) | 0 | 13 (29) | 2 (4) |
| Tremor | 1 (17) | 0 | 8 (35) | 0 | 4 (25) | 0 | 13 (29) | 0 (0) |
| Decreased appetite | 0 | 0 | 9 (39) | 2 (9) | 3 (19) | 0 | 12 (27) | 2 (4) |
| Hyperglycemia | 1 (17) | 0 | 6 (26) | 0 | 5 (31) | 1 (6) | 12 (27) | 1 (2) |
| Hypomagnesemia | 2 (33) | 0 | 8 (35) | 0 | 2 (13) | 0 | 12 (27) | 0 (0) |
| Hyponatremia | 3 (50) | 2 (33) | 7 (30) | 3 (13) | 2 (13) | 0 | 12 (27) | 5 (11) |
| Edema peripheral | 1 (17) | 0 | 7 (30) | 1 (4) | 4 (25) | 0 | 12 (27) | 1 (2) |

*Table includes adverse events of any grade occurring in ≥25% of all patients

CRS was reported in 42 patients (93%); 14 patients (31%) experienced grade ≥3 CRS (Table 19). Common grade ≥3 symptoms of CRS were pyrexia (45%), hypotension (36%), and hypoxia (17%). Vasopressors were used for the treatment of CRS in 12 patients (27%). The median time to CRS onset post-infusion was 2 days (range, 1-12); the median durations of any grade and grade ≥3 CRS were 9 and 4.5 days, respectively. CRS-associated events resolved in all but the 2 patients who experienced grade 5 anti-CD19 CAR T cell-related AEs. One patient treated with $2\times10^6$ CAR T cells/kg had multiorgan failure secondary to CRS (day 6). One patient treated with $0.5\times10^6$ cells/kg developed cerebrovascular accident (stroke) in the context of CRS and NE (day 7). No other anti-CD19 CAR T cell-related grade 5 AEs were reported.

NE were reported in 35 patients (78%); grade ≥3 events occurred in 17 patients (38%; Table 19). Grade ≥3 NE occurring in 55% of patients were encephalopathy (22%), aphasia (16%), and confusional state (9%). There were no cases of cerebral edema and no grade 5 NE. The median time to onset of NE was 6 days (range, 1-31) after infusion; the median durations of any grade and grade ≥3 NE were 12 and 9 days, respectively. NE resolved in 31/35 patients (89%); 1 patient died from progressive disease and 3 patients died from AEs considered unrelated to anti-CD19 CAR T cells (sepsis [n=1], cerebrovascular accident [n=1], herpes simplex viremia [n=1]) prior to neurologic event resolution.

Fifty-three percent of all patients received tocilizumab, and 36% also received steroids for management of CRS; 31% and 44% received tocilizumab and steroids, respectively, for NE. Improved overall safety was observed for the 9 patients treated under revised AE management guidelines relative to the 14 patients treated at the same dose under the original guidelines (Table 20). Four of 14 patients treated at $1\times10^6$ CAR T cells/kg under the original guidelines had grade 3 or 4 CRS. With revised AE management, 3/9 patients treated at $1\times10^6$ CAR T cells/kg had grade 3 CRS, with no grade 4 CRS reported. These patients also had a shorter median duration of grade ≥3 CRS (4 vs. 7 days) than patients receiving $1\times10^6$ CAR T cells/kg under original AE guidelines, and a longer time to onset of grade ≥3 symptoms (6 vs. 4.5 days, respectively). Notably, 9/14 patients in the $1\times10^6$ CAR T cells/kg dose cohort managed with the original guidelines experienced grade 3/4 NE, compared to one grade 3 and no grade 4 events inpatients receiving the same dose under revised management guidelines (Table 20). Based on the review of all available safety and efficacy data, the benefit/risk ratio was considered most favorable at the dose of $1\times10^6$ CAR T cells/kg, resulting in this dose being the RP2D. All phase 2 patients were being treated under revised AE management guidelines.

TABLE 20

Cytokine release syndrome and neurologic events including with revised AE management guidelines

| n (%) | 2 × $10^6$ (n = 6) | 1 × $10^6$ Original AE Management (n = 14) | 1 × $10^6$ Revised AE Management (n = 9) | 0.5 × $10^6$ (n = 16) |
|---|---|---|---|---|
| Steroids | | | | |
| For treatment of CRS | 1 (17) | 5 (36) | 5 (56) | 5 (31) |
| For treatment of NE | 3 (50) | 7 (50) | 5 (56) | 5 (31) |
| Tocilizumab | | | | |
| For treatment of CRS | 1 (17) | 9 (64) | 9 (100) | 5 (31) |
| For treatment of NE | 4 (67) | 5 (36) | 4 (44) | 1 (6) |

| Adverse event, n (%) | Any grade | Grade ≥3 | Any grade | Grade ≥3 | Any grade | Grade ≥3 | Any grade | Grade ≥3 |
|---|---|---|---|---|---|---|---|---|
| Cytokine release syndrome | 6 (100) | 3 (50) | 14 (100) | 4 (29) | 9 (100) | 3 (33) | 13 (81) | 4 (25) |
| Pyrexia | 6 (100) | 3 (50) | 12 (86) | 5 (36) | 9 (100) | 6 (67) | 10 (77) | 5 (31) |
| Hypotension | 4 (67) | 3 (50) | 11 (79) | 6 (43) | 6 (67) | 3 (33) | 8 (62) | 3 (19) |
| Sinus tachycardia | 2 (33) | 0 | 6 (43) | 0 | 4 (44) | 1 (11) | 2 (15) | 0 |
| Chills | 1 (17) | 0 | 5 (36) | 0 | 4 (44) | 0 | 2 (15) | 0 |
| Tachycardia | 1 (17) | 1 (17) | 4 (29) | 1 (7) | 2 (22) | 0 | 4 (31) | 0 |
| Tachypnea | 0 | 0 | 4 (29) | 1 (7) | 0 | 0 | 0 | 0 |
| Hypoxia | 2 (33) | 1 (17) | 2 (14) | 2 (14) | 3 (33) | 2 (22) | 3 (23) | 2 (15) |
| Nausea | 0 | 0 | 2 (14) | 0 | 0 | 0 | 0 | 0 |
| Fatigue | 0 | 0 | 1 (7) | 0 | 3 (33) | 0 | 1 (8) | 0 |
| Headache | 0 | 0 | 1 (7) | 0 | 2 (22) | 0 | 3 (23) | 0 |
| Hyponatremia | 0 | 0 | 1 (7) | 0 | 1 (11) | 0 | 1 (8) | 0 |
| Any neurologic event | 5 (83) | 3 (50) | 13 (93) | 9 (64) | 7 (78) | 1 (11) | 10 (63) | 4 (25) |
| Confusional state | 2 (33) | 1 (17) | 3 (21) | 0 | 6 (67) | 1 (11) | 5 (31) | 2 (13) |
| Tremor | 1 (17) | 0 | 4 (29) | 0 | 4 (44) | 0 | 4 (25) | 0 |
| Aphasia | 0 | 0 | 6 (43) | 4 (29) | 2 (22) | 1 (11) | 2 (13) | 2 (13) |
| Encephalopathy | 4 (67) | 2 (33) | 9 (64) | 6 (43) | 2 (22) | 0 | 2 (13) | 2 (13) |
| Lethargy | 0 | 0 | 1 (7) | 0 | 2 (22) | 0 | 2 (13) | 0 |
| Mental status changes | 0 | 0 | 0 | 0 | 2 (22) | 0 | 0 | 0 |
| Agitation | 0 | 0 | 4 (29) | 1 (7) | 1 (11) | 1 (11) | 2 (13) | 0 |
| Dysarthria | 0 | 0 | 1 (7) | 1 (7) | 1 (11) | 0 | 0 | 0 |
| Restlessness | 0 | 0 | 1 (7) | 1 (7) | 1 (11) | 1 (11) | 0 | 0 |
| Seizure | 1 (17) | 0 | 2 (14) | 2 (14) | 1 (11) | 0 | 1 (6) | 0 |
| Ataxia | 0 | 0 | 1 (7) | 0 | 1 (11) | 0 | 0 | 0 |

AE, adverse event;
CRS, cytokine release syndrome;
NE, neurologic events

Twenty-six treated patients (58%) died from causes that included disease progression in 19 (42%) and AEs in 7 patients (16%), including the 2 above-mentioned treatment-related deaths. The remaining 5 AE-related deaths occurred at a median 63 days (range, 48-579) after infusion of anti-CD19 CAR T cells and were considered unrelated to anti-CD19 CAR T cells. They included sepsis (n=2), cerebrovascular accident (n=1), herpes simplex viremia (n=1) and bacteremia (n=1).

Efficacy

All 45 treated patients were eligible for efficacy analysis. At a median follow-up of 22.1 months (range, 7.1-36.1), the overall remission rate (ORR) was 69%, with 51% of patients achieving CR and 18% CRi (Table 21). Among the 23 patients treated with 1×$10^6$ CAR T cells/kg, the ORR was 83%, with 14 achieving CR (61%) and 5 (22%) CRi. Six of 9 patients who received revised AE management achieved CR/CRi (4 CR, 2 CRi). The median time to CR/CRi across dose levels was 30 days (range, 26-192), which included 1 patient with blast-free hypoplastic/aplastic bone marrow (BFBM) at day 28 who did not meet CR criteria until month 6. ORR was generally consistent across key covariates, including refractory patients (56%), prior transplant (77%), prior blinatumomab (57%) or inotuzumab ozogamicin (50%), and Ph+ disease patients (100%) (FIG. 5). Undetectable bone marrow MRD was achieved at day 28 in 100% of responders, including the 31 patients with CR/CRi, 1 patient with partial response, and 1 with BFBM. Residual disease assessment was unavailable in 1 patient with BFBM. Two of 6 patients who underwent the optional bone marrow assessment at day 7-14 had undetectable MRD; the 5 patients with data available at day 30 had undetectable MRD.

TABLE 21

| Response to anti-CD19 CAR T cells | | | | |
|---|---|---|---|---|
| Response Category, n (%) | 2 × $10^6$ (n = 6) | 1 × $10^6$ (n = 23) | 0.5 × $10^6$ (n = 16) | Total (N = 45) |
| Complete remission | 4 (67) | 19 (83) | 8 (50) | 31 (69) |
| Complete remission | 3 (50) | 14 (61) | 6 (38) | 23 (51) |
| Complete remission with incomplete hematologic recovery | 1 (17) | 5 (22) | 2 (13) | 8 (18) |
| Blast-free hypoplastic/aplastic bone marrow | 0 | 1 (4) | 1 (6) | 2 (4) |
| Partial remission | 0 | 1 (4)* | 0 | 1 (2) |
| No response | 1 (17) | 2 (9) | 6 (3) | 8 (18) |
| Unknown or not evaluable | 1 (17)† | 0 | 1 (6)‡ | 2 (4) |

*Patient had extramedullary disease at response assessment.

†Patient died on day 6 due to multiorgan failure secondary to CRS.

Figure 6A:
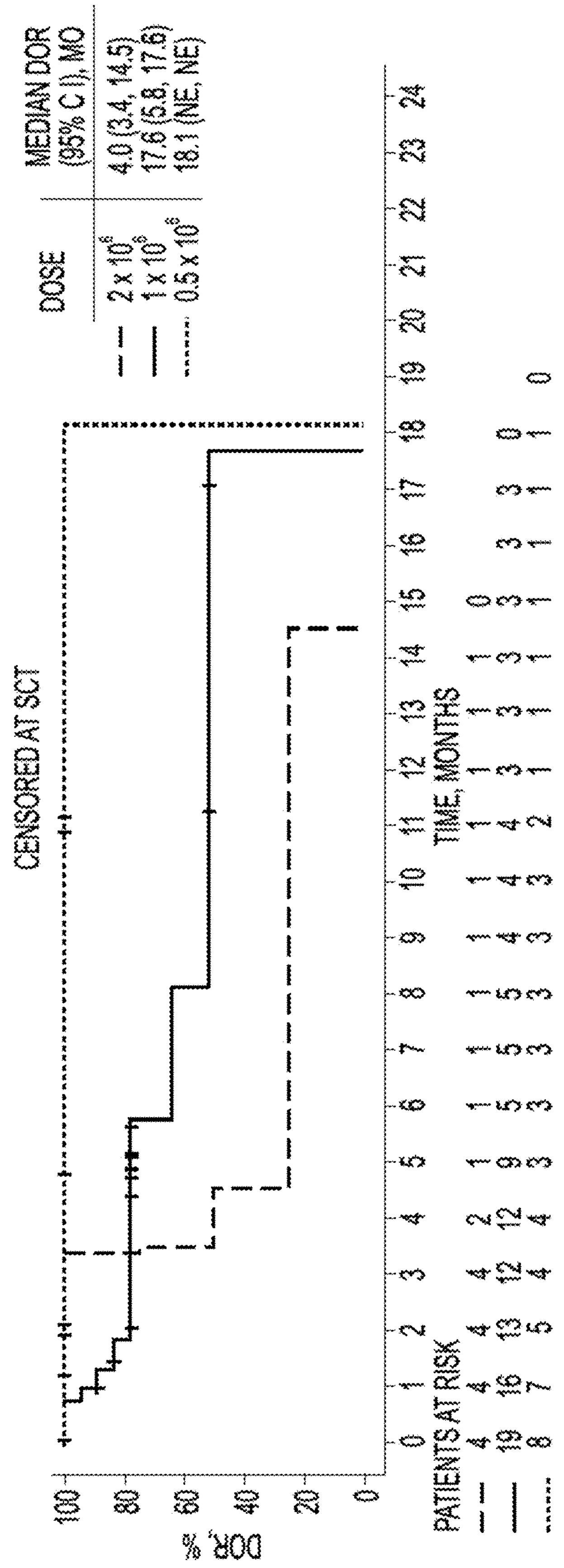
Figure 6B:
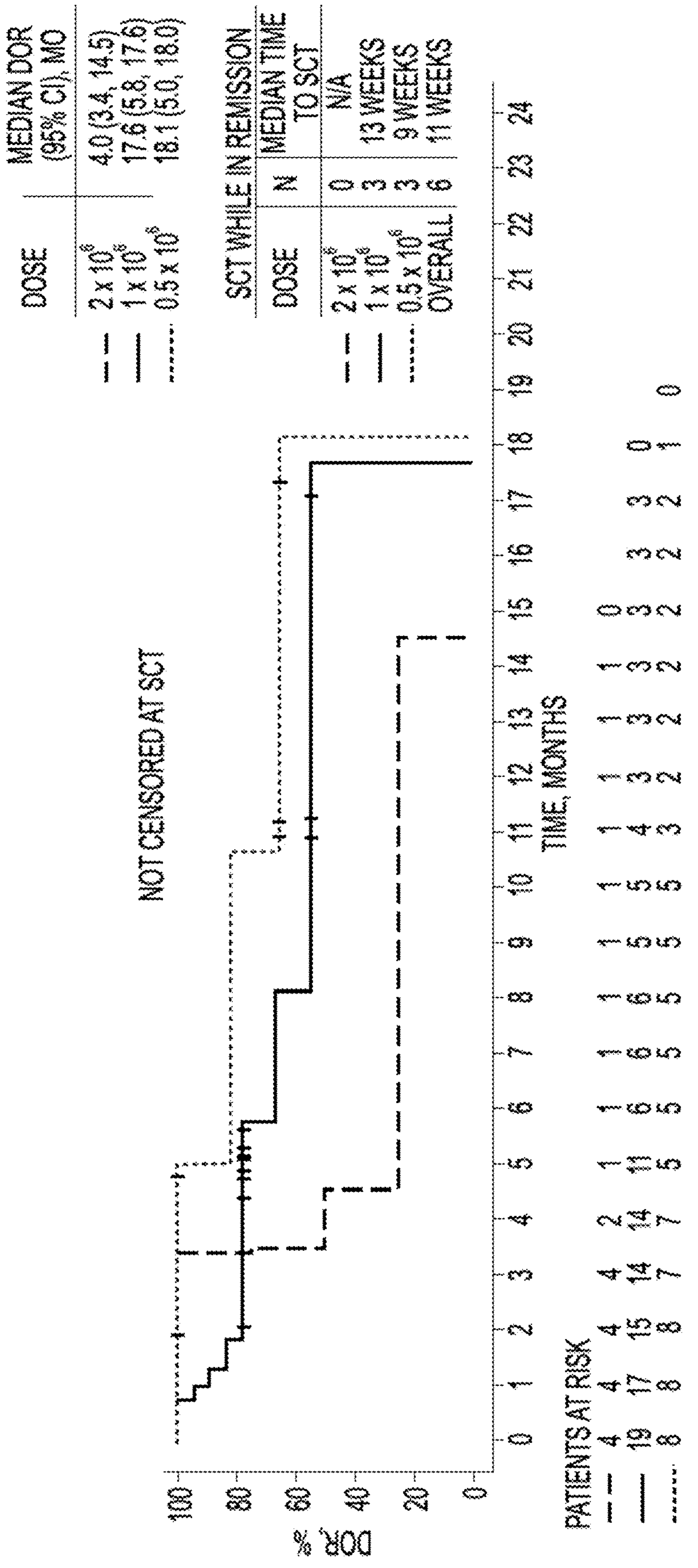
Figure 6C:
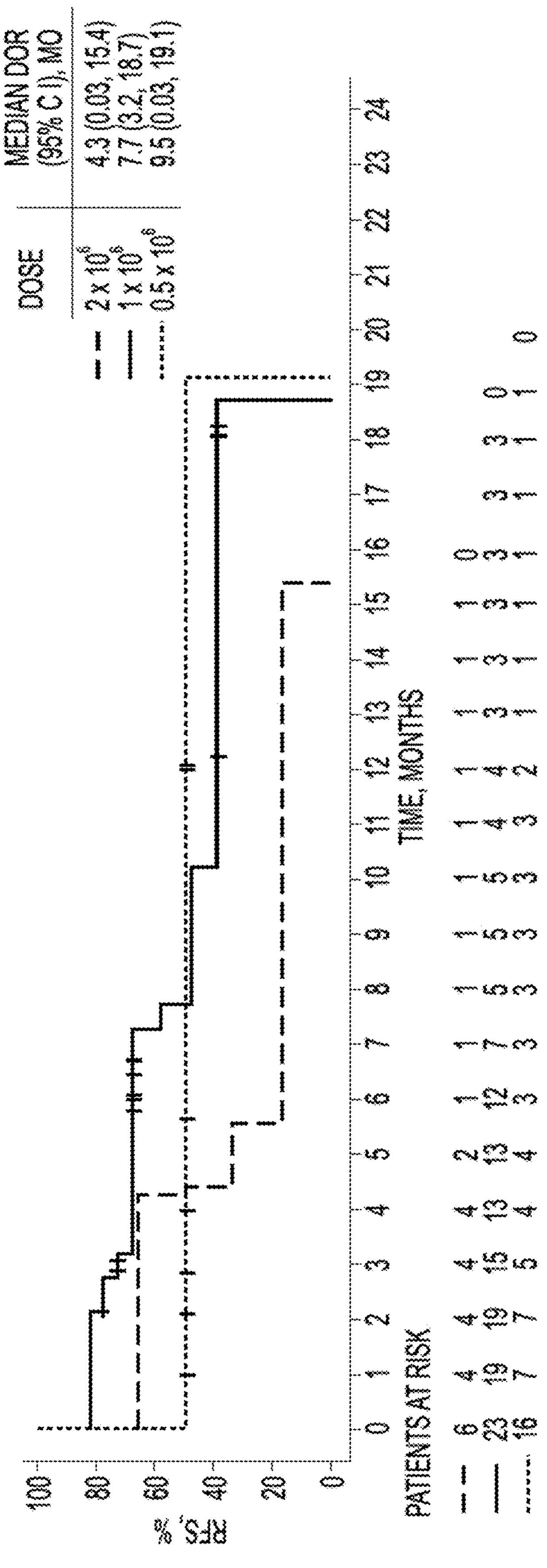
Figure 6D:
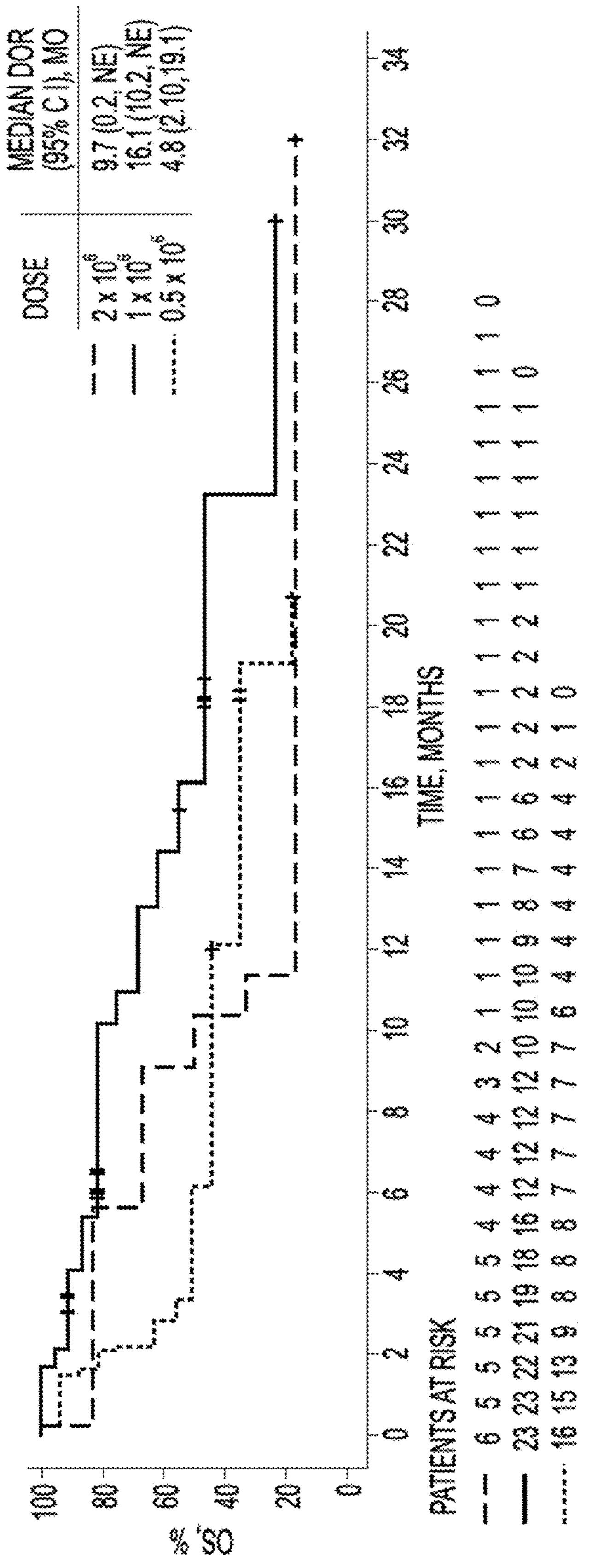

‡Patient died on day 7 due to cerebrovascular accident (stroke) in the context of CRS and neurologic events The median DOR for the 31 patients achieving CR/CRi was 14.5 months (95% CI, 5.8-18.1; FIG. 6A), and 17.6 months (95% oCI, 5.8-17.6) in patients treated with 1x$10^6$ CAR T cells/kg. Median DOR was similar regardless of censoring for SCT post-anti-CD 19 CAR T cells (FIG. 6B). As of the data cutoff, 8 patients (260%) had ongoing CRs, including 2 who received 0.5x$10^6$ CAR T cells/kg and 6 who received 1x$10^6$ CAR T cells/kg, with a median follow-up of 6.3 months (range, 5.9-18.2). Six patients (2CR and 1 partial response treated with 1x$10^6$ CAR T cells/kg; 3CR treated with 0.5x$10^6$ cells/kg) underwent SCT at a median of 2.7 months (range, 1.7-4.3) post-infusion. As of this analysis, 3 of these remained in CR (2 treated with 1x$10^6$ CAR T cells/kg and 1 with 0.5x$10^6$ cells/kg). Across all dose levels, the median duration of relapse-free survival was 7.3 months (95% CI, 2.7-18.7) vs. 7.7 months (95% CI, 3.2-18.7) in patients receiving 1x$10^6$ CAR T cells/kg (FIG. 6C). The median OS was 12.1 months (95% CI, 6.1-19.1) across all dose levels and 16.1 months (95% CI, 10.2-not estimable) with 1x$10^6$ CAR cells/kg (FIG. 6D).

As of the data cutoff, 1 patient (2%) withdrew consent, 1 (20%) was lost to follow-up, and 17 (38%) were alive, including 11/23 patients (50%) treated with 1x$10^6$ cells/kg. Four patients received a second infusion of anti-CD19 CAR T cells; one was in CR at 15 months post-re-dosing, 2 had relapsed by the month-3 assessment, and 1 withdrew consent prior to the first response assessment.

Clinical Pharmacology

CAR T-cell levels measured by CAR gene copies per g DNA in blood peaked 7-14 days post-anti-CD19 CART cells infusion for most patients and remained detectable in 2/12 evaluable patients at 12 months, both of whom were in CR (FIG. 7A; Table 22).

TABLE 22

| CAR gene copies in blood over time | | | | |
|---|---|---|---|---|
| CAR Gene Copies per µg DNA in Blood | 2 × $10^6$ | 1 × $10^6$ Original AE Management | 1 × $10^6$ Revised AE Management | 0.5 × $10^6$ |
| Baseline | (n = 6) | (n = 14) | (n = 9) | (n = 16) |
| Median | 0 | 0 | 0 | 0 |
| Range | 0-0 | 0-0 | 0-0 | 0-0 |
| Day 7 | (n = 4) | (n = 12) | (n = 9) | (n = 15) |
| Median | 62,411 | 154,386 | 91,287 | 3702 |
| Range | 11,097-162,972 | 12,231-443,880 | 0-353,160 | 0-375,030 |
| Week 2 | (n = 5) | (n = 14) | (n = 8) | (n = 13) |
| Median | 44,064 | 48,114 | 60,507 | 3669 |
| Range | 2228-106,110 | 7614-283,500 | 10,935-224,370 | 0-100,845 |
| Week 4 | (n = 5) | (n = 11) | (n = 9) | (n = 13) |
| Median | 1304 | 3119 | 16,200 | 1588 |
| Range | 405-4860 | 1029-95,580 | 235-56,052 | 0-27,540 |
| Week 8 | (n = 0) | (n = 5) | (n = 7) | (n = 7) |
| Median | — | 0 | 527 | 219 |
| Range | — | 0-907 | 0-972 | 0-9882 |
| Month 3 | (n = 4) | (n = 11) | (n = 6) | (n = 9) |
| Median | 0 | 203 | 99 | 0 |
| Range | 0-0 | 0-1458 | 0-478 | 0-5508 |
| Month 6 | (n = 3) | (n = 8) | (n = 0) | (n = 7) |
| Median | 0 | 0 | — | 0 |
| Range | 0-0 | 0-105 | — | 0-518 |
| Month 9 | (n = 1) | (n = 6) | (n = 0) | (n = 4) |
| Median | 0 | 0 | — | 0 |
| Range | 0-0 | 0-138 | — | 0-0 |
| Month 12 | (n = 1) | (n = 4) | (n = 0) | (n = 3) |
| Median | 65 | 0 | — | 0 |
| Range | 65-65 | 0-0 | — | 0-57 |

AE, adverse event;

CAR, chimeric antigen receptor

CAR T cells were undetectable in the 5 patients with data available at relapse. Median peak CAR T-cell levels were highest with 1×10$^{6}$ CAR T cells/kg and were similar between patients who received original vs. revised AE management (FIG. 7B; FIG. 8). Patients achieving CR/CRi had greater median peak expansion than non-responders, as did patients with undetectable vs. detectable MRD (FIG. 7C-D; FIG. 84B-C). Higher median peak expansion was also observed in patients with grade ≥3 vs. those with grade ≤2 NE (FIG. 7E-F; FIG. 8D-E). Of 13 patients who relapsed, 7 had detectable CD19-positive cells at relapse, 3 had no detectable CD19-positive cells, and 3 had no data available.

Peak levels of key cytokines, chemokines, and pro-inflammatory markers occurred by day 7, with some trending higher in patients dosed with 2×10$^{6}$ compared with 1×10$^{6}$ CAR T cells/kg (IL-15, CRP, SAA, CXCL10, IFNγ), or lower in those with revised AE management vs those with original AE management (IL-6, Ferritin, IL-1RA, IFNγ, IL-8, CXCL10, MCP-1) FIG. 9; FIG. 10). While peak IL-15 serum levels were surprisingly lower in patients with grade ≥3 CRS, median peak levels of several pro-inflammatory markers trended higher in patients with grade ≥3 CRS and those with grade ≥3 NE (IFNγ, IL-8, GM-CSF, IL-1RA, CXCL10, MCP-1, Granzyme B; FIG. 11).

Four patients tested positive during screening assays for anti-CAR antibodies, but all were negative in confirmatory assays at leukapheresis. Characteristics of manufactured CAR T-cell products were as anticipated and previously reported (Table 23).

treated, high rates of remission and undetectable bone marrow MRD were achieved, particularly in those treated at the 1×10$^{6}$ dose level; the ORR was 8300 including 61% CR and 22% CRi, all of whom had undetectable MRD. Based on these results showing that anti-CD19 CAR T cells are safe and have promising efficacy, the 1×10$^{6}$ CAR T cells/kg dose was chosen for further evaluation in phase 2 of ZUMA-3.

Use of anti-CD19 CAR T cells to treat adult R/R B-ALL has proven difficult owing to the highly proliferative nature of this disease and inability to tolerate treatment-related AEs. A previous CAR T-cell trial in this population was closed early due to fatal NE, including 5 cases of cerebral edema. DeAngelo D J, Ghobadi A, Park J H, et al. *Journal for Immuno Therapy of Cancer.* 2017; 5 (Suppl 2):P217. Under the original AE management guidelines in ZUMA-3, 2 patients died from grade 5 AEs considered related to anti-CD19 CAR T cells either secondary to CRS or in the context of CRS and NE outside the DLT-assessment time-frame. In addition to evaluating multiple doses to identify the dose with the most manageable toxicities, revised AE management guidelines requiring earlier steroid intervention for neurotoxicity and the use of tocilizumab only for CRS were implemented among 9 patients enrolled at the 1×10$^{6}$ CAR T cells/kg dose level. This resulted in a shorter duration of CRS events and lower incidence, severity, and duration of NE compared with 14 patients treated at the same dose under the original guidelines.

At a median follow-up of 22.1 months, responses were ongoing in 26% of patients, most of whom received 1×10$^{6}$

TABLE 23

| Product characteristics | | | | |
|---|---|---|---|---|
| Median characteristic (range) | 2 × 10$^{6}$ (n = 6) | 1 × 10$^{6}$ Original AE Management (n = 14) | 1 × 10$^{6}$ Revised AE Management (n = 9) | 0.5 × 10$^{6}$ (n = 16) |
| T-cell subsets, % | | | | |
| Naïve | 32.9 (16.4-60.5) | 41.1 (9.9-73.2) | 30.2 (0.1-65.0) | 33.1 (12.5-80.9) |
| Central memory | 34.5 (15.1-42.7) | 21.9 (14.6-40.7) | 19.3 (3.2-36.3) | 18.0 (3.0-48.2) |
| Effector | 8.9 (3.7-13.4) | 8.9 (4.5-41.6) | 14.5 (2.4-20.9) | 14.3 (2.4-38.1) |
| Effector memory | 20.7 (15.5-52.4) | 18.4 (4.8-60.0) | 19.9 (3.9-94.3) | 22.6 (1.0-45.3) |
| CD4, % | 44.7 (33.9-58.8) | 47.6 (21.9-76.8) | 56.8 (41.0-93.7) | 58.8 (28.5-85.9) |
| CD8, % | 55.4 (41.2-66.2) | 49.0 (23.2-78.1) | 43.3 (6.3-59.0) | 41.2 (14.1-71.4) |
| CD4/CD8 ratio | 0.8 (0.5-1.4) | 1.0 (0.3-3.3) | 1.4 (0.7-14.9) | 1.4 (0.4-6.1) |
| IFNγ production in co-culture (pg/mL)* | 7944.0 (1679.5-11214.4) | 9980.5 (3025.0-37921.9) | 10317.3 (5255.0-45235.7) | 9059.5 (1040.6-27859.1) |

*Co-culture experiments were performed using Toledo cells mixed in a 1:1 ratio with anti-CD19 CAR T cells product. IFNγ was measured in cell culture media 24 h post-incubation using a qualified ELISA.
AE, adverse event;
IFNγ, interferon gamma ZUMA-3 is the first multicenter study evaluating CAR T-cell therapy in adult R/RB-ALL to complete phase 1. In the phase 1 portion, no protocol-defined DLTs were observed with anti-CD 19 CAR T cells, and the AEs reported were consistent with prior studies of an-CD19 CAR T-cell therapies. Neelapu S S. et al. *N Engl J Med.* 2017; 377(26): 2531-2544; Maude S L et al. *N Engl J Med.* 2018; 378(5): 439-448. The 1×10$^{6}$ CAR T cells/kg dose coupled with revised AE management guidelines had the most favorable risk/benefit ratio without compromising activity. Although patients had high disease burden and were heavily pre- CAR T cells/kg (32% ongoing CR/CRi). Responses tended to occur early after treatment. Most occurred within the first month, though 1 patient with extramedullary disease achieved CR at month 6. High response rates were observed across all prespecified subgroups, including a 100% CR rate in patients with Ph+ disease. Response (CR/CRi) was associated with higher expansion of CAR T cells measured within 2 weeks post-treatment. Similarly, in a single-center, phase 1 study using an anti-CD19 CAR T-cell therapy also containing a CD3ζ and CD28 co-stimulatory domain (Park J H et a. *N Engl J Med.* 2018; 378(5):449-459), the overall CR rate was 83%, although post-bridging therapy, only half of the patients had ≥5% blasts in the bone marrow, 28% had MRD, and 11% had undetectable MRD. Nevertheless, those trial results largely paralleled those of the present study, further supporting the potential utility of anti-CD19 CAR T-cell therapies using a CD3ζ and CD28 co-stimulatory domain in adult R/R B-ALL.

Tisagenlecleucel, an anti-CD19 CAR T-cell therapy containing a CD3ζ T-cell activation domain and a 4-1BB co-stimulatory domain, is approved for the treatment of R/R B-ALL in children and young adults (≤25 years). Maude S L et al. *N Engl J Med.* 2018; 378(5):439-448; KYMRIAH (tisagenlecleucel) [package insert]. Novartis. East Hanover, NJ; 2018. The dosing regimen for tisagenlecleucel in younger patients, however, resulted in substantial toxicity and CRS-related deaths in adults with R/R B-ALL. Frey N V. et al. *J Clin Oncol.* 2020; 38(5):415-422. In a single-center study in adult R/R B-ALL across two clinical trials, administering the dose in fractions resulted in manageable CRS and a 90% CR rate. Frey N V et al. *J Clin Oncol.* 2020; 38(5):415-422. Similar to ZUMA-3 observations, optimized dosing and toxicity management strategies may enable patients vulnerable to life-threatening treatment-related toxicities to benefit from CAR T-cell therapy.

Despite differences in trial designs, patient populations, and OS methodology, the median OS with $1\times10^6$ CAR T cells/kg in the present study was 16.1 months, whereas the median OS previously reported with blinatumomab, which also targets CD19, was 6.1-7.7 months in adult R/R B-ALL. Topp M S et al. *Lancet Oncol.* 2015; 16(1):57-66; Kantarjian H. et al. *N Engl J Med.* 2017; 376(9):836-847. Of 10 patients evaluable at relapse for CD19 blast expression, 3 showed lack of CD19 expression, reminiscent of other reports attributing target-loss to selection of exon splice variants and mutations. Sotillo E et al. *Cancer Discov.* 2015; 5(12):1282-1295. In the present study, only 1/8 patients (13%) with blinatumomab as last prior therapy responded to blinatumomab. This may suggest immunologic incompetence in unmanipulated T cells in some patients with R/R ALL, possibly limiting the utility of bispecific T-cell engager therapy. Of the 21 patients with prior blinatumomab in any line, 12 (57%) achieved CR/CRi following anti-CD19 CAR T cell therapy. As previously reported (Shah B D. et al. *J Clin Oncol.* 2018; 36 (suppl):abstr 7006), responses to anti-CD19 CAR T cells were similar regardless of prior blinatumomab exposure inpatients with continued CD19 positivity. In addition, 6 patients achieving CR underwent SCT and were censored at the time of SCT; 3 remained in remission.

Adults with R/R B-ALL achieved high rates of CR and undetectable bone marrow MRD with a tolerable safety profile after treatment with anti-CD19 CAR T cells. The successful manufacture for all enrolled patients and the relatively rapid turnaround time supported the feasibility of providing this cellular-therapy treatment to patients with rapidly progressing disease who need prompt treatment. By carefully evaluating a range of doses and adopting safety strategies, including use of tocilizumab or steroids and conditions under which they should be administered to manage AEs, it was possible to transition the study from phase 1 to an international phase 2 study. There were no fatal cerebral edema cases in phase 1, a limitation of prior studies in this population. Phase 2 of ZUMA-3 was ongoing at the $1\times10^6$ CAR T cells/kg dose with revised AE management guidelines.

Example 10

This Example described the results of CD19ΔTyr260 in CD19 in B-ALL associated with resistance to a CAR T cell therapy treatment. After failing several therapies, including blinatumomab prior to KTE-X19, a B-ALL patient received a target dose of $1\times10^6$ CAR T cell/kg. The patient did not respond clinically; no CAR T and CD19-expressing lymphocytes were detectable at Day 28. Peripheral blood mononuclear cells (PBMCs) were collected the patient with B-ALL pre- and post-KTE-X19 infusion at various time points. Multicolor flow cytometry was used to examine CD19 (clone FMC63, HIB19, SJ25C1) surface expression on patient PBMCs and Jurkat cell lines engineered to be CD19-wildtype (WT) or to express CD19ΔTyr260. The presence of genetic variants was assessed using enhanced whole genome and RNA sequencing (TruSeq Stranded Total RNA). Location of cellular protein expression was assessed using Western blot with and without deglycosylating enzymes.

While local pathology concluded that preinfusion B lymphoblasts were uniformly $CD19^{dim}$, additional analyses of the same sample with FMC63 (the single-chain variable fragment of KTE-X19) revealed that CD19 was not detectable in preinfusion B lymphoblasts. Results of RNA sequencing showed an in-frame deletion within the intracellular domain of CD19 at Tyr260 (CD19ΔTyr260) in circulating leukemia blasts. Additional analysis using flow cytometry showed that CD19 expression was not detected on Jurkat CD19ΔTyr260 cells but was present on Jurkat CD19-WT cells, which suggested that the lack of visualization of cells carrying this point mutation and their resistance to CAR T cell therapy. Longitudinal RNA and DNA sequencing analysis showed that the mutation had occurred prior to infusion of CAR-T therapy. Fractionated cellular lysates showed WT CD19 in the cell membrane having a high and lower molecular weight band, as well as CD19ΔTyr260 expressed on the surface with a single low molecular weight band. Under deglycosylating conditions, only 1 band was present in both WT CD19 and CD19ΔTyr260 cellular fractions. Without being bound to any scientific theories or hypotheses, it is likely that the CD19ΔTyr260 mutation may result in lack of suitable or functional CD19 glycosylation and/or inhibiting detection. The mutation in B-ALL malignant cells may have potential implications for other anti-CD19 CAR or non-CD19 CAR cell therapy.

Example 11

Patients with MCL who progress after BTKi therapy typically have a poor prognosis, with an overall survival of only 5.8 months with salvage therapies. Martin P, et al. *Blood.* 2016; 127:1559-1563. In Phase 2 ZUMA-2 study, KTE-X19 was evaluated in patients with MCL who were R/R to 1-5 prior therapies, including a BTKi. Wang M, et al. *N Engl J Med.* 2020; 382:1331-1342. At a median follow-up of 12.3 months, the ORR was 93% (67% complete responses) in the primary efficacy analysis of ZUMA-2 (N=60). Aggressive disease variants, including blastoid or pleomorphic MCL, are generally associated with poor clinical outcomes, yet ORR was comparable across patients with various histologies in ZUMA-2. Wang M, et al. *N Engl J Med.* 2020; 382:1331-1342; Jain P and Wang M. *Am J Hematol.* 2019; 94:710-725. In this study, the pharmacological profile and clinical outcomes in patient subgroups defined by MCL morphology and prior BTKi exposure in ZUMA-2 were compared, accompanied by a characterization of product attributes and other pre-treatment factors. Patients underwent leukapheresis and conditioning chemotherapy followed by a single infusion of CD19 CAR-T cells at a target dose of $2\times10^6$ CAR T cells/kg, by single IV infusion on Day 0. Some patients received bridging therapy with dexamethasone (20-40 mg or equivalent PO or IV daily for 1-4 days), ibrutinib (560 mg PO daily), or acalabrutinib (100 mg PO twice daily), administered after leukapheresis and completed ≤5 days before initiating conditioning chemotherapy; PET-CT was required post-bridging. Primary endpoint was objective response rate (ORR [complete response (CR)+partial response]). Secondary endpoints were duration of response (DOR), progression-free survival (PFS), OS, frequency of adverse events (AEs), levels of CAR T cells in blood, and levels of cytokines in serum. Efficacy and safety analyses included all patients who received CD19 CAR-T cell therapy. The first tumor assessment was done on Day 28. Bone marrow biopsy was done at screening, and if positive, not done, or indeterminate, a biopsy was needed to confirm CR.

Of the 60 patients in ZUMA-2 with MCL treated with KTE-X19 with a median follow-up of 12.3 months, there was a 93% ORR, 67% CR rate, and 57% of all patients and 78% of patients in CR had ongoing responses. CRS and neurologic events were mostly reversible (N=68 treated patients). About 15% had Grade ≥3 CRS, 31% Grade ≥3 neurologic events, and 2 Grade 5 AEs (1 KTE-X19-related). Patient subgroups were defined by morphological characteristics (classical, blastoid, or pleomorphic MCL) and by prior exposure to ibrutinib only, acalabrutinib only, or both ibrutinib and acalabrutinib. Table 24. Baseline characteristics were generally comparable across these groups. There was a trend toward higher pre-treatment tumor burden in patients previously treated with ibrutinib. Product attributes, CAR T cell levels in blood, and cytokine levels in serum were analyzed using previously described methods. Locke F L, et al. Mo Ther. 2017; 25:285-295. Product T cell attributes were generally comparable across MCL morphology subgroups. There were trends toward increased product co-culture IFN-γ and percentage of CCR7+ cells in products from patients with pleomorphic morphology. Table 25. Product T cell Attributes were also generally comparable across prior BTKi subgroups. There was a trend toward increased product co-culture IFN-γ in patients previously treated with ibrutinib. Table 26.

TABLE 24

Patient baseline characteristics.

| | Ibrutinib (n = 52) | Acalabrutinib (n = 10) | Both (n = 6) |
|---|---|---|---|
| Median age (range), years | 65 (45-79) | 57 (38-73) | 62 (55-72) |
| ≥65 years, n (%) | 32 (62) | 4 (40) | 3 (50) |
| Male, n (%) | 43 (83) | 9 (90) | 5 (83) |
| Stage IV disease, n (%) | 44 (85) | 9 (90) | 5 (83) |
| ECOG 0/1, n (%) | 52 (100) | 10 (100) | 6 (100) |
| Median tumor burden[a] (range), $mm^2$ | 2697 (386-16878) | 1144 (293-14390) | 536 (260-1174) |
| Ki-67 proliferation index, n/N (%) | | | |
| ≥50 | 25/38 (66) | 3/5 (60) | 6/6 (100) |
| <50 | 13/38 (34) | 2/5 (40) | 0 |
| MCL morphology | | | |
| Classical | 30 (58) | 6 (60) | 4 (67) |
| Pleomorphic | 1 (2) | 2 (20) | 1 (17) |
| Blastoid | 12 (23) | 3 (30) | 2 (33) |
| Bone marrow involvement, n (%) | 28 (54) | 3 (30) | 6 (100) |
| Extranodal disease, n (%) | 31 (60) | 3 (30) | 4 (67) |
| Median no. prior therapies (range) | 3 (1-5) | 3 (2-5) | 3 (3-4) |
| Prior bendamustine, n (%) | 28 (54) | 7 (70) | 2 (33) |

[a]As measured by the sum of product dimensions of all target lesions at baseline. For subjects who had bridging therapy, the measurement after bridging therapy is used as baseline.

TABLE 25

Cell characterizations and MCL morphology.

| | MCL Morphology | | |
|---|---|---|---|
| Median (range) | Classical (n = 40) | Blastoid (n = 17) | Pleomorphic (n = 4) |
| Transduction rate, % | 58.1 (35.0-82.4) | 60.0 (46.0-79.4) | 61.9 (50.0-77.1) |
| CD4/CD8 ratio | 0.7 (0.04-2.8)[a] | 0.6 (0.2-1.1)[a] | 0.7 (0.5-2.0) |
| CCR7+ T cells, % | 40.0 (2.6-88.8)[a] | 35.3 (14.3-73.4)[a] | 80.8 (57.3-88.8) |
| CCR7− effector + effector memory T cells, % | 59.9 (11.1-97.4)[a] | 64.8 (26.6-85.7)[a] | 19.2 (11.1-42.7) |

TABLE 25-continued

| Cell characterizations and MCL morphology. | | | |
|---|---|---|---|
| | MCL Morphology | | |
| Median (range) | Classical (n = 40) | Blastoid (n = 17) | Pleomorphic (n = 4) |
| (CCR7+ T cells)/(CCR7− effector + effector memory T cells) ratio | 0.7 (0.03-8.0)[a] | 0.5 (0.2-2.8)[a] | 4.7 (1.3-8.0) |
| IFN-γ by coculture, pg/mL | 6309.5 (424.0-2.0 × $10^4$) | 6510.0 (2709.0-1.8 × $10^4$) | 7687.5 (424.0-1.2 × $10^4$) |

[a]Based on available data: classical, n = 38; blastoid, n = 16

TABLE 26

| Cell characterizations and BTKi subgroups. | | | |
|---|---|---|---|
| | BTKi Exposure | | |
| Median (range) | Ibrutinib (n = 52) | Acalabrutinib (n = 10) | Both (n = 6) |
| Transduction rate, % | 56.7 (32.0-82.4) | 65.0 (35.0-74.0) | 58.5 (46.0-67.0) |
| CD4/CD8 ratio | 0.7 (0.04-3.7)[a] | 0.6 (0.3-1.2) | 1.0 (0.7-1.9) |
| CCR7+ T cells, % | 39.3 (2.6-86.4)[a] | 42.7 (16.3-88.8) | 49.5 (14.3-83.0) |
| CCR7− effector + effector memory T cells, % | 60.6 (13.7-97.4)[a] | 57.3 (11.1-83.8) | 50.6 (17.0-85.7) |
| (CCR7+ T cells)/(CCR7− effector + effector memory T cells) ratio | 0.7 (0.03-6.3)[a] | 0.8 (0.2-8.0) | 1.2 (0.2-4.9) |
| IFN-γ by coculture, pg/mL | 6496.0 (424.0-2.0 × $10^4$) | 5972.5 (2502.0-1.8 × $10^4$) | 7985.5 (2709.0-1.2 × $10^4$) |

aBased on available data: ibrutinib, n = 49

High rates of response were achieved across MCL morphology and prior BTKi subgroups. Table 27. Clinical benefit from KTE-X19 treatment was observed in all subgroups defined by MCL morphology or prior BTKi. A trend toward a higher ongoing response rate at 6 months was observed in patients previously treated with ibrutinib. Table 27. CRS and neurological events were generally comparable across MCL morphology and prior BTKi subgroups. Table 28. A trend toward increased rate of Grade ≥3 neurological events was observed in patients with non-blastoid morphology or previously treated with ibrutinib. Table 28.

TABLE 27

| Rate of response | | | | | | |
|---|---|---|---|---|---|---|
| | MCL Morphology | | | BTKi Exposure | | |
| | Classical (n = 35) | Blastoid (n = 14) | Pleomorphic (n = 4) | Ibrutinib (n = 45) | Acalabrutinib (n = 9) | Both (n = 6) |
| ORR, n (%) | 32 (91)[1] | 13 (93)[1] | 4 (100)[1] | 43 (96) | 7 (78) | 6 (100) |
| CR, n (%) | 22 (63)[1] | 9 (64)[1] | 3 (75)[1] | 30 (67) | 4 (44) | 6 (100) |
| Ongoing response at 6 mo, n (%) | 18 (51) | 8 (57) | 3 (75) | 25 (56) | 3 (33) | 6 (100) |
| 12-mo OS, % (95% CI) | 85.7 (69.0-93.8)[1] | 71.4 (40.6-88.2)[1] | 100.0 (NE-NE)[1] | 82.0 (67.2-90.6) | 77.8 (36.5-93.9) | 100.0 (NE-NE) |

[1]Wang M, et al. *N Engl J Med.* 2020; 382: 1331-1342.
CR, complete response;
MCL, mantle cell lymphoma;
NE, not evaluable;
ORR, objective response rate;
OS, overall survival

TABLE 28

| Adverse Events | | | | | | |
|---|---|---|---|---|---|---|
| | MCL Morphology | | | BTKi Exposure | | |
| n (%) | Classical (n = 40) | Blastoid (n = 17) | Pleomorphic (n = 4) | Ibrutinib (n = 52) | Acalabrutinib (n = 10) | Both (n = 6) |
| CRS | | | | | | |
| Any grade | 36 (90) | 15 (88) | 4 (100) | 50 (96) | 6 (60) | 6 (100) |
| Grade ≥3 | 6 (15) | 1 (6) | 1 (25) | 9 (17) | 1 (10) | 0 |
| Neurologic events | | | | | | |
| Any grade | 25 (63) | 11 (65) | 3 (75) | 33 (63) | 4 (40) | 6 (100) |
| Grade ≥3 | 15 (38) | 3 (18) | 2 (50) | 16 (31) | 1 (10) | 4 (67) |

Comparisons across subgroups were conducted using the Kruskal-Wallis test; Dunn's post-hoc test was used to compare between groups. Pharmacological profile, product attributes, and safety data were reported for all 68 patients treated with KTE-X19 ($2\times10^6$ cells/kg). The pharmacological and pharmacodynamic profile of KTE-X19 across MCL morphology subgroups suggested increased CAR T cell expansion and select pro-inflammatory cytokines in patients with classical morphology compared with patients with blastoid morphology (FIGS. 12 and 13) or in patients previously treated with ibrutinib compared with acalabrutinib alone FIGS. 14 and 15). Pre-treatment patient and product characteristics were generally comparable across MCL morphologies and subsets with different prior therapies. Patients with blastoid morphology exhibited decreased CAR T cell expansion, circulating myeloid-related cytokines and chemokines, and rate of Grade ≥3 CRS and neurologic events, while the clinical efficacy was comparable with that of patients with classical morphology. The trend towards an improved safety profile in patients with blastoid morphology was commensurate with lower peak CAR T cell expansion and decreased peak levels of cytokines associated with myeloid-related inflammation. Patients previously treated with ibrutinib exhibited increased CAR T cell expansion, circulating inflammatory cytokines and chemokines, and rate of Grade ≥3 neurologic events; as well as increased ongoing response rate at 6 months and an ORR comparable with that of patients previously treated with acalabrutinib alone. Patients previously treated with acalabrutinib exhibited decreased CAR T cell expansion and circulating T1-related cytokines and chemokines, which was consistent with an improved safety profile.

Example 12

This example characterized two anti-CD19 CAR T therapies, KTE-X19 prepared according to Example 5 and axicabtagene ciloleucel. Cells were labeled with fluorescently-conjugated antibodies to CD3 (pan T cell marker), CD14, CD19 (B cell marker), CD45 (pan-leukocyte marker), and CD56 (activation and NK marker) and assessed by flow cytometry. Cell viability was assessed using negative staining of a viability dye (SYTOX near-IR). The lower limit of quantification (LLOQ) of the assay was 0.2% and for NK cells and monocytes was 5%. The percentage of NK cells was determined (NK cells were $CD45^+$, $CD14^-$, $CD3^-$, and $CD56^+$; T cells were $CD45^+$, $CD14^-$, and $CD3^-$). The median percentages of NK cells from 23 lots of axicabtagene ciloleucel and 97 lots of KTE-X19 were 1.9% (range 0.8%-3.2%) and 0.1% (range 0.0%-2.8%), respectively. The median percentage of $CD3^-$ cellular impurities from the same lots of axicabtagene ciloleucel and KTE-X19 were 2.4% (range 0.9%-4.6%) and 0.5% (range 0.3%-3.9%), respectively. The results of KTE-X19 and axicabtagene ciloleucel in cell viability were ≥72% and ≥80%, respectively; in anti-CD19 CAR expression were ≥24% and ≥15%, respectively; in IFN-γ production were ≥190 μg/mL and ≥520 μg/mL, respectively; and in percentage of $CD3^+$ cells were ≥90% and ≥85%, respectively.

Example 13

Additional results of patients receiving $2\times10^6$ KTE-X19 cells/kg in a single infusion in prior examples including EXAMPLE 2 and EXAMPLE 7 were provided. ORR by IRRC assessment was 92% (95% CI, 82-97) and CR Rate was 67% (95% CI, 53-78). At a median follow-up of 17.5 months (range, 12.3-37.6), 29 patients remained in ongoing responses. Ongoing response rates were largely consistent among patients with high-risk disease characteristics. The first 28 patients treated had a median follow-up of 32.3 months (range, 30.6-37.6). 39% of patients remained in continued remission with no further therapy. In all enrolled patients (N=74), ORR was 84% (59% CR rate). The medians for DOR, PFS, and OS were not reached after a median follow-up of 17.5 months. Table 29. The ongoing response rate was consistent across adverse prognostic groups. FIG. 16. At a median follow-up of 17.5 months, the ZUMA-2 study continued to show substantial and durable clinical benefit of KTE-X19 therapy in patients with R/R MCL. No new safety signals were observed with additional follow-up. No new CRS or new Grade 5 events occurred since the previous reports. Table 30. AE rates decreased over time. KTE-X19 therapy showed a manageable safety profile with extended follow-up.

TABLE 29

Duration of response, progression-free survival, and overall survival.

| | DOR | | PFS | | OS | |
|---|---|---|---|---|---|---|
| | Median (95% CI), mo | 15-Mo Rate (95% CI) | Median (95% CI), mo | 15-Mo Rate (95% CI) | Median (95% CI), mo | 15-Mo Rate (95% CI) |
| Evaluable pts (N = 60) | NR (13.6-NE)[a] | 58.6 (42.5-71.7)[a] | NR (9.6-NE) | 59.2 (44.6-71.2) | NR (NE, NE) | 76.0 (62.8, 85.1) |
| Pts in CR (n = 40) | NR (14.4-NE) | 69.7 (49.3-83.2) | NR (15.3-NE) | 75.1 (56.8-86.5) | NR (NE, NE) | 91.7 (76.2, 97.2) |
| Pts in PR (n = 15) | 2.2 (1.4-4.3) | 24.1 (5.9-48.9) | 3.1 (2.3-5.2) | 24.1 (5.9-48.9) | 12.6 (3.3, NE) | 46.7 (21.2, 68.7) |

[a]Out of 55 total responding patients.

TABLE 30

Safety Analysis

| | All Treated Patients (N = 68) | | | |
|---|---|---|---|---|
| | On/After 3 Months Post-Infusion | | On/After 6 Months Post-Infusion | |
| AE, n (%)[a] | Any Grade | Grade ≥3 | Any Grade | Grade ≥3 |
| Any AE | 55 (81) | 33 (48) | 49 (72) | 25 (37) |
| Anemia | 22 (32) | 9 (13) | 13 (19) | 4 (6) |
| Neutropenia | 20 (29) | 16 (24) | 14 (21) | 11 (16) |
| Thrombocytopenia | 20 (29) | 14 (21) | 14 (21) | 9 (13) |
| White blood cell count decrease | 16 (24) | 9 (13) | 12 (18) | 6 (9) |
| Fatigue | 10 (15) | 0 | 10 (15) | 0 |
| Pneumonia | 9 (13) | 5 (7) | 6 (9) | 4 (6) |
| Cough | 8 (12) | 0 | 7 (10) | 0 |
| Hypogammaglobulinemia | 8 (12) | 0 | 7 (10) | 0 |
| Upper respiratory tract infection | 7 (10) | 2 (3) | 5 (7) | 1 (1) |

[a]Includes AEs of any grade occurring in ≥10% of patients.

Of 57 efficacy-evaluable patients with data available, 48 (840%) had detectable B cells at baseline. Among patients with ongoing responses at 12 months, more than 50% of evaluable patients had detectable B cells and gene-marked CAR T cells at months 6, 12, 15, and 24. Among patients in ongoing response at 12 months, the percentage of patients with gene-marked CAR T cells generally decreased over time, with 100%, 93%, 82%, 89%, 80%, and 56% at 3, 6, 12, 15, 18, and 24 months, respectively. There was a decreased CAR T cell peak expansion in patients that failed to respond to KTE-X19. Peak CAR T cell expansion was increased in patients with an ongoing response at 12 months or in those who relapsed at 12 months, compared to nonresponding patients. Elevated CAR T cell levels were initially observed in patients who later relapsed, possibly pointing to alternate mechanisms for secondary treatment failure. CAR T cell peak levels normalized by baseline tumor burden and ongoing response at 12-month data cut are shown in FIG. 17A (INV) and 17B (CEN).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the disclosure.

We claim:

1. A method for treating relapsed or refractory mantle cell lymphoma (MCL) in a subject in need thereof that has a Ki-67 tumor proliferation index ≥50% or presence of a TP53 mutation, comprising administering to the subject a therapeutically effective amount of a composition which comprises autologous T cells expressing an anti-CD19 chimeric antigen receptor (CAR) wherein the T cells comprise CD4+ and CD8+ CAR T cells that are prepared from peripheral blood mononuclear cells (PBMCs) by positive enrichment and partial or complete depletion of circulating cancer cells and wherein the anti-CD19 CAR comprises an anti-CD19 single-chain variable fragment (scFv) comprising the heavy chain and light chain variable regions of FMC63, a CD28 intracellular signaling region, and a CD3-zeta signaling domain.

2. The method of claim 1, wherein the MCL is refractory to, or has relapsed following, one or more of chemotherapy, radiotherapy, immunotherapy, an autologous stem cell transplant, or any combination thereof.

3. The method of claim 1, wherein the subject has received 1-5 prior treatments, optionally wherein at least one of the prior treatments is selected from autologous SCT, anti-CD20 antibody, anthracycline- or bendamustine-containing chemotherapy, and/or a Bruton Tyrosine Kinase inhibitor (BTKi).

4. The method of claim 3, wherein the BTKi is ibrutinib or acalabrutinib.

5. The method of claim 1, wherein the subject receives a bridging therapy after leukapheresis to obtain the PBMCs and before the consequent partial or complete depletion of circulating cancer cells.

6. The method of claim 5, wherein the bridging therapy is selected from dexamethasone, ibrutinib, and/or acalabrutinib.

7. The method of claim 1, wherein the subject receives a lymphodepleting chemotherapy regimen of cyclophosphamide 500 mg/$m^2$ intravenously and fludarabine 30 mg/$m^2$ intravenously, both given on each of the fifth, fourth, and third days before T cell infusion.

8. The method of claim 1, wherein the PBMC are enriched for T cells by selection for CD4+ and CD8+ cells, activated with anti-CD3 and anti-CD28 antibodies in the presence of IL-2, and then transduced with a replication-incompetent viral vector containing a polynucleotide encoding the anti-CD19 CAR.

9. The method of claim 1, wherein the subject is administered a dose of $1\times10^6$ to $2\times10^6$ CAR positive viable T cells per kg body weight, with a maximum of $2\times10^8$ CAR positive viable T cells.

* * * * *